US012649723B2

(12) United States Patent
Pae et al.

(10) Patent No.: US 12,649,723 B2
(45) Date of Patent: Jun. 9, 2026

(54) CARBONOHYDRAZONOYL DICYANIDE COMPOUNDS COMPRISING 2 OR MORE ARYL OR HETEROARYL CONNECTED VIA LINKER AND USE THEREOF

(71) Applicant: KOREA INSTITUTE OF SCIENCE AND TECHNOLOGY, Seoul (KR)

(72) Inventors: Ae Nim Pae, Seoul (KR); Yun Kyung Kim, Seoul (KR); Sang Min Lim, Seoul (KR); Sungsu Lim, Seoul (KR); Haeun Lee, Seoul (KR); Woo Seung Son, Seoul (KR); Hye Yeon Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 671 days.

(21) Appl. No.: 18/011,469

(22) PCT Filed: Jun. 18, 2021

(86) PCT No.: PCT/KR2021/007694
§ 371 (c)(1),
(2) Date: Dec. 19, 2022

(87) PCT Pub. No.: WO2021/256902
PCT Pub. Date: Dec. 23, 2021

(65) Prior Publication Data
US 2023/0278965 A1 Sep. 7, 2023

(30) Foreign Application Priority Data
Jun. 19, 2020 (KR) ........................ 10-2020-0075042

(51) Int. Cl.

| | |
|---|---|
| ***C07D 241/24*** | (2006.01) |
| ***C07D 213/75*** | (2006.01) |
| ***C07D 237/08*** | (2006.01) |
| ***C07D 277/56*** | (2006.01) |
| ***C07D 333/60*** | (2006.01) |
| ***C07D 401/14*** | (2006.01) |
| ***C07D 409/12*** | (2006.01) |
| ***C07D 413/12*** | (2006.01) |
| ***C07D 417/12*** | (2006.01) |

(52) U.S. Cl.
CPC ......... *C07D 241/24* (2013.01); *C07D 213/75* (2013.01); *C07D 237/08* (2013.01); *C07D 277/56* (2013.01); *C07D 333/60* (2013.01); *C07D 401/14* (2013.01); *C07D 409/12* (2013.01); *C07D 413/12* (2013.01); *C07D 417/12* (2013.01)

(58) Field of Classification Search
CPC .................................................... C07D 241/24
See application file for complete search history.

(56) References Cited

U.S. PATENT DOCUMENTS

| | | | |
|---|---|---|---|
| 3,202,698 | A | 8/1965 | Prichard |
| 4,485,827 | A | 12/1984 | Komossa et al. |
| 8,809,302 | B2 | 8/2014 | Cohen et al. |
| 9,962,384 | B1 | 5/2018 | Kim et al. |
| 2014/0107125 | A1 | 4/2014 | Zhang et al. |

FOREIGN PATENT DOCUMENTS

| | | | |
|---|---|---|---|
| EP | 1 612 204 | A1 | 1/2006 |
| EP | 3 424 908 | A1 | 1/2019 |
| EP | 3 901 139 | A1 | 10/2021 |
| JP | 7-206800 | A | 8/1995 |
| JP | 2005-519878 | A | 7/2005 |
| JP | 7375019 | B2 | 11/2023 |
| KR | 10-2018-0050130 | A | 5/2018 |
| KR | 10-2020-0076808 | A | 6/2020 |
| WO | WO 2006/024858 | A1 | 3/2006 |

OTHER PUBLICATIONS

Pluta R et al. Tau Protein-Targeted Therapies in Alzheimer's Disease: Current State and Future Perspectives. In: Huang X, editor. Alzheimer's Disease: Drug Discovery [Internet]. Brisbane (AU): Exon Publications; Dec. 18, 2020. Chapter 4. Available from: https://www.ncbi.nlm.nih.gov/books/NBK566118/ (Year: 2020).*
CAS Registry No. 511241-38-6, Chemical Library, *Ambinter*, May 6, 2003, (1 page in English).
CAS Registry No. 903727-31-1, Chemical Library, *Scientific Exchange, Inc.*, Aug. 23, 2006, (1 page in English).
Korean Office Action issued on Jun. 30, 2023, in counterpart Korean Patent Application No. 10-2021-0079537 (8 pages in Korean).
Cankař, Petr, et al. "Heterocyclic Amine I*. The Cycloaddition Reaction of Malonodinitrile and Some of its Derivatives with Hydrazine and Their Use for the Preparation of 3,5-Diamino-4-Arylazo-Pyrazoles Derived from Sulfonamides" Acta Universitatis Palackianae Olomucensis Facultas Rerum Naturalium 2002 Chemica 41., (9 pages).
Barak, Dinesh S., et al. "Iodine-Catalyzed Diazenylation with Arylhydrazine Hydrochlorides in Air." The Journal of Organic Chemistry 83.7 (2018): 3537-3546.
Fouda, Ahmed M., et al. "Synthesis, In Vitro Antimicrobial and Cytotoxic Activities of Some New Pyrazolo [1,5-a] pyrimidine Derivatives." Molecules 24.6 (2019): 1080., (20 pages).
El-Sayed, Elsherbiny Hamdy, et al., "Synthesis and Antimicrobial Evaluation of Some New Pyrazolo [1, 5-a] pyrimidine and Pyrazolo [1, 5-c] triazine Derivatives Containing Sulfathiazole Moiety." Acta Chimica Slovenica 67.4 (2020): 1024-1034.

(Continued)

*Primary Examiner* — Alicia L Otton
(74) *Attorney, Agent, or Firm* — NSIP Law

(57) ABSTRACT

Provided are novel carbonohydrazonoyl dicyanide compounds including two or more aryl or heteroaryl groups connected via a linker and uses thereof.

9 Claims, No Drawings

(56) References Cited

OTHER PUBLICATIONS

Extended European search report issued on Jun. 10, 2024, in counterpart European Patent Application No. 21826659.1 (13 pages).
Crowe, Alex, et al. "Compound screening in cell-based models of tau inclusion formation: Comparison of primary neuron and HEK293 cell assays." *Journal of Biological Chemistry* vol. 295. Issue 12 (2020). pp 4001-4013.
Chinese Office Action issued on Oct. 17, 2024, in counterpart Chinese Patent Application No. 202180050494.2 (10 pages in English, 10 pages in Chinese).
Abdel-Gawad, F.M., et al. "New Sulphonamido-4-Hydrazonomesoxalonitriles with Spectrophotometric and Potentiometric Studies." Egyptian journal of chemistry 39.1 (1996): 73-82.
Eli-Gaby, Mohamed SA, et al. "Preparation of Some Novel 3,5-Diaminopyrazole, Pyrazolo-[1,5-a] [1, 3, 5] Triazine and Pyrazolo [1, 5-a]-Pyrimidine Derivatives Containing Sulfonamido Moieties as Antimicrobial Agents." Acta Chim. Slov 49 (2002): 159-171.
Hassan, Saber M., et al. "Chemistry and tautomerism of coupling products of diazotised sulfamethoxazole with some compounds containing an active methylene group." Journal of Chemical Research 2002.2 (2002): 64-65.
Kryštof, Vladimír, et al. "4-Arylazo-3,5-diamino-1 H-pyrazole CDK inhibitors: SAR study, Crystal Structure in Complex with CDK2, Selectivity, and Cellular Effects." Journal of medicinal chemistry 49.22 (2006): 6500-6509.
Registry(STN) CAS Registry No. 906726-39-4, Sep. 15, 2006.
Le Corre, Laurent, et al. "Microwave-assisted preparation of 4-amino-3-cyano-5-methoxycarbonyl-N-arylpyrazoles as building blocks for the diversity-oriented synthesis of pyrazole-based polycyclic scaffolds." Organic & Biomolecular Chemistry 13.2 (2015): 409-423.
Japanese Office Action issued on Dec. 19, 2023, in counterpart Japanese Patent Application No. 2022-577422 (3 pages in Japanese).

* cited by examiner

CARBONOHYDRAZONOYL DICYANIDE COMPOUNDS COMPRISING 2 OR MORE ARYL OR HETEROARYL CONNECTED VIA LINKER AND USE THEREOF

CROSS-REFERENCE TO RELATED APPLICATIONS

This application is a U.S. National Stage Application of International Application No. PCT/KR2021/007694, filed on Jun. 18, 2021, which claims the benefit under 35 USC 119(a) and 365(b) of Korean Patent Application No. 10-2020-0075042, filed on Jun. 19, 2020, in the Korean Intellectual Property Office, the entire disclosures of which are incorporated herein by reference for all purposes.

TECHNICAL FIELD

The present invention relates to novel carbonohydrazonoyl dicyanide compounds including two or more aryl or heteroaryl groups connected via a linker and uses thereof.

BACKGROUND ART

Tau protein (tau (T) protein), which is a microtubule-associated protein (MAP) mainly expressed in axons of nerve cells with a molecular weight of 50,000 to 70,000, serves to stabilize microtubules, and represents molecular diversity through phosphorylation. In humans, tau protein is formed into six isoforms by the insertion of 29 or 58 amino acid residues at the N-terminus and the alternative splicing of mRNA of 3 or 4 repeating structures (referred to as microtubule binding domain) at the C-terminus.

In healthy nerves, tau protein stabilizes microtubules by promoting growth from axons and nerve cell polarization. When pathological hyperphosphorylation occurs, tau protein separates from microtubules, resulting in insoluble aggregation. Further, a structural skeleton inducing the aggregation of tau protein has been proposed, and evidence has been provided that insoluble filaments are formed from 10 soluble monomers, and that these filaments are bound into high-dimensional structures called neurofibrillary tangles (NFTs). Human full-length tau protein includes a microtubule binding domain consisting of four repetitive conserved sequences. Among these repetitive sequences, positively charged residues have an important function in binding to highly negatively charged microtubules (20 to 30 electrons per αβ-tubulin dimer). The binding affinity to tau microtubules is also actively regulated by the phosphorylation of tau protein, and this phosphorylation causes dynamic rearrangement of microtubule networks. When tau protein is phosphorylated abnormally excessively, the balance of this dynamic rearrangement is disrupted, and the affinity to microtubules is rapidly decreased.

The hyperphosphorylation and/or aggregation of tau proteins cause abnormal accumulation of these tau proteins in nerve cells, which is pointed to as a cause of various neurodegenerative diseases and the like. Tau protein aggregates are mainly found in the cell bodies and dendrites of nerve cells, and these tau protein aggregates are called neurofibrillary tangles (NFTs) and neuropil threads. Examination of the microstructures of neurofibrillary tangles (NFTs) reveals that such microstructures thereof consist of paired helical filaments (PHFs) in which tau proteins are entangled like fine threads and are aggregated and hyperphosphorylated, unlike normal tau protein. An abnormal tau protein aggregation phenomenon appears also in tauopathy.

In this case, although it is not known exactly what role the aggregation of tau protein plays in the progress of tauopathy, this tau protein aggregation phenomenon appears similar to an aggregation phenomenon that is common in general neurodegenerative diseases.

As such, although it is known that hyperphosphorylation and/or aggregation of tau protein causes various neurodegenerative diseases comprising Alzheimer's disease and tauopathy, the specific mechanism how these abnormal tau species cause changes in the signaling pathway and elicit neurotoxicity has not yet been verified, and there are no effective treatment methods or therapeutic agents yet available to treat these diseases.

DISCLOSURE

Technical Problem

As a result of intensive efforts to develop novel small-molecule compounds capable of inhibiting aggregation and/or hyperphosphorylation of tau protein, the present inventors have found that a series of novel carbonohydrazonoyl dicyanide compounds including two or more aryl or heteroaryl groups connected via a linker effectively inhibit aggregation of tau protein without exhibiting cytotoxicity at effective concentrations, thereby completing the present invention.

Technical Solution

An object of the present invention is to provide a compound represented by Formula 1 below or a pharmaceutically acceptable salt thereof:

[Formula 1]

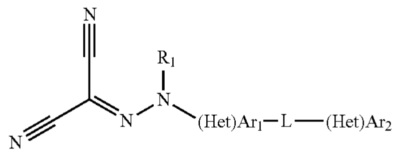

in Formula 1 above,

L is —NHCO—, —CONH—, —$NHSO_2$—, —$SO_2NH$—, or -(straight-chain or branched $C_{0-3}$ alkylene)'-O-(straight-chain or branched $C_{0-3}$ alkylene)"-;

$R_1$ is hydrogen, $C_{1-6}$ alkyl, or $C_{1-6}$ alkylcarbonyl;

$(Het)Ar_1$ is $C_{6-10}$ arylene or 5- to 10-membered heteroarylene; and $(Het)Ar_2$ is $C_{6-10}$ aryl or 5- to 10-membered heteroaryl;

wherein the $C_{6-10}$ aryl(ene) and 5- to 10-membered heteroaryl(ene) are each independently unsubstituted or substituted with at least one selected from the group consisting of $C_{1-6}$ alkyl, $C_{1-6}$ alkoxy, halogen, cyano, $C_{1-6}$ haloalkyl, and $C_{1-6}$ haloalkoxy.

Another object of the present invention is to provide a method of preparing the compound of the compound described above.

Still another object of the present invention is to provide a composition for inhibiting aggregation of tau protein including the compound described above as an active ingredient.

Still another object of the present invention is to provide a composition for inhibiting hyperphosphorylation of tau protein including the compound described above as an active ingredient.

Still another object of the present invention is to provide a pharmaceutical composition for preventing or treating a disease caused by aggregation or hyperphosphorylation of tau protein including the compound described above as an active ingredient.

Still another object of the present invention is to provide a method of preventing or treating a disease caused by aggregation or hyperphosphorylation of tau protein, the method including administering the pharmaceutical composition described above to a subject in need thereof.

Advantageous Effects

The novel carbonohydrazonoyl dicyanide compounds including two or more aryl or heteroaryl groups connected via a linker of the present invention may effectively inhibit aggregation and/or hyperphosphorylation of tau protein, and thus may be effectively used in prevention or treatment of diseases caused thereby such as Alzheimer's disease and various tauopathies.

BEST MODE

A first aspect of the present invention provides a compound represented by Formula 1 below or a pharmaceutically acceptable salt thereof:

[Formula 1]

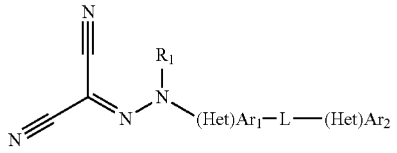

in Formula 1 above,

L is —NHCO—, —CONH—, —$NHSO_2$—, —$SO_2NH$—, or -(straight-chain or branched $C_{0-3}$ alkylene)'-O-(straight-chain or branched $C_{0-3}$ alkylene)"-;

$R_1$ is hydrogen, $C_{1-6}$ alkyl, or $C_{1-6}$ alkylcarbonyl;

(Het)$Ar_1$ is $C_{6-10}$ arylene or 5- to 10-membered heteroarylene; and (Het)$Ar_2$ is $C_{6-10}$ aryl or 5- to 10-membered heteroaryl;

wherein the $C_{6-10}$ aryl(ene) and 5- to 10-membered heteroaryl(ene) are each independently unsubstituted or substituted with at least one selected from the group consisting of $C_{1-3}$ alkyl, $C_{1-6}$ alkoxy, halogen, cyano, $C_{1-6}$ haloalkyl, and $C_{1-6}$ haloalkoxy.

For example, in the compound of the present invention, L may be —NHCO—, —CONH—, —$NHSO_2$—, —$SO_2NH$—, —O—, —O—$CH_2$—, —O—$(CH_2)_2$—, or —O—$CH(CH_3)$—, without being limited thereto.

For example, in the compound of the present invention, $R_1$ is hydrogen, methyl, or acetyl;

(Het)$Ar_1$ is phenylene, pyridinylene, pyrazinylene, pyrimidinylene, pyrazolylene, pyridazinylene, thiophenylene, benzothiazolylene, thiazolopyridinylene, quinoxalinylene, thiazolylene, isoxazolylene, oxazolylene, furanylene, benzoimidazolylene, benzothiophenylene, or benzooxazolylene; and (Het)$Ar_2$ is phenyl, pyridinyl, pyrazinyl, pyrimidinyl, pyrazolyl, pyridazinyl, thiophenyl, benzothiazolyl, thiazolopyridinyl, quinoxalinyl, thiazolyl, isoxazolyl, oxazolyl, furanyl, benzoimidazolyl, benzothiophenyl, or benzooxazolyl, wherein the (Het)$Ar_1$ and (Het)$Ar_2$ are each independently unsubstituted or substituted with at least one selected from the group consisting of methyl, methoxy, fluoro, chloro, cyano, and trifluoromethyl, without being limited thereto.

Specifically, in the compound of the present invention, $R_1$ is hydrogen, methyl, or acetyl;

(Het)$Ar_1$ is phenylene, pyridinylene, or thiazolopyridinylene; and (Het)$Ar_2$ is phenyl, pyridinyl, pyrazinyl, pyrimidinyl, pyrazolyl, pyridazinyl, thiophenyl, benzothiazolyl, quinoxalinyl, thiazolyl, isoxazolyl, oxazolyl, furanyl, benzoimidazolyl, benzothiophenyl, or benzooxazolyl, wherein the (Het)$Ar_1$ and (Het)$Ar_2$ are each independently unsubstituted or substituted with at least one selected from the group consisting of methyl, methoxy, fluoro, chloro, cyano, and trifluoromethyl, without being limited thereto.

More specifically, the compound may be 1, (6-(5-methylpyrazine-2-carboxamido)pyridin-3-yl)carbonohydrazonoyl dicyanide, 2. (4-(5-methylpyrazine-2-carboxamido)phenyl)carbonohydrazonoyl dicyanide, 3. (2-fluoro-4-(5-methylpyrazine-2-carboxamido)phenyl)carbonohydrazonoyl dicyanide, 4. (2-methoxy-4-(5-methylpyrazine-2-carboxamido)phenyl)carbonohydrazonoyl dicyanide, 5. (2-chloro-4-(5-methylpyrazine-2-carboxamido)phenyl)carbonohydrazonoyl dicyanide, 6. (2-methyl-4-(5-methylpyrazine-2-carboxamido)phenyl)carbonohydrazonoyl dicyanide, 7. (3-fluoro-4-(5-methylpyrazine-2-carboxamido)phenyl)carbonohydrazonoyl dicyanide, 8. (3-methyl-4-(5-methylpyrazine-2-carboxamido)phenyl)carbonohydrazonoyl dicyanide, 9. methyl(3-methyl-4-(5-methylpyrazine-2-carboxamido)phenyl)carbonohydrazonoyl dicyanide, 10. (3-methoxy-4-(5-methylpyrazine-2-carboxamido)phenyl)carbonohydrazonoyl dicyanide, 11. (3-chloro-4-(5-methylpyrazine-2-carboxamido)phenyl)carbonohydrazonoyl dicyanide, 12. (5-methyl-6-(5-methylpyrazine-2-carboxamido)pyridin-3-yl)carbonohydrazonoyl dicyanide, 13. (4-methyl-6-(5-methylpyrazine-2-carboxamido)pyridin-3-yl)carbonohydrazonoyl dicyanide, 14. (5-(5-methylpyrazine-2-carboxamido)pyridin-2-yl)carbonohydrazonoyl dicyanide, 15. (6-benzamidopyridin-3-yl)carbonohydrazonoyl dicyanide, 16. (6-(4-fluorobenzamido)pyridin-3-yl)carbonohydrazonoyl dicyanide, 17. (6-(2-fluorobenzamido)pyridin-3-yl)carbonohydrazonoyl dicyanide, 18. (6-(3-fluorobenzamido)pyridin-3-yl)carbonohydrazonoyl dicyanide, 19. (6-(3-fluoro-5-methylbenzamido)pyridin-3-yl)carbonohydrazonoyl dicyanide, 20. (6-(2-fluoro-3-methylbenzamido)pyridin-3-yl)carbonohydrazonoyl dicyanide, 21. (6-(4-fluoro-3-methylbenzamido)pyridin-3-yl)carbonohydrazonoyl dicyanide, 22. (6-(3-fluoro-4-methylbenzamido)pyridin-3-yl)carbonohydrazonoyl dicyanide, 23. (6-(4-methylbenzamido)pyridin-3-yl)carbonohydrazonoyl dicyanide, 24. (6-(3-methylbenzamido)pyridin-3-yl)carbonohydrazonoyl dicyanide, 25. (6-(2-methylbenzamido)pyridin-3-yl)carbonohydrazonoyl dicyanide,
26. (6-(3-(trifluoromethyl)benzamido)pyridin-3-yl)carbonohydrazonoyl dicyanide,
27. (6-(4-(trifluoromethyl)benzamido)pyridin-3-yl)carbonohydrazonoyl dicyanide,
28. (6-(2-(trifluoromethyl)benzamido)pyridin-3-yl)carbonohydrazonoyl dicyanide,
29. (6-(pyrimidine-2-carboxamido)pyridin-3-yl)carbonohydrazonoyl dicyanide,
30. (6-(thiophene-2-carboxamido)pyridin-3-yl)carbonohydrazonoyl dicyanide,
31. (6-(benzo[d]thiazole-2-carboxamido)pyridin-3-yl)carbonohydrazonoyl dicyanide,
32. (6-(quinoxaline-2-carboxamido)pyridin-3-yl)carbonohydrazonoyl dicyanide,
33. (2-(5-methylpyrazine-2-carboxamido)thiazolo[4,5-b]pyridin-6-yl)carbonohydrazonoyl dicyanide,
34. (6-(p-tolylcarbamoyl)pyridin-3-yl)carbonohydrazonoyl dicyanide,
35. (6-(4-methoxyphenylcarbamoyl)pyridin-3-yl)carbonohydrazonoyl dicyanide,
36. (6-(5-methylpyrazin-2-ylcarbamoyl)pyridin-3-yl)carbonohydrazonoyl dicyanide,
37. (6-(4-chlorophenylcarbamoyl)pyridin-3-yl)carbonohydrazonoyl dicyanide,
38. (6-(6-methylpyridin-3-ylcarbamoyl)pyridin-3-yl)carbonohydrazonoyl dicyanide,
39 (6-(5-methylpyridin-3-ylcarbamoyl)pyridin-3-yl)carbonohydrazonoyl dicyanide,
40. (6-(pyridin-3-ylcarbamoyl)pyridin-3-yl)carbonohydrazonoyl dicyanide,
41. (6-(6-methylpyrazin-2-ylcarbamoyl)pyridin-3-yl)carbonohydrazonoyl dicyanide,
42. (6-(pyrimidin-5-ylcarbamoyl)pyridin-3-yl)carbonohydrazonoyl dicyanide,
43. (6-(pyrimidin-2-ylcarbamoyl)pyridin-3-yl)carbonohydrazonoyl dicyanide,
44. (4-(4-methoxyphenylcarbamoyl)phenyl)carbonohydrazonoyl dicyanide,
45. (4-(5-methylpyrazin-2-ylcarbamoyl)phenyl)carbonohydrazonoyl dicyanide,
46. (4-(6-methylpyrazin-2-ylcarbamoyl)phenyl)carbonohydrazonoyl dicyanide,
47. (4-(6-methylpyridin-3-ylcarbamoyl)phenyl)carbonohydrazonoyl dicyanide,
48. (4-(5-methylpyridin-3-ylcarbamoyl)phenyl)carbonohydrazonoyl dicyanide,
49. (4-(pyridin-3-ylcarbamoyl)phenyl)carbonohydrazonoyl dicyanide,
50. (4-(pyrimidin-5-ylcarbamoyl)phenyl)carbonohydrazonoyl dicyanide,
51 (2-methoxy-4-(5-methylpyrazin-2-ylcarbamoyl)phenyl)carbonohydrazonoyl dicyanide,
52. (3-methyl-4-(5-methylpyrazin-2-ylcarbamoyl)phenyl)carbonohydrazonoyl dicyanide,
53. (3-methyl-4-(6-methylpyridin-3-ylcarbamoyl)phenyl)carbonohydrazonoyl dicyanide,
54. (3-methyl-4-(6-methylpyrazin-2-ylcarbamoyl)phenyl)carbonohydrazonoyl dicyanide,
55. (2-methyl-4-(6-methylpyridin-3-ylcarbamoyl)phenyl)carbonohydrazonoyl dicyanide,
56. (2-fluoro-4-(5-methylpyrazin-2-ylcarbamoyl)phenyl)carbonohydrazonoyl dicyanide,
57. (2-methoxy-4-(6-methylpyridin-3-ylcarbamoyl)phenyl)carbonohydrazonoyl dicyanide,
58. (6-(phenylsulfonamido)pyridin-3-yl)carbonohydrazonoyl dicyanide,
59. (6-(4-methoxyphenylsulfonamido)pyridin-3-yl)carbonohydrazonoyl dicyanide,
60. (6-(pyridine-3-sulfonamido)pyridin-3-yl)carbonohydrazonoyl dicyanide,
61. (6-(1-methyl-1H-pyrazole-4-sulfonamido)pyridin-3-yl)carbonohydrazonoyl dicyanide,
62. (6-(thiophene-2-sulfonamido)pyridin-3-yl)carbonohydrazonoyl dicyanide,
63. (6-(4-methylphenylsulfonamido)pyridin-3-yl)carbonohydrazonoyl dicyanide,
64. (6-(4-fluorophenylsulfonamido)pyridin-3-yl)carbonohydrazonoyl dicyanide,
65. (4-(N-(6-methylpyridin-3-yl)sulfamoyl)phenyl)carbonohydrazonoyl dicyanide,
66. (4-(N-(4-methoxyphenyl)sulfamoyl)phenyl)carbonohydrazonoyl dicyanide,
67. (4-(N-(5-methylpyrazin-2-yl)sulfamoyl)phenyl)carbonohydrazonoyl dicyanide,
68. (6-phenoxypyridin-3-yl)carbonohydrazonoyl dicyanide,
69. (6-(3-fluorophenoxy)pyridin-3-yl)carbonohydrazonoyl dicyanide,
70. (5-phenoxypyridin-2-yl)carbonohydrazonoyl dicyanide,
71. (3-fluoro-4-phenoxyphenyl)carbonohydrazonoyl dicyanide,
72. (3-fluoro-4-(pyridin-3-yloxy)phenyl)carbonohydrazonoyl dicyanide,
73. (4-phenoxy-3-(trifluoromethyl)phenyl)carbonohydrazonoyl dicyanide,
74. (3-methyl-4-(pyridin-3-yloxy)phenyl)carbonohydrazonoyl dicyanide,
75. methyl(5-phenoxypyridin-2-yl)carbonohydrazonoyl dicyanide,
76. (6-(3-fluorophenoxy)pyridin-3-yl)(methyl)carbonohydrazonoyl dicyanide,
77. (3-fluoro-4-phenoxyphenyl)(methyl)carbonohydrazonoyl dicyanide,
78. methyl(4-phenoxy-3-(trifluoromethyl)phenyl)carbonohydrazonoyl dicyanide,
79. (3-methyl-4-(pyridin-4-yloxy)phenyl)carbonohydrazonoyl dicyanide,
80. (3-fluoro-4-(pyridin-4-yloxy)phenyl)carbonohydrazonoyl dicyanide,
81. (3-methyl-4-(pyrimidin-5-yloxy)phenyl)carbonohydrazonoyl dicyanide,
82. (3-fluoro-4-(pyrimidin-5-yloxy)phenyl)carbonohydrazonoyl dicyanide,
83. (4-(pyridin-2-yloxy)phenyl)carbonohydrazonoyl dicyanide,
34. (4-(pyrazin-2-yloxy)phenyl)carbonohydrazonoyl dicyanide,
35. (4-(pyridin-3-yloxy)phenyl)carbonohydrazonoyl dicyanide,
86. (4-(2-cyanophenoxy)phenyl)carbonohydrazonoyl dicyanide,
87. (4-(4-cyanophenoxy)phenyl)carbonohydrazonoyl dicyanide,
38. (4-(3-cyanophenoxy)phenyl)carbonohydrazonoyl dicyanide,
89. (4-(6-(trifluoromethyl)pyridin-3-yloxy)phenyl)carbonohydrazonoyl dicyanide,
90. (4-(5-(trifluoromethyl)pyridin-2-yloxy)phenyl)carbonohydrazonoyl dicyanide,
91. (4-(pyrimidin-2-yloxy)phenyl)carbonohydrazonoyl dicyanide, 92. (4-(pyridazin-3-yloxy)phenyl)carbonohydrazonoyl dicyanide,
93. (4-(2-fluorophenoxy)phenyl)carbonohydrazonoyl dicyanide,
94. (4-(3-fluorophenoxy)phenyl)carbonohydrazonoyl dicyanide,
95. (6-(benzyloxy)pyridin-3-yl)carbonohydrazonoyl dicyanide,
96. (6-(4-(trifluoromethyl)benzyloxy)pyridin-3-yl)carbonohydrazonoyl dicyanide,
97. (4-(benzyloxy)-3-(trifluoromethyl)phenyl)carbonohydrazonoyl dicyanide,
98. (3-(trifluoromethyl)-4-(4-(trifluoromethyl)benzyloxy)phenyl)carbonohydrazonoyl dicyanide,
99. (6-(4-methylbenzyloxy)pyridin-3-yl)carbonohydrazonoyl dicyanide,
100. (6-phenethoxypyridin-3-yl)carbonohydrazonoyl dicyanide,
101. (4-phenethoxy-3-(trifluoromethyl)phenyl)carbonohydrazonoyl dicyanide,
102. (6-(4-methoxyphenethoxy)pyridin-3-yl)carbonohydrazonoyl dicyanide,
103. (6-(4-(trifluromethyl)phenethoxy)pyridin-3-yl)carbonohydrazonoyl dicyanide,
104. (3-methoxy-4-(5-methylpyrazin-2-ylcarbamoyl)phenyl)carbonohydrazonoyl dicyanide,
105. (3-methoxy-4-(6-methylpyrazin-2-ylcarbamoyl)phenyl)carbonohydrazonoyl dicyanide,
106. (3-chloro-4-(5-methylpyrazin-2-ylcarbamoyl)phenyl)carbonohydrazonoyl dicyanide,
107. (3-methoxy-4-(5-methylpyridin-3-ylcarbamoyl)phenyl)carbonohydrazonoyl dicyanide,
108. (3-methoxy-4-(p-tolylcarbamoyl)phenyl)carbonohydrazonoyl dicyanide,
109. (3-methoxy-4-(4-methoxyphenylcarbamoyl)phenyl)carbonohydrazonoyl dicyanide,
110. (6-(furan-3-carboxamido)pyridin-3-yl)carbonohydrazonoyl dicyanide,
111. (3-methyl-4-(thiazole-4-carboxamido)phenyl)carbonohydrazonoyl dicyanide,
112. (6-(thiazole-4-carboxamide)pyridin-3-yl)carbonohydrazonoyl dicyanide,
113. (6-(oxazole-4-carboxamido)pyridin-3-yl)carbonohydrazonoyl dicyanide,
114. (6-(oxazole-5-carboxamido)pyridin-3-yl)carbonohydrazonoyl dicyanide,
115. (6-(isoxazole-3-carboxamido)pyridin-3-yl)carbonohydrazonoyl dicyanide,
116. (4-(thiazol-2-yloxy)phenyl)carbonohydrazonoyl dicyanide,
117. (4-(benzyloxy)phenyl)carbonohydrazonoyl dicyanide,
118. (4-(4-(trifluoromethyl)benzyloxy)phenyl)carbonohydrazonoyl dicyanide,
119. (4-(4-methylbenzyloxy)phenyl)carbonohydrazonoyl dicyanide,
120. (4-(4-methoxyphenethoxy)phenyl)carbonohydrazonoyl dicyanide,
121. (4-(4-(trifluoromethyl)phenethoxy)phenyl)carbonohydrazonoyl dicyanide,
122. (4-phenethoxyphenyl)carbonohydrazonoyl dicyanide,
123. (4-(4-chlorophenethoxy)phenyl)carbonohydrazonoyl dicyanide,
124. (4-(pyridin-3-ylmethoxy)phenyl)carbonohydrazonoyl dicyanide,
125. (4-(pyrazin-2-ylmethoxy)phenyl)carbonohydrazonoyl dicyanide,
126. (4-((1H-benzo[d]imidazol-2-yl)methoxy)phenyl)carbonohydrazonoyl dicyanide,
127. (4-(pyridazin-3-ylmethoxy)phenyl)carbonohydrazonoyl dicyanide,
128. (4-(benzo[d]oxazol-2-ylmethoxy)phenyl)carbonohydrazonoyl dicyanide,
129. (4-(benzo[d]thiazol-2-ylmethoxy)phenyl)carbonohydrazonoyl dicyanide,
130. (4-(benzo[b]thiophen-2-ylmethoxy)phenyl)carbonohydrazonoyl dicyanide,
131. (6-(4-chlorophenethoxy)pyridin-3-yl)carbonohydrazonoyl dicyanide,
132. (4-(4-methylbenzyloxy)-3-(trifluoromethyl)phenyl)carbonohydrazonoyl dicyanide,
133. (4-(4-chlorophenethoxy)-3-(trifluoromethyl)phenyl)carbonohydrazonoyl dicyanide,
134. (4-(4-methoxyphenethoxy)-3-(trifluoromethyl)phenyl)carbonohydrazonoyl dicyanide,
135. (3-(trifluormethyl)-4-(4-(trifluoromethyl)phenethoxy)phenyl)carbonohydrazonoyl dicyanide,
136. (4-(pyrimidin-2-ylmethoxy)phenyl)carbonohydrazonoyl dicyanide,
137. (4-((1H-pyrazol-4-yl)methoxy)phenyl)carbonohydrazonoyl dicyanide,
138. (4-((5-methylpyrazin-2-yl)methoxy)phenyl)carbonohydrazonoyl dicyanide,
139. (4-(1-(4-(trifluoromethyl)phenyl)ethoxy)phenyl)carbonohydrazonoyl dicyanide,
140. (4-(1-(pyridin-3-yl)ethoxy)phenyl)carbonohydrazonoyl dicyanide,
141. (4-(benzyloxy)-3-methylphenyl)carbonohydrazonoyl dicyanide,
142. (3-methyl-4-(4-methylbenzyloxy)phenyl)carbonohydrazonoyl dicyanide,
143. 3-methyl-4-(pyrimidin-2-ylmethoxy)phenyl)carbonohydrazonoyl dicyanide,
144. (3-methyl-4-(pyrazin-2-ylmethoxy)phenyl)carbonohydrazonoyl dicyanide,
145. (3-methyl-4-(pyridin-3-ylmethoxy)phenyl)carbonohydrazonoyl dicyanide,
146. (4-((1H-benzo[d]imidazol-2-yl)methoxy)-3-methylphenyl)carbonohydrazonoyl dicyanide,
147. (3-methyl-4-((5-methylpyrazin-2-yl)methoxy)phenyl)carbonohydrazonoyl dicyanide,
148. (3-methyl-4-(4-(trifluoromethyl)benzyloxy)phenyl)carbonohydrazonoyl dicyanide,
149. (3-methyl-4-(pyridazin-3-ylmethoxy)phenyl)carbonohydrazonoyl dicyanide,
150. (4-(benzo[b]thiophen-2-ylmethoxy)-3-methylphenyl)carbonohydrazonoyl dicyanide,
151. (4-((1H-pyrazol-3-yl)methoxy)-3-methylphenyl)carbonohydrazonoyl dicyanide,
152. (3-methyl-4-(thiazol-4-ylmethoxy)phenyl)carbonohydrazonoyl dicyanide,
153. (4-(benzyloxy)-3-methoxyphenyl)carbonohydrazonoyl dicyanide,
154. (3-methoxy-4-(4-methylbenzyloxy)phenyl)carbonohydrazonoyl dicyanide,
155. (3-methoxy-4-(4-(trifluoromethyl)benzyloxy)phenyl)carbonohydrazonoyl dicyanide,
156. (4-(benzo[d]oxazol-2-ylmethoxy)-3-methylphenyl)carbonohydrazonoyl dicyanide,
157. (4-(benzo[d]thiazol-2-ylmethoxy)-3-methylphenyl)carbonohydrazonoyl dicyanide,
158. (4-(benzo[b]thiophen-2-ylmethoxy)-3-methoxyphenyl)carbonohydrazonoyl dicyanide, 159. (3-methoxy-4-(pyrazin-2-ylmethoxy)phenyl)carbonohydrazonoyl dicyanide,
160. (3-methoxy-4-(pyridin-3-ylmethoxy)phenyl)carbonohydrazonoyl dicyanide,
161. (3-methoxy-4-(pyrimidin-2-ylmethoxy)phenyl)carbonohydrazonoyl dicyanide,
162. (3-methoxy-4-((5-methylpyrazin-2-yl)methoxy)phenyl)carbonohydrazonoyl dicyanide,
163. (4-((1H-benzo[d]imidazol-2-yl)methoxy)-3-methoxyphenyl)carbonohydrazonoyl dicyanide,
164. (3-methoxy-4-(pyridazin-3-ylmethoxy)phenyl)carbonohydrazonoyl dicyanide,
165. (4-(benzo[d]thiazol-2-ylmethoxy)-3-methoxyphenyl)carbonohydrazonoyl dicyanide,
166. (4-(benzo[d]oxazol-2-ylmethoxy)-3-methoxyphenyl)carbonohydrazonoyl dicyanide,
167. (3-methoxy-4-(thiazol-4-ylmethoxy)phenyl)carbonohydrazonoyl dicyanide,
168. (4-((1H-pyrazol-3-yl)methoxy)-3-methoxyphenyl)carbonohydrazonoyl dicyanide,
169. (3-methoxy-4-(pyridin-2-ylmethoxy)phenyl)carbonohydrazonoyl dicyanide,
170. (3-methoxy-4-((6-methylpyridin-3-yl)methoxy)phenyl)carbonohydrazonoyl dicyanide,
171. (3-methoxy-4-((2-methylthiazol-4-yl)methoxy)phenyl)carbonohydrazonoyl dicyanide,
172. (3-methoxy-4-(thiophen-2-ylmethoxy)phenyl)carbonohydrazonoyl dicyanide,
173. (3-methoxy-4-(thiophen-3-ylmethoxy)phenyl)carbonohydrazonoyl dicyanide,
174. (3-methoxy-4-((1-methyl-1H-pyrazol-4-yl)methoxy)phenyl)carbonohydrazonoyl dicyanide, or
175. acetyl(3-methyl-4-(4-methylbenzyloxy)phenyl)carbonohydrazonoyl dicyanide.

Furthermore, these compounds may be compounds represented by formulae shown in Table 1 below.

TABLE 1

| Example | |
|---|---|
| 1 | 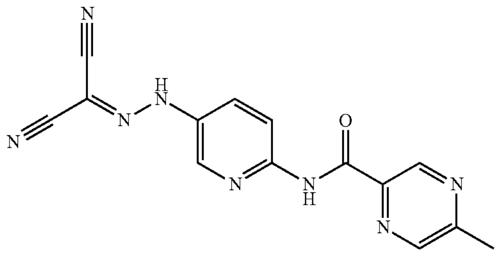 |
| 2 | 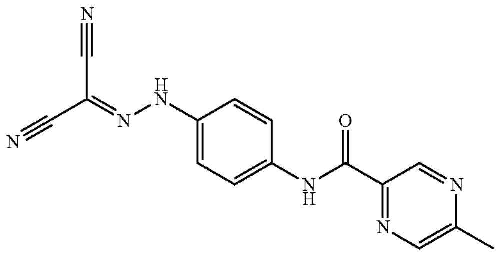 |
| 3 | 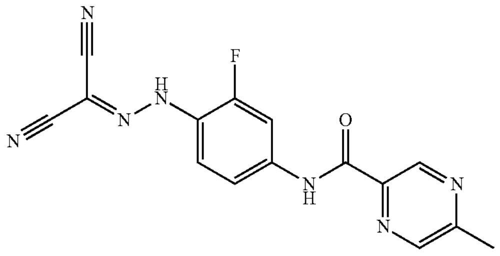 |
| 4 | 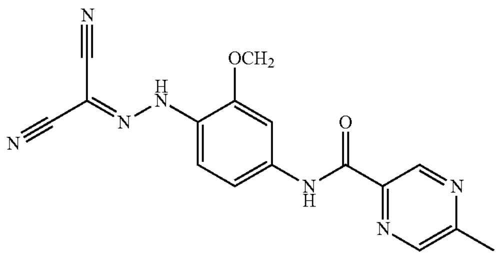 |

TABLE 1-continued
| Example | |
|---|---|
| 5 | 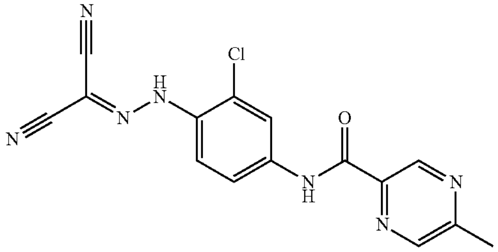 [SMILES: Cc1cnc(C(=O)Nc2ccc(NN=C(C#N)C#N)c(Cl)c2)cn1] |
| 6 | 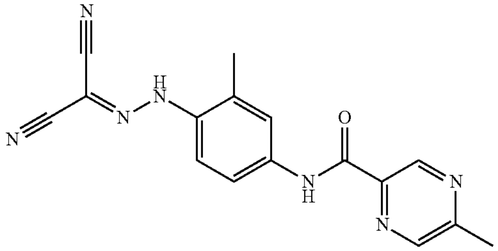 [SMILES: Cc1cnc(C(=O)Nc2ccc(NN=C(C#N)C#N)c(C)c2)cn1] |
| 7 | 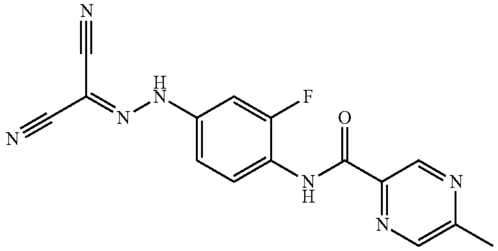 [SMILES: Cc1cnc(C(=O)Nc2ccc(NN=C(C#N)C#N)cc2F)cn1] |
| 8 | 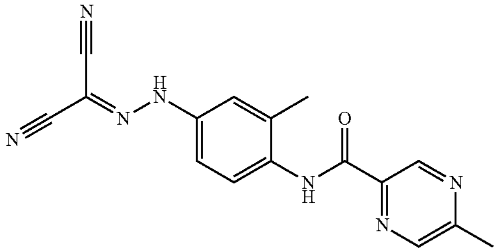 [SMILES: Cc1cnc(C(=O)Nc2ccc(NN=C(C#N)C#N)cc2C)cn1] |
| 9 | 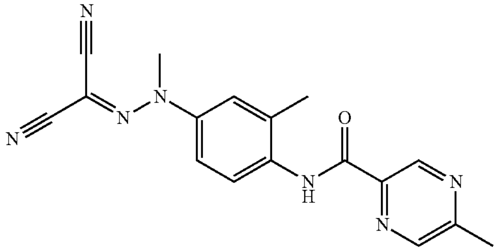 [SMILES: Cc1cnc(C(=O)Nc2ccc(N(C)N=C(C#N)C#N)cc2C)cn1] |
| 10 | 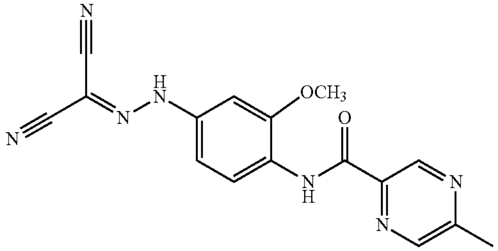 [SMILES: COc1cc(NN=C(C#N)C#N)ccc1NC(=O)c1cnc(C)cn1] |

TABLE 1-continued
| Example | |
|---|---|
| 11 | 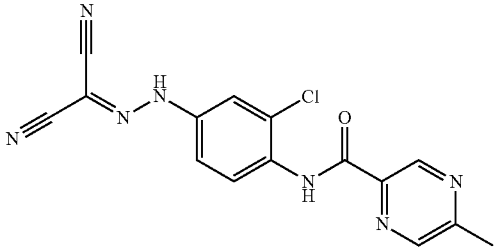 |
| 12 | 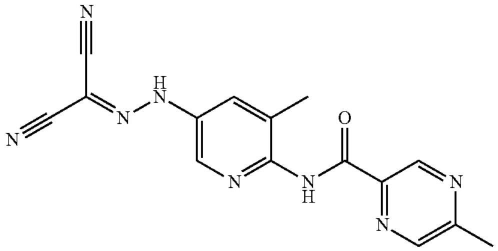 [SMILES: Cc1cnc(C(=O)Nc2ncc(NN=C(C#N)C#N)cc2C)cn1] |
| 13 | 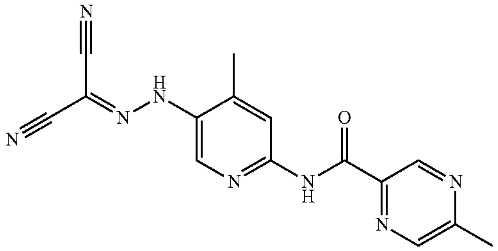 |
| 14 | 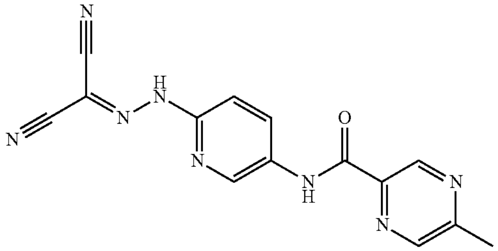 [SMILES: Cc1cnc(C(=O)Nc2ccc(NN=C(C#N)C#N)nc2)cn1] |
| 15 | 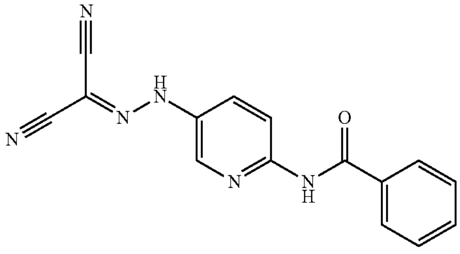 [SMILES: N#CC(C#N)=NNc1ccc(NC(=O)c2ccccc2)nc1] |
| 16 | 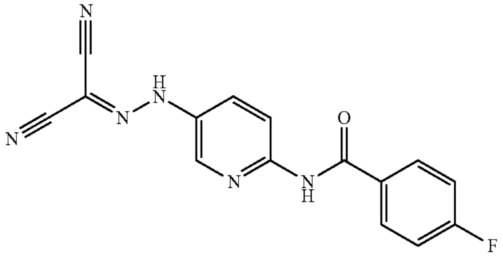 [SMILES: N#CC(C#N)=NNc1ccc(NC(=O)c2ccc(F)cc2)nc1] |

TABLE 1-continued
| Example | |
|---|---|
| 17 | 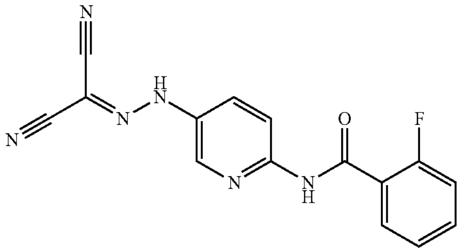 [SMILES: N#CC(C#N)=NNc1ccc(NC(=O)c2ccccc2F)nc1] |
| 18 | 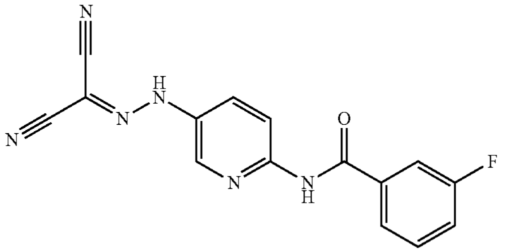 [SMILES: N#CC(C#N)=NNc1ccc(NC(=O)c2cccc(F)c2)nc1] |
| 19 | 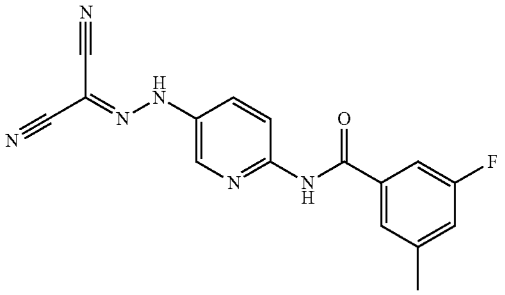 [SMILES: Cc1cc(F)cc(C(=O)Nc2ccc(NN=C(C#N)C#N)cn2)c1] |
| 20 | 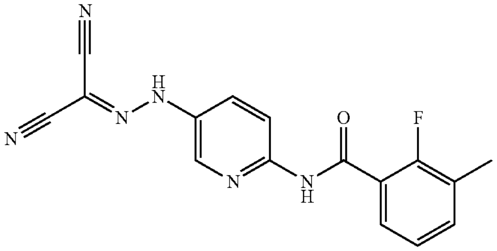 [SMILES: Cc1cccc(C(=O)Nc2ccc(NN=C(C#N)C#N)cn2)c1F] |
| 21 | 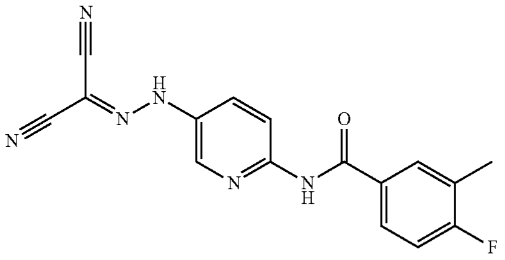 [SMILES: Cc1cc(C(=O)Nc2ccc(NN=C(C#N)C#N)cn2)ccc1F] |
| 22 | 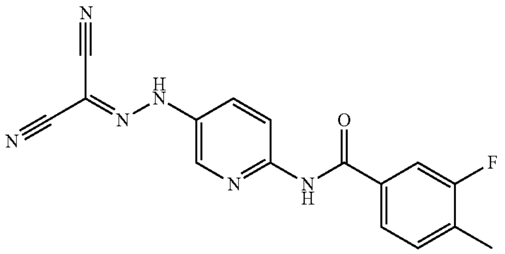 [SMILES: Cc1ccc(C(=O)Nc2ccc(NN=C(C#N)C#N)cn2)cc1F] |

TABLE 1-continued
| Example | |
|---|---|
| 23 | 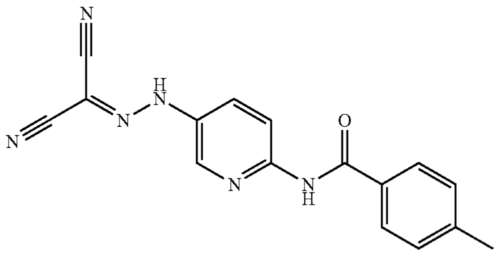 [SMILES: Cc1ccc(C(=O)Nc2ccc(NN=C(C#N)C#N)cn2)cc1] |
| 24 | 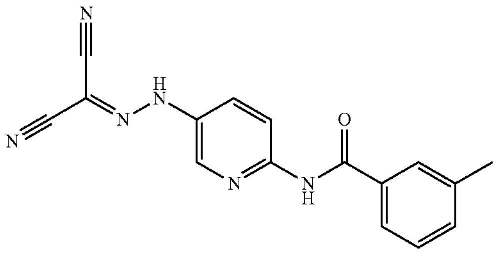 [SMILES: Cc1cccc(C(=O)Nc2ccc(NN=C(C#N)C#N)cn2)c1] |
| 25 | 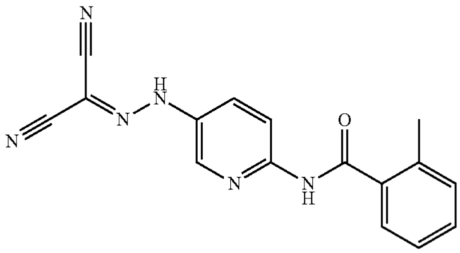 [SMILES: Cc1ccccc1C(=O)Nc1ccc(NN=C(C#N)C#N)cn1] |
| 26 | 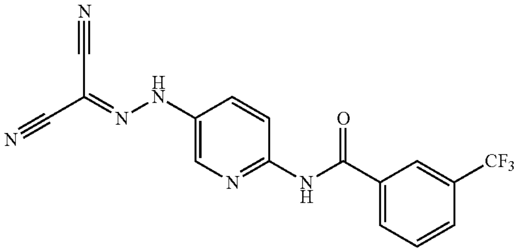 [SMILES: N#CC(C#N)=NNc1ccc(NC(=O)c2cccc(C(F)(F)F)c2)nc1] |
| 27 | 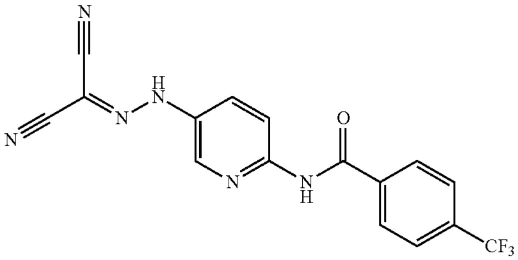 [SMILES: N#CC(C#N)=NNc1ccc(NC(=O)c2ccc(C(F)(F)F)cc2)nc1] |
| 28 | 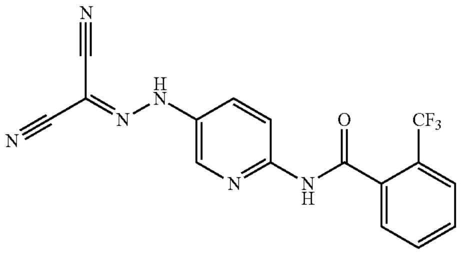 [SMILES: N#CC(C#N)=NNc1ccc(NC(=O)c2ccccc2C(F)(F)F)nc1] |

TABLE 1-continued
| Example | |
|---|---|
| 29 | 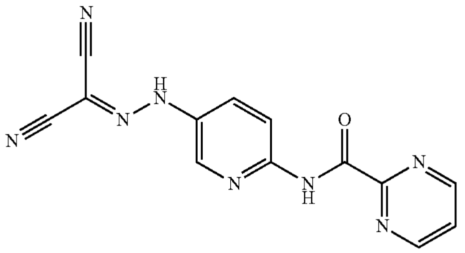 [SMILES: N#CC(C#N)=NNc1ccc(NC(=O)c2ncccn2)nc1] |
| 30 | 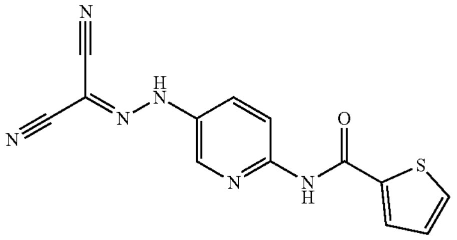 [SMILES: N#CC(C#N)=NNc1ccc(NC(=O)c2cccs2)nc1] |
| 31 | 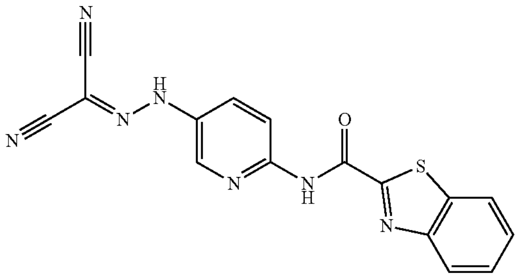 [SMILES: N#CC(C#N)=NNc1ccc(NC(=O)c2nc3ccccc3s2)nc1] |
| 32 | 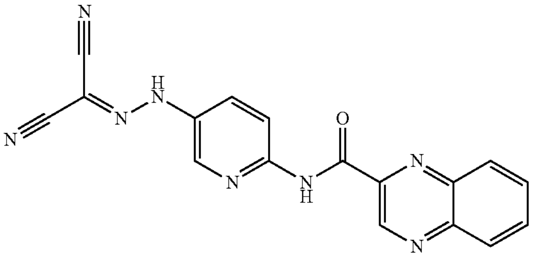 [SMILES: N#CC(C#N)=NNc1ccc(NC(=O)c2cnc3ccccc3n2)nc1] |
| 33 | 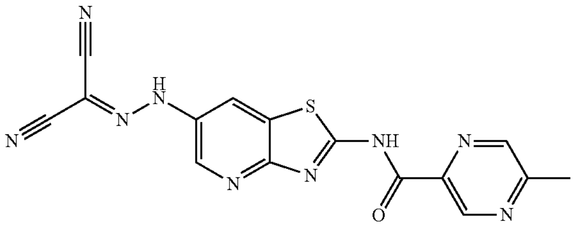 [SMILES: Cc1cnc(C(=O)Nc2nc3ncc(NN=C(C#N)C#N)cc3s2)cn1] |
| 34 | 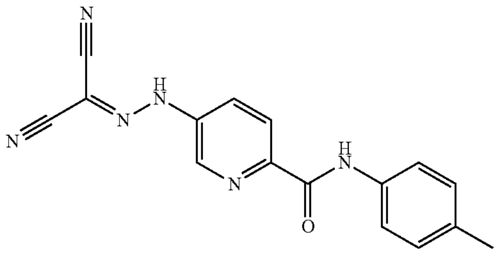 [SMILES: Cc1ccc(NC(=O)c2ccc(NN=C(C#N)C#N)cn2)cc1] |

TABLE 1-continued
| Example | |
|---|---|
| 35 | 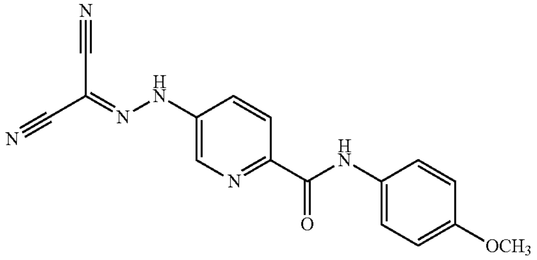 [SMILES: COc1ccc(NC(=O)c2ccc(NN=C(C#N)C#N)cn2)cc1] |
| 36 | 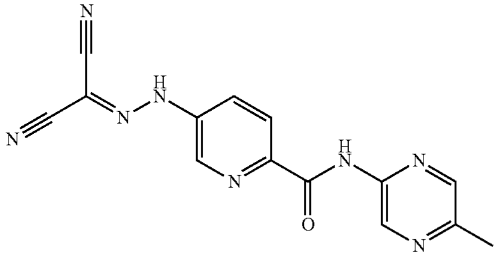 [SMILES: Cc1cnc(NC(=O)c2ccc(NN=C(C#N)C#N)cn2)cn1] |
| 37 | 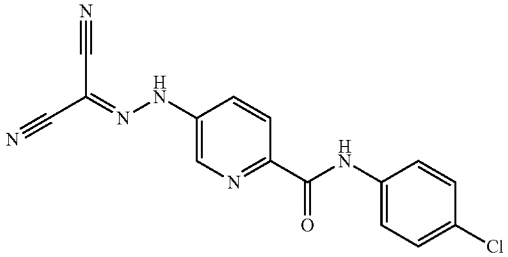 [SMILES: N#CC(C#N)=NNc1ccc(C(=O)Nc2ccc(Cl)cc2)nc1] |
| 38 | 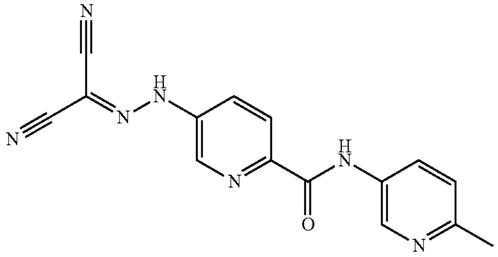 [SMILES: Cc1ccc(NC(=O)c2ccc(NN=C(C#N)C#N)cn2)cn1] |
| 39 | 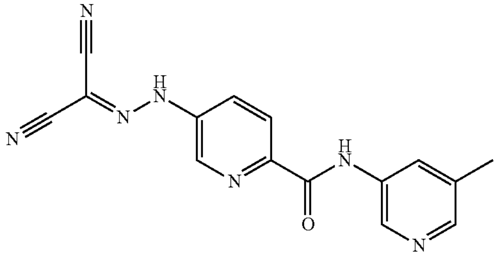 [SMILES: Cc1cncc(NC(=O)c2ccc(NN=C(C#N)C#N)cn2)c1] |
| 40 | 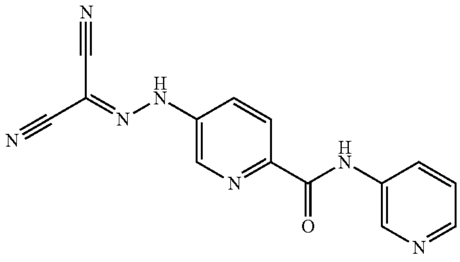 [SMILES: N#CC(C#N)=NNc1ccc(C(=O)Nc2cccnc2)nc1] |

TABLE 1-continued
| Example | |
|---|---|
| 41 | 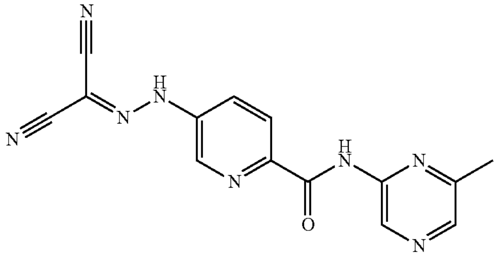 [SMILES: Cc1cncc(NC(=O)c2ccc(NN=C(C#N)C#N)cn2)n1] |
| 42 | 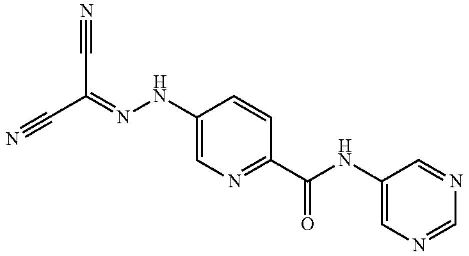 [SMILES: N#CC(C#N)=NNc1ccc(C(=O)Nc2cncnc2)nc1] |
| 43 | 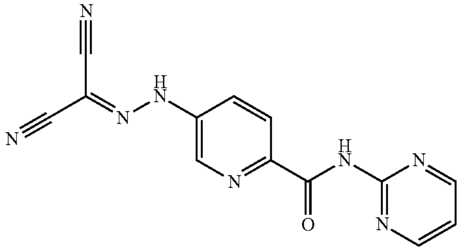 [SMILES: N#CC(C#N)=NNc1ccc(C(=O)Nc2ncccn2)nc1] |
| 44 | 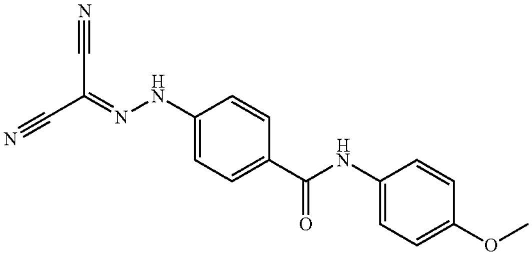 [SMILES: COc1ccc(NC(=O)c2ccc(NN=C(C#N)C#N)cc2)cc1] |
| 45 | 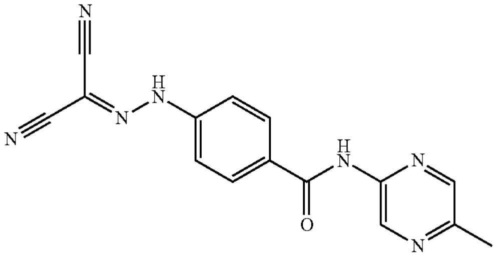 [SMILES: Cc1cnc(NC(=O)c2ccc(NN=C(C#N)C#N)cc2)cn1] |
| 46 | 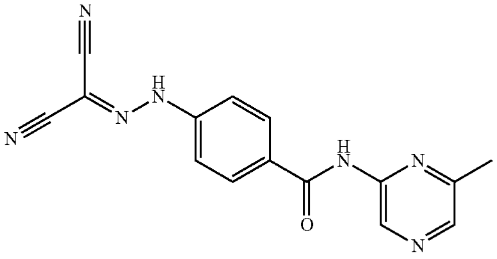 [SMILES: Cc1cncc(NC(=O)c2ccc(NN=C(C#N)C#N)cc2)n1] |

TABLE 1-continued
| Example | |
|---|---|
| 47 | 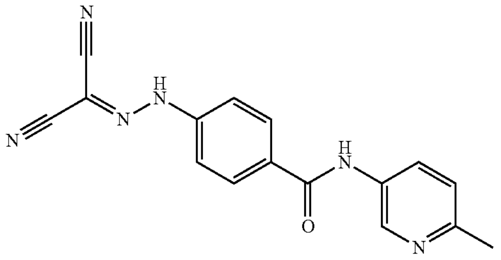 [SMILES: Cc1ccc(NC(=O)c2ccc(NN=C(C#N)C#N)cc2)cn1] |
| 48 | 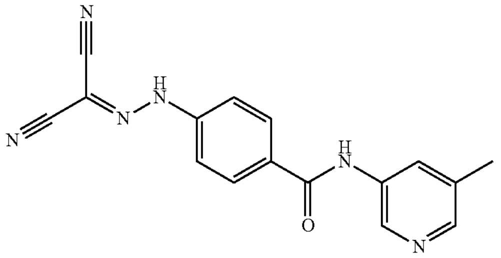 [SMILES: Cc1cncc(NC(=O)c2ccc(NN=C(C#N)C#N)cc2)c1] |
| 49 | 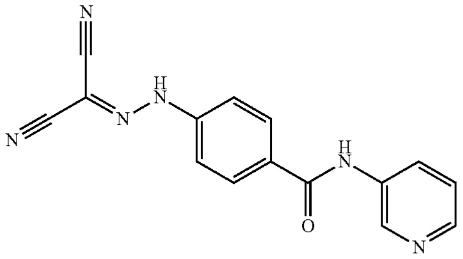 [SMILES: N#CC(C#N)=NNc1ccc(C(=O)Nc2cccnc2)cc1] |
| 50 | 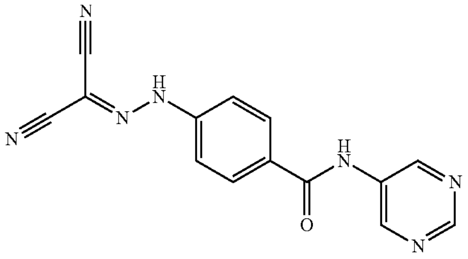 [SMILES: N#CC(C#N)=NNc1ccc(C(=O)Nc2cncnc2)cc1] |
| 51 | 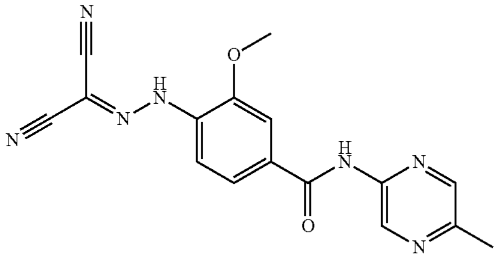 [SMILES: COc1cc(C(=O)Nc2cnc(C)cn2)ccc1NN=C(C#N)C#N] |
| 52 | 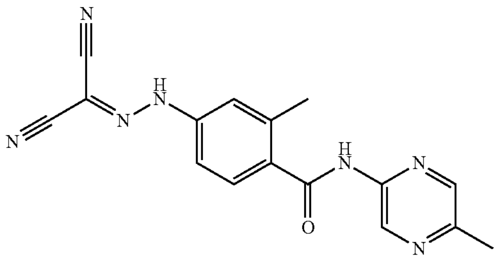 [SMILES: Cc1cnc(NC(=O)c2ccc(NN=C(C#N)C#N)cc2C)cn1] |

TABLE 1-continued
| Example | |
|---|---|
| 53 | 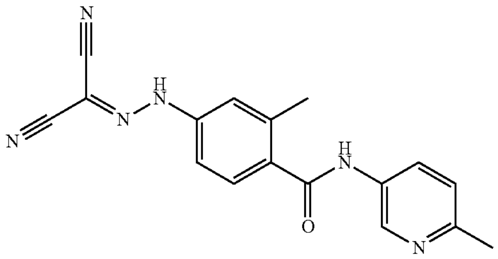 [SMILES: Cc1ccc(NC(=O)c2ccc(NN=C(C#N)C#N)cc2C)cn1] |
| 54 | 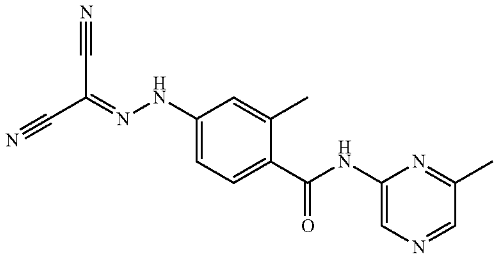 [SMILES: Cc1cncc(NC(=O)c2ccc(NN=C(C#N)C#N)cc2C)n1] |
| 55 | 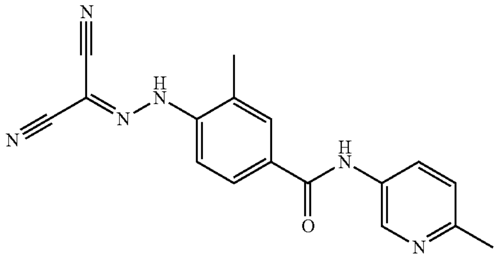 [SMILES: Cc1ccc(NC(=O)c2ccc(NN=C(C#N)C#N)c(C)c2)cn1] |
| 56 | 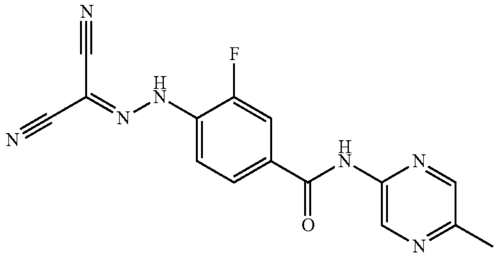 [SMILES: Cc1cnc(NC(=O)c2ccc(NN=C(C#N)C#N)c(F)c2)cn1] |
| 57 | 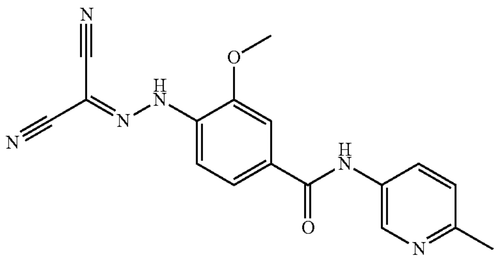 [SMILES: COc1cc(C(=O)Nc2ccc(C)nc2)ccc1NN=C(C#N)C#N] |
| 58 | 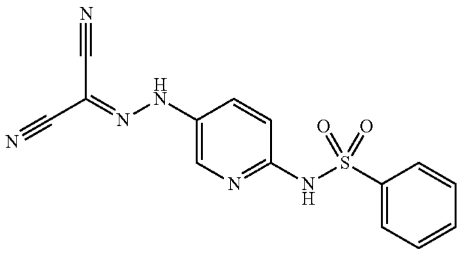 [SMILES: N#CC(C#N)=NNc1ccc(NS(=O)(=O)c2ccccc2)nc1] |

TABLE 1-continued
| Example | |
|---|---|
| 59 | 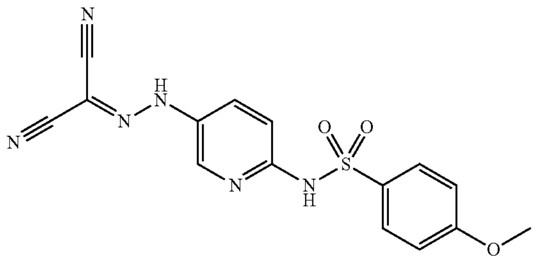 [SMILES: COc1ccc(S(=O)(=O)Nc2ccc(NN=C(C#N)C#N)cn2)cc1] |
| 60 | 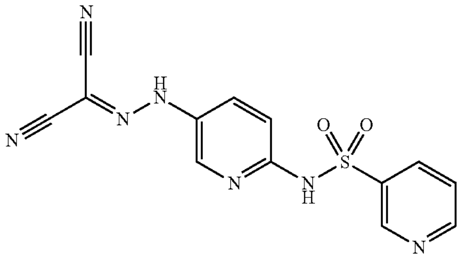 [SMILES: N#CC(C#N)=NNc1ccc(NS(=O)(=O)c2cccnc2)nc1] |
| 61 | 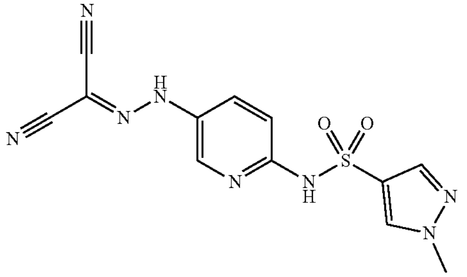 [SMILES: Cn1cc(S(=O)(=O)Nc2ccc(NN=C(C#N)C#N)cn2)cn1] |
| 62 | 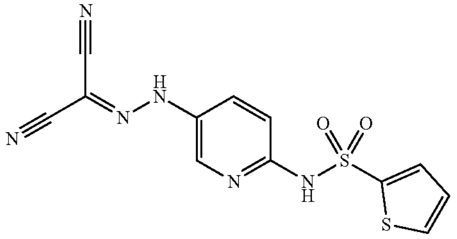 [SMILES: N#CC(C#N)=NNc1ccc(NS(=O)(=O)c2cccs2)nc1] |
| 63 | 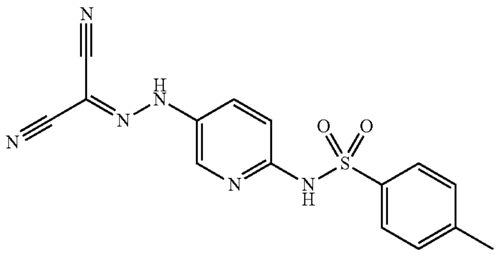 [SMILES: Cc1ccc(S(=O)(=O)Nc2ccc(NN=C(C#N)C#N)cn2)cc1] |
| 64 | 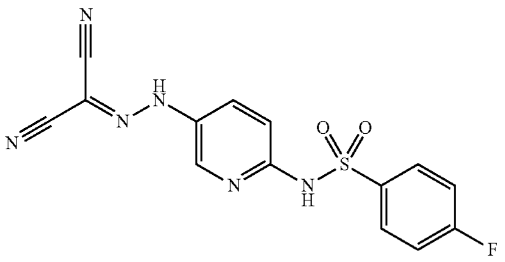 [SMILES: N#CC(C#N)=NNc1ccc(NS(=O)(=O)c2ccc(F)cc2)nc1] |

TABLE 1-continued
| Example | |
|---|---|
| 65 | 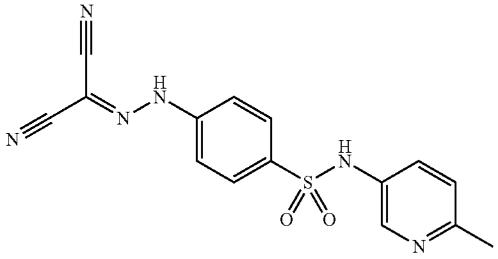 [SMILES: Cc1ccc(NS(=O)(=O)c2ccc(NN=C(C#N)C#N)cc2)cn1] |
| 66 | 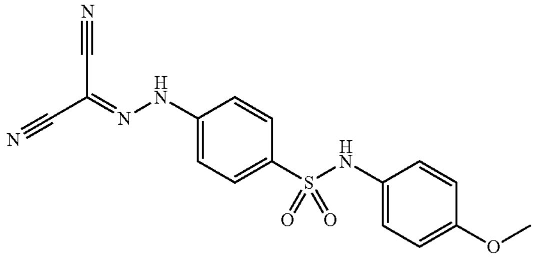 [SMILES: COc1ccc(NS(=O)(=O)c2ccc(NN=C(C#N)C#N)cc2)cc1] |
| 67 | 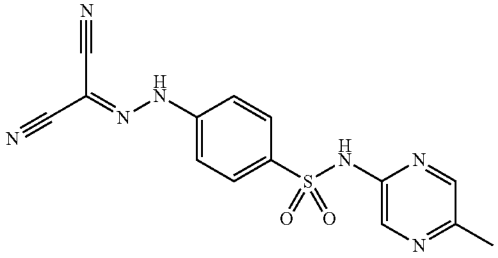 [SMILES: Cc1cnc(NS(=O)(=O)c2ccc(NN=C(C#N)C#N)cc2)cn1] |
| 68 | 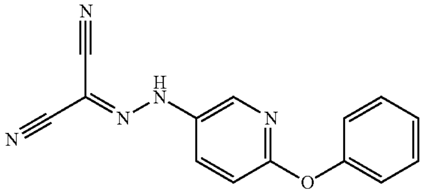 [SMILES: N#CC(C#N)=NNc1ccc(Oc2ccccc2)nc1] |
| 69 | 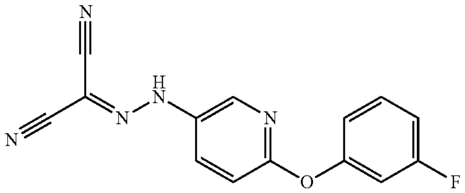 [SMILES: N#CC(C#N)=NNc1ccc(Oc2cccc(F)c2)nc1] |
| 70 | 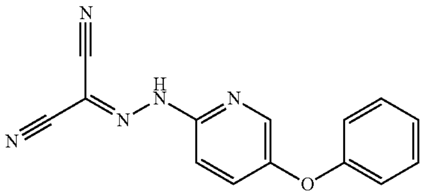 [SMILES: N#CC(C#N)=NNc1ccc(Oc2ccccc2)cn1] |

TABLE 1-continued
| Example | |
|---|---|
| 71 | 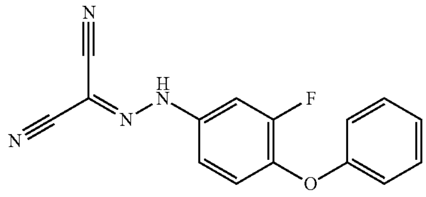 [SMILES: N#CC(C#N)=NNc1ccc(Oc2ccccc2)c(F)c1] |
| 72 | 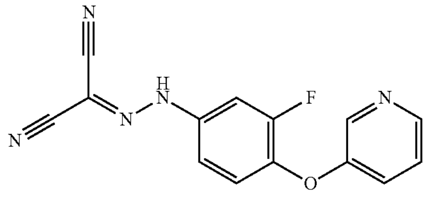 [SMILES: N#CC(C#N)=NNc1ccc(Oc2cccnc2)c(F)c1] |
| 73 | 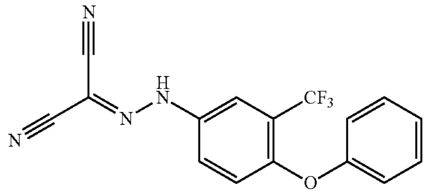 [SMILES: N#CC(C#N)=NNc1ccc(Oc2ccccc2)c(C(F)(F)F)c1] |
| 74 | 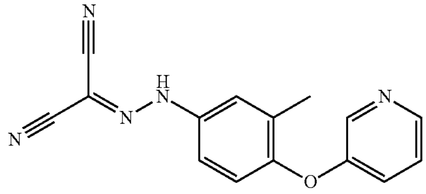 [SMILES: Cc1cc(NN=C(C#N)C#N)ccc1Oc1cccnc1] |
| 75 | 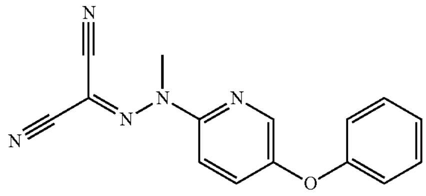 [SMILES: CN(N=C(C#N)C#N)c1ccc(Oc2ccccc2)cn1] |
| 76 | 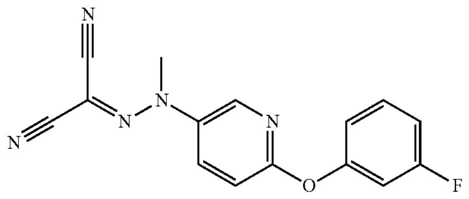 [SMILES: CN(N=C(C#N)C#N)c1ccc(Oc2cccc(F)c2)nc1] |
| 77 | 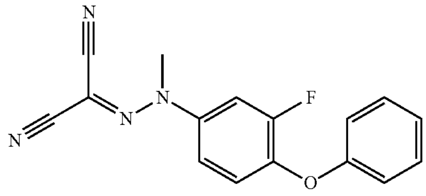 [SMILES: CN(N=C(C#N)C#N)c1ccc(Oc2ccccc2)c(F)c1] |

TABLE 1-continued
| Example | |
|---|---|
| 78 | 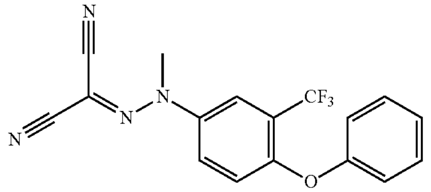 [SMILES: CN(N=C(C#N)C#N)c1ccc(Oc2ccccc2)c(C(F)(F)F)c1] |
| 79 | 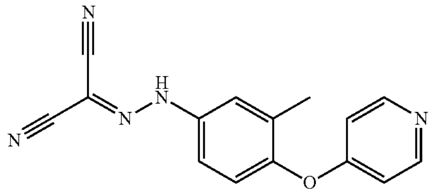 |
| 80 | 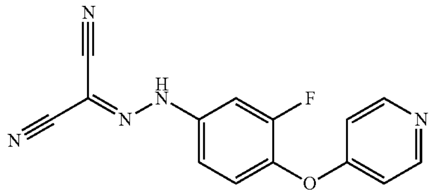 [SMILES: Cc1cc(NN=C(C#N)C#N)ccc1Oc1ccncc1] |
| 81 | 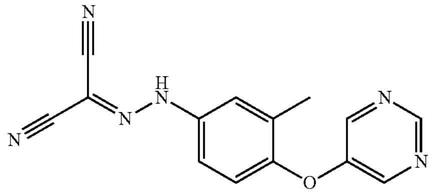 [SMILES: Cc1cc(NN=C(C#N)C#N)ccc1Oc1cncnc1] |
| 82 | 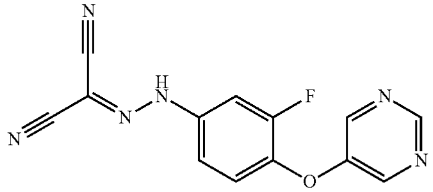 [SMILES: N#CC(C#N)=NNc1ccc(Oc2cncnc2)c(F)c1] |
| 83 | 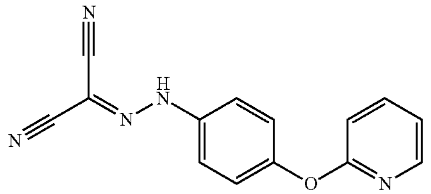 [SMILES: N#CC(C#N)=NNc1ccc(Oc2ccccn2)cc1] |
| 84 | 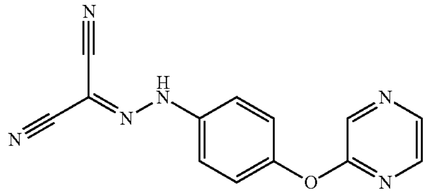 [SMILES: N#CC(C#N)=NNc1ccc(Oc2cnccn2)cc1] |

TABLE 1-continued
| Example | |
|---|---|
| 85 | 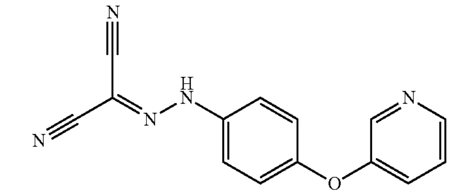 [SMILES: N#CC(C#N)=NNc1ccc(Oc2cccnc2)cc1] |
| 86 | 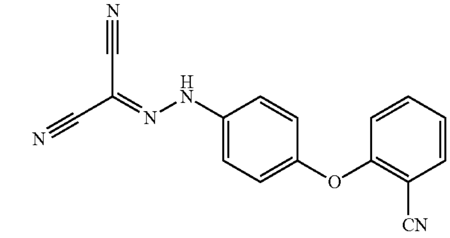 [SMILES: N#CC(C#N)=NNc1ccc(Oc2ccccc2C#N)cc1] |
| 87 | 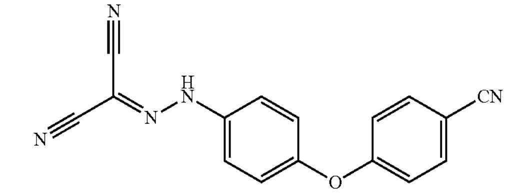 [SMILES: N#CC(C#N)=NNc1ccc(Oc2ccc(C#N)cc2)cc1] |
| 88 | 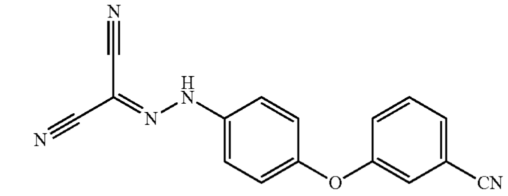 [SMILES: N#CC(C#N)=NNc1ccc(Oc2cccc(C#N)c2)cc1] |
| 89 | 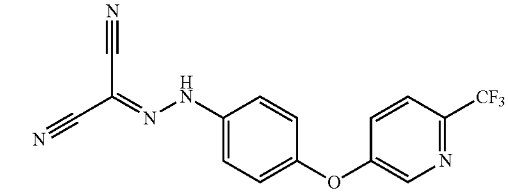 [SMILES: N#CC(C#N)=NNc1ccc(Oc2ccc(C(F)(F)F)nc2)cc1] |
| 90 | 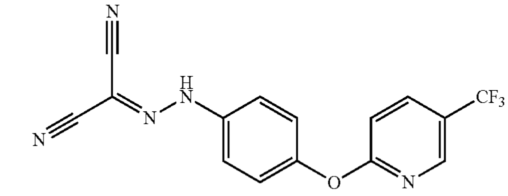 [SMILES: N#CC(C#N)=NNc1ccc(Oc2ccc(C(F)(F)F)cn2)cc1] |
| 91 | 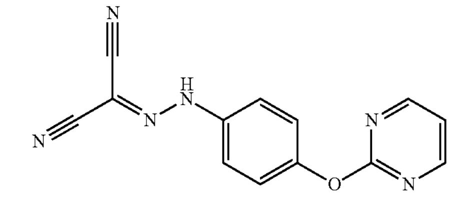 [SMILES: N#CC(C#N)=NNc1ccc(Oc2ncccn2)cc1] |

TABLE 1-continued
| Example | |
|---|---|
| 92 | 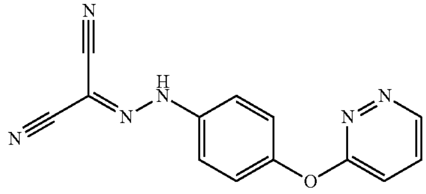 [SMILES: N#CC(C#N)=NNc1ccc(Oc2cccnn2)cc1] |
| 93 | 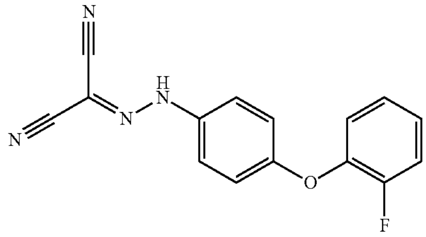 [SMILES: N#CC(C#N)=NNc1ccc(Oc2ccccc2F)cc1] |
| 94 | 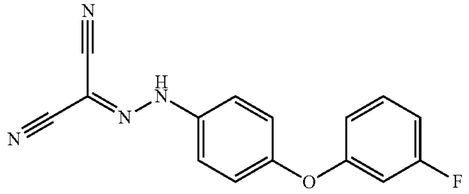 [SMILES: N#CC(C#N)=NNc1ccc(Oc2cccc(F)c2)cc1] |
| 95 | 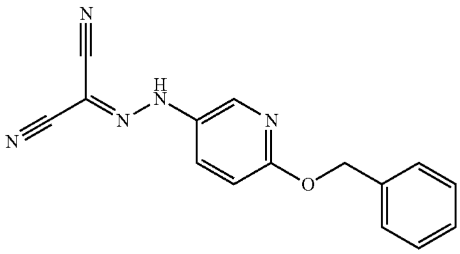 [SMILES: N#CC(C#N)=NNc1ccc(OCc2ccccc2)nc1] |
| 96 | 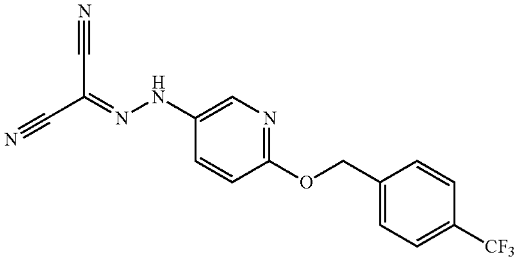 [SMILES: N#CC(C#N)=NNc1ccc(OCc2ccc(C(F)(F)F)cc2)nc1] |
| 97 | 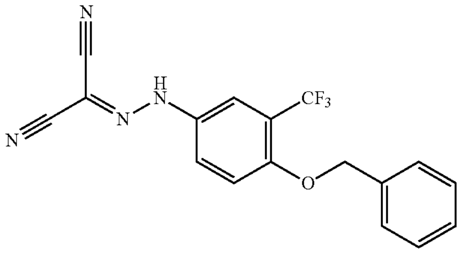 [SMILES: N#CC(C#N)=NNc1ccc(OCc2ccccc2)c(C(F)(F)F)c1] |

TABLE 1-continued
| Example | |
|---|---|
| 98 | 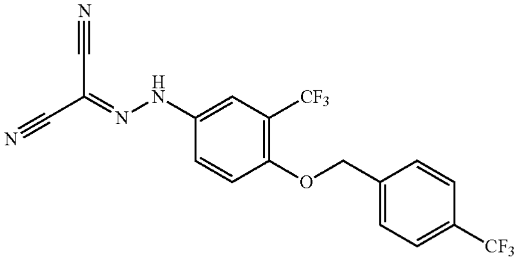 [SMILES: N#CC(C#N)=NNc1ccc(OCc2ccc(C(F)(F)F)cc2)c(C(F)(F)F)c1] |
| 99 | 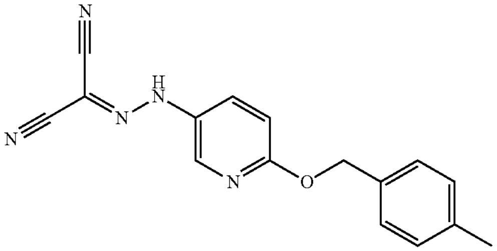 [SMILES: Cc1ccc(COc2ccc(NN=C(C#N)C#N)cn2)cc1] |
| 100 | 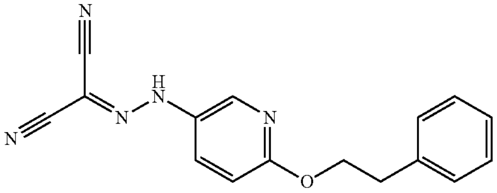 [SMILES: N#CC(C#N)=NNc1ccc(OCCc2ccccc2)nc1] |
| 101 | 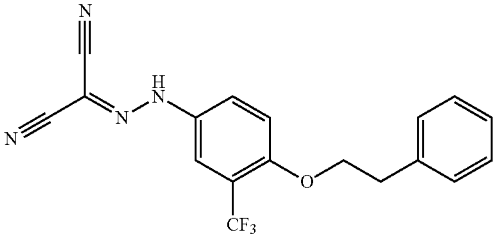 [SMILES: N#CC(C#N)=NNc1ccc(OCCc2ccccc2)c(C(F)(F)F)c1] |
| 102 | 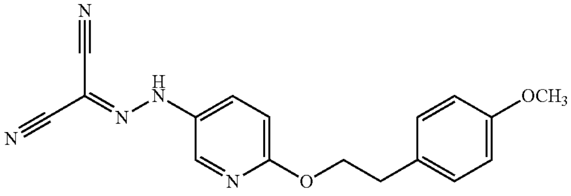 [SMILES: COc1ccc(CCOc2ccc(NN=C(C#N)C#N)cn2)cc1] |
| 103 | 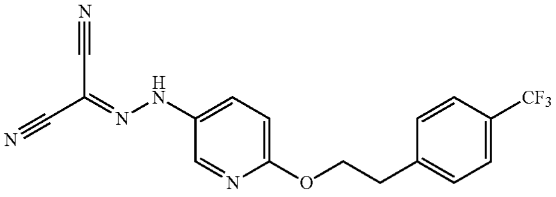 [SMILES: N#CC(C#N)=NNc1ccc(OCCc2ccc(C(F)(F)F)cc2)nc1] |

TABLE 1-continued
| Example | |
|---|---|
| 104 | 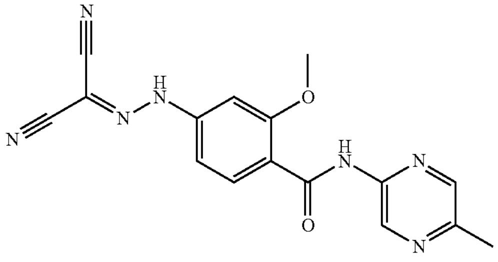 [SMILES: COc1cc(NN=C(C#N)C#N)ccc1C(=O)Nc1cnc(C)cn1] |
| 105 | 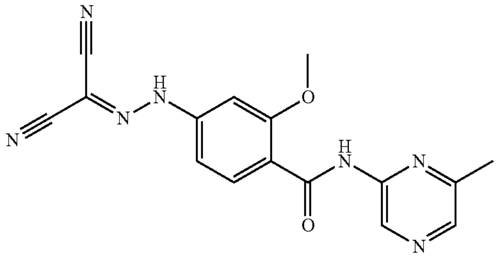 [SMILES: COc1cc(NN=C(C#N)C#N)ccc1C(=O)Nc1cncc(C)n1] |
| 106 | 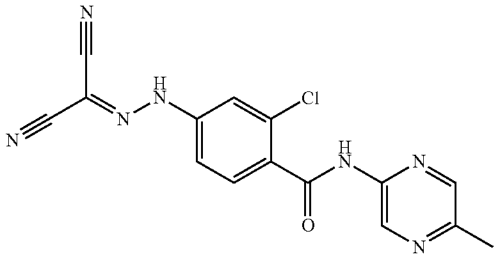 |
| 107 | 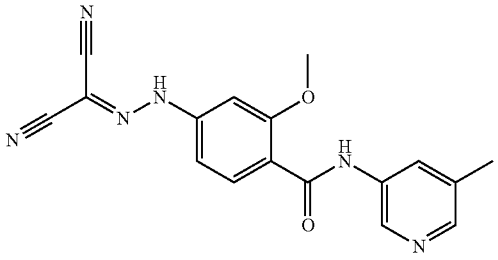 [SMILES: COc1cc(NN=C(C#N)C#N)ccc1C(=O)Nc1cncc(C)c1] |
| 108 | 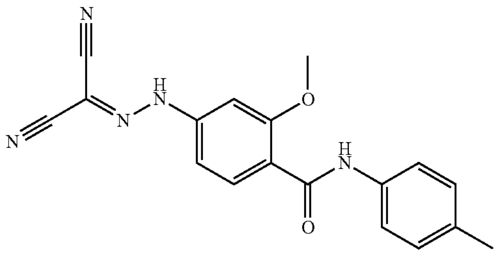 [SMILES: COc1cc(NN=C(C#N)C#N)ccc1C(=O)Nc1ccc(C)cc1] |
| 109 | 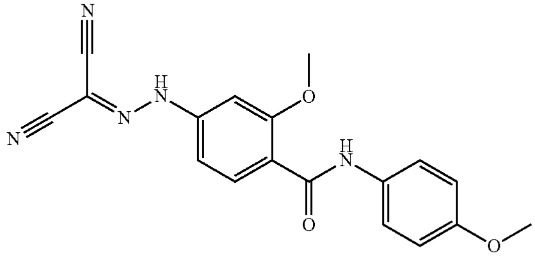 [SMILES: COc1ccc(NC(=O)c2ccc(NN=C(C#N)C#N)cc2OC)cc1] |

TABLE 1-continued
| Example | |
|---|---|
| 110 | 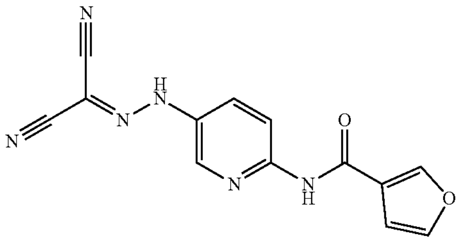 [SMILES: N#CC(C#N)=NNc1ccc(NC(=O)c2ccoc2)nc1] |
| 111 | 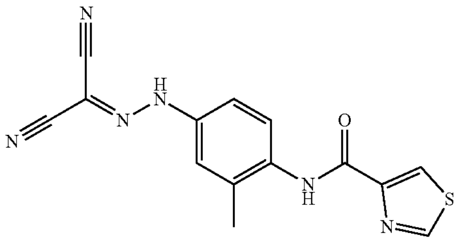 [SMILES: Cc1cc(NN=C(C#N)C#N)ccc1NC(=O)c1cscn1] |
| 112 | 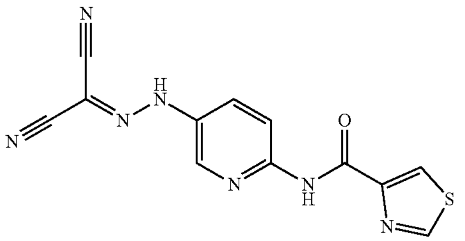 [SMILES: N#CC(C#N)=NNc1ccc(NC(=O)c2cscn2)nc1] |
| 113 | 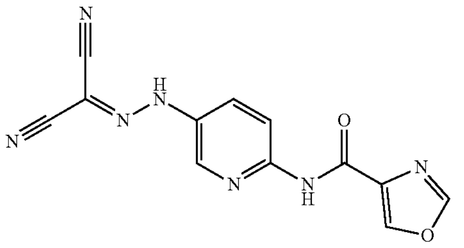 [SMILES: N#CC(C#N)=NNc1ccc(NC(=O)c2cocn2)nc1] |
| 114 | 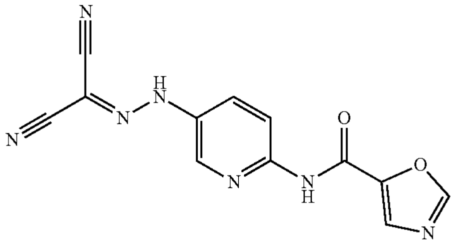 [SMILES: N#CC(C#N)=NNc1ccc(NC(=O)c2cnco2)nc1] |
| 115 | 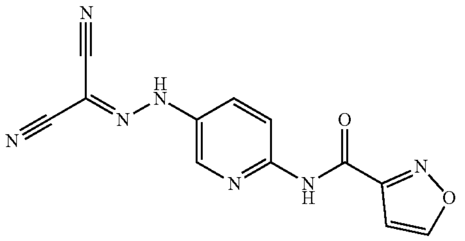 [SMILES: N#CC(C#N)=NNc1ccc(NC(=O)c2ccon2)nc1] |

TABLE 1-continued
| Example | |
|---|---|
| 116 | 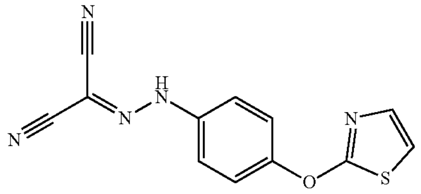 [SMILES: N#CC(C#N)=NNc1ccc(Oc2nccs2)cc1] |
| 117 | 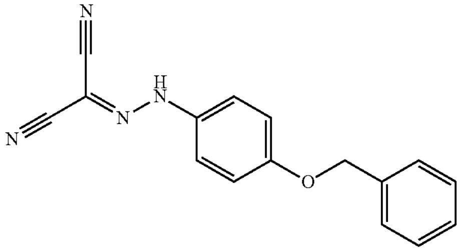 |
| 118 | 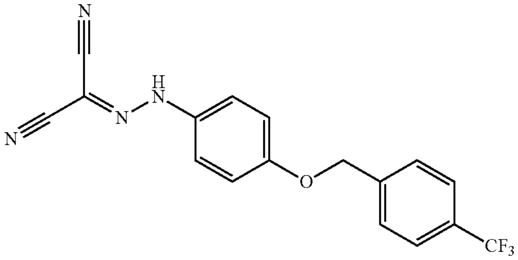 [SMILES: N#CC(C#N)=NNc1ccc(OCc2ccc(C(F)(F)F)cc2)cc1] |
| 119 | 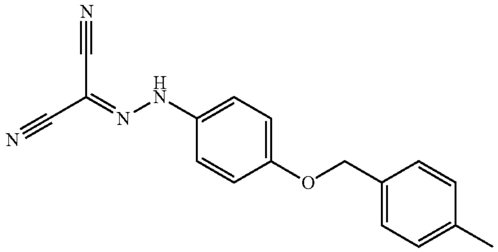 [SMILES: Cc1ccc(COc2ccc(NN=C(C#N)C#N)cc2)cc1] |
| 120 | 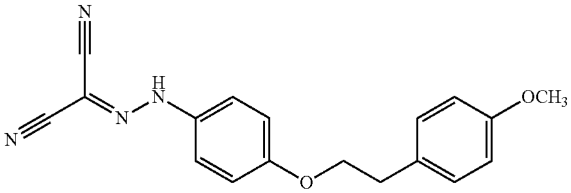 |
| 121 | 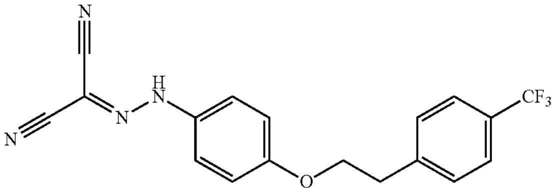 [SMILES: N#CC(C#N)=NNc1ccc(OCCc2ccc(C(F)(F)F)cc2)cc1] |
| 122 | 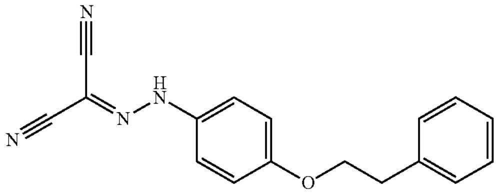 [SMILES: N#CC(C#N)=NNc1ccc(OCCc2ccccc2)cc1] |

TABLE 1-continued
| Example | |
|---|---|
| 123 | 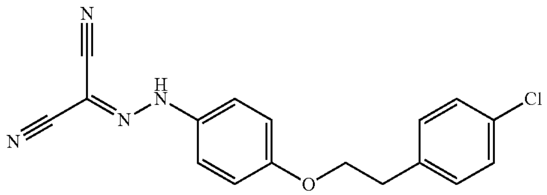 [SMILES: N#CC(C#N)=NNc1ccc(OCCc2ccc(Cl)cc2)cc1] |
| 124 | 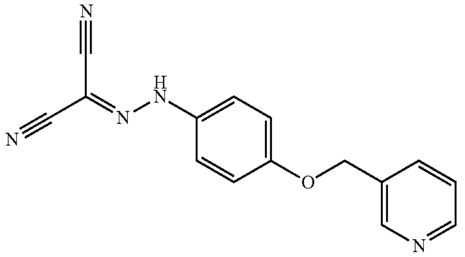 [SMILES: N#CC(C#N)=NNc1ccc(OCc2cccnc2)cc1] |
| 125 | 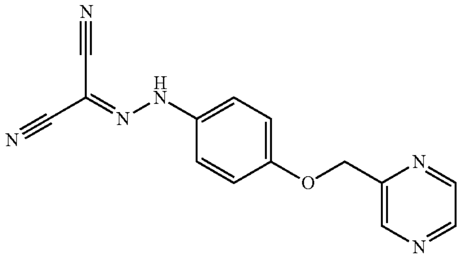 [SMILES: N#CC(C#N)=NNc1ccc(OCc2cnccn2)cc1] |
| 126 | 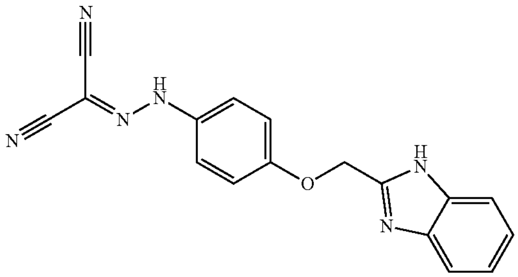 [SMILES: N#CC(C#N)=NNc1ccc(OCc2nc3ccccc3[nH]2)cc1] |
| 127 | 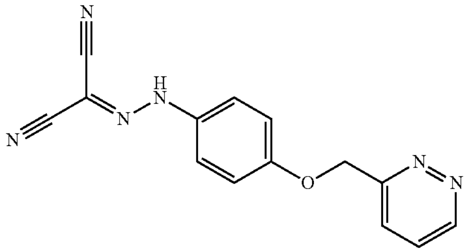 [SMILES: N#CC(C#N)=NNc1ccc(OCc2cccnn2)cc1] |
| 128 | 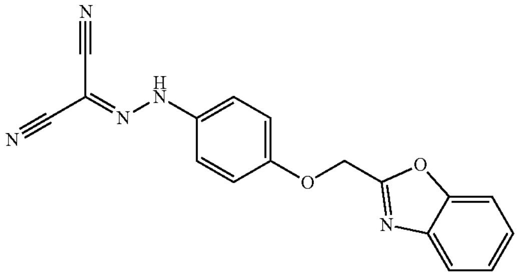 [SMILES: N#CC(C#N)=NNc1ccc(OCc2nc3ccccc3o2)cc1] |

TABLE 1-continued
| Example | |
|---|---|
| 129 | 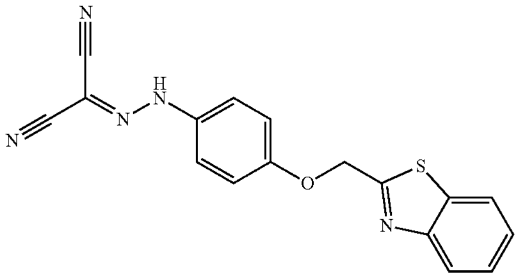 [SMILES: N#CC(C#N)=NNc1ccc(OCc2nc3ccccc3s2)cc1] |
| 130 | 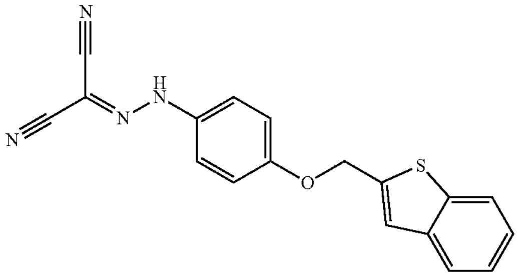 [SMILES: N#CC(C#N)=NNc1ccc(OCc2cc3ccccc3s2)cc1] |
| 131 | 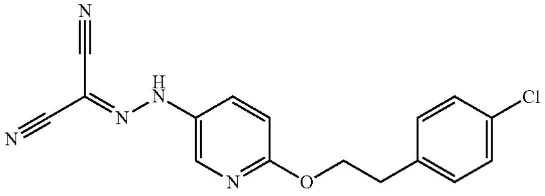 [SMILES: N#CC(C#N)=NNc1ccc(OCCc2ccc(Cl)cc2)nc1] |
| 132 | 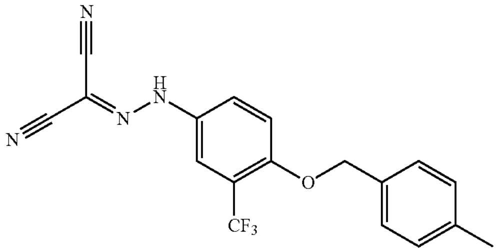 [SMILES: Cc1ccc(COc2ccc(NN=C(C#N)C#N)cc2C(F)(F)F)cc1] |
| 133 | 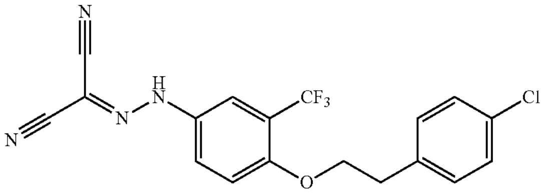 [SMILES: N#CC(C#N)=NNc1ccc(OCCc2ccc(Cl)cc2)c(C(F)(F)F)c1] |
| 134 | 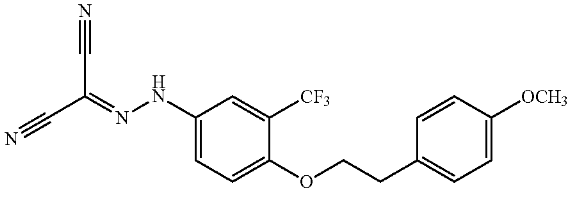 [SMILES: COc1ccc(CCOc2ccc(NN=C(C#N)C#N)cc2C(F)(F)F)cc1] |

TABLE 1-continued
| Example | |
|---|---|
| 135 | 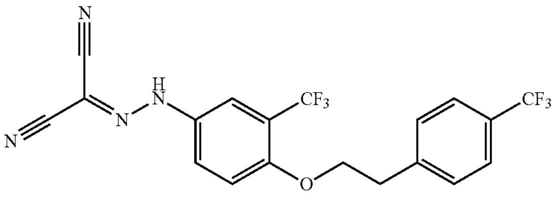 [SMILES: N#CC(C#N)=NNc1ccc(OCCc2ccc(C(F)(F)F)cc2)c(C(F)(F)F)c1] |
| 136 | 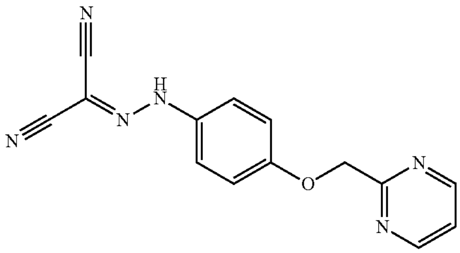 [SMILES: N#CC(C#N)=NNc1ccc(OCc2ncccn2)cc1] |
| 137 | 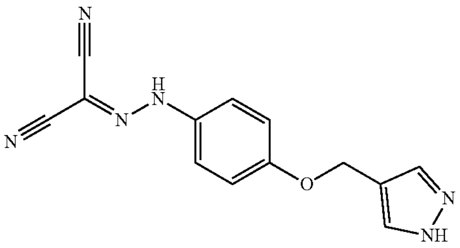 [SMILES: N#CC(C#N)=NNc1ccc(OCc2cn[nH]c2)cc1] |
| 138 | 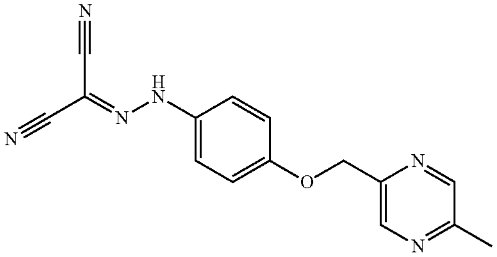 [SMILES: Cc1cnc(COc2ccc(NN=C(C#N)C#N)cc2)cn1] |
| 139 | 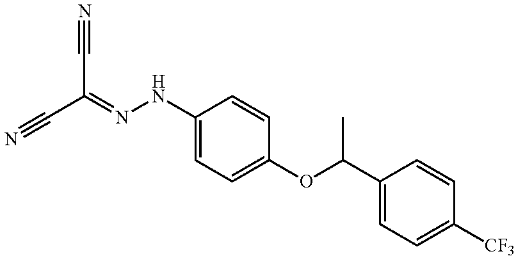 [SMILES: CC(Oc1ccc(NN=C(C#N)C#N)cc1)c1ccc(C(F)(F)F)cc1] |
| 140 | 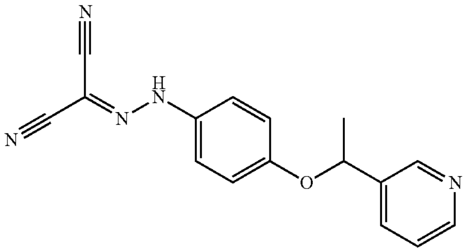 [SMILES: CC(Oc1ccc(NN=C(C#N)C#N)cc1)c1cccnc1] |

TABLE 1-continued
| Example | |
|---|---|
| 141 | 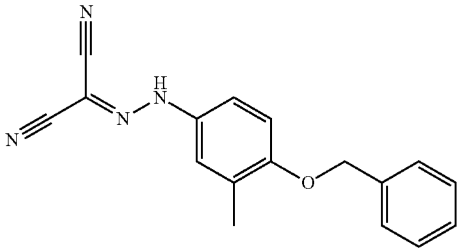 [SMILES: Cc1cc(NN=C(C#N)C#N)ccc1OCc1ccccc1] |
| 142 | 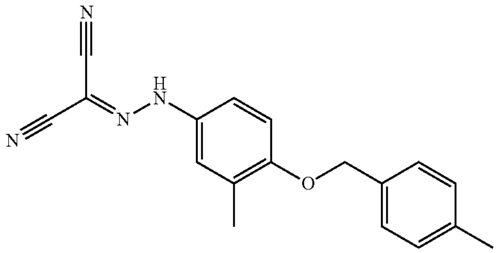 [SMILES: Cc1ccc(COc2ccc(NN=C(C#N)C#N)cc2C)cc1] |
| 143 | 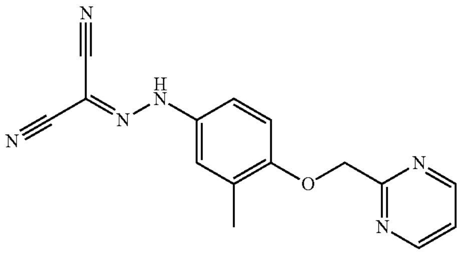 [SMILES: Cc1cc(NN=C(C#N)C#N)ccc1OCc1ncccn1] |
| 144 | 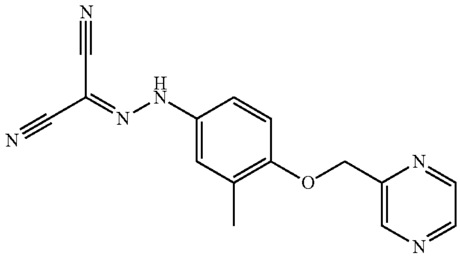 [SMILES: Cc1cc(NN=C(C#N)C#N)ccc1OCc1cnccn1] |
| 145 | 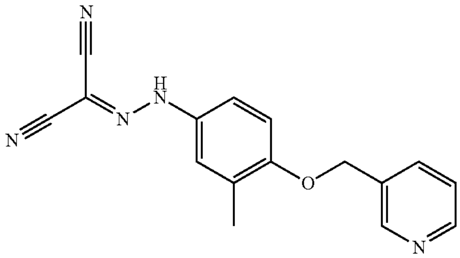 [SMILES: Cc1cc(NN=C(C#N)C#N)ccc1OCc1cccnc1] |
| 146 | 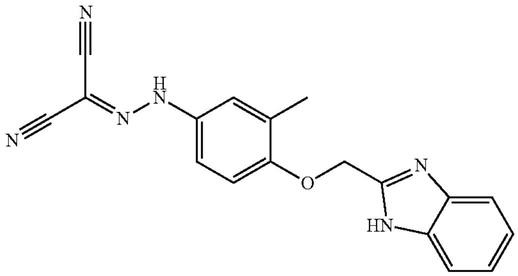 [SMILES: Cc1cc(NN=C(C#N)C#N)ccc1OCc1nc2ccccc2[nH]1] |

TABLE 1-continued
| Example | |
|---|---|
| 147 | 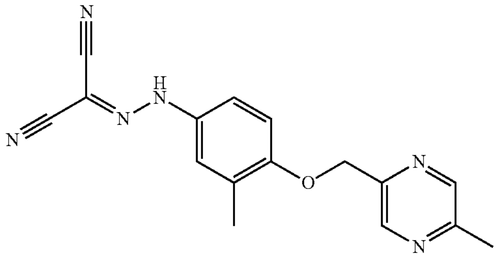 [SMILES: Cc1cnc(COc2ccc(NN=C(C#N)C#N)cc2C)cn1] |
| 148 | 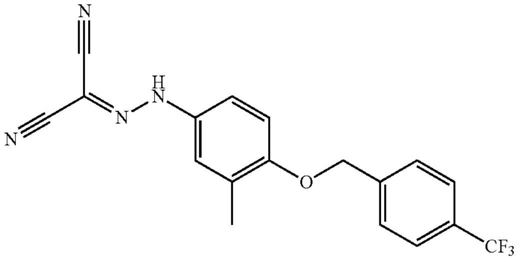 [SMILES: Cc1cc(NN=C(C#N)C#N)ccc1OCc1ccc(C(F)(F)F)cc1] |
| 149 | 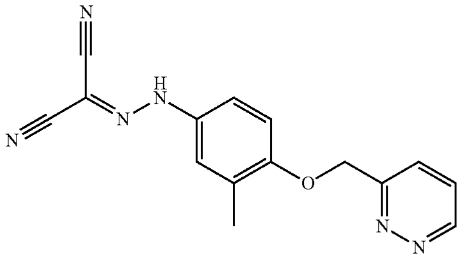 [SMILES: Cc1cc(NN=C(C#N)C#N)ccc1OCc1cccnn1] |
| 150 | 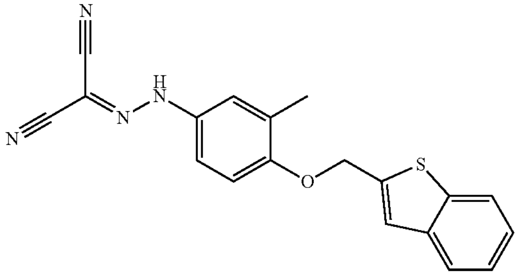 [SMILES: Cc1cc(NN=C(C#N)C#N)ccc1OCc1cc2ccccc2s1] |
| 151 | 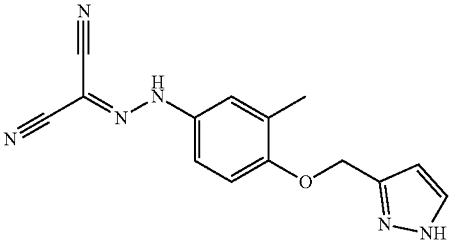 [SMILES: Cc1cc(NN=C(C#N)C#N)ccc1OCc1cc[nH]n1] |
| 152 | 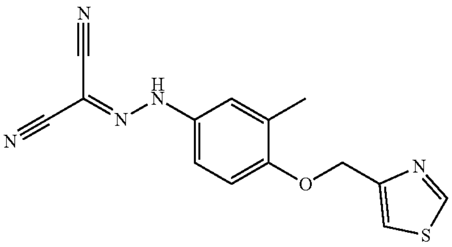 [SMILES: Cc1cc(NN=C(C#N)C#N)ccc1OCc1cscn1] |

TABLE 1-continued
| Example | |
|---|---|
| 153 | 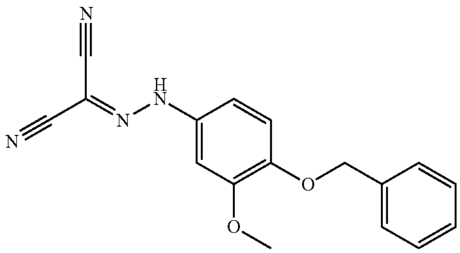 |
| 154 | 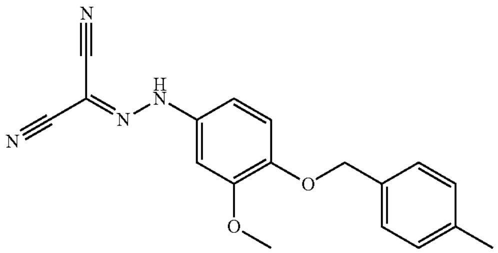 [SMILES: COc1cc(NN=C(C#N)C#N)ccc1OCc1ccc(C)cc1] |
| 155 | 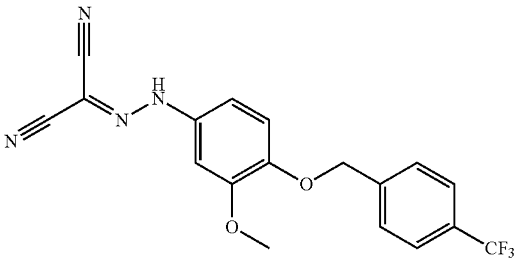 |
| 156 | 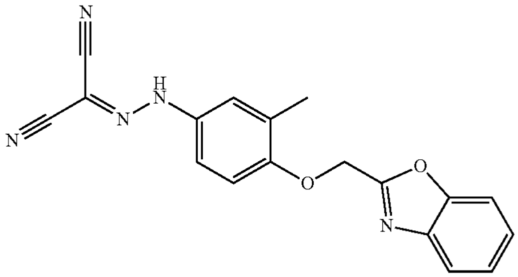 |
| 157 | 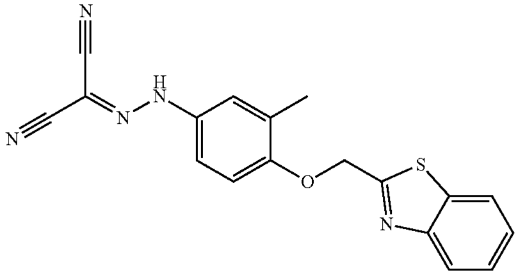 [SMILES: Cc1cc(NN=C(C#N)C#N)ccc1OCc1nc2ccccc2o1] |

TABLE 1-continued
| Example | |
|---|---|
| 158 | 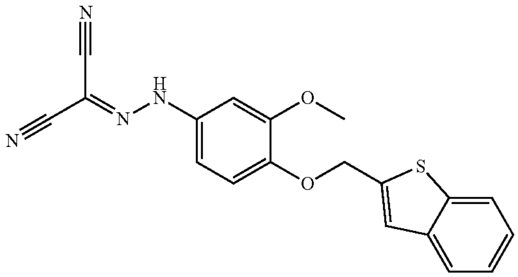 [SMILES: COc1cc(NN=C(C#N)C#N)ccc1OCc1cc2ccccc2s1] |
| 159 | 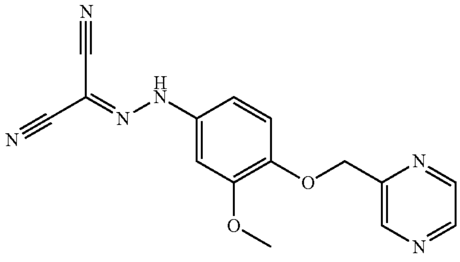 [SMILES: COc1cc(NN=C(C#N)C#N)ccc1OCc1cnccn1] |
| 160 | 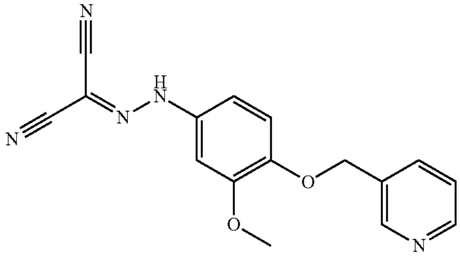 [SMILES: COc1cc(NN=C(C#N)C#N)ccc1OCc1cccnc1] |
| 161 | 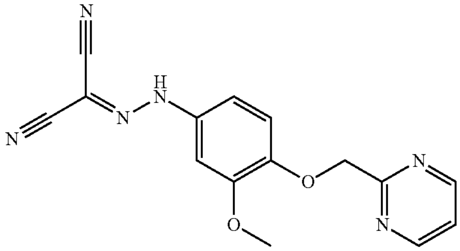 [SMILES: COc1cc(NN=C(C#N)C#N)ccc1OCc1ncccn1] |
| 162 | 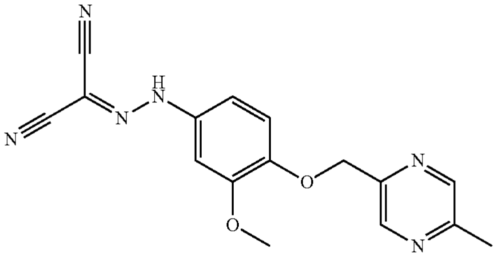 [SMILES: COc1cc(NN=C(C#N)C#N)ccc1OCc1cnc(C)cn1] |

TABLE 1-continued
| Example | |
|---|---|
| 163 | 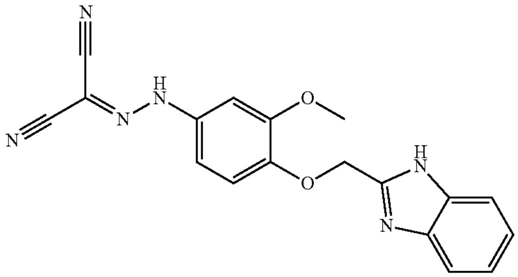 [SMILES: COc1cc(NN=C(C#N)C#N)ccc1OCc1nc2ccccc2[nH]1] |
| 164 | 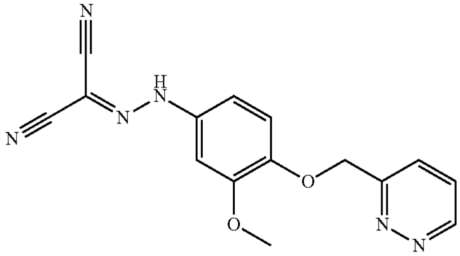 [SMILES: COc1cc(NN=C(C#N)C#N)ccc1OCc1cccnn1] |
| 165 | 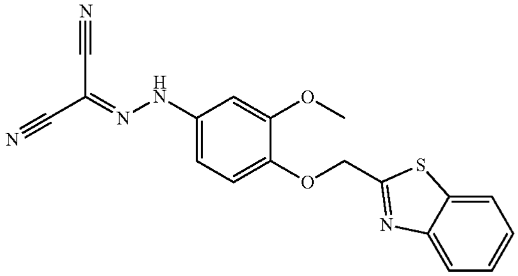 [SMILES: COc1cc(NN=C(C#N)C#N)ccc1OCc1nc2ccccc2s1] |
| 166 | 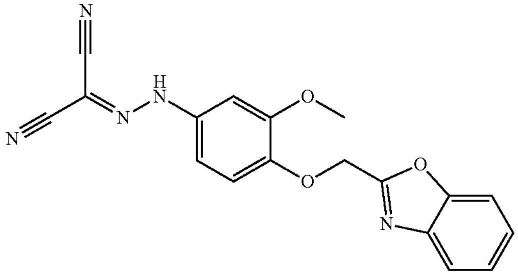 [SMILES: COc1cc(NN=C(C#N)C#N)ccc1OCc1nc2ccccc2o1] |
| 167 | 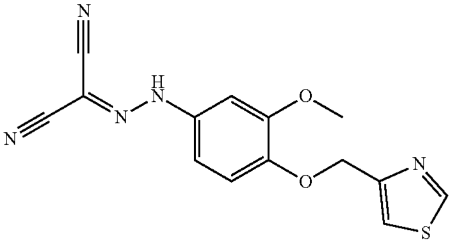 [SMILES: COc1cc(NN=C(C#N)C#N)ccc1OCc1cscn1] |
| 168 | 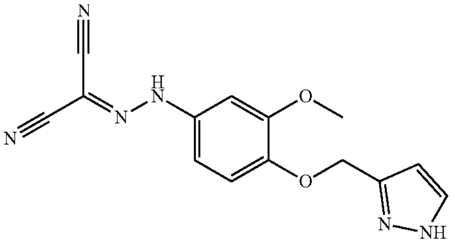 [SMILES: COc1cc(NN=C(C#N)C#N)ccc1OCc1cc[nH]n1] |

TABLE 1-continued
| Example | |
|---|---|
| 169 | 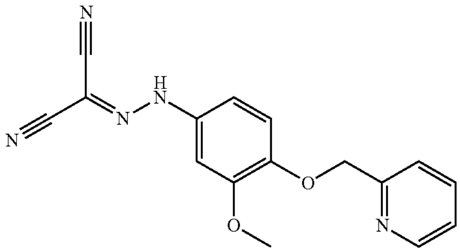 [SMILES: COc1cc(NN=C(C#N)C#N)ccc1OCc1ccccn1] |
| 170 | 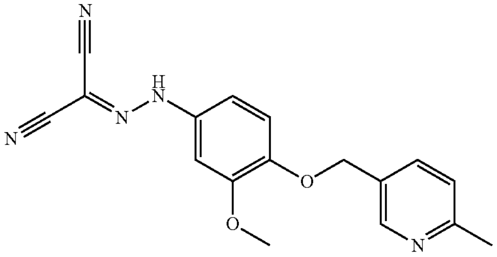 [SMILES: COc1cc(NN=C(C#N)C#N)ccc1OCc1ccc(C)nc1] |
| 171 | 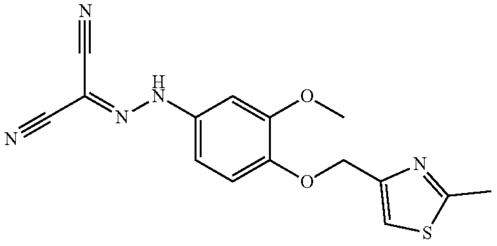 [SMILES: COc1cc(NN=C(C#N)C#N)ccc1OCc1csc(C)n1] |
| 172 | 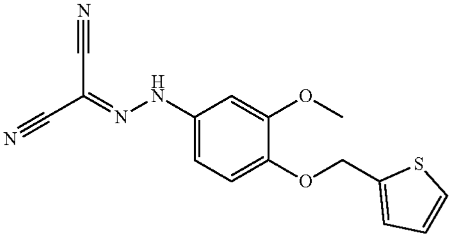 [SMILES: COc1cc(NN=C(C#N)C#N)ccc1OCc1cccs1] |
| 173 | 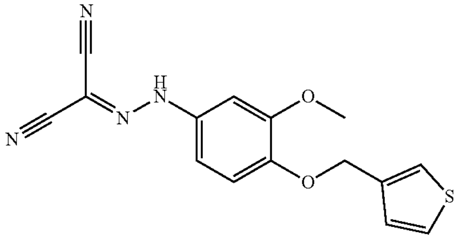 [SMILES: COc1cc(NN=C(C#N)C#N)ccc1OCc1ccsc1] |
| 174 | 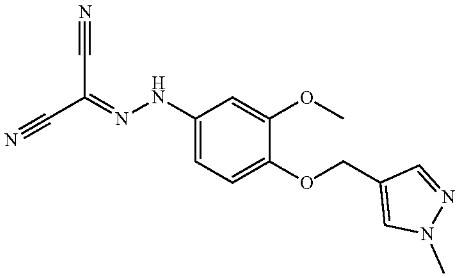 [SMILES: COc1cc(NN=C(C#N)C#N)ccc1OCc1cnn(C)c1] |

TABLE 1-continued

| Example | |
|---|---|
| 175 | 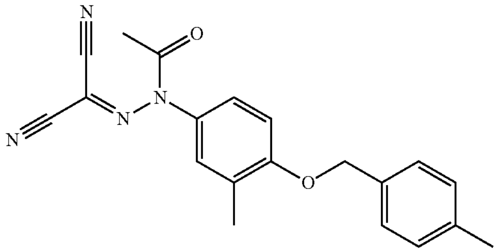 [SMILES: CC(=O)N(N=C(C#N)C#N)c1ccc(OCc2ccc(C)cc2)c(C)c1] |

Meanwhile, the compound of the present invention may exist in the form of a pharmaceutically acceptable salt. As the salt, an acid salt formed by a pharmaceutically acceptable free acid is useful. As used herein, the term "pharmaceutically acceptable salt" refers to any organic or inorganic addition salt of the compound represented by Formula 1 which is relatively non-toxic and harmless to patients, and side effects caused by this salt do not compromise the beneficial effects of this compound.

An acid addition salt is prepared by way of a conventional method, for example, by dissolving a compound in an excess amount of an aqueous acid solution and precipitating this solution using a water-miscible organic solvent such as methanol, ethanol, acetone, or acetonitrile. The same molar amounts of the compound and acid or alcohol (for example, glycol monoethyl ether) in water are heated, and subsequently the mixture may be evaporated and dried, or the precipitated salt may be suction-filtered.

In this case, as the free acid, an organic acid or an inorganic acid may be used. As the inorganic acid, hydrochloric acid, phosphoric acid, sulfuric acid, nitric acid, tartaric acid, or the like may be used. As the organic acid, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbon acid, vanillic acid, hydroiodic acid, or the like may be used. However, the present invention is not limited thereto.

Further, a pharmaceutically acceptable metal salt may be made using a base. An alkali metal salt or alkaline earth metal salt is obtained by dissolving the compound in an excess amount of an alkali metal hydroxide or alkaline earth metal hydroxide solution, filtering a non-soluble compound salt, and then evaporating and drying the filtrate. In this case, it is suitable for pharmaceutical use to prepare a sodium, potassium, or calcium salt as the metal salt, but the present invention is not limited thereto. Further, the corresponding silver salt may be obtained by reacting an alkali metal or alkaline earth metal salt with a suitable silver salt (for example, silver nitrate).

Pharmaceutically acceptable salts of the compounds of the present invention include salts of acidic or basic groups that may be present in the compound of Formula 1, unless otherwise indicated. For example, pharmaceutically acceptable salts may include sodium, calcium, and potassium salts of hydroxy groups, and other pharmaceutically acceptable salts of amino groups may include hydrobromide, sulfate, hydrogen sulfate, phosphate, hydrogen phosphate, dihydrogen phosphate, acetate, succinate, citrate, tartrate, lactate, mandelate, methanesulfonate (mesylate), and p-toluenesulfonate (tosylate). These pharmaceutically acceptable salts may be prepared by way of preparation methods of salts known in the art.

As the salts of the compound of Formula 1 of the present invention, any salt, as a pharmaceutically acceptable salt, may be used without limitation as long as it exhibits pharmacological activity equivalent to the compound of Formula 1, for example, it inhibits the aggregation and/or hyperphosphorylation of tau protein.

Further, the compound represented by Formula 1 according to the present invention include, without limitation, pharmaceutically acceptable salts thereof, as well as solvates such as possible hydrates that may be prepared therefrom, and all possible stereoisomers. The solvates and stereoisomers of the compound represented by Formula 1 may be prepared from the compound represented by Formula 1 using any method known in the art.

Moreover, the compound represented by Formula 1 according to the present invention may be prepared in a crystalline or amorphous form, and may be optionally hydrated or solvated if prepared in a crystalline form. In the present invention, compounds containing various amounts of water as well as stoichiometric hydrates of the compound represented by Formula 1 may be provided. The solvates of the compound represented by Formula 1 according to the present invention include both stoichiometric solvates and non-stoichiometric solvates.

A second aspect of the present invention provides a method of preparing the compound of Formula 1.

For example, the compound of the present invention may be prepared by way of a process including:

a first step of reacting a compound represented by Formula 2 below including a reactive amine group at one end with sodium nitrite and malononitrile in the presence of an acid to form an imine bond; and optionally, a second step of introducing an $R_1$ substituent into a product obtained in the previous step when $R_1$ is a substituent other than hydrogen:

$H_2N$—(Het)$Ar_1$-L-(Het)$Ar_2$ [Formula 2]

In Formula 2 above, L, (Het)$Ar_1$, (Het)$Ar_2$, and $R_1$ are as defined above in the first aspect.

Specifically, the first step of the process may be performed by way of a series of processes including the steps of:

1-1) dissolving the compound of Formula 2 and sodium nitrite in a $C_{1-4}$ lower alcohol solvent and adding an aqueous acid solution thereto at a temperature of −5° C. to 5° C. to form a diazonium salt, 1-2) adding malononitrile to a reaction solution including the diazonium salt obtained in step 1-1) and performing a reaction at a temperature of 15° C. to 40° C., and 1-3) neutralizing the reaction solution of step 1-2) by adding an aqueous base solution thereto, without being limited thereto.

For example, the first step may be proceeded by performing the reaction of step 1-1) at a low temperature around 0° C. for 2 minutes to 1 hour using a 1 M hydrochloric acid solution, and then performing the reaction of step 1-2) at room temperature for 2 minutes to 1 hour, without being limited thereto.

For example, the second step may be performed by reacting the carbonohydrazonoyl dicyanide compound obtained in the previous step, in which $R_1$ is other than hydrogen, with a halogenated derivative of $R_1$ in an organic solvent. Specifically, when $R_1$ is $C_{1-6}$ alkyl, the second step may be performed by dissolving the carbonohydrazonoyl dicyanide compound obtained in the previous step, in which $R_1$ is other than hydrogen, in an organic solvent such as DMF, and adding a haloalkane such as alkane iodide corresponding to $R_1$ to the reaction solution, and performing a reaction at a temperature of 50° C. to 70° C., wherein the reaction solution may further include potassium tert-butoxide. However, the present invention is not limited thereto. Specifically, when $R_1$ is $C_{1-6}$ alkylcarbonyl, the second step may be performed by dissolving the carbonohydrazonoyl dicyanide compound obtained in the previous step, in which $R_1$ is other than hydrogen, in a lower alcohol such as methanol, followed by reaction with a base such as potassium hydroxide and solidification to obtain a product, and reacting the product with a halogenated alkylcarbonyl such as acetyl chloride corresponding to the $C_{1-6}$ alkylcarbonyl in an organic solvent such as acetonitrile in the presence of triethylamine. However, the present invention is not limited thereto.

For example, the compound represented by Formula 2 including a reactive amine group at one end and used in the preparation of the compound of the present invention may be prepared from a compound represented by Formula 3 below including a nitro group by way of a reduction reaction, without being limited thereto:

$O_2N$-(Het)$Ar_1$-L-(Het)$Ar_2$ [Formula 3]

Specifically, the reduction may be performed via a reaction in an organic solvent such as a 1,4-dioxane or methanol solvent in the presence of a Pd/C catalyst, via a reaction with AcOH in the presence of Fe, or via a reaction with ammonium chloride in the presence of Fe, without being limited thereto.

For example, when L is —NHCO— or —CONH—, the compound of Formula 3 may be prepared by way of:

i) a reaction between a (Het)$Ar_1$ derivative including carboxyl groups at sites linked to the nitro group and L and a (Het)$Ar_2$ derivative including an amine group at a site linked to L; or ii) a reaction between a (Het)$Ar_1$ derivative including amine groups at sites linked to the nitro group and L and a (Het)$Ar_2$ derivative including a carboxyl group at a site linked to L, without being limited thereto.

Specifically, the compound of Formula 3 may be prepared by dissolving a carboxylic acid derivative of one of (Het)$Ar_1$ and (Het)$Ar_2$ in an organic solvent, MeCN, ACN, or the like, adding HATU and TEA thereto, and stirring the mixture at room temperature for several hours to prepare a reaction solution; adding an amine derivative of the other of (Het)$Ar_1$ and (Het)$Ar_2$ to the reaction solution; and refluxing the resultant for 12 to 48 hours, without being limited thereto.

As another example, the compound of Formula 3 may be prepared by dissolving a carboxylic acid derivative of one of (Het)$Ar_1$ and (Het)$Ar_2$ in an organic solvent, anhydrous DCM, adding $(COCl)_2$ and a small amount of DMF thereto at 0° C., and concentrating the mixture under reduced pressure for 1 hour while stirring to prepare a concentrate; and dissolving an amine derivative of the other of (Het)$Ar_1$ and (Het)$Ar_2$ and the concentrate in an organic solvent, pyridine; and stirring the mixture at room temperature for 3 to 24 hours, without being limited thereto.

For example, when L is —$NHSO_2$— or —$SO_2NH$—, the compound of Formula 3 may be prepared by way of:

i) a reaction between a (Het)$Ar_1$ derivative including amine groups at sites linked to the nitro group and L and a (Het)$Ar_2$ derivative including a chlorosulfonyl group at a site linked to L; or ii) a reaction between a (Het)$Ar_1$ derivative including halosulfonyl groups at sites linked to the nitro group and L and a (Het)$Ar_2$ derivative including an amine group at a site linked to L, without being limited thereto.

Specifically, the compound of Formula 3 may be prepared by dissolving an amine derivative of one of (Het)$Ar_1$ and (Het)$Ar_2$ in an organic solvent, THF, or the like, lowering a reaction temperature to around 0° C., adding sodium hydride thereto, and stirring the mixture for several to several tens of minutes to prepare a reaction solution; adding a halosulfonyl derivative such as a sulfonyl chloride derivative of the other of (Het)$Ar_1$ and (Het)$Ar_2$ thereto, and stirring the resultant at room temperature for 1 to 12 hours, without being limited thereto.

For example, when L is -(straight-chain or branched $C_{0-3}$ alkylene)'-O-(straight-chain or branched $C_{0-3}$ alkylene)"-, the compound of Formula 3 may be prepared by way of:

i) a reaction between a (Het)$Ar_1$ derivative including -(straight-chain or branched $C_{0-3}$ alkylene)'-OH at sites linked to the nitro group and L and a (Het)$Ar_2$ derivative including -(straight-chain or branched $C_{0-3}$ alkylene)"-X (where X is halogen) at a site linked to L; or ii) a reaction between a (Het)$Ar_1$ derivative including -(straight-chain or branched $C_{0-3}$ alkylene)'-X at sites linked to the nitro group and L and a (Het)$Ar_2$ derivative including -(straight-chain or branched $C_{0-3}$ alkylene)"-OH at a site linked to L, without being limited thereto.

Specifically, the compound of Formula 3 may be prepared by dissolving a haloalkyl (-(straight-chain or branched $C_{0-3}$ alkylene)-X) derivative of one of (Het)$Ar_1$ and (Het)$Ar_2$ in an organic solvent, DMF, or the like; adding a hydroxyalkyl (-(straight-chain or branched $C_{0-3}$ alkylene)-OH) derivative of the other of (Het)$Ar_1$ and (Het)$Ar_2$ and a base such as potassium carbonate thereto; and stirring the mixture at a temperature of 130° C. to 170° C. for several minutes to several hours, without being limited thereto. In this regard, the stirring may be performed using a microwave, without being limited thereto.

For example, commercially available compounds may be used as purchased as reactants and intermediates used in each step of the method of the present invention, or the reactants and intermediates used in each step may be synthesized using commercially available compounds via reactions well known in the art alone or in combination, but the present invention is not limited thereto.

In addition, if required, the method may further include processes of isolating and/or purifying a product after each reaction, and these processes may be performed using various methods well known in the art.

A third aspect of the present invention is to provide a composition for inhibiting aggregation of tau protein including the compound of the present invention as an active ingredient.

A fourth aspect of the present invention is to provide a composition for inhibiting hyperphosphorylation of tau protein including the compound of the present invention as an active ingredient.

A fifth aspect of the present invention is to provide a pharmaceutical composition for preventing or treating a disease caused by aggregation or hyperphosphorylation of tau protein including the compound of the present invention as an active ingredient.

A sixth aspect of the present invention is to provide a method of preventing or treating a disease caused by aggregation or hyperphosphorylation of tau protein, the method including administering the compound of the present invention into a subject in need thereof.

In specific embodiments of the present invention, a total of 175 compounds, numbered 1 to 175 and represented by Formula 1, were newly synthesized, and the effects thereof on inhibiting aggregation and hyperphosphorylation of tau protein were confirmed. Moreover, in order to confirm the possibility of use as a pharmaceutical composition, it was confirmed that these compounds do not exhibit cytotoxicity.

As used herein, the term "prevention" refers to any action that inhibits or delays the occurrence, spread, and recurrence of a disease induced by aggregation or hyperphosphorylation of tau protein by administration of the pharmaceutical composition of the present invention, and the term "treatment" refers to any action in which symptoms of the disease are improved or beneficially changed by administration of the pharmaceutical composition of the present invention.

As described above, since the compound of the present invention not only inhibits aggregation or hyperphosphorylation of tau protein, but also does not exhibit toxicity to cells, the pharmaceutical composition containing this compound as an active ingredient may be used for the prevention or treatment of diseases caused by aggregation or hyperphosphorylation of tau protein. The disease caused by aggregation or hyperphosphorylation of tau protein to which the pharmaceutical composition of the present invention may be applied may be Alzheimer's disease, Parkinson's disease, vascular dementia, acute stroke, trauma, cerebrovascular disease, brain cord trauma, spinal cord trauma, peripheral neuropathy, retinopathy, glaucoma, or tauopathy. Non-limiting examples of the tauopathy may include chronic traumatic encephalopathy (CTE), primary age-related tauopathy, progressive supranuclear palsy, corticobasal degeneration, Pick's disease, argyrophilic grain disease (AGD), frontotemporal dementia (FTD), parkinsonism linked to chromosome 17, Lytico-bodig disease (Parkinsonism-dementia complex of Guam), ganglioglioma, gangliocytoma, meningioangiomatosis, postencephalitic Parkinsonism, subacute sclerosing panencephalitis, lead encephalopathy, tuberous sclerosis, pantothenate kinase-associated neurodegeneration, lipofuscinosis, post-traumatic stress disorder, and traumatic brain injury.

For example, the composition of the present invention may further include a pharmaceutically acceptable carrier, a diluent, or an excipient, may be formulated and used in various forms such as oral formulations such as powders, granules, tablets, capsules, suspensions, emulsions, syrups, aerosols, and injection drugs of sterile injection solutions according to a general method for each purpose of use, and may be administered orally or may be administered through various routes including intravenous, intraperitoneal, subcutaneous, rectal, and topical administrations. Examples of the suitable carrier, excipient, or diluent included in this composition may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, and mineral oil. The composition of the present invention may further include a filler, an anti-aggregating agent, a lubricant, a humectant, a flavoring agent, an emulsifying agent, a preservative, and the like.

Solid preparations for oral administration include tablets, pills, powders, granules, capsules, and the like, and such a solid preparation is formulated by mixing one or more excipients, such as starch, calcium carbonate, sucrose, lactose, and gelatin with the composition. Meanwhile, in addition to a simple excipient, a lubricant such as magnesium stearate or talc may be used.

As the oral liquid formulation, a suspension, a solution for internal use, an emulsion, a syrup, and the like may be exemplified, and the oral liquid formulation may include various excipients, such as a humectant, a sweetening agent, a fragrance, and a preservative in addition to water and liquid paraffin, which are commonly used as a simple diluent.

Preparations for parenteral administration include an aqueous solvent, a non-aqueous solvent, a suspension agent, an emulsifying agent, a lyophilized preparation, and a suppository, which are sterilized. As the non-aqueous solvent or the suspension agent, propylene glycol, polyethylene glycol, plant oil such as olive oil, injectable ester such as ethyloleate, or the like may be used. As a base of the suppository, witepsol, macrogol, twin 61, cacao oil, laurin oil, glycerogelatin, or the like may be used. Meanwhile, injectables may include conventional additives such as a solubilizing agent, an isotonic agent, a suspension agent, an emulsifying agent, a stabilizing agent, and a preservative.

The formulation may be prepared by way of a conventional mixing, granulating, or coating method, and may contain an active ingredient in an amount of about 0.1 wt % to 75 wt %, preferably about 0.1 wt % to 50 wt %. The unit formulation for a mammal weighing about 50 kg to 70 kg contains about 10 mg to 200 mg of an active ingredient.

In this case, the composition of the present invention is administered in a pharmaceutically effective amount. As used herein, the term "pharmaceutically effective amount" refers to an amount sufficient to treat a disease at a reasonable benefit/risk ratio applicable to medical treatment and not cause side effects, and the level of the effective amount may be determined depending on patient's health status, type of disease, severity, activity of drug, sensitivity to drug, administration method, administration time, administration route, excretion rate, treatment period, factors including drugs used in combination or concurrently, and other factors well known in the medical field. The composition of the present invention may be administered as an individual therapeutic agent or administered in combination with other therapeutic agents, may be administered sequentially or simultaneously with a conventional therapeutic agent, and may be administered in a single dose or multiple doses. It is important to administer a minimum amount capable of obtaining the maximum effect without side effects in consideration of all of the above factors, which may be easily determined by those skilled in the art.

For example, since a dosage may increase or decrease depending on administration route, disease severity, sex, weight, age, and the like, the dosage does not limit the scope of the present invention in any way.

A preferred dosage of the compound of the present invention varies depending on the condition and weight of a patient, severity of disease, the form of drug, and the route and duration of administration, but may be appropriately selected by those skilled in the art. However, for a desired effect, the compound of the present invention may be administered in an amount of 0.0001 mg/kg to 100 mg/kg (body weight), preferably 0.001 mg/kg to 100 mg/kg (body weight) per day. The compound may be administered once a day or several times a day at divided doses via an oral or parenteral route.

A seventh aspect of the present invention is to provide a method for preventing or treating a disease caused by aggregation or hyperphosphorylation of tau protein, the method including administering the pharmaceutical composition of the present invention to a subject in need thereof.

As used herein, the term "subject" refers to any animal including monkeys, cows, horses, sheep, pigs, chickens, turkeys, quails, cats, dogs, mice, rabbits, and guinea pigs in addition to humans, which have developed or may develop a disease caused by aggregation or hyperphosphorylation of tau protein. The diseases may be effectively prevented or treated by administering the pharmaceutical composition of the present invention to the subject. Further, since the pharmaceutical composition of the present invention exhibits a therapeutic effect by inhibiting aggregation or hyperphosphorylation of tau protein, a synergistic effect may be exhibited by administering this composition in combination with a conventional therapeutic agent.

As used herein, the term "administration" refers to providing a predetermined substance to a patient by any suitable method, and the administration route of the composition of the present invention may be any general route as long as the substance is able to reach a target tissue. The composition may be administered through intraperitoneal administration, intravenous administration, intramuscular administration, subcutaneous administration, intradermal administration, oral administration, topical administration, intranasal administration, intrapulmonary administration, or rectal administration, but the present invention is not limited thereto. Also, the pharmaceutical composition of the present invention may be administered by any device capable of moving an active substance to a target cell. Preferred administrations and formulations include intravenous injection drugs, subcutaneous injection drugs, intradermal injection drugs, intramuscular injection drugs, and dropwise injection drugs. The injection drugs may be prepared using an aqueous solvent such as a physiological saline solution or Ringer's solution, or a non-aqueous solvent such as plant oil, higher fatty acid ester (for example, ethyl oleate), or alcohol (for example, ethanol, benzyl alcohol, propylene glycol, or glycerin), and may include a pharmaceutical carrier such as a stabilizing agent for preventing denaturing (for example, ascorbic acid, sodium hydrogen sulfite, sodium pyrosulfite, BHA, tocopherol, or EDTA), an emulsifying agent, a buffering agent for pH control, or a preservative for inhibiting the growth of microorganisms (for example, phenylmercury nitrate, thimerosal, benzalkonium chloride, phenol, cresol, or benzyl alcohol).

MODE FOR INVENTION

Hereinafter, the present invention will be described in more detail with reference to examples and experimental examples. However, these examples and experimental examples are only illustrative of the present invention, and the scope of the present invention is not limited to these examples and experimental examples.

Example 1: Preparation of (6-(5-methylpyrazine-2-carboxamido)pyridin-3-yl)carbonohydrazonoyl dicyanide (Compound 1)

Step 1-1: Preparation of 5-methyl-N-(5-nitropyridin-2-yl)pyrazine-2-carboxamide After 5-methylpyrazine-2-carboxylic acid (500 mg, 3.62 mmol) was dissolved in MeCN under a nitrogen atmosphere, 1-[bis(dimethylamino)methylene]-1H-1,2,3-triazolo [4,5-b]pyridinium 3-oxide hexafluorophosphate, hexafluorophosphate azabenzotriazole tetramethyl uronium (HATU, 1.65 g, 4.34 mmol), and triethylamine (TEA, 0.8 mL, 5.43 mmol) were added thereto, and the reaction mixture was stirred at room temperature for 4 hours. Then, 5-nitropyridine-2-amine (503 mg, 3.62 mmol) was added thereto, and the reaction mixture was refluxed for 24 hours. Upon completion of the reaction, a product was filtered using MeCN to obtain 476 mg (yield: 51%) of the title compound.

$^1$H NMR (400 MHz, DMSO-$d_6$) δ 10.83 (s, 1H), 9.29-9.15 (m, 2H), 8.74 (d, J=8.7 Hz, 2H), 8.45 (d, J=9.2 Hz, 1H), 2.66 (s, 3H).

Step 1-2: Preparation of N-(5-aminopyridin-2-yl)-5-methylpyrazine-2-carboxamide 5-Methyl-N-(5-nitropyridin-2-yl)pyrazine-2-carboxamide (400 mg, 1.54 mmol) obtained in Step 1-1 above and 10% Pd/C (328 mg, 0.31 mmol) were dissolved in 1,4-dioxane, and the reaction mixture was stirred under a hydrogen atmosphere at 60° C. for 2 hours. Upon completion of the reaction, the reaction mixture was filtered using ethyl acetate. The filtrate was concentrated under reduced pressure, solidified using ether, and filtered to obtain 47 mg (yield: 13%) of the title compound in a solid state.

$^1$H NMR (400 MHz, DMSO-$d_6$) δ 9.92 (s, 1H), 9.16 (d, J=1.4 Hz, 1H), 8.68 (d, J=1.5 Hz, 1H), 7.93 (d, J=8.7 Hz, 1H), 7.74 (d, J=2.8 Hz, 1H), 7.06 (dd, J=8.7 Hz, 2.9 Hz, 1H), 5.27 (s, 2H), 2.63 (s, 3H).

Step 1-3: Preparation of (6-(5-methylpyrazine-2-carboxamido)pyridin-3-yl)carbonohydrazonoyl dicyanide N-(5-Aminopyridin-2-yl)-5-methylpyrazine-2-carboxamide (40 mg, 0.17 mmol) obtained in Step 1-2 above and sodium nitrite (18 mg, 0.26 mmol) were dissolved in ethanol under a nitrogen atmosphere, and a 1.0 M aqueous hydrochloric acid solution (0.5 mL, 0.52 mmol) was added thereto at 0° C. The reaction mixture was stirred at 0° C. for 10 minutes to form a diazonium salt. Malononitrile (23 mg, 0.35 mmol) was added to the reaction mixture including the diazonium salt, and the mixture was stirred at room temperature for 10 minutes. Thereafter, the pH of the reaction mixture was adjusted to 6.0 using an aqueous sodium hydroxide solution, and the reaction mixture was further stirred at room temperature for 1 hour. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 48 mg (yield: 89%) of the title compound.

$^1$H NMR (400 MHz, DMSO-$d_6$) δ 10.36 (s, 1H), 9.19 (d, J=1.4 Hz, 1H), 8.71 (d, J=1.4 Hz, 1H), 8.49 (d, J=2.7 Hz, 1H), 8.27 (d, J=9.0 Hz, 1H), 7.95 (dd, J=9.0 Hz, 2.7 Hz, 1H), 2.64 (s, 3H).

Example 2: Preparation of (4-(5-methylpyrazine-2-carboxamido)phenyl)carbonohydrazonoyl dicyanide (Compound 2)

Step 2-1: Preparation of 5-methyl-N-(4-nitrophenyl)pyrazine-2-carboxamide 776 mg (yield: 83%) of the title compound was obtained in the same manner as in Step 1-1 of Example 1 above, except that N-nitroaniline (500 mg, 3.62 mmol) was used instead of 5-nitropyridine-2-amine.

$^1$H NMR (400 MHz, DMSO-$d_6$) δ 11.26 (s, 1H), 9.20 (d, J=1.5 Hz, 1H), 8.74 (d, J=1.4 Hz, 1H), 8.35-8.16 (m, 4H), 2.65 (s, 3H).

) Step 2-2: Preparation of N-(4-aminophenyl)-5-methylpyrazine-2-carboxamide 435 mg (yield: 66%) of the title compound was obtained in the same manner as in Step 1-2 of Example 1 above, except that 5-methyl-N-(4-nitrophenyl)pyrazine-2-carboxamide (750 mg, 2.90 mmol) obtained in Step 2-1 was used instead of 5-methyl-N-(5-nitropyridin-2-yl)pyrazine-2-carboxamide.

$^1$H NMR (400 MHz, DMSO-$d_6$) δ 7.35 (d, J=9.5 Hz, 1H), 7.11 (d, J=8.7 Hz, 2H), 6.92 (d, J=9.4 Hz, 1H), 6.59 (d, J=8.7 Hz, 2H), 5.31 (s, 2H), 2.28 (s, 3H).

Step 2-3: Preparation of (4-(5-methylpyrazine-2-carboxamido)phenyl)carbonohydrazonoyl dicyanide 113 mg (yield: 30%) of the title compound was obtained in the same manner as in Step 1-3 of Example 1 above, except that N-(4-aminophenyl)-5-methylpyrazine-2-carboxamide (284 mg, 1.24 mmol) obtained in Step 2-2 was used instead of N-(5-aminopyridin-2-yl)-5-methylpyrazine-2-carboxamide.

$^1$H NMR (400 MHz, DMSO-$d_6$) δ 13.06 (s, 1H), 10.79 (s, 1H), 9.16 (s, 1H), 8.70 (s, 1H), 7.97 (d, J=8.6 Hz, 2H), 7.48 (d, J=8.6 Hz, 2H), 2.64 (s, 3H).

Example 3: Preparation of (2-fluoro-4-(5-methylpyrazine-2-carboxamido)phenyl)carbonohydrazonoyl dicyanide (Compound 3)

Step 3-1: Preparation of N-(3-fluoro-4-nitrophenyl)-5-methylpyrazine-2-carboxamide 778 mg (yield: 83%) of the title compound was obtained in the same manner as in Step 1-1 of Example 1 above, except that 3-fluoro-4-nitroaniline (500 mg, 3.62 mmol) was used instead of 5-nitropyridine-2-amine.

$^1$H NMR (400 MHz, DMSO-$d_6$) δ 11.26 (s, 1H), 9.20 (d, J=1.5 Hz, 1H), 8.74 (d, J=1.4 Hz, 1H), 8.35-8.16 (m, 4H), 2.65 (s, 3H).

Step 3-2: Preparation of N-(4-amino-3-fluorophenyl)-5-methylpyrazine-2-carboxamide 41 mg (yield: 13%) of the title compound was obtained in the same manner as in Step 1-2 of Example 1 above, except that N-(3-fluoro-4-nitrophenyl)-5-methylpyrazine-2-carboxamide (350 mg, 1.27 mmol) obtained in Step 3-1 was used instead of 5-methyl-N-(5-nitropyridin-2-yl)pyrazine-2-carboxamide.

$^1$H NMR (400 MHz, DMSO-$d_6$) δ 10.47 (s, 1H), 9.12 (d, J=1.5 Hz, 1H), 8.67 (s, 1H), 7.66 (dd, J=13.7 Hz, 2.3 Hz, 1H), 7.48-7.34 (m, 1H), 6.74 (dd, J=10.1 Hz, 8.6 Hz, 1H), 5.02 (s, 2H), 2.62 (s, 3H).

Step 3-3: Preparation of (2-fluoro-4-(5-methylpyrazine-2-carboxamido)phenyl)carbonohydrazonoyl dicyanide 113 mg (yield: 30%) of the title compound was obtained in the same manner as in Step 1-3 of Example 1 above, except that N-(4-amino-3-fluorophenyl)-5-methylpyrazine-2-carboxamide (284 mg, 1.24 mmol) obtained in Step 3-2 was used instead of N-(5-aminopyridin-2-yl)-5-methylpyrazine-2-carboxamide.

$^1$H NMR (400 MHz, DMSO-$d_6$) δ 13.06 (s, 1H), 10.79 (s, 1H), 9.16 (s, 1H), 8.70 (s, 1H), 7.97 (d, J=8.6 Hz, 2H), 7.48 (d, J=8.6 Hz, 2H), 2.64 (s, 3H).

Example 4: Preparation of (2-methoxy-4-(5-methylpyrazine-2-carboxamido)phenyl)carbonohydrazonoyl dicyanide (Compound 4)

Step 4-1: Preparation of N-(3-methoxy-4-nitrophenyl)-5-methylpyrazine-2-carboxamide 496 mg (yield: 79%) of the title compound was obtained in the same manner as in Step 1-1 of Example 1 above, except that 3-methoxy-4-nitroaniline (365 mg, 2.17 mmol) was used instead of 5-nitropyridine-2-amine.

$^1$H NMR (400 MHz, DMSO-$d_6$) δ 11.12 (s, 1H), 9.20 (s, 1H), 8.73 (s, 1H), 8.08-7.94 (m, 2H), 778 (dd, J=9.0 Hz, 2.0 Hz, 1H), 3.93 (s, 3H), 2.65 (s, 3H).

Step 4-2: Preparation of N-(4-amino-3-methoxyphenyl)-5-methylpyrazine-2-carboxamide 192 mg (yield: 48%) of the title compound was obtained in the same manner as in Step 1-2 of Example 1 above, except that N-(3-methoxy-4-nitrophenyl)-5-methylpyrazine-2-carboxamide (450 mg, 1.56 mmol) obtained in Step 4-1 was used instead of 5-methyl-N-(5-nitropyridin-2-yl)pyrazine-2-carboxamide.

$^1$H NMR (400 MHz, DMSO-$d_6$) δ 10.28 (s, 1H), 9.13 (s, 1H), 8.67 (s, 1H), 7.46 (s, 1H), 7.32-7.21 (m, 1H), 660 (dd, J=8.5 Hz, 2.0 Hz, 1H), 4.68-4.60 (m, 3H), 3.77 (d, J=2.0 Hz, 3H), 2.62 (d, J=2.0 Hz, 3H).

Step 4-3: Preparation of (2-methoxy-4-(5-methylpyrazine-2-carboxamido)phenylcarbohydrazonoyl Dicyanide 214 mg (yield: 91%) of the title compound was obtained in the same manner as in Step 1-3 of Example 1 above, except that N-(4-amino-3-methoxyphenyl)-5-methylpyrazine-2-carboxamide (180 mg, 0.70 mmol) obtained in Step 4-2 was used instead of N-(5-aminopyridin-2-yl)-5-methylpyrazine-2-carboxamide.

$^1$H NMR (400 MHz, DMSO-$d_6$) δ 11.87 (s, 1H), 10.80 (s, 1H), 9.17 (d, J=14 Hz, 1H), 8.71 (s, 1H), 7.86 (d, J=2.1 Hz, 1H), 7.67 (dd, J=8.8 Hz, 2.1 Hz, 1H), 7.39 (d, J=8.8 Hz, 1H), 3.91 (s, 3H), 2.64 (s, 3H).

Example 5: Preparation of (2-chloro-4-(5-methylpyrazine-2-carboxamido)phenyl)carbonohydrazonoyl dicyanide (Compound 5)

Step 5-1: Preparation of N-(3-chloro-4-nitrophenyl)-5-methylpyrazine-2-carboxamide 339 mg (yield: 53%) of the title compound was obtained in the same manner as in Step 1-1 of Example 1 above, except that 3-chloro-4-nitroaniline (375 mg, 2.17 mmol) was used instead of 5-nitropyridine-2-amine.

$^1$H NMR (400 MHz, DMSO-$d_6$) δ 11.33 (s, 1H), 9.19 (d, J=1.4 Hz, 1H), 8.73 (d, J=1.4 Hz, 1H), 8.38 (d, J=2.1 Hz, 1H), 8.22-8.09 (m, 2H), 2.65 (s, 3H).

Step 5-2: Preparation of N-(4-amino-3-chlorophenyl)-5-methylpyrazine-2-carboxamide 489 mg (yield: 50%) of the title compound was obtained in the same manner as in Step 1-2 of Example 1 above, except that N-(3-chloro-4-nitrophenyl)-5-methylpyrazine-2-carboxamide (300 mg, 1.03 mmol) obtained in Step 5-1 was used instead of 5-methyl-N-(5-nitropyridin-2-yl)pyrazine-2-carboxamide.

$^1$H NMR (400 MHz, DMSO-$d_6$) δ 10.47 (s, 1H), 9.12 (d, J=1.4 Hz, 1H), 8.67 (d, J=1.5 Hz, 1H), 7.85 (d, J=2.3 Hz, 1H), 7.51 (dd, J=8.7 Hz, 2.4 Hz, 1H), 6.78 (d, J=8.7 Hz, 1H), 5.24 (s, 2H), 2.62 (s, 3H).

Step 5-3: Preparation of 2-chloro-4-(5-methylpyrazine-2-carboxamido)phenyl)carbonohydrazonoyl dicyanide 119 mg (yield: 77%) of the title compound was obtained in the same manner as in Step 1-3 of Example 1 above, except that N-(4-amino-3-chlorophenyl)-5-methylpyrazine-2-carboxamide (120 mg, 0.46 mmol) obtained in Step 5-2 was used instead of N-(5-aminopyridin-2-yl)-5-methylpyrazine-2-carboxamide.

$^1$H NMR (400 MHz, DMSO-$d_6$) δ 10.95 (s, 1H), 9.17 (s, 1H), 8.71 (s, 1H), 8.18 (s, 1H), 7.93 (d, J=8.9 Hz, 1H), 7.50 (d, J=8.9 Hz, 1H), 2.64 (s, 3H).

Example 6: Preparation of (2-methyl-4-(5-methylpyrazine-2-carboxamido)phenyl)carbonohydrazonoyl dicyanide (Compound 6)

Step 6-1: Preparation of 5-methyl-N-(3-methyl-4-nitrophenyl)pyrazine-2-carboxamide 489 mg (yield: 83%) of the title compound was obtained in the same manner as in Step 1-1 of Example 1 above, except that 3-methyl-4-nitroaniline (331 mg, 2.17 mmol) was used instead of 5-nitropyridine-2-amine.

$^1$H NMR (400 MHz, DMSO-$d_6$) δ 11.09 (s, 1H), 9.18 (s, 1H), 8.73 (s, 1H), 8.18-7.95 (m, 3H), 2.65 (s, 3H), 2.56 (s, 3H).

Step 6-2: Preparation of N-(4=amino-3-methylphenyl-5-methylpyrazine-2-carboxamide 268 mg (yield: 63%) of the title compound was obtained in the same manner as in Step 1-2 of Example 1 above, except that 5-methyl-N-(3-methyl-4-nitrophenyl)pyrazine-2-carboxamide (480 mg, 1.69 mmol) obtained in Step 6-1 was used instead of 5-methyl-N-(5-nitropyridin-2-yl)pyrazine-2-carboxamide.

$^1$H NMR (400 MHz, DMSO-$d_6$) δ 10.20 (s, 1H), 9.11 (s, 1H), 8.66 (s, 1H), 7.46 (s, 1H), 7.40 (dd, J=8.5 Hz, 2.5 Hz, 1H), 6.62 (d, J=8.5 Hz, 1H), 5.16 (s, 2H), 2.62 (s, 3H), 207 (s, 3H).

Step 6-3: Preparation of (2-methyl-4-(5-methylpyrazine-2-carboxamido)phenyl)carbonohydrazonoyl dicyanide 112 mg (yield: 33%) of the title compound was obtained in the same manner as in Step 1-3 of Example 1 above, except that N-(4-amino-3-methylphenyl)-5-methylpyrazine-2-carboxamide (260 mg, 1.07 mmol) obtained in Step 6-2 was used instead of N-(5-aminopyridin-2-yl)-5-methylpyrazine-2-carboxamide.

$^1$H NMR (400 MHz, DMSO-$d_6$) δ 12.30 (s, 1H), 10.71 (s, 1H), 9.16 (d, J=1.4 Hz, 1H), 8.70 (d, J=1.4 Hz, 1H), 7.91-7.75 (m, 2H), 7.34 (d, J=8.5 Hz, 1H), 2.64 (s, 3H), 2.36 (s, 3H).

Example 7: Preparation of (3-fluoro-4-(5-methylpyrazine-2-carboxamido)phenyl)carbonohydrazonoyl dicyanide (Compound 7)

Step 7-1: Preparation of N-(2-fluoro-4-nitrophenyl)-5-methylpyrazine-2-carboxamide 309 mg (yield: 51%) of the title compound was obtained in the same manner as in Step 1-1 of Example 1 above, except that 2-fluoro-4-nitroaniline (339 mg, 2.61 mmol) was used instead of 5-nitropyridine-2-amine.

$^1$H NMR (400 MHz, DMSO-$d_6$) δ 10.60 (s, 1H), 9.21 (s, 0H), 8.75 (s, 1H), 8.39 (t, J=8.3 Hz, 1H), 8.29 (dd, J=10.7 Hz, 2.6 Hz, 1H), 8.21 (dd, J=9.1 Hz, 2.6 Hz, 1H), 2.66 (s, 3H).

Step 7-2: Preparation of N-(4-amino-2-fluorophenyl)-5-methylpyrazine-2-carboxamide 97 mg (yield: 44%) of the title compound was obtained in the same manner as in Step 1-2 of Example 1 above, except that N-(2-fluoro-4-nitrophenyl)-5-methylpyrazine-2-carboxamide (250 mg, 0.91 mmol) obtained in Step 7-1 was used instead of 5-methyl-N-(5-nitropyridin-2-yl)pyrazine-2-carboxamide.

$^1$H NMR (400 MHz, DMSO-$d_6$) δ 9.96 (s, 1H), 9.11 (d, J=1.4 Hz, 1H), 8.67 (d, J=1.4 Hz, 1H), 7.37 (t, J=8.7 Hz, 1H), 6.51-6.29 (m, 2H), 5.39 (s, 2H), 2.62 (s, 3H).

Step 7-3: Preparation of (3-fluoro-4-(5-methylpyrazine-2-carboxamido)phenyl)carbonohydrazonoyl dicyanide 110 Mg (yield: 93%) of the title compound was obtained in the same manner as in Step 1-3 of Example 1 above, except that N-(4-amino-2-fluorophenyl)-5-methylpyrazine-2-carboxamide (90 mg, 0.37 mmol) obtained in Step 7-2 was used instead of N-(5-aminopyridin-2-yl)-5-methylpyrazine-2-carboxamide.

$^1$H NMR (400 MHz, DMSO-$d_6$) δ 13.10 (s, 1H), 10.35 (s, 1H), 9.16 (d, J=1.4 Hz, 1H), 8.72 (d, J=1.4 Hz, 1H), 7.95 (t, J=8.5 Hz, 1H), 7.46-7.29 (m, 2H), 2.64 (s, 3H).

Example 8: Preparation of (3-methyl-4-(5-methylpyrazine-2-carboxamido)phenyl)carbonohydrazonoyl dicyanide (Compound 8)

Step 8-1: Preparation of 5-methyl-N-(2-methyl-4-nitrophenyl)pyrazine-2-carboxamide 514 mg (yield: 87%) of the title compound was obtained in the same manner as in Step 1-1 of Example 1 above, except that 2-methyl-4-nitroaniline (331 mg, 2.17 mmol) was used instead of 5-nitropyridine-2-amine.

$^1$H NMR (400 MHz, DMSO-$d_6$) δ 10.42 (s, 1H), 9.21 (s, 1H), 8.75 (s, 1H), 8.23 (s, 1H), 8.17 (s, 2H), 2.65 (s, 3H), 2.45 (s, 3H).

Step 8-2: Preparation of N-(4-amino-2-methylphenyl)-5-methylpyrazine-2-carboxamide 277 mg (yield: 57%) of the title compound was obtained in the same manner as in Step 1-2 of Example 1 above, except that 5-methyl-V-(2-methyl-4-nitrophenyl)pyrazine-2-carboxamide (460 mg, 1.69 mmol) obtained in Step 8-1 was used instead of 5-methyl-N-(5-nitropyridin-2-yl)pyrazine-2-carboxamide.

$^1$H NMR (400 MHz, DMSO-$d_6$) δ 9.87 (s, 1H), 9.11 (s, 1H), 8.66 (d, J=1.5 Hz, 1H), 7.15 (d, J=8.4 Hz, 1H), 6.46 (d, J=2.6 Hz, 1H), 6.41 (dd, J=8.3 Hz, 2.6 Hz, 1H), 5.01 (s, 2H), 2.62 (s, 3H), 2.10 (s, 3H).

Step 8-3: Preparation of (3-methyl-4-(5-methylpyrazine-2-carboxamido)phenyl)carbonohydrazonoyl dicyanide 168 mg (yield: 42%) of the title compound was obtained in the same manner as in Step 1-3 of Example 1 above, except that N-(4-amino-2-methylphenyl)-5-methylpyrazine-2-carboxamide (260 mg, 1.07 mmol) obtained in Step 8-2 was used instead of N-(5-aminopyridin-2-yl)-5-methylpyrazine-2-carboxamide.

$^1$H NMR (400 MHz, DMSO-$d_6$) δ 13.03 (s, 1H), 10.21 (s, 1H), 9.15 (s, 1H), 8.70 (s, 1H), 7.72 (d, J=8.6 Hz, 1H), 7.46-7.22 (m, 2H), 2.63 (s, 3H), 2.30 (s, 3H).

Example 9: Preparation of Methyl(3-methyl-4-(5-methylpyrazine-2-carboxamido)phenyl)carbonohydrazonoyl dicyanide (Compound 9)

(3-Methyl-4-(5-methylpyrazine-2-carboxamido)phenyl) carbonohydrazonoyl dicyanide (100 mg, 0.31 mmol) obtained in Example 8 above was dissolved in dimethylformamide (DMF), and potassium tert-butoxide (46 mg, 0.41 mmol) was added thereto at room temperature, and then iodomethane (39 μL, 0.63 mmol) was added thereto. The reaction mixture was stirred at 60° C. for 12 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 4 mg (yield: 3%) of the title compound.

$^1$H NMR (400 MHz, DMSO-$d_6$) δ 10.28 (s, 1H), 9.16 (d, J=1.5 Hz, 1H), 8.71 (d, J=1.4 Hz, 1H), 7.79 (d, J=8.6 Hz, 1H), 7.44 (d, J=2.8 Hz, 1H), 7.38 (dd, J=8.7 Hz, 2.8 Hz, 1H), 4.06 (s, 3H), 2.64 (s, 3H), 2.33 (s, 3H).

Example 10: Preparation of (3-methoxy-4-(5-methylpyrazine-2-carboxamido)phenyl)carbonohydrazonoyl dicyanide (Compound 10)

Step 10-1: Preparation of a-(2-methoxy-4-nitrophenyl)-5-methylpyrazine-2-carboxamide 454 mg (yield: 75%) of the title compound was obtained in the same manner as in Step 1-1 of Example 1 above, except that 2-methoxy-4-nitroaniline (365 mg, 2.17 mmol) was used instead of 5-nitropyridine-2-amine.

$^1$H NMR (400 MHz, DMSO-$d_6$) δ 10.41 (s, 1H), 9.23 (s, 1H), 8.74 (s, 1H), 8.66 (d, J=9.0 Hz, 1H), 8.08-7.99 (m, 1H), 7.92 (d, J=2.5 Hz, 1H), 4.09 (s, 3H), 2.65 (s, 3H).

Step 10-2: Preparation of N-(4-amino-2-methoxyphenyl)-5-methylpyrazine-2-carboxamide 290 mg (yield: 72%) of the title compound was obtained in the same manner as in Step 1-2 of Example 1 above, except that N-(2-methoxy-4-nitrophenyl)-5-methylpyrazine-2-carboxamide (447 mg, 1.55 mmol) obtained in Step 10-1 was used instead of 5-methyl-N-(5-nitropyridin-2-yl)pyrazine-2-carboxamide.

$^1$H NMR (400 MHz, DMSO-$d_6$) δ 9.82 (s, 1H), 9.13 (s, 1H), 8.66 (s, 1H), 7.98 (d, J=8.5 Hz, 1H), 6.36 (d, J=2.4 Hz, 1H), 6.18 (dd, J=8.6 Hz, 2.4 Hz, 1H), 5.11 (s, 2H), 3.82 (s, 3H), 2.62 (s, 3H).

Step 10-3: Preparation of (3-methoxy-4-(5-methylpyrazine-2-carboxamido)phenyl)carbonohydrazonoyl dicyanide 181 mg (yield: 50%) of the title compound was obtained in the same manner as in Step 1-3 of Example 1 above, except that N-(4-amino-2-methoxyphenyl)-5-methylpyrazine-2-carboxamide (280 mg, 1.08 mmol) obtained in Step 10-2 was used instead of N-(5-aminopyridin-2-yl)-5-methylpyrazine-2-carboxamide.

$^1$H NMR (400 MHz, DMSO-$d_6$) δ 13.02 (s, 1H), 10.10 (s, 1H), 9.17 (s, 1H), 8.69 (s, 1H), 8.40 (d, J=8.8 Hz, 1H), 7.22 (s, 1H), 7.13 (dd, J=8.8 Hz, 2.3 Hz, 1H), 3.96 (s, 3H), 2.63 (s, 3H).

Example 11: Preparation of (3-chloro-4-(5-methylpyrazine-2-carboxamido)phenyl)carbonohydrazonoyl dicyanide (Compound 11)

Step 11-1: Preparation of N-(2-chloro-4-nitrophenyl)-5-methylpyrazine-2-carboxamide 5-Methylpyrazine-2-carboxylic acid (300 mg, 2.17 mmol) was dissolved in anhydrous dichloromethane under a nitrogen atmosphere, and oxalyl chloride (0.56 mL, 6.52 mmol) and DMF (1 to 2 drops) were added thereto at 0° C. The reaction mixture was stirred at 0° C. for 1 hour and concentrated under reduced pressure. The concentrate and 2-chloro-4-nitroaniline (375 mg, 2.17 mmol) were dissolved in pyridine under a nitrogen atmosphere, and the reaction mixture was stirred at room temperature for 12 hours. Upon completion of the reaction, a reaction product was extracted using an aqueous ammonium chloride solution and dichloromethane to obtain an organic layer, and the organic layer was dried over anhydrous magnesium sulfate and filtered to obtain 162 mg (yield: 25%) of the title compound in a solid state.

$^1$H NMR (400 MHz, DMSO-$d_6$) δ 10.64 (s, 1H), 9.25 (d, J=1.4 Hz, 1H), 8.76 (d, J=1.4 Hz, 1H), 8.66 (d, J=9.2 Hz, 1H), 8.49 (d, J=2.7 Hz, 1H), 8.35 (dd, J=9.1 Hz, 2.7 Hz, 1H), 2.66 (s, 3H).

Step 11-2: Preparation of N-(4-amino-2-chlorophenyl)-5-methylpyrazine-2-carboxamide 89 mg (yield: 66%) of the title compound was obtained in the same manner as in Step 1-2 of Example 1 above, except that N-(2-chloro-4-nitrophenyl)-5-methylpyrazine-2-carboxamide (150 mg, 0.51 mmol) obtained in Step 11-1 was used instead of 5-methyl-N-(5-nitropyridin-2-yl)pyrazine-2-carboxamide.

$^1$H NMR (400 MHz, DMSO-$d_6$) δ 10.02 (s, 1H), 9.13 (s, 1H), 8.68 (s, 1H), 7.64 (d, J=8.7 Hz, 1H), 6.71 (d, J=2.5 Hz, 1H), 6.57 (dd, J=8.7 Hz, 2.5 Hz, 1H), 5.39 (s, 2H), 2.62 (s, 3H).

Step 11-3: Preparation of (3-chloro-4-(5-methylpyrazine-2-carboxamido)phenyl)carbonohydrazonoyl dicyanide 86 mg (yield: 89%) of the title compound was obtained in the same manner as in Step 1-3 of Example 1 above, except that N-(4-amino-2-chlorophenyl)-5-methylpyrazine-2-carboxamide (75 mg, 0.28 mmol) obtained in Step 11-2 was used instead of N-(5-aminopyridin-2-yl)-5-methylpyrazine-2-carboxamide.

$^1$H NMR (400 MHz, DMSO-$d_6$) δ 1306 (s, 1H), 10.32 (s, 1H), 9.17 (d, J=1.4 Hz, 1H), 8.71 (d, J=1.4 Hz, 1H), 8.24 (d, J=9.0 Hz, 1H), 7.61 (d, J=2.4 Hz, 1H), 7.49 (dd, J=8.9 Hz, 2.5 Hz, 1H), 2.64 (s, 3H).

Example 12: Preparation of (5-methyl-6-(5-methylpyrazine-2-carboxamido)pyridin-3-yl)carbonohydrazonoyl dicyanide (Compound 12)

Step 12-1: Preparation of 5-methyl-N-(3-methyl-5-nitropyridin-2-yl)pyrazine-2-carboxamide 410 mg (yield: 69%) of the title compound was obtained in the same manner as in Step 1-1 of Example 1 above, except that 3-methyl-5-nitropyridine-2-amine (332 mg, 2.17 mmol) was used instead of 5-nitropyridine-2-amine.

$^1$H NMR (400 MHz, DMSO-$d_6$) δ 10.99 (s, 1H), 9.17 (d, J=1.4 Hz, 1H), 9.13 (d, J=2.7 Hz, 1H), 8.73 (d, J=1.4 Hz, 1H), 8.61 (d, J=2.7 Hz, 1H), 2.65 (s, 3H), 2.40 (s, 3H).

Step 12-2: Preparation of N-(5-amino-3-methylpyridin-2-yl)-5-methylpyrazine-2-carboxamide 211 mg (yield: 59%) of the title compound was obtained in the same manner as in Step 1-2 of Example 1 above, except that 5-methyl-N-(3-methyl-5-nitropyridin-2-yl)pyrazine-2-carboxamide (400 mg, 1.46 mmol) obtained in Step 12-1 was used instead of 5-methyl-N-(5-nitropyridin-2-yl) pyrazine-2-carboxamide.

$^1$H NMR (400 MHz, DMSO-$d_6$) δ 10.19 (s, 1H), 9.10 (d, J=1.6 Hz, 1H), 8.67 (s, 1H), 7.64 (d, J=2.7 Hz, 1H), 6.86 (d, J=2.7 Hz, 1H), 5.26 (s, 2H), 2.62 (s, 3H), 2.07 (s, 3H).

Step 12-3: Preparation of (5-methyl-G-(5-methylpyrazine-2-carboxamido)pyridin-3-yl)carbonohydrazonoyl dicyanide 231 mg (yield: 88%) of the title compound was obtained in the same manner as in Step 1-3 of Example 1 above, except that N-(5-amino-3-methylpyridin-2-yl)-5-methylpyrazine-2-carboxamide (200 mg, 0.82 mmol) obtained in Step 12-2 was used instead of N-(5-aminopyridin-2-yl)-5-methylpyrazine-2-carboxamide.

$^1$H NMR (400 MHz, DMSO-$d_6$) δ 10.70 (s, 1H), 9.14 (s, 1H), 8.71 (d, J=1.4 Hz, 1H), 8.44 (d, J=2.6 Hz, 1H), 7.88-7.78 (m, 1H), 2.64 (s, 3H), 2.28 (s, 3H).

Example 13: Preparation of (4-methyl-6-(5-methylpyrazine-2-carboxamido)pyridin-3-yl)carbonohydrazonoyl dicyanide (Compound 13)

Step 13-1: Preparation of 5-methyl-N-(4-methyl-5-nitropyridin-2-yl)pyrazine-2-carboxamide 265 mg (yield: 45%) of the title compound was obtained in the same manner as in Step 1-1 of Example 1 above, except that 4-methyl-5-nitropyridine-2-amine (332 mg, 2.17 mmol) was used instead of 5-nitropyridine-2-amine.

$^1$H NMR (400 MHz, DMSO-$d_6$) δ 10.70 (s, 1H), 9.22 (d, J=1.5 Hz, 1H), 9.06 (s, 1H), 8.75 (d, J=1.5 Hz, 1H), 8.32 (s, 1H), 2.66 (d, J=5.6 Hz, 6H).

Step 13-2: Preparation of N-(5-amino-4-methylpyridin-2-yl)-5-methylpyrazine-2-carboxamide 28 mg (yield: 13%) of the title compound was obtained in the same manner as in Step 1-2 of Example 1 above, except that 5-methyl-N-(4-methyl-5-nitropyridin-2-yl)pyrazine-2-carboxamide (250 mg, 0.91 mmol) obtained in Step 13-1 was used instead of 5-methyl-N-(5-nitropyridin-2-yl)pyrazine-2-carboxamide.

$^1$H NMR (400 MHz, DMSO-$d_6$) δ 9.87 (s, 1H), 9.16 (d, J=1.4 Hz, 1H), 8.68 (d, J=1.4 Hz, 1H), 7.87 (s, 1H), 7.72 (s, 1H), 5.05 (s, 2H), 2.63 (s, 3H), 2.14 (s, 3H).

Step 13-3: Preparation of (4-methyl-6-(5-methylpyrazine-2-carboxamido)pyridin-3-yl)carbonohydrazonoyl dicyanide 20 mg (yield: 61%) of the title compound was obtained in the same manner as in Step 1-3 of Example 1 above, except that N-(5-amino-4-methylpyridin-2-yl)-5-methylpyrazine-2-carboxamide (25 mg, 0.10 mmol) obtained in Step 13-2 was used instead of N-(5-aminopyridin-2-yl)-5-methylpyrazine-2-carboxamide.

$^1$H NMR (400 MHz, DMSO-$d_6$) δ 10.56 (s, 1H), 9.20 (d, J=1.4 Hz, 1H), 8.72 (d, J=1.5 Hz, 1H), 8.25 (s, 1H), 8.10 (s, 1H), 2.65 (s, 3H), 2.45 (s, 3H).

Example 14: Preparation of (5-(5-methylpyrazine-2-carboxamido)pyridin-2-yl)carbonohydrazonoyl dicyanide (Compound 14)

Step 14-1: Preparation of 5-methyl-N-(6-nitropyridin-3-yl)pyrazine-2-carboxamide 304 mg (yield: 54%) of the title compound was obtained in the same manner as in Step 1-1 of Example 1 above, except that 6-nitropyridine-3-amine (302 mg, 2.17 mmol) was used instead of 5-nitropyridine-2-amine.

$^1$H NMR (400 MHz, DMSO-$d_6$) δ 11.54 (s, 1H), 9.22 (d, J=1.4 Hz, 1H), 9.15 (d, J=2.5 Hz, 1H), 8.77-8.72 (m, 2H), 8.41 (d, J=8.9 Hz, 1H), 2.66 (s, 3H).

Step 14-2: Preparation of N-(6-aminopyridin-3-yl)-"-methylpyrazine-2-carboxamide 103 mg (yield: 40%) of the title compound was obtained in the same manner as in Step 1-2 of Example 1 above, except that 5-methyl-N-(6-nitropyridin-3-yl)pyrazine-2-carboxamide (290 mg, 1.12 mmol) obtained in Step 14-1 was used instead of 5-methyl-N-(5-nitropyridin-2-yl)pyrazine-2-carboxamide.

$^1$H NMR (400 MHz, DMSO-$d_6$) δ 10.45 (s, 1H), 9.12 (d, J=1.5 Hz, 1H), 8.67 (d, J=1.4 Hz, 1H), 8.35 (d, J=2.6 Hz, 1H), 7.80 (dd, J=8.8 Hz, 2.7 Hz, 1H), 6.45 (d, J=8.8 Hz, 1H), 5.82 (s, 2H), 2.62 (s, 3H).

Step 14-3: Preparation of (5-(5-methylpyrazine-2-carboxamido)pyridin-2-yl)carbonohydrazonoyl dicyanide 34 mg (yield: 28%) of the title compound was obtained in the same manner as in Step 1-3 of Example 1 above, except that N-(6-aminopyridin-3-yl)-5-methylpyrazine-2-carboxamide (90 mg, 0.39 mmol) obtained in Step 14-2 was used instead of N-(5-aminopyridin-2-yl)-5-methylpyrazine-2-carboxamide.

$^1$H NMR (400 MHz, DMSO-$d_6$) δ 11.46 (s, 1H), 10.59 (s, 1H), 9.12 (d, J=1.4 Hz, 1H), 8.68 (d, J=1.4 Hz, 1H), 8.06 (d, J=2.9 Hz, 1H), 7.84 (dd, J=9.7 Hz, 2.9 Hz, 1H), 6.38 (d, J=9.7 Hz, 1H), 2.62 (s, 3H).

Example 15: Preparation of (6-benzamidopyridin-3-yl)carbonohydrazonoyl dicyanide (Compound 15)

Step 15-1: Preparation of N-(5-nitropyridin-2-yl)benzamide 424 mg (yield: 71%) of the title compound was obtained in the same manner as in Step 11-1 of Example 11 above, except that benzoic acid (300 mg, 2.46 mmol) was used instead of 5-methylpyrazine-2-carboxylic acid, and 2-amino-5-nitropyridine (342 mg, 2.46 mmol) was used instead of 2-chloro-4-nitroaniline.

$^1$H NMR (400 MHz, DMSO-$d_6$) δ 11.55 (s, 1H), 9.24 (d, J=2.8 Hz, 1H), 8.67 (dd, J=9.3 Hz, 2.9 Hz, 1H), 8.45 (d, J=9.3 Hz, 1H), 8.14-7.94 (m, 2H), 7.64 (t, J=7.4 Hz, 1H), 7.54 (t, J=7.6 Hz, 2H).

Step 15-2: Preparation of N-(5-aminopyridin-2-yl)benzamide 328 mg (yield: 91%) of the title compound was obtained in the same manner as in Step 1-2 of Example 1 above, except that N-(5-nitropyridin-2-yl)benzamide (410 mg, 1.69 mmol) obtained in Step 15-1 was used instead of 5-methyl-N-(5-nitropyridin-2-yl)pyrazine-2-carboxamide.

$^1$H NMR (400 MHz, DMSO-$d_6$) δ 10.32 (s, 1H), 7.99 (d, J=7.3 Hz, 2H), 7.81 (d, J=8.7 Hz, 1H), 7.75 (d, J=2.8 Hz, 1H), 7.61-7.53 (m, 1H), 7.52-7.43 (m, 2H), 7.02 (dd, J=8.7 Hz, 2.9 Hz, 1H), 5.17 (s, 2H).

Step 15-3: Preparation of (6-benzamidopyridin-3-yl)carbonohydrazonoyl Dicyanide 86 mg (yield: 89%) of the title compound was obtained in the same manner as in Step 1-3 of Example 1 above, except that N-(5-aminopyridin-2-yl)benzamide (320 mg, 1.50 mmol) obtained in Step 15-2 was used instead of N-(5-aminopyridin-2-yl)-5-methylpyrazine-2-carboxamide.

$^1$H NMR (400 MHz, DMSO-$d_6$) δ 10.96 (s, 1H), 8.51 (d, J=2.7 Hz, 1H), 8.25 (d, J=9.0 Hz, 1H), 8.03 (d, J=7.2 Hz, 2H), 7.93 (dd. J=9.1 Hz, 2.7 Hz, 1H), 7.61 (t, J=7.3 Hz, 1H), 7.52 (t, J=7.6 Hz, 2H).

Example 16: Preparation of (6-(4-fluorobenzamido)pyridin-3-yl)carbonohydrazonoyl dicyanide (Compound 16)

Step 16-1: Preparation of 4-fluoro-N-(6-nitropyridin-2-yl)benzamide 369 mg (yield: 66%) of the title compound was obtained in the same manner as in Step 11-1 of Example 11 above, except that 4-fluorobenzoic acid (300 mg, 2.14 mmol) was used instead of 5-methylpyrazine-2-carboxylic acid, and 2-amino-5-nitropyridine (298 mg, 2.14 mmol) was used instead of 2-chloro-4-nitroaniline.

$^1$H NMR (400 MHz, DMSO-$d_6$) δ 11.59 (s, 1H), 9.24 (d, J=2.8 Hz, 1H), 8.67 (dd, J=9.3 Hz, 2.8 Hz, 1H), 8.43 (d, J=9.2 Hz, 1H), 8.13 (dd, J=8.8 Hz, 5.5 Hz, 2H), 7.38 (t, J=8.9 Hz, 2H).

Step 16-2: Preparation of N-(5-aminopyridin-2-yl)-4-fluorobenzamide 273 mg (yield: 88%) of the title compound was obtained in the same manner as in Step 1-2 of Example 1 above, except that 4-fluoro-N-(5-nitropyridin-2-yl)benzamide (350 mg, 1.34 mmol) obtained in Step 16-1 was used instead of 5-methyl-N-(5-nitropyridin-2-yl)pyrazine-2-carboxamide.

$^1$H NMR (400 MHz, DMSO-$d_6$) δ 10.39 (s, 1H), 8.07 (dd, J=8.6 Hz, 5.5 Hz, 2H), 7.83-7.72 (m, 2H), 7.31 (t, J=8.8 Hz, 2H), 7.03 (dd, J=8.8 Hz, 2.8 Hz, 1H), 5.18 (s, 2H).

Step 16-3: Preparation of (6-(4-fluorobenzamido)pyridin-3-yl)carbonohydrazonoyl dicyanide 160 mg (yield: 46%) of the title compound was obtained in the same manner as in Step 1-3 of Example 1 above, except that N-(5-aminopyridin-2-yl)-4-fluorobenzamide (260 mg, 1.12 mmol) obtained in Step 16-2 was used instead of N-(5-aminopyridin-2-yl)-5-methylpyrazine-2-carboxamide.

$^1$H NMR (400 MHz, DMSO-$d_6$) δ 13.01 (s, 1H), 11.01 (s, 1H), 8.51 (d, J=2.7 Hz, 1H), 8.23 (d, J=9.1 Hz, 1H), 8.11 (dd, J=8.6 Hz, 5.5 Hz, 2H), 7.92 (dd, J=9.0 Hz, 2.8 Hz, 1H), 7.35 (t, J=8.8 Hz, 2H).

Example 17: Preparation of (6-(2-fluorobenzamido)pyridin-3-yl)carbonohydrazonoyl dicyanide (Compound 17)

Step 17-1: Preparation of 2-fluoro-N-(5-nitropyridin-2-yl)benzamide 358 mg (yield: 64%) of the title compound was obtained in the same manner as in Step 11-1 of Example 11 above, except that 2-fluorobenzoic acid (300 mg, 2.14 mmol) was used instead of 5-methylpyrazine-2-carboxylic acid, and 2-amino-5-nitropyridine (298 mg, 2.14 mmol) was used instead of 2-chloro-4-nitroaniline.

$^1$H NMR (400 MHz, DMSO-$d_6$) δ 11.59 (s, 1H), 9.22 (d, J=2.8 Hz, 1H), 8.68 (dd, J=9.2 Hz, 2.8 Hz, 1H), 8.42 (d, J=9.2 Hz, 1H), 7.73 (t, J=7.4 Hz, 1H), 7.63 (q, J=6.2 Hz, 5.8 Hz, 1H), 7.35 (q, J=8.3 Hz, 7.1 Hz, 2H).

Step 17-2: Preparation of N-(5-aminopyridin-2-yl)-2-fluorobenzamide 204 mg (yield: 68%) of the title compound was obtained in the same manner as in Step 1-2 of Example 1 above, except that 2-fluoro-N-(5-nitropyridin-2-yl)benzamide (340 mg, 1.30 mmol) obtained in Step 17-1 was used instead of 5-methyl-N-(5-nitropyridin-2-yl)pyrazine-2-carboxamide.

$^1$H NMR (400 MHz, DMSO-$d_6$) δ 10.42-10.03 (m, 1H), 7.85 (d, J=8.8 Hz, 1H), 7.73-7.63 (m, 2H), 7.58-7.52 (m, 1H), 7.35-7.26 (m, 2H), 7.02 (dd, J=8.7 Hz, 2.9 Hz, 1H), 5.18 (s, 2H).

Step 17-3: Preparation of (6-(2-fluorobenzamido) pyridin-3-yl)carbonohydrazonoyl dicyanide 161 mg (yield: 63%) of the title compound was obtained in the same manner as in Step 1-3 of Example 1 above, except that N-(5-aminopyridin-2-yl)-2-fluorobenzamide (190 mg, 0.82 mmol) obtained in Step 17-2 was used instead of N-(5-aminopyridin-2-yl)-5-methylpyrazine-2-carboxamide.

$^1$H NMR (400 MHz, DMSO-$d_6$) δ 10.93 (s, 1H), 8.49 (d, J=2.8 Hz, 1H), 8.25 (d, J=9.1 Hz, 1H), 7.93 (dd, J=9.0 Hz, 2.7 Hz, 1H), 7.70 (td, J=7.5 Hz, 1.8 Hz, 1H), 7.64-7.56 (m, 1H), 7.40-7.28 (m, 2H).

Example 18: Preparation of (6-(3-fluorobenzamido) pyridin-3-yl)carbonohydrazonoyl dicyanide (Compound 18)

Step 18-1: Preparation of 3-fluoro-N-(5-nitropyridin-2-yl)benzamide 288 mg (yield: 51%) of the title compound was obtained in the same manner as in Step 11-1 of Example 11 above, except that 3-fluorobenzoic acid (300 mg, 2.14 mmol) was used instead of 5-methylpyrazine-2-carboxylic acid, and 2-amino-5-nitropyridine (298 mg, 2.14 mmol) was used instead of 2-chloro-4-nitroaniline.

$^1$H NMR (400 MHz, DMSO-$d_6$) δ 11.64 (s, 1H), 9.25 (d, J=2.2 Hz, 0H), 8.68 (dd, J=9.3 Hz, 2.8 Hz, 1H), 8.43 (dd, J=9.3 Hz, 0.7 Hz, 1H), 7.94-7.85 (m, 2H), 7.60 (td, J=8.1 Hz, 5.9 Hz, 1H), 7.55-7.47 (m, 1H).

Step 18-2: Preparation of N-(5-aminopyridin-2-yl)-3-fluorobenzamide 188 mg (yield: 85%) of the title compound was obtained in the same manner as in Step 1-2 of Example 1 above, except that 3-fluoro-N-(5-nitropyridin-2-yl)benzamide (250 mg, 0.96 mmol) obtained in Step 18-1 was used instead of 5-methyl-N-(5-nitropyridin-2-yl)pyrazine-2-carboxamide.

$^1$H NMR (400 MHz, DMSO-$d_6$) δ 10.44 (s, 1H), 7.87-7.78 (m, 3H), 7.75 (dd, J=2.9 Hz, 0.7 Hz, 1H), 7.54 (td, J=8.0 Hz, 5.9 Hz, 1H), 7.43-7.37 (m, 2H), 5.20 (s, 2H).

Step 18-3: Preparation of (6-(3-fluorobenzamido) Pyridin-3-yl)carbonohydrazonoyl dicyanide 75 mg (yield: 38%) of the title compound was obtained in the same manner as in Step 1-3 of Example 1 above, except that N-(5-aminopyridin-2-yl)-3-fluorobenzamide (150 mg, 0.65 mmol) obtained in Step 18-2 was used instead of N-(5-aminopyridin-2-yl)-5-methylpyrazine-2-carboxamide.

$^1$H NMR (400 MHz, DMSO-$d_6$) δ 11.06 (s, 1H), 8.53 (d, J=2.8 Hz, 1H), 8.24 (d, J=9.0 Hz, 1H), 7.96-7.82 (m, 3H), 7.58 (td, J=8.0 Hz, 5.8 Hz, 1H), 7.49-7.42 (m, 1H).

Example 19: Preparation of (6-(3-fluoro-5-methylbenzamido)pyridin-3-yl)carbonohydrazonoyl dicyanide (Compound 19)

Step 19-1: Preparation of 3-fluoro-5-methyl-N-(5-nitropyridin-2-yl)benzamide 403 mg (yield: 75%) of the title compound was obtained in the same manner as in Step 11-1 of Example 11 above, except that 3-fluoro-5-methylbenzoic acid (300 mg, 1.95 mmol) was used instead of 5-methylpyrazine-2-carboxylic acid, and 2-amino-5-nitropyridine (271 mg, 1.95 mmol) was used instead of 2-chloro-4-nitroaniline.

$^1$H NMR (400 MHz, DMSO-$d_6$) δ 11.55 (s, 1H), 9.24 (d, J=2.8 Hz, 1H), 8.67 (dd, J=9.2 Hz, 2.9 Hz, 1H), 8.42 (d, J=9.3 Hz, 1H), 7.75 (s, 1H), 7.66 (dt, J=9.6 Hz, 2.0 Hz, 1H), 7.36-7.31 (m, 1H), 2.41 (s, 3H).

Step 19-2: Preparation of N-(5-aminopyridin-2-yl)-3-fluoro-5-methylbenzamide 182 mg (yield: 54%) of the title compound was obtained in the same manner as in Step 1-2 of Example 1 above, except that 3-fluoro-5-methyl-N-(5-nitropyridin-2-yl)benzamide (380 mg, 1.38 mmol) obtained in Step 19-1 was used instead of 5-methyl-N-(5-nitropyridin-2-yl)pyrazine-2-carboxamide.

$^1$H NMR (400 MHz, DMSO-$d_6$) δ 10.35 (s, 1H), 7.79 (d, J=8.8 Hz, 1H), 7.74 (d, J=2.8 Hz, 1H), 7.69 (s, 1H), 7.59 (d, J=9.8 Hz, 1H), 7.24 (d, J=9.6 Hz, 1H), 7.02 (dd, J=8.8 Hz, 2.8 Hz, 1H), 5.19 (s, 2H), 2.38 (s, 3H).

Step 19-3: Preparation of (6-(3-fluoro-5-methylbenzamido)pyridin-3-yl)carbonohydrazonoyl dicyanide 114 mg (yield: 58%) of the title compound was obtained in the same manner as in Step 1-3 of Example 1 above, except that N-(5-aminopyridin-2-yl)-3-fluoro-5-methylbenzamide (150 mg, 0.61 mmol) obtained in Step 19-2 was used instead of N-(5-aminopyridin-2-yl)-5-methylpyrazine-2-carboxamide.

$^1$H NMR (400 MHz, DMSO-$d_6$) δ 10.97 (s, 1H), 8.52 (d, J=2.8 Hz, 1H), 8.23 (d, J=9.0 Hz, 1H), 7.92 (dd, J=9.1 Hz, 2.8 Hz, 1H), 7.73 (s, 1H), 7.63 (dt, J=9.7 Hz, 2.1 Hz, 1H), 7.37-7.23 (m, 1H), 2.40 (s, 3H).

Example 20: Preparation of (6-(2-fluoro-3-methylbenzamido)pyridin-3-yl)carbonohydrazonoyl dicyanide (Compound 20)

Step 20-1: Preparation of 2-fluoro-3-methyl-N-(5-nitropyridin-2-yl)benzamide 396 mg (yield: 74%) of the title compound was obtained in the same manner as in Step 11-1 of Example 11 above, except that 2-fluoro-3-methylbenzoic acid (300 mg, 1.95 mmol) was used instead of 5-methylpyrazine-2-carboxylic acid, and 2-amino-5-nitropyridine (271 mg, 1.95 mmol) was used instead of 2-chloro-4-nitroaniline.

$^1$H NMR (400 MHz, DMSO-$d_6$) δ 11.55 (s, 1H), 9.21 (d, J=2.8 Hz, 1H), 8.68 (dd, J=9.2 Hz, 2.8 Hz, 1H), 8.42 (d,

J=9.2 Hz, 1H), 7.51 (qd, J=7.4 Hz, 3.7 Hz, 2H), 7.22 (t, J=7.6 Hz, 1H), 2.30 (d, J=2.1 Hz, 3H).

Step 20-2: Preparation of N-(5-aminopyridin-2-yl)-2-fluoro-3-methylbenzamide 268 mg (yield: 79%) of the title compound was obtained in the same manner as in Step 1-2 of Example 1 above, except that 2-fluoro-3-methyl-N-(5-nitropyridin-2-yl)benzamide (380 mg, 1.38 mmol) obtained in Step 20-1 was used instead of 5-methyl-N-(5-nitropyridin-2-yl)pyrazine-2-carboxamide.

$^1$H NMR (400 MHz, DMSO-$d_6$) δ 10.19 (d, J=2.3 Hz, 1H), 7.84 (d, J=8.8 Hz, 1H), 7.71 (d, J=2.8 Hz, 1H), 7.55-7.37 (m, 2H), 7.17 (t, J=7.6 Hz, 1H), 7.01 (dd, J=8.7 Hz, 2.9 Hz, 1H), 5.17 (s, 2H), 2.28 (d, J=2.1 Hz, 3H).

Step 20-3: Preparation of (6-(2-fluoro-3-methylbenzamido)pyridin-3-yl)carbonohydrazonoyl dicyanide 292 mg (yield: 89%) of the title compound was obtained in the same manner as in Step 1-3 of Example 1 above, except that N-(5-aminopyridin-2-yl)-2-fluoro-3-methylbenzamide (250 mg, 1.02 mmol) obtained in Step 20-2 was used instead of N-(5-aminopyridin-2-yl)-5-methylpyrazine-2-carboxamide.

$^1$H NMR (400 MHz, DMSO-$d_6$) δ 10.89 (s, 1H), 8.48 (d, J=2.7 Hz, 1H), 8.24 (d, J=9.1 Hz, 1H), 7.92 (dd, J=9.1 Hz, 2.8 Hz, 1H), 7.56-7.42 (m, 2H), 7.20 (t, J=7.6 Hz, 1H), 2.29 (d, J=2.1 Hz, 3H).

Example 21: Preparation of (6-(4-fluoro-3-methylbenzamido)pyridin-3-yl)carbonohydrazonoyl dicyanide (Compound 21)

Step 21-1: Preparation of 4-fluoro-3-methyl-N-(5-nitropyridin-2-yl)benzamide 349 mg (yield: 65%) of the title compound was obtained in the same manner as in Step 11-1 of Example 11 above, except that 4-fluoro-3-methylbenzoic acid (300 mg, 1.95 mmol) was used instead of 5-methylpyrazine-2-carboxylic acid, and 2-amino-5-nitropyridine (271 mg, 1.95 mmol) was used instead of 2-chloro-4-nitroaniline.

$^1$H NMR (400 MHz, DMSO-$d_6$) δ 11.50 (s, 1H), 9.30-9.15 (m, 1H), 8.66 (dd, J=9.3 Hz, 2.8 Hz, 1H), 8.42 (dd, J=9.3 Hz, 0.7 Hz, 1H), 8.05 (dd, J=7.4 Hz, 1.5 Hz, 1H), 7.94 (ddd, J=8.0 Hz, 5.0 Hz, 2.5 Hz, 1H), 7.30 (dd, J=9.6 Hz, 8.6 Hz, 1H), 2.31 (d, J=2.0 Hz, 3H).

Step 21-2: Preparation of N-(5-aminopyridin-2-yl)-4-fluoro-3-methylbenzamide 235 mg (yield: 85%) of the title compound was obtained in the same manner as in Step 1-2 of Example 1 above, except that 4-fluoro-3-methyl-N-(5-nitropyridin-2-yl)benzamide (310 mg, 1.13 mmol) obtained in Step 21-1 was used instead of 5-methyl-N-(5-nitropyridin-2-yl)pyrazine-2-carboxamide.

$^1$H NMR (400 MHz, DMSO-$d_6$) δ 10.28 (s, 1H), 7.98 (dd, J=7.3 Hz, 1.8 Hz, 1H), 7.87 (ddd, J=7.9 Hz, 5.1 Hz, 2.4 Hz, 1H), 7.81-7.77 (m, 1H), 7.74 (dd, J=2.8 Hz, 0.7 Hz, 1H), 7.23 (dd, J=9.7 Hz, 8.5 Hz, 1H), 7.02 (dd, J=8.7 Hz, 2.9 Hz, 1H), 5.17 (s, 2H), 2.29 (d, J=2.0 Hz, 3H).

Step 21-3: Preparation of (6-(4-fluoro-3-methylbenzamido)pyridin-3-yl)carbonohydrazonoyl dicyanide 145 mg (yield: 55%) of the title compound was obtained in the same manner as in Step 1-3 of Example 1 above, except that N-(5-aminopyridin-2-yl)-4-fluoro-3-methylbenzamide (200 mg, 0.81 mmol) obtained in Step 21-2 was used instead of N-(5-aminopyridin-2-yl)-5-methylpyrazine-2-carboxamide.

$^1$H NMR (400 MHz, DMSO-$d_6$) δ 10.91 (s, 1H), 8.51 (d, J=2.7 Hz, 1H), 8.22 (d, J=9.0 Hz, 1H), 8.01 (dd, J=7.6 Hz, 2.4 Hz, 1H), 7.92 (dd, J=8.9 Hz, 2.8 Hz, 2H), 7.27 (t, J=9.1 Hz, 1H), 2.31 (d, J=1.9 Hz, 3H).

Example 22: Preparation of (6-(3-fluoro-4-methylbenzamido)pyridin-3-yl)carbonohydrazonoyl dicyanide (Compound 22)

Step 22-1: Preparation of 3-fluoro-4-methyl-N—(S-nitropyridin-2-yl)benzamide 380 mg (yield: 71%) of the title compound was obtained in the same manner as in Step 11-1 of Example 11 above, except that 3-fluoro-4-methylbenzoic acid (300 mg, 1.95 mmol) was used instead of 5-methylpyrazine-2-carboxylic acid, and 2-amino-5-nitropyridine (271 mg, 1.95 mmol) was used instead of 2-chloro-4-nitroaniline.

$^1$H NMR (400 MHz, DMSO-$d_6$) δ 11.55 (s, 1H), 9.24 (dd, J=2.9 Hz, 0.7 Hz, 1H), 8.66 (dd, J=9.3 Hz, 2.9 Hz, 1H), 8.42 (dd, J=9.2 Hz, 0.7 Hz, 1H), 8.04-7.72 (m, 2H), 7.51-7.35 (m, 1H), 2.32 (d, J=1.9 Hz, 3H).

Step 22-2: Preparation of N-(5-aminopyridin-2-yl)-3-fluoro-4-methylbenzamide 259 mg (yield: 83%) of the title compound was obtained in the same manner as in Step 1-2 of Example 1 above, except that 3-fluoro-4-methyl-N-(5-nitropyridin-2-yl)benzamide (350 mg, 1.27 mmol) obtained in Step 22-1 was used instead of 5-methyl-N-(5-nitropyridin-2-yl)pyrazine-2-carboxamide.

$^1$H NMR (400 MHz, DMSO-$d_6$) δ 10.35 (s, 1H), 7.85-7.72 (m, 4H), 7.40 (t, J=7.8 Hz, 1H), 7.02 (dd, J=8.7 Hz, 2.9 Hz, 1H), 5.18 (s, 2H), 2.30 (d, J=2.1 Hz, 3H).

Step 22-3: Preparation of (6-(3-fluoro-4-methylbenzamido)pyridin-3-yl)carbonohydrazonoyl dicyanide 18 mg (yield: 6%) of the title compound was obtained in the same manner as in Step 1-3 of Example 1 above, except that N-(5-aminopyridin-2-yl)-3-fluoro-4-methylbenzamide (240 mg, 0.98 mmol) obtained in Step 22-2 was used instead of N-(5-aminopyridin-2-yl)-5-methylpyrazine-2-carboxamide.

$^1$H NMR (400 MHz, DMSO-$d_6$) δ 10.97 (s, 1H), 8.51 (d, J=2.7 Hz, 1H), 8.23 (d, J=9.1 Hz, 1H), 7.92 (dd, J=9.1 Hz, 2.8 Hz, 1H), 7.85-7.77 (m, 2H), 7.44 (t, J=7.8 Hz, 1H), 2.31 (d, J=1.9 Hz, 3H).

Example 23: Preparation of (6-(4-methylbenzamido)pyridin-3-yl)carbonohydrazonoyl dicyanide (Compound 23)

Step 23-1: Preparation of 4-methyl-N-(5-nitropyridin-2-yl)benzamide 412 mg (yield: 73%) of the title compound was obtained in the same manner as in Step 11-1 of Example 11 above, except that p-toluic acid (300 mg, 2.20 mmol) was used instead of 5-methylpyrazine-2-carboxylic acid, and 2-amino-5-nitropyridine (306 mg, 2.20 mmol) was used instead of 2-chloro-4-nitroaniline.

$^1$H NMR (400 MHz, DMSO-$d_6$) δ 11.45 (s, 1H), 9.23 (d, J=2.8 Hz, 1H), 8.65 (dd, J=9.3 Hz, 2.8 Hz, 1H), 8.44 (d, J=9.3 Hz, 1H), 7.97 (d, J=8.1 Hz, 2H), 7.34 (d, J=8.0 Hz, 2H), 2.40 (s, 3H).

Step 23-2: Preparation of N-(5-aminopyridin-2-yl)-4-methylbenzamide 265 mg (yield: 75%) of the title compound was obtained in the same manner as in Step 1-2 of Example 1 above, except that 4-methyl-N-(5-nitropyridin-2-yl)benzamide (400 mg, 1.55 mmol) obtained in Step 23-1 was used instead of 5-methyl-N-(5-nitropyridin-2-yl)pyrazine-2-carboxamide.

$^1$H NMR (400 MHz, DMSO-$d_6$) δ 10.21 (s, 1H), 7.90 (d, J=8.1 Hz, 2H), 7.80 (d, J=8.7 Hz, 1H), 7.74 (d, J=2.8 Hz, 1H), 7.28 (d, J=8.0 Hz, 2H), 7.01 (dd, J=8.7 Hz, 2.9 Hz, 1H), 5.15 (s, 2H), 2.37 (s, 3H).

Step 23-3: Preparation of (6-(4-methylbenzamido) pyridin-3-yl)carbonohydrazonoyl dicyanide 269 mg (yield: 80%) of the title compound was obtained in the same manner as in Step 1-3 of Example 1 above, except that N-(5-aminopyridin-2-yl)-4-methylbenzamide (250 mg, 1.10 mmol) obtained in Step 23-2 was used instead of N-(5-aminopyridin-2-yl)-5-methylpyrazine-2-carboxamide.

$^1$H NMR (400 MHz, DMSO-$d_6$) δ 10.87 (s, 1H), 8.50 (d, J=2.7 Hz, 1H), 8.23 (d, J=9.1 Hz, 1H), 7.98-7.89 (m, 3H), 7.32 (d, J=8.0 Hz, 2H), 2.38 (s, 3H).

Example 24: Preparation of (6-(3-methylbenzamido)pyridin-3-yl)carbonohydrazonoyl dicyanide (Compound 24)

Step 24-1: Preparation of 3-methyl-N-(5-nitropyridin-2-yl)benzamide 432 mg (yield: 76%) of the title compound was obtained in the same manner as in Step 11-1 of Example 11 above, except that m-toluic acid (300 mg, 2.20 mmol) was used instead of 5-methylpyrazine-2-carboxylic acid, and 2-amino-5-nitropyridine (306 mg, 2.20 mmol) was used instead of 2-chloro-4-nitroaniline.

$^1$H NMR (400 MHz, DMSO-$d_6$) δ 11.46 (s, 1H), 9.23 (d, J=2.8 Hz, 1H), 8.66 (dd, J=9.3 Hz, 2.8 Hz, 1H), 8.44 (d, J=9.3 Hz, 1H), 7.97-7.78 (m, 2H), 7.52-7.37 (m, 2H), 2.40 (s, 3H).

Step 24-2: Preparation of N-(5-aminopyridin-2-yl)-3-methylbenzamide 308 mg (yield: 87%) of the title compound was obtained in the same manner as in Step 1-2 of Example 1 above, except that 3-methyl-N-(5-nitropyridin-2-yl)benzamide (400 mg, 1.55 mmol) obtained in Step 24-1 was used instead of 5-methyl-N-(5-nitropyridin-2-yl)pyrazine-2-carboxamide.

$^1$H NMR (400 MHz, DMSO-$d_6$) δ 10.22 (s, 1H), 7.84-7.73 (m, 3H), 7.36 (d, J=5.2 Hz, 1H), 7.02 (dd, J=8.7 Hz, 2.9 Hz, 1H), 5.16 (s, 2H), 2.37 (s, 3H).

Step 24-3: Preparation of (6-(3-methylbenzamido) pyridin-3-yl)carbonohydrazonoyl dicyanide 370 mg (yield: 99%) of the title compound was obtained in the same manner as in Step 1-3 of Example 1 above, except that N-(5-aminopyridin-2-yl)-3-methylbenzamide (280 mg, 1.23 mmol) obtained in Step 24-2 was used instead of N-(5-aminopyridin-2-yl)-5-methylpyrazine-2-carboxamide.

$^1$H NMR (400 MHz, DMSO-$d_6$) δ 10.88 (s, 1H), 8.51 (d, J=2.7 Hz, 1H), 8.24 (d, J=9.1 Hz, 1H), 7.92 (dd, J=9.1 Hz, 2.8 Hz, 1H), 7.86 (s, 1H), 7.83-7.80 (m, 1H), 7.40 (d, J=6.2 Hz, 2H), 2.39 (s, 3H).

Example 26: Preparation of (6-(2-methylbenzamido)pyridin-3-yl)carbonohydrazonoyl dicyanide (Compound 25)

Step 25-1: Preparation of 2-methyl-N-(5-nitropyridin-2-yl)benzamide 396 mg (yield: 70%) of the title compound was obtained in the same manner as in Step 11-1 of Example 11 above, except that o-toluic acid (300 mg, 2.20 mmol) was used instead of 5-methylpyrazine-2-carboxylic acid, and 2-amino-5-nitropyridine (306 mg, 2.20 mmol) was used instead of 2-chloro-4-nitroaniline.

$^1$H NMR (400 MHz, DMSO-$d_6$) δ 11.53 (s, 1H), 9.20 (d, J=2.7 Hz, 1H), 8.66 (dd, J=9.2 Hz, 2.9 Hz, 1H), 8.44 (d, J=9.3 Hz, 1H), 7.56-7.51 (m, 1H), 7.42 (td, J=7.5 Hz, 1.4 Hz, 1H), 7.34-7.27 (m, 2H), 2.40 (s, 3H).

Step 25-2: Preparation of N-(5-aminopyridin-2-yl)-2-methylbenzamide 260 mg (yield: 79%) of the title compound was obtained in the same manner as in Step 1-2 of Example 1 above, except that 2-methyl-N-(5-nitropyridin-2-yl)benzamide (370 mg, 1.44 mmol) obtained in Step 25-1 was used instead of 5-methyl-N-(5-nitropyridin-2-yl)pyrazine-2-carboxamide.

$^1$H NMR (400 MHz, DMSO-$d_6$) δ 10.21 (s, 1H), 7.82 (d, J=8.7 Hz, 1H), 7.70 (d, J=2.8 Hz, 1H), 7.44-7.39 (m, 1H), 7.34 (td, J=7.4 Hz, 1.5 Hz, 1H), 7.28-7.21 (m, 2H), 7.01 (dd, J=8.7 Hz, 2.9 Hz, 1H), 5.13 (s, 2H), 2.37 (s, 3H).

Step 25-3: Preparation of (6-(2-methylbenzamido) pyridin-3-yl)carbonohydrazonoyl dicyanide 226 mg (yield: 68%) of the title compound was obtained in the same manner as in Step 1-3 of Example 1 above, except that N-(5-aminopyridin-2-yl)-2-methylbenzamide (250 mg, 1.10 mmol) obtained in Step 25-2 was used instead of N-(5-aminopyridin-2-yl)-5-methylpyrazine-2-carboxamide.

$^1$H NMR (400 MHz, DMSO-$d_6$) δ 10.93 (s, 1H), 8.47 (d, J=2.7 Hz, 1H), 8.24 (d, J=9.1 Hz, 1H), 7.92 (dd, J=9.1 Hz, 2.8 Hz, 1H), 7.50-7.46 (m, 1H), 7.39 (td, J=7.5 Hz, 1.4 Hz, 1H), 7.33-7.25 (m, 2H), 2.39 (s, 3H).

Example 26: Preparation of (6-(3-(trifluoromethyl) benzamido)pyridin-3-yl)carbonohydrazonoyl dicyanide (Compound 26)

Step 26-1: Preparation of N-(5-nitropyridin-2-yl)-3-(trifluoromethyl)benzamide

The title compound was obtained in the same manner as in Step 11-1 of Example 11 above, except that 3-(trifluoromethyl)benzoic acid (300 mg, 1.58 mmol) was used instead of 5-methylpyrazine-2-carboxylic acid, and 2-amino-5-nitropyridine (219 mg, 1.58 mmol) was used instead of 2-chloro-4-nitroaniline, and the solvent was removed therefrom to use the title compound in the next step without additional purification.

Step 26-2: Preparation of N-(6-aminopyridin-2-yl)-3-(trifluoromethyl)benzamide 134 mg (yield: 65%) of the title compound was obtained in the same manner as in Step 1-2 of Example 1 above, except that N-(5-nitropyridin-2-yl)-3-(trifluoromethyl)benzamide (230 mg, 0.74 mmol) obtained in Step 26-1 was used instead of 5-methyl-N-(5-nitropyridin-2-yl)pyrazine-2-carboxamide.

$^1$H NMR (400 MHz, DMSO-$d_6$) δ 10.69 (s, 1H), 8.34 (s, 1H), 8.28 (d, J=7.8 Hz, 1H), 7.93 (d, J=7.8 Hz, 1H), 7.83 (d, J=8.7 Hz, 1H), 7.78-7.70 (m, 2H), 7.04 (dd, J=8.7 Hz, 2.9 Hz, 1H), 5.22 (s, 2H).

Step 26-3: Preparation of (6-(3-(trifluoromethyl)benzamido)pyridin-3-yl)carbonohydrazonoyl dicyanide 133 mg (yield: 87%) of the title compound was obtained in the same manner as in Step 1-3 of Example 1 above, except that N-(5-aminopyridin-2-yl)-3-(trifluoromethyl)benzamide (120 mg, 0.43 mmol) obtained in Step 26-2 was used instead of N-(5-aminopyridin-2-yl)-5-methylpyrazine-2-carboxamide.

$^1$H NMR (400 MHz, DMSO-$d_6$) δ 11.28 (s, 1H), 8.53 (d, J=2.7 Hz, 1H), 8.38 (s, 1H), 8.31 (d, J=7.8 Hz, 1H), 8.26 (d, J=9.1 Hz, 1H), 8.01-7.91 (m, 2H), 7.77 (t, J=7.8 Hz, 1H).

Example 27: Preparation of (6-(4-(trifluoromethyl)benzamido)pyridin-3-yl)carbonohydrazonoyl dicyanide (Compound 27)

Step 27-1: Preparation of N-(5-nitropyridin-2-yl)-4-(trifluoromethyl)benzamide

The title compound was obtained in the same manner as in Step 11-1 of Example 11 above, except that 4-(trifluoromethyl)benzoic acid (300 mg, 1.58 mmol) was used instead of 5-methylpyrazine-2-carboxylic acid, and 2-amino-5-nitropyridine (219 mg, 1.58 mmol) was used instead of 2-chloro-4-nitroaniline, and the solvent was removed therefrom to use the title compound in the next step without additional purification.

Step 27-2: Preparation of N-(5-aminopyridin-2-yl)-4-(trifluoromethyl)benzamide 130 mg (yield: 58%) of the title compound was obtained in the same manner as in Step 1-2 of Example 1 above, except that N-(5-nitropyridin-2-yl)-4-(trifluoromethyl)benzamide (250 mg, 0.80 mmol) obtained in Step 27-1 was used instead of 5-methyl-N-(5-nitropyridin-2-yl)pyrazine-2-carboxamide.

$^1$H NMR (400 MHz, DMSO-$d_6$) δ 10.62 (s, 1H), 8.16 (d, J=8.1 Hz, 2H), 7.84 (dd, J=14.0 Hz, 8.4 Hz, 3H), 7.76 (d, J=2.8 Hz, 1H), 7.03 (dd, J=8.7 Hz, 2.9 Hz, 1H), 5.22 (s, 2H).

Step 27-3: Preparation of (6-(4-(trifluoromethyl)benzamido)pyridin-3-yl)carbonohydrazonoyl dicyanide 138 mg (yield: 98%) of the title compound was obtained in the same manner as in Step 1-3 of Example 1 above, except that N-(5-aminopyridin-2-yl)-4-(trifluoromethyl)benzamide (110 mg, 0.39 mmol) obtained in Step 27-2 was used instead of N-(5-aminopyridin-2-yl)-5-methylpyrazine-2-carboxamide.

$^1$H NMR (400 MHz, DMSO-$d_6$) δ 11.22 (s, 1H), 8.53 (d, J=2.8 Hz, 1H), 8.26 (d, J=9.1 Hz, 1H), 8.20 (d, J=8.1 Hz, 2H), 7.94 (dd, J=9.0 Hz, 2.8 Hz, 1H), 7.89 (d, J=8.1 Hz, 2H).

Example 28: Preparation of (6-(2-(trifluoromethyl)benzamido)pyridin-3-yl)carbonohydrazonoyl dicyanide (Compound 28)

Step 28-1: Preparation of N-(5-nitropyridin-2-yl)-2-(trifluoromethyl)benzamide 138 mg (yield: 28%) of the title compound was obtained in the same manner as in Step 11-1 of Example 11 above, except that 2-(trifluoromethyl)benzoic acid (300 mg, 1.58 mmol) was used instead of 5-methylpyrazine-2-carboxylic acid, and 2-amino-5-nitropyridine (219 mg, 1.58 mmol) was used instead of 2-chloro-4-nitroaniline.

$^1$H NMR (400 MHz, DMSO-$d_6$) δ 11.87 (s, 1H), 9.21 (d, J=2.8 Hz, 1H), 8.68 (dd, J=9.2 Hz, 2.9 Hz, 1H), 8.39 (d, J=9.2 Hz, 1H), 7.86 (d, J=7.8 Hz, 1H), 7.82-7.71 (m, 3H).

Step 28-2: Preparation of N-(6-aminopyridin-2-yl)-2-(trifluoromethyl)benzamide 84 mg (yield: 78%) of the title compound was obtained in the same manner as in Step 1-2 of Example 1 above, except that N-(5-nitropyridin-2-yl)-2-(trifluoromethyl)benzamide (120 mg, 0.39 mmol) obtained in Step 28-1 was used instead of 5-methyl-N-(5-nitropyridin-2-yl)pyrazine-2-carboxamide.

$^1$H NMR (400 MHz, DMSO-$d_6$) δ 10.56 (s, 1H), 7.79 (d, J=8.7 Hz, 2H), 7.76-7.59 (m, 4H), 7.02 (dd, J=8.8 Hz, 2.9 Hz, 1H), 5.17 (s, 2H).

Step 28-3: Preparation of (6-(4-(trifluoromethyl)benzamido)pyridin-3-yl)carbonohydrazonoyl dicyanide 58 mg (yield: 61%) of the title compound was obtained in the same manner as in Step 1-3 of Example 1 above, except that N-(5-aminopyridin-2-yl)-2-(trifluoromethyl)benzamide (75 mg, 0.27 mmol) obtained in Step 28-2 was used instead of N-(5-aminopyridin-2-yl)-5-methylpyrazine-2-carboxamide.

$^1$H NMR (400 MHz, DMSO-$d_6$) δ 11.24 (s, 1H), 8.48 (d, J=2.8 Hz, 1H), 8.21 (d, J=9.1 Hz, 1H), 7.93 (dd, J=9.1 Hz, 2.8 Hz, 1H), 7.83 (d, J=7.7 Hz, 1H), 7.80-7.67 (m, 3H).

Example 29: Preparation of (6-(pyrimidine-2-carboxamido)pyridin-3-yl)carbonohydrazonoyl dicyanide (Compound 29)

Step 29-1: Preparation of N-(5-nitropyridin-2-yl)pyrimidine-2-carboxamide 180 mg (yield: 30%) of the title compound was obtained in the same manner as in Step 11-1 of Example 11 above, except that pyrimidine-2-carboxylic acid (300 mg, 2.42 mmol) was used instead of 5-methylpyrazine-2-carboxylic acid, and 2-amino-5-nitropyridine (336 mg, 2.42 mmol) was used instead of 2-chloro-4-nitroaniline.

$^1$H NMR (400 MHz, DMSO-$d_6$) δ 11.12 (s, 1H), 9.25 (d, J=2.8 Hz, 1H), 9.09 (d, J=4.9 Hz, 2H), 8.74 (dd, J=9.2 Hz, 2.8 Hz, 1H), 8.48 (d, J=9.2 Hz, 1H), 7.82 (t, J=4.9 Hz, 1H).

Step 29-2: Preparation of N-(5-aminopyridin-2-yl)pyrimidine-2-carboxamide 52 mg (yield: 40%) of the title compound was obtained in the same manner as in Step 1-2 of Example 1 above, except that N-(5-nitropyridin-2-yl)pyrimidine-2-carboxamide (150 mg, 0.61 mmol) obtained in Step 29-1 was used instead of 5-methyl-N-(5-nitropyridin-2-yl)pyrazine-2-carboxamide.

$^1$H NMR (400 MHz, DMSO-$d_6$) δ 10.19 (s, 1H), 9.03 (d, J=4.9 Hz, 2H), 7.96 (d, J=8.7 Hz, 1H), 7.83-7.67 (m, 2H), 7.07 (dd, J=8.8 Hz, 2.9 Hz, 1H), 5.27 (s, 2H).

Step 29-3: Preparation of (6-(pyrimidine-2-carboxamido)pyridin-3-yl)carbonohydrazonoyl dicyanide 36 mg (yield: 67%) of the title compound was obtained in the same manner as in Step 1-3 of Example 1 above, except that N-(5-aminopyridin-2-yl)pyrimidine-2-carboxamide (40 mg, 0.19 mmol) obtained in Step 29-2 was used instead of N-(5-aminopyridin-2-yl)-5-methylpyrazine-2-carboxamide.

$^1$H NMR (400 MHz, DMSO-$d_6$) δ 10.65 (s, 1H), 9.06 (d, J=4.9 Hz, 2H), 8.50 (d, J=2.7 Hz, 1H), 8.31 (d, J=9.0 Hz, 1H), 7.96 (dd, J=9.0 Hz, 2.7 Hz, 1H), 7.78 (t, J=4.9 Hz, 1H).

Example 30: Preparation of (6-(thiophene-2-carboxamido)pyridin-3-yl)carbonohydrazonoyl dicyanide (Compound 30)

Step 30-1: Preparation of N-(5-nitropyridin-2-yl)thiophene-2-carboxamide 459 mg (yield: 79%) of the title compound was obtained in the same manner as in Step 11-1 of Example 11 above, except that thiophene-2-carboxylic acid (300 mg, 2.34 mmol) was used instead of 5-methylpyrazine-2-carboxylic acid, and 2-amino-5-nitropyridine (326 mg, 2.34 mmol) was used instead of 2-chloro-4-nitroaniline.

$^1$H NMR (400 MHz, DMSO-$d_6$) δ 11.63 (s, 1H), 9.24 (d, J=2.8 Hz, 1H), 8.65 (dd, J=9.3 Hz, 2.8 Hz, 1H), 8.39 (d, J=9.3 Hz, 1H), 8.33 (dd, J=3.8 Hz, 1.1 Hz, 1H), 7.98 (dd, J=5.0 Hz, 1.1 Hz, 1H), 7.25 (dd, J=5.0 Hz, 3.8 Hz, 1H).

Step 30-2: Preparation of N-(5-aminopyridin-2-yl)thiophene-2-carboxamide 244 mg (yield: 64%) of the title compound was obtained in the same manner as in Step 1-2 of Example 1 above, except that N-(5-nitropyridin-2-yl)thiophene-2-carboxamide (430 mg, 172 mmol) obtained in Step 30-1 was used instead of 5-methyl-N-(5-nitropyridin-2-yl)pyrazine-2-carboxamide.

$^1$H NMR (400 MHz, DMSO-$d_6$) δ 10.45 (s, 1H), 8.13 (dd, J=3.8 Hz, 1.1 Hz, 1H), 7.81 (dd, J=5.0 Hz, 1.1 Hz, 1H), 7.78-7.69 (m, 2H), 7.17 (dd, J=5.0 Hz, 3.8 Hz, 1H), 7.01 (dd, J=8.7 Hz, 3.0 Hz, 1H), 5.18 (s, 2H).

Step 30-3: Preparation of (6-(thiophene-2-carboxamido)pyridin-3-yl)carbonohydrazonoyl dicyanide 130 mg (yield: 96%) of the title compound was obtained in the same manner as in Step 1-3 of Example 1 above, except that N-(5-aminopyridin-2-yl)thiophene-2-carboxamide (100 mg, 0.46 mmol) obtained in Step 30-2 was used instead of N-(5-aminopyridin-2-yl)-5-methylpyrazine-2-carboxamide.

$^1$H NMR (400 MHz, DMSO-$d_6$) δ 11.05 (s, 1H), 8.52 (d, J=2.7 Hz, 1H), 8.24 (d, J=3.8 Hz, 1H), 8.19 (d, J=9.1 Hz, 1H), 7.96-7.86 (m, 2H), 7.22 (dd, J=5.0 Hz, 3.7 Hz, 1H).

Example 31: Preparation of (6-(benzo[d]thiazole-2-carboxamido)pyridin-3-yl)carbonohydrazonoyl dicyanide (Compound 31)

Step 31-1: Preparation of N-(6-nitropyridin-2-yl)benzo[d]thiazole-2-carboxamide 112 mg (yield: 22%) of the title compound was obtained in the same manner as in Step 11-1 of Example 11 above, except that benzo[d]thiazole-2-carboxylic acid (300 mg, 1.67 mmol) was used instead of 5-methylpyrazine-2-carboxylic acid, and 2-amino-5-nitropyridine (233 mg, 1.67 mmol) was used instead of 2-chloro-4-nitroaniline.

$^1$H NMR (400 MHz, DMSO-$d_6$) δ 11.19 (s, 1H), 9.27 (d, J=2.8 Hz, 1H), 8.74 (dd, J=9.2 Hz, 2.8 Hz, 1H), 8.37 (d, J=9.2 Hz, 1H), 8.33-8.24 (m, 2H), 7.80-7.58 (m, 2H).

Step 31-2: Preparation of N-(5-aminopyridin-2-yl)benzo[d]thiazole-2-carboxamide 55 mg (yield: 61%) of the title compound was obtained in the same manner as in Step 1-2 of Example 1 above, except that N-(5-nitropyridin-2-yl)benzo[d]thiazole-2-carboxamide (100 mg, 0.33 mmol) obtained in Step 31-1 was used instead of 5-methyl-N-(5-nitropyridin-2-yl)pyrazine-2-carboxamide.

$^1$H NMR (400 MHz, DMSO-$d_6$) δ 10.05 (s, 1H), 8.32-8.16 (m, 2H), 7.85-7.77 (m, 2H), 7.72-7.58 (m, 2H), 7.07 (dd, J=8.7 Hz, 2.9 Hz, 1H), 5.34 (s, 2H).

Step 31-3: Preparation of (6-(benzo[d]thiazole-2-carboxamido)pyridin-3-yl)carbonohydrazonoyl dicyanide 34 mg (yield: 66%) of the title compound was obtained in the same manner as in Step 1-3 of Example 1 above, except that N-(5-aminopyridin-2-yl)benzo[d]thiazole-2-carboxamide (40 mg, 0.15 mmol) obtained in Step 31-2 was used instead of N-(5-aminopyridin-2-yl)-5-methylpyrazine-2-carboxamide.

$^1$H NMR (400 MHz, DMSO-$d_6$) δ 10.61 (s, 1H), 8.53 (d, J=2.7 Hz, 1H), 8.37-8.15 (m, 3H), 7.96 (dd, J=9.1 Hz, 2.7 Hz, 1H), 7.66 (dt, J=20.0 Hz, 7.3 Hz, 2H).

Example 32: Preparation of (6-(quinoxaline-2-carboxamido)pyridin-3-yl)carbonohydrazonoyl dicyanide (Compound 32)

Step 32-1: Preparation of N-(5-nitropyridin-2-yl)quinoxaline-2-carboxamide 183 mg (yield: 36%) of the title compound was obtained in the same manner as in Step 11-1 of Example 11 above, except that quinoxaline-2-carboxylic acid (300 mg, 1.72 mmol) was used instead of 5-methylpyrazine-2-carboxylic acid, and 2-amino-5-nitropyridine (240 mg, 1.72 mmol) was used instead of 2-chloro-4-nitroaniline.

$^1$H NMR (400 MHz, DMSO-$d_6$) δ 11.13 (s, 1H), 9.61 (s, 1H), 9.29 (d, J=2.8 Hz, 1H), 8.77 (dd, J=9.2 Hz, 2.8 Hz, 1H), 8.52 (d, J=9.2 Hz, 1H), 8.41-8.33 (m, 1H), 8.30-8.19 (m, 1H), 8.09-8.03 (m, 2H).

Step 32-2: Preparation of N-(5-aminopyridin-2-yl)quinoxaline-2-carboxamide 37 mg (yield: 24%) of the title compound was obtained in the same manner as in Step 1-2 of Example 1 above, except that N-(5-nitropyridin-2-yl)quinoxaline-2-carboxamide (170 mg, 0.58 mmol) obtained in Step 32-1 was used instead of 5-methyl-N-(5-nitropyridin-2-yl)pyrazine-2-carboxamide.

$^1$H NMR (400 MHz, DMSO-$d_6$) δ 10.20 (s, 1H), 9.58 (s, 1H), 8.36-8.29 (m, 1H), 8.27-8.19 (m, 1H), 8.09-7.95 (m, 3H), 7.79 (d, J=2.8 Hz, 1H), 7.10 (dd, J=8.7 Hz, 2.8 Hz, 1H), 5.31 (s, 2H).

Step 32-3: Preparation of (6-(quinoxaline-2-carboxamido)pyridin-3-yl)carbonohydrazonoyl dicyanide 34 mg (yield: 88%) of the title compound was obtained in the same manner as in Step 1-3 of Example 1 above, except that N-(5-aminopyridin-2-yl)quinoxaline-2-carboxamide (30 mg, 0.11 mmol) obtained in Step 32-2 was used instead of N-(5-aminopyridin-2-yl)-5-methylpyrazine-2-carboxamide.

$^1$H NMR (400 MHz, DMSO-$d_6$) δ 10.57 (s, 1H), 9.56 (s, 1H), 8.51 (s, 1H), 8.31 (t, J=8.0 Hz, 2H), 8.25-8.17 (m, 1H), 8.06-8.00 (m, 2H), 7.94 (d, J=9.0 Hz, 1H).

Example 33: Preparation of (2-(5-methylpyrazine-2-carboxamido)thiazolo[4,5-b]pyridin-6-yl)carbonohydrazonoyl dicyanide (Compound 33)

Step 33-1: Preparation of 5-methyl-N-(6-nitrothiazolo[4,5-b]pyridin-2-yl)pyrazine-2-carboxamide After 5-methylpyrazine-2-carboxylic acid (211 mg, 1.53 mmol) was dissolved in MeCN under a nitrogen atmosphere, HATU (698 mg, 1.84 mmol) and TEA (0.26 mL, 1.84 mmol) were added thereto, and the reaction mixture was stirred at room temperature for 2 hours. Thereafter, 6-nitrothiazolo[4,5-b]pyridine-2-amine (300 mg, 1.53 mmol) was added thereto, and the reaction mixture was refluxed for 24 hours. Upon completion of the reaction, a reaction product was filtered using MeCN to obtain 413 mg (yield: 85%) of the title compound.

$^1$H NMR (400 MHz, DMSO-$d_6$) δ 13.50 (s, 1H), 9.46 (d, J=2.8 Hz, 1H), 9.40 (d, J=2.8 Hz, 1H), 9.26 (s, 1H), 8.79 (s, 1H), 2.57 (s, 3H).

Step 33-2: Preparation of N-(6-aminothiazolo[4,5-b]pyridin-2-yl)-5-methylpyrazine-2-carboxamide 5-Methyl-N-(6-nitrothiazolo[4,5-b]pyridin-2-yl)pyrazine-2-carboxamide (200 mg, 0.63 mmol) obtained in Step 33-1 and 10% Pd/C (135 mg, 0.13 mmol) were dissolved in DMF, and the reaction mixture was stirred at 60° C. for 2 hours under a hydrogen atmosphere. Upon completion of the reaction, a reaction product was filtered using DMF, and the filtrate was concentrated under reduced pressure. Then, the product was solidified using ethyl acetate and filtered to obtain 101 mg (yield: 56%) of the title compound in a solid state.

$^1$H NMR (400 MHz, DMSO-$d_6$) δ 12.51 (s, 1H), 9.19 (d, J=1.3 Hz, 1H), 8.74 (s, 1H), 8.00 (d, J=2.6 Hz, 1H), 7.51 (d, J=2.6 Hz, 1H), 5.45 (s, 2H), 2.65 (s, 3H).

Step 33-3: Preparation of (2-(5-methylpyrazine-2-carboxamido)thiazolo[4,5-b]pyridin-6-yl)carbonohydrazonoyl dicyanide 52 mg (yield: 60%) of the title compound was obtained in the same manner as in Step 1-3 of Example 1 above, except that N-(6-aminothiazolo[4,5-b]pyridin-2-yl)-5-methylpyrazine-2-carboxamide (70 mg, 0.37 mmol) obtained in Step 33-2 was used instead of N-(5-aminopyridin-2-yl)-5-methylpyrazine-2-carboxamide.

$^1$H NMR (400 MHz, DMSO-$d_6$) δ 10.47 (s, 1H), 8.74 (s, 1H), 8.14 (d, J=8.5 Hz, 1H), 7.96 (dd, J=8.6 Hz, 2.5 Hz, 1H), 7.78 (d, J=8.1 Hz, 2H), 7.16 (d, J=8.1 Hz, 2H), 2.29 (s, 3H).

Example 34: Preparation of (6-(p-tolylcarbamoyl)pyridin-3-yl)carbonohydrazonoyl dicyanide (Compound 34)

Step 34-1: Preparation of 5-nitro-N-p-toylpicolinamide

After 5-nitrocholic acid (300 mg, 1.78 mmol) was dissolved in acetonitrile (18 mL) under a nitrogen atmosphere, HATU (814 mg, 2.14 mmol), TEA (376 μL, 2.68 mmol), and p-toluidine (191 mg, 1.78 mmol) were sequentially added thereto, and the reaction mixture was refluxed for 16 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by recrystallization using ethyl acetate to obtain 401 mg (yield: 87%) of the title compound.

$^1$H NMR (400 MHz, Chloroform-$d_6$) δ 9.83 (s, 1H), 9.43 (d, J=2.4 Hz, 1H), 8.69 (dd, J=8.8 Hz, 2.4 Hz, 1H), 8.52 (d, J=8.8 Hz, 1H), 7.67 (d, J=8.4 Hz, 2H), 7.22 (d, J=8.4 Hz, 2H), 2.37 (s, 3H).

Step 34-2: Preparation of 5-amino-N-p-tolviolcolinamide

5-Nitro-N-p-tolylpicolinamide (200 mg, 0.78 mmol) obtained in Step 34-1 and 10% Pd/C (92 mg, 0.08 mmol) were dissolved in DMF (5 mL) and the reaction mixture was stirred at 60° C. for 1 hour under a hydrogen atmosphere. Upon completion of the reaction, the reaction mixture was filtered using celite to remove the catalyst from the reaction mixture. The filtrate was concentrated under reduced pressure to obtain 169 mg (yield: 96%) of the title compound.

$^1$H NMR (400 MHz, Chloroform-d) δ 9.70 (s, 1H), 8.08 (d, J=8.4 Hz, 1H), 8.00 (d, J=2.7 Hz, 1H), 7.64 (d, J=8.4 Hz, 2H), 7.17 (d, J=8.2 Hz, 2H), 7.07 (dd, J=8.5 Hz, 2.8 Hz, 1H), 4.05 (s, 2H), 2.33 (s, 3H).

Step 34-3: Preparation of (6-p-tolylcarbamoyl)pyridin-3-yl)carbonohydrazonoyl dicyanide 4 mg (yield: 7%) of the title compound was obtained in the same manner as in Step 1-3 of Example 1 above, except that 5-amino-N-p-tolylpicolinamide (40 mg, 0.18 mmol) obtained in Step 34-2 was used instead of N-(5-aminopyridin-2-yl)-5-methylpyrazine-2-carboxamide.

$^1$H NMR (400 MHz, DMSO-$d_6$) δ 10.47 (s, 1H), 8.74 (s, 1H), 8.14 (d, J=8.5 Hz, 1H), 7.96 (dd, J=8.6 Hz, 2.5 Hz, 1H), 7.78 (d, J=8.1 Hz, 2H), 7.16 (d, J=8.1 Hz, 2H), 2.29 (s, 3H).

Example 35: Preparation of (6-(4-methoxyphenylcarbamoyl)pyridin-3-yl)carbonohydrazonoyl dicyanide (Compound 35)

Step 35-1: Preparation of N-(4-methoxyphenyl)-5-nitropicolinamide 267 mg (yield: 82%) of the title compound was obtained in the same manner as in Step 34-1 of Example 34 above, except that p-anisidine (147 mg, 1.19 mmol) was used instead of p-toluidine.

$^1$H NMR (400 MHz, DMSO-$d_6$) δ 10.79 (s, 1H), 9.44 (d, J=2.5 Hz, 1H), 8.82 (dd, J=8.6 Hz, 2.5 Hz, 1H), 8.38 (d, J=8.6 Hz, 1H), 7.84 (d, J=9.0 Hz, 2H), 6.96 (d, J=9.0 Hz, 2H), 3.76 (s, 3H).

Step 35-2: Preparation of 5-amino-N-(4-methoxyphenyl)picolinamide 124 mg (yield: 93%) of the title compound was obtained in the same manner as in Step 34-2 of Example 34 above, except that N-(4-methoxyphenyl)-5-nitropicolinamide (150 mg, 0.55 mmol) obtained in Step 35-1 was used instead of 5-nitro-N-p-tolylpicolinamide.

$^1$H NMR (400 MHz, DMSO-$d_6$) δ 10.08 (s, 1H), 8.01 (dd, J=2.6 Hz, 0.7 Hz, 1H), 7.85-7.81 (m, 1H), 7.77 (d, J=9.1 Hz, 2H), 7.04 (dd, J=8.5 Hz, 2.7 Hz, 1H), 6.91 (d, J=9.0 Hz, 1H), 6.07 (s, 2H), 3.75 (s, 3H).

Step 35-3: Preparation of (6-(4-methoxyphenylcarbamoyl)pyridin-3-yl)carbonohydrazonoyl dicyanide 9 mg (yield: 5%) of the title compound was obtained in the same manner as in Step 1-3 of Example 1 above, except that 5-amino-N-(4-methoxyphenyl)picolinamide (124 mg, 0.51 mmol) obtained in Step 35-2 was used instead of N-(5-aminopyridin-2-yl)-5-methylpyrazine-2-carboxamide.

$^1$H NMR (400 MHz, DMSO-$d_6$) δ 10.46 (s, 1H), 8.73 (d, J=2.5 Hz, 1H), 8.14 (d, J=8.6 Hz, 1H), 7.96 (dd, J=8.6 Hz, 2.4 Hz, 1H), 7.81 (d, J=9.0 Hz, 2H), 6.93 (d, J=9.0 Hz, 2H), 3.75 (s, 3H).

Example 36: Preparation of (6-(5-methylpyrazin-2-ylcarbamoyl)pyridin-3-yl)carbonohydrazonoyl dicyanide (Compound 36)

Step 36-1: Preparation of N-(5-methylpyrazin-2-yl)-5-nitropicolinamide 91 mg (yield: 38%) of the title compound was obtained in the same manner as in Step 34-1 of Example 34 above, except that 5-methylpyrazine-2-amine (101 mg, 0.92 mmol) was used instead of p-toluidine.

$^1$H NMR (400 MHz, Chloroform-d) δ 10.29 (s, 1H), 9.61 (d, J=1.5 Hz, 1H), 9.47 (d, J=2.5 Hz, 1H), 8.73 (dd, J=8.6 Hz, 2.5 Hz, 1H), 8.54 (dd, J=8.6 Hz, 0.8 Hz, 1H), 8.24 (d, J=1.5 Hz, 1H), 2.59 (s, 3H).

Step 36-2: Preparation of 5-amino-N-(5-methylpyrazin-2-yl)picolinamide 78 mg (yield: 81%) of the title compound was obtained in the same manner as in Step 34-2 of Example 34 above, except that N-(5-methylpyrazin-2-yl)-5-nitropicolinamide (110 mg, 0.42 mmol) obtained in Step 36-1 was used instead of 5-nitro-N-p-tolylpicolinamide.

$^1$H NMR (400 MHz, DMSO-$d_6$) δ 10.13 (s, 1H), 9.36 (d, J=1.5 Hz, 1H), 8.32 (t, J=1.0 Hz, 1H), 8.00 (d, J=2.6 Hz, 1H), 7.88 (d, J=8.5 Hz, 1H), 7.06 (dd, J=8.6 Hz, 2.6 Hz, 1H), 6.30 (s, 2H), 2.47 (s, 3H).

Step 36-3: Preparation of (6-(5-methylpyrazin-2-ylcarbamoyl)pyridin-3-yl)carbonohydrazonoyl dicyanide 13 mg (yield: 13%) of the title compound was obtained in the same manner as in Step 1-3 of Example 1 above, except that 5-amino-N-(5-methylpyrazin-2-yl)picolinamide (75 mg, 0.65 mmol) obtained in Step 36-2 was used instead of N-(5-aminopyridin-2-yl)-5-methylpyrazine-2-carboxamide.

$^1$H NMR (400 MHz, DMSO-$d_6$) δ 10.37 (s, 1H), 9.37 (d, J=1.5 Hz, 1H), 8.55 (d, J=2.4 Hz, 1H), 8.36 (s, 1H), 8.07 (d, J=8.5 Hz, 1H), 7.79 (dd, J=8.5 Hz, 2.4 Hz, 1H), 2.49 (s, 3H).

Example 37: Preparation of (6-(4-chlorophenylcarbamoyl)pyridin-3-yl)carbonohydrazonoyl dicyanide (Compound 37)

Step 37-1: Preparation of N-(4-chlorophenyl)-5-nitropicolinamide 267 mg (yield: 81%) of the title compound was obtained in the same manner as in Step 34-1 of Example 34 above, except that p-chloroaniline (152 mg, 1.19 mmol) was used instead of p-toluidine.

$^1$H NMR (400 MHz, DMSO-$d_6$) δ 11.06 (s, 1H), 9.45 (d, J=2.5 Hz, 1H), 8.83 (dd, J=8.6 Hz, 2.5 Hz, 1H), 8.39 (d, J=8.6 Hz, 1H), 7.98 (d, J=8.9 Hz, 2H), 7.45 (d, J=8.9 Hz, 2H).

Step 37-2: Preparation of 5-amino-N-(4-chlorophenyl)picolinamide 174 mg (yield: 73%) of the title compound was obtained in the same manner as in Step 34-2 of Example 34 above, except that N-(4-chlorophenyl)-5-nitropicolinamide (267 mg, 0.96 mmol) obtained in Step 37-1 was used instead of 5-nitro-N-p-tolylpicolinamide and 1,4-dioxane was used, as a solvent, instead of DMF.

$^1$H NMR (400 MHz, DMSO-$d_6$) δ 10.35 (s, 1H), 8.01 (d, J=2.6 Hz, 1H), 7.92 (d, J=8.9 Hz, 2H), 7.84 (d, J=8.5 Hz, 1H), 7.37 (d, J=8.9 Hz, 2H), 7.04 (dd, J=8.5 Hz, 2.7 Hz, 1H), 6.13 (s, 2H).

Step 37-3: Preparation of (6-(4-chlorophenylcarbamoyl)pyridin-3-yl)carbonohydrazonoyl dicyanide 14 mg (yield: 6%) of the title compound was obtained in the same manner as in Step 1-3 of Example 1 above, except that 5-amino-N-(4-chlorophenyl)picolinamide (167 mg, 0.67 mmol) obtained in Step 37-2 was used instead of N-(5-aminopyridin-2-yl)-5-methylpyrazine-2-carboxamide.

$^1$H NMR (400 MHz, DMSO-$d_6$) δ 10.70 (s, 1H), 8.63 (d, J=2.4 Hz, 1H), 8.08 (d, J=8.6 Hz, 1H), 7.97 (d, J=8.9 Hz, 2H), 7.85 (dd. J=8.6 Hz, 2.5 Hz, 1H), 7.41 (d, J=8.9 Hz, 2H).

Example 38: Preparation of (6-(6-methylpyridin-3-ylcarbamoyl)pyridin-3-yl)carbonohydrazonoyl dicyanide (Compound 38)

Step 38-1: Preparation of N-(6-methylpyridin-3-yl)-5-nitropicolinamide 202 mg (yield: 66%) of the title compound was obtained in the same manner as in Step 34-1 of Example 34 above, except that 6-methylpyridine-3-amine (129 mg, 1.19 mmol) was used instead of p-toluidine.

$^1$H NMR (400 MHz, DMSO-$d_6$) δ 11.07 (s, 1H), 9.45 (d, J=2.5 Hz, 1H), 8.95 (d, J=2.5 Hz, 1H), 8.83 (dd, J=8.6 Hz, 2.6 Hz, 1H), 8.39 (d, J=8.6 Hz, 1H), 8.19 (dd, J=8.4 Hz, 2.6 Hz, 1H), 7.28 (d, J=8.4 Hz, 1H), 2.46 (s, 3H).

Step 38-2: Preparation of 5-amino-N-(6-methylpyridin-3-yl)picolinamide 120 mg (yield: 69%) of the title compound was obtained in the same manner as in Step 34-2 of Example 34 above, except that N-(6-methylpyridin-3-yl)-5-nitropicolinamide (198 mg, 0.77 mmol) obtained in Step 38-1 was used instead of 5-nitro-N-p-tolylpicolinamide.

$^1$H NMR (400 MHz, DMSO-$d_6$) δ 10.35 (s, 1H), 8.89 (d, J=2.5 Hz, 1H), 8.15 (dd, J=8.4 Hz, 2.6 Hz, 1H), 8.02 (d, J=2.7 Hz, 1H), 7.84 (d, J=8.5 Hz, 1H), 7.21 (d, J=8.4 Hz, 1H), 7.04 (dd, J=8.5 Hz, 2.6 Hz, 1H), 6.13 (s, 2H), 2.42 (s, 3H).

Step 38-3: Preparation of (6-(6-methylpyridin-3-ylcarbamoyl)pyridin-3-yl)carbonohydrazonoyl dicyanide 8 mg (yield: 5%) of the title compound was obtained in the same manner as in Step 1-3 of Example 1 above, except that 5-amino-N-(6-methylpyridin-3-yl)picolinamide (115 mg, 0.50 mmol) obtained in Step 38-2 was used instead of N-(5-aminopyridin-2-yl)-5-methylpyrazine-2-carboxamide.

$^1$H NMR (400 MHz, DMSO-$d_6$) δ 11.08 (s, 1H), 9.14 (d, J=2.5 Hz, 1H), 8.62 (d, J=2.4 Hz, 1H), 8.54 (d, J=8.6 Hz, 1H), 8.08 (d, J=8.5 Hz, 1H), 7.84 (dd, J=8.6 Hz, 2.4 Hz, 1H), 7.59 (d, J=8.6 Hz, 1H), 2.56 (s, 3H).

Example 39: Preparation of (6-(5-methylpyridin-3-ylcarbamoyl)pyridin-3-yl)carbonohydrazonoyl dicyanide (Compound 39)

Step 39-1: Preparation of N-(5-methylpyridin-3-yl)-6-nitropicolinamide 148 mg (yield: 48%) of the title compound was obtained in the same manner as in Step 34-1 of Example 34 above, except that 5-methylpyridine-3-amine (129 mg, 1.19 mmol) was used instead of p-toluidine.

$^1$H NMR (400 MHz, DMSO-$d_6$) δ 11.08 (s, 1H), 9.46 (d, J=2.5 Hz, 1H), 8.87 (d, J=2.3 Hz, 1H), 8.84 (dd, J=8.6 Hz, 2.6 Hz, 1H), 8.40 (d, J=8.5 Hz, 1H), 8.22 (s, 1H), 8.18 (s, 1H), 2.33 (s, 3H).

Step 39-2: Preparation of 5-amino-N-(5-methylpyridin-3-yl)picolinamide 85 mg (yield: 67%) of the title compound was obtained in the same manner as in Step 34-2 of Example 34 above, except that N-(5-methylpyridin-3-yl)-5-nitropicolinamide (143 mg, 0.55 mmol) obtained in Step 39-1 was used instead of 5-nitro-N-p-tolylpicolinamide.

$^1$H NMR (400 MHz, DMSO-$d_6$) δ 10.36 (s, 1H), 8.81 (d, J=2.3 Hz, 1H), 8.14 (s, 1H), 8.12 (s, 1H), 8.02 (d, J=2.6 Hz, 1H), 7.84 (d, J=8.5 Hz, 1H), 7.04 (dd, J=8.5 Hz, 2.7 Hz, 1H), 6.15 (s, 2H), 2.30 (s, 3H).

Step 39-3: Preparation of (6-(5-methylpyridin-3-ylcarbamoyl)pyridin-3-yl)carbonohydrazonoyl dicyanide 47 mg (yield: 28%) of the title compound was obtained in the same manner as in Step 1-3 of Example 1 above, except that 5-amino-N-(5-methylpyridin-3-yl)picolinamide (85 mg, 0.37 mmol) obtained in Step 39-2 was used instead of N-(5-aminopyridin-2-yl)-5-methylpyrazine-2-carboxamide.

$^1$H NMR (400 MHz, DMSO-$d_6$) δ 11.15 (s, 1H), 9.15-9.11 (m, 1H), 8.68 (d, J=2.4 Hz, 1H), 8.58 (d, J=2.3 Hz, 1H), 8.39 (s, 1H), 8.12 (d, J=8.6 Hz, 1H), 7.90 (dd, J=8.6 Hz, 2.4 Hz, 1H), 2.43 (s, 3H).

Example 40: Preparation of (6-(pyridin-3-ylcarbamoyl)pyridin-3-yl)carbonohydrazonoyl dicyanide (Compound 40)

Step 40-1: Preparation of 5-nitro-N-(pyridin-3-yl)picolinamide 161 mg (yield: 55%) of the title compound was obtained in the same manner as in Step 34-1 of Example 34 above, except that 5-methylpyridine-3-amine (112 mg, 1.19 mmol) was used instead of p-toluidine.

$^1$H NMR (400 MHz, DMSO-$d_6$) δ 11.18 (s, 1H), 9.49-9.44 (m, 1H), 9.12-9.07 (m, 1H), 8.85 (dd, J=8.6 Hz, 2.6 Hz, 1H), 8.42 (dd, J=8.6 Hz, 0.7 Hz, 1H), 8.41-8.30 (m, 2H), 7.44 (ddd, J=8.3 Hz, 4.7 Hz, 0.8 Hz, 1H), 2.70 (s, 3H).

Step 40-2: Preparation of 5-amino-N-(pyridin-3-yl)picolinamide 79 mg (yield: 56%) of the title compound was obtained in the same manner as in Step 34-2 of Example 34 above, except that 5-nitro-N-(pyridin-3-yl)picolinamide (161 mg, 0.66 mmol) obtained in Step 40-1 was used instead of 5-nitro-N-p-tolylpicolinamide.

$^1$H NMR (400 MHz, DMSO-$d_6$) δ 10.45 (s, 1H), 9.04 (d, J=2.5 Hz, 1H), 8.33-8.25 (m, 2H), 8.04 (d, J=2.6 Hz, 1H), 7.86 (d, J=8.5 Hz, 1H), 7.37 (dd, J=8.3 Hz, 4.7 Hz, 1H), 7.06 (dd, J=8.5 Hz, 2.7 Hz, 1H), 6.16 (s, 2H).

Step 40-3: Preparation of (6-(pyridin-3-ylcarbamoyl)pyridin-3-yl)carbonohydrazonoyl dicyanide 30 mg (yield: 27%) of the title compound was obtained in the same manner as in Step 1-3 of Example 1 above, except that 5-amino-N-(pyridin-3-yl)picolinamide (79 mg, 0.37 mmol) obtained in Step 40-2 was used instead of N-(5-aminopyridin-2-yl)-5-methylpyrazine-2-carboxamide.

$^1$H NMR (400 MHz, DMSO-$d_6$) δ 11.19 (s, 1H), 9.32-9.26 (m, 1H), 8.72 (d, J=2.4 Hz, 1H), 8.64 (ddd, J=8.5 Hz, 2.5 Hz, 1.4 Hz, 1H), 8.49 (d, J=5.1 Hz, 1H), 8.15 (d, J=8.6 Hz, 1H), 7.93 (dd, J=8.6 Hz, 2.4 Hz, 1H), 7.73 (dd, J=8.5 Hz, 5.1 Hz, 1H).

Example 41: Preparation of (6-(6-methylpyrazin-2-ylcarbamoyl)pyridin-3-yl)carbonohydrazonoyl dicyanide (Compound 41)

Step 41-1: Preparation of N-(6-methylpyrazin-2-yl)-5-nitropicolinamide 161 mg (yield: 55%) of the title compound was obtained in the same manner as in Step 34-1 of Example 34 above, except that 6-methylpyrazine-2-amine (130 mg, 1.19 mmol) was used instead of p-toluidine.

$^1$H NMR (400 MHz, Chloroform-d) δ 10.28 (s, 1H), 9.54 (s, 1H), 9.47 (d, J=2.5 Hz, 1H), 8.73 (dd, J=8.5 Hz, 2.5 Hz, 1H), 8.55 (d, J=8.5 Hz, 1H), 8.33 (s, 1H), 2.55 (s, 3H).

Step 41-2: Preparation of 5-amino-N-(6-methylpyrazin-2-yl)picolinamide 134 mg (yield: 92%) of the title compound was obtained in the same manner as in Step 34-2 of Example 34 above, except that N-(6-methylpyrazin-2-yl)-5-nitropicolinamide (165 mg, 0.64 mmol) obtained in Step 41-1 was used instead of 5-nitro-N-p-tolylpicolinamide.

$^1$H NMR (400 MHz, DMSO-$d_6$) δ 10.13 (s, 1H), 9.30 (s, 1H), 8.30 (s, 1H), 8.01 (d, J=2.6 Hz, 1H), 7.89 (d, J=8.5 Hz, 1H), 7.07 (dd, J=8.5 Hz, 2.6 Hz, 1H), 6.32 (s, 2H), 2.46 (s, 3H).

Step 41-3: Preparation of (6-(6-methylpyrazin-2-ylcarbamoyl)pyridin-3-yl)carbonohydrazonoyl dicyanide 35 mg (yield: 20%) of the title compound was obtained in the same manner as in Step 1-3 of Example 1 above, except that 5-amino-N-(6-methylpyrazin-2-yl)picolinamide (130 mg, 0.57 mmol) obtained in Step 41-2 was used instead of N-(5-aminopyridin-2-yl)-5-methylpyrazine-2-carboxamide.

$^1$H NMR (400 MHz, DMSO-$d_6$) δ 10.34 (s, 1H), 9.32 (s, 1H), 8.55 (d, J=2.3 Hz, 1H), 8.34 (s, 1H), 8.07 (d, J=8.5 Hz, 1H), 7.79 (dd. J=8.5 Hz, 2.4 Hz, 1H), 2.48 (s, 3H).

Example 42: Preparation of (6-(pyrimidin-6-ylcarbamoyl)pyridin-3-yl)carbonohydrazonoyl dicyanide (Compound 42)

Step 42-1: Preparation of 5-nitro-N-(pyrimidin-5-yl)picolinamide 192 mg (yield: 65%) of the title compound was obtained in the same manner as in Step 34-1 of Example 34 above, except that pyrimidine-5-amine (113 mg, 1.19 mmol) was used instead of p-toluidine.

$^1$H NMR (400 MHz, DMSO-$d_6$) δ 11.43 (s, 1H), 9.48 (dd, J=2.6 Hz, 0.7 Hz, 1H), 9.33 (s, 2H), 8.99 (s, 1H), 8.87 (dd, J=8.6 Hz, 2.6 Hz, 1H), 8.43 (dd, J=8.6 Hz, 0.7 Hz, 1H).

Step 42-2: Preparation of 5-amino-N-(pyrimidin-6-yl)picolinamide 117 mg (yield: 76%) of the title compound was obtained in the same manner as in Step 34-2 of Example 34 above, except that 5-nitro-N-(pyrimidin-5-yl)picolinamide (173 mg, 0.71 mmol) obtained in Step 42-1 was used instead of 5-nitro-N-p-tolylpicolinamide.

$^1$H NMR (400 MHz, DMSO-$d_6$) δ 10.70 (s, 1H), 9.28 (s, 2H), 8.88 (s, 1H), 8.05 (d, J=2.6 Hz, 1H), 7.87 (d, J=8.5 Hz, 1H), 7.05 (dd, J=8.5 Hz, 2.6 Hz, 1H), 6.22 (s, 2H).

Step 42-3: Preparation of (6-(pyrimidin-5-ylcarbamoyl)pyridin-3-yl)carbonohydrazonoyl dicyanide 33 mg (yield: 21%) of the title compound was obtained in the same manner as in Step 1-3 of Example 1 above, except that 5-amino-N-(pyrimidin-5-yl)picolinamide (115 mg, 0.53 mmol) obtained in Step 42-2 was used instead of N-(5-aminopyridin-2-yl)-5-methylpyrazine-2-carboxamide.

$^1$H NMR (400 MHz, DMSO-$d_6$) δ 11.10 (s, 1H), 9.31 (s, 2H), 8.93 (s, 1H), 8.75 (d, J=2.5 Hz, 1H), 8.17 (d, J=8.6 Hz, 1H), 7.96 (dd, J=8.6 Hz, 2.5 Hz, 1H).

Example 43: Preparation of (6-(pyrimidin-2-ylcarbamoyl)pyridin-3-yl)carbonohydrazonoyl dicyanide (Compound 43)

Step 43-1: Preparation of 5-nitro-N-(pyrimidin-2-yl)picolinamide 194 mg (yield: 66%) of the title compound was obtained in the same manner as in Step 34-1 of Example 34 above, except that pyrimidine-2-amine (113 mg, 1.19 mmol) was used instead of p-toluidine.

$^1$H NMR (400 MHz, Chloroform-d) δ 10.58 (s, 1H), 9.47 (d, J=2.5 Hz, 1H), 8.78-8.68 (m, 3H), 8.59 (dd, J=8.6 Hz, 0.8 Hz, 1H), 7.14 (t, J=4.8 Hz, 1H).

Step 43-2: Preparation of 5-amino-N-(pyrimidin-2-yl)picolinamide 98 mg (yield: 67%) of the title compound was obtained in the same manner as in Step 34-2 of Example 34 above, except that 5-nitro-N-(pyrimidin-2-yl)picolinamide (165 mg, 0.67 mmol) obtained in Step 43-1 was used instead of 5-nitro-N-p-tolylpicolinamide.

$^1$H NMR (400 MHz, DMSO-$d_6$) δ 10.36 (s, 1H), 8.70 (d, J=4.8 Hz, 2H), 7.99 (dd, J=2.7 Hz, 0.6 Hz, 1H), 7.90-7.84 (m, 1H), 7.22 (t, J=4.8 Hz, 1H), 7.06 (dd. J=8.6 Hz, 2.7 Hz, 1H), 6.27 (s, 2H).

Step 43-3: Preparation of (6-(pyrimidin-2-ylcarbamoyl)pyridin-3-yl)carbonohydrazonoyl dicyanide 25 mg (yield: 19%) of the title compound was obtained in the same manner as in Step 1-3 of Example 1 above, except that 5-amino-N-(pyrimidin-2-yl)picolinamide (97 mg, 0.45 mmol) obtained in Step 43-2 was used instead of N-(5-aminopyridin-2-yl)-5-methylpyrazine-2-carboxamide.

$^1$H NMR (400 MHz, DMSO-$d_6$) δ 10.56 (s, 1H), 8.81-8.73 (m, 3H), 8.20 (dd, J=8.7 Hz, 0.7 Hz, 1H), 8.02 (dd, J=8.6 Hz, 2.5 Hz, 1H), 7.29 (t, J=4.8 Hz, 1H).

Example 44: Preparation of (4-(4-methoxyphenylcarbamoyl)phenyl)carbonohydrazonoyl dicyanide (Compound 44)

Step 44-1: Preparation of N-(4-methoxyphenyl)-4-nitrobenzamide 174 mg (yield: 53%) of the title compound was obtained in the same manner as in Step 34-1 of Example 34 above, except that 4-nitrobenzoic acid (200 mg, 1.20 mmol) was used instead of 5-nitrocholic acid, and p-anisidine (147 mg, 1.20 mmol) was used instead of p-toluidine.

$^1$H NMR (400 MHz, DMSO-$d_6$) δ 10.45 (s, 1H), 8.37 (d, J=8.8 Hz, 2H), 8.18 (d, J=8.8 Hz, 2H), 7.69 (d, J=9.0 Hz, 2H), 6.96 (d, J=9.0 Hz, 2H), 3.76 (s, 3H).

Step 44-2: Preparation of 4-amino-N-(4-methoxyphenyl)benzamide 137 mg (yield: 92%) of the title compound was obtained in the same manner as in Step 34-2 of Example 34 above, except that N-(4-methoxyphenyl)-4-nitrobenzamide (168 mg, 0.62 mmol) obtained in Step 44-1 was used instead of 5-nitro-N-p-tolylpicolinamide.

$^1$H NMR (400 MHz, DMSO-$d_6$) δ 9.64 (s, 1H), 7.70 (d, J=8.6 Hz, 2H), 7.63 (d, J=9.0 Hz, 2H), 6.89 (d, J=9.0 Hz, 2H), 6.59 (d, J=8.6 Hz, 2H), 5.71 (s, 2H), 3.74 (s, 3H).

Step 44-3: Preparation of (4-(4-methoxyphenylcarbamoyl)phenyl)carbonohydrazonoyl Dicyanide 20 mg (yield: 11%) of the title compound was obtained in the same manner as in Step 1-3 of Example 1 above, except that 4-amino-N-(4-methoxyphenyl)benzamide (135 mg, 0.56 mmol) obtained in Step 44-2 was used instead of N-(5-aminopyridin-2-yl)-5-methylpyrazine-2-carboxamide.

$^1H$ NMR (400 MHz, DMSO-$d_6$) δ 13.19 (s, 1H), 10.13 (s, 1H), 8.02 (d, J=8.8 Hz, 2H), 7.68 (d, J=9.0 Hz, 2H), 7.58 (d, J=8.8 Hz, 2H), 6.94 (d, J=9.0 Hz, 2H), 3.76 (s, 3H).

Example 45: Preparation of (4-(5-methylpyrazin-2-ylcarbamoyl)phenyl)carbonohydrazonoyl dicyanide (Compound 45)

Step 45-1: Preparation of N-(5-methylpyrazin-2-yl)-4-nitrobenzamide 84 mg (yield: 13%) of the title compound was obtained in the same manner as in Step 44-1 of Example 44 above, except that 5-methylpyrazine-2-amine (131 mg, 1.20 mmol) was used instead of p-anisidine.

$^1H$ NMR (400 MHz, Chloroform-d) δ 9.59-9.54 (m, 1H), 8.47 (s, 1H), 8.42-8.34 (m, 2H), 8.21-8.16 (m, 1H), 8.15-8.07 (m, 2H), 2.59 (s, 3H).

Step 45-2: Preparation of 4-amino-N-(5-methylpyrazin-2-yl)benzamide 56 mg (yield: 84%) of the title compound was obtained in the same manner as in Step 34-2 of Example 34 above, except that N-(5-methylpyrazin-2-yl)-4-nitrobenzamide (76 mg, 0.29 mmol) obtained in Step 45-1 was used instead of 5-nitro-N-p-tolylpicolinamide.

$^1H$ NMR (400 MHz, DMSO-$d_6$) δ 10.41 (s, 1H), 9.26 (d, J=1.5 Hz, 1H), 8.31 (d, J=1.5 Hz, 1H), 7.85-7.77 (m, 2H), 6.63-6.54 (m, 2H), 5.87 (s, 2H), 2.46 (s, 3H).

Step 45-3: Preparation of (4-(5-methylpyrazin-2-ylcarbamoyl)phenyl)carbonohydrazonoyl dicyanide 37 mg (yield: 59%) of the title compound was obtained in the same manner as in Step 1-3 of Example 1 above, except that 4-amino-N-(5-methylpyrazin-2-yl)benzamide (46 mg, 0.20 mmol) obtained in Step 45-2 was used instead of N-(5-aminopyridin-2-yl)-5-methylpyrazine-2-carboxamide.

$^1H$ NMR (400 MHz, DMSO-$d_6$) δ 13.14 (s, 1H), 10.99 (s, 1H), 9.28 (d, J=1.5 Hz, 1H), 8.37 (d, J=1.5 Hz, 1H), 8.14-8.08 (m, 2H), 7.60-7.54 (m, 2H), 2.49 (s, 3H).

Example 46: Preparation of (4-(6-methylpyrazin-2-ylcarbamoyl)phenyl)carbonohydrazonoyl dicyanide (Compound 46)

Step 46-1: Preparation of N-(6-methylpyrazin-2-yl)-4-nitrobenzamide 156 mg (yield: 33%) of the title compound was obtained in the same manner as in Step 44-1 of Example 44 above, except that 6-methylpyrazine-2-amine (196 mg, 1.80 mmol) was used instead of p-anisidine.

$^1H$ NMR (400 MHz, Chloroform-d) δ 9.49 (s, 1H), 8.46 (s, 1H), 8.42-8.35 (m, 2H), 8.33 (s, 1H), 8.16-8.08 (m, 2H), 2.52 (d, J=0.7 Hz, 3H).

Step 46-2: Preparation of 4-amino-N-(6-methylpyrazin-2-yl)benzamide 135 mg (yield: 99%) of the title compound was obtained in the same manner as in Step 34-2 of Example 34 above, except that N-(6-methylpyrazin-2-yl)-4-nitrobenzamide (154 mg, 0.60 mmol) obtained in Step 46-1 was used instead of 5-nitro-N-p-tolylpicolinamide.

$^1H$ NMR (400 MHz, DMSO-$d_6$) δ 10.45 (s, 1H), 9.21 (s, 1H), 8.24 (s, 1H), 7.86-7.78 (m, 2H), 6.62-6.54 (m, 2H), 5.88 (s, 2H), 2.46 (s, 3H).

Step 46-3: Preparation of (4-(6-methylpyrazin-2-ylcarbamoyl)phenyl)carbonohydrazonoyl dicyanide 25 mg (yield: 18%) of the title compound was obtained in the same manner as in Step 1-3 of Example 1 above, except that 4-amino-N-(6-methylpyrazin-2-yl)benzamide (105 mg, 0.46 mmol) obtained in Step 46-2 was used instead of N-(5-aminopyridin-2-yl)-5-methylpyrazine-2-carboxamide.

$^1H$ NMR (400 MHz, DMSO-$d_6$) δ 13.06 (s, 1H), 11.05 (s, 1H), 9.25 (s, 1H), 8.32 (s, 1H), 8.12 (d, 2H), 7.57 (d, 2H), 2.50 (s, 3H).

Example 47: Preparation of (4-(6-methylpyridin-3-ylcarbamoyl)phenyl)carbonohydrazonoyl dicyanide (Compound 47)

Step 47-1: Preparation of N-(6-methylpyridin-3-yl)-4-nitrobenzamide 157 mg (yield: 51%) of the title compound was obtained in the same manner as in Step 44-1 of Example 44 above, except that 6-methylpyridine-3-amine (129 mg, 1.20 mmol) was used instead of p-anisidine.

$^1H$ NMR (400 MHz, DMSO-$d_6$) δ 10.69 (s, 1H), 8.80 (d, J=2.6 Hz, 1H), 8.39 (d, 2H), 8.21 (d, 2H), 8.08 (dd, J=8.4 Hz, 2.6 Hz, 1H), 7.28 (d, J=8.4 Hz, 1H), 2.46 (s, 3H).

Step 47-2: Preparation of 4-amino-N-(6-methylpyridin-3-yl)benzamide 95 mg (yield: 68%) of the title compound was obtained in the same manner as in Step 34-2 of Example 34 above, except that N-(6-methylpyridin-3-yl)-4-nitrobenzamide (157 mg, 0.61 mmol) obtained in Step 47-1 was used instead of 5-nitro-N-p-tolylpicolinamide.

$^1H$ NMR (400 MHz, DMSO-$d_6$) δ 9.86 (s, 1H), 8.76 (d, J=2.5 Hz, 1H), 8.03 (dd, J=8.4 Hz, 2.6 Hz, 1H), 7.72 (d, 2H), 7.20 (d, J=8.4 Hz, 1H), 6.60 (d, 2H), 5.79 (s, 2H), 2.42 (s, 3H).

Step 47-3: Preparation of (4-(6-methylpyridin-3-ylcarbamoyl)phenyl)carbonohydrazonoyl dicyanide 91 mg (yield: 73%) of the title compound was obtained in the same manner as in Step 1-3 of Example 1 above, except that 4-amino-N-(6-methylpyridin-3-yl)benzamide (92 mg, 0.40 mmol) obtained in Step 47-2 was used instead of N-(5-aminopyridin-2-yl)-5-methylpyrazine-2-carboxamide.

$^1H$ NMR (400 MHz, DMSO-$d_6$) δ 10.49 (s, 1H), 8.91 (d, J=2.5 Hz, 1H), 8.21 (dd, J=8.5 Hz, 2.6 Hz, 1H), 8.02 (d, 2H), 7.55 (d, 2H), 7.43 (d, J=8.5 Hz, 1H), 3.45 (m, 3H).

Example 48: Preparation of (4-(5-methylpyridin-3-ylcarbamoyl)phenyl)carbonohydrazonoyl dicyanide (Compound 48)

Step 48-1: Preparation of N(5-methylpyridin-3-yl)-4-nitrobenzamide 195 mg (yield: 63%) of the title compound was obtained in the same manner as in Step 44-1 of Example 44 above, except that 5-methylpyridine-3-amine (129 mg, 1.20 mmol) was used instead of p-anisidine.

$^1H$ NMR (400 MHz, DMSO-$d_6$) δ 10.71 (s, 1H), 8.74 (d, J=2.4 Hz, 1H), 8.40 (d, 2H), 8.21 (d, 3H), 8.05 (t, J=2.3 Hz, 1H), 2.33 (s, 3H).

Step 48-2: Preparation of 4-amino-N-(5-methylpyridin-3-yl)benzamide 78 mg (yield: 49%) of the title compound was obtained in the same manner as in Step 34-2 of Example 34 above, except that N-(5-methylpyridin-3-yl)-4-nitrobenzamide (179 mg, 0.70 mmol) obtained in Step 48-1 was used instead of 5-nitro-N-p-tolylpicolinamide.

$^1H$ NMR (400 MHz, DMSO-$d_6$) δ 9.92 (s, 1H), 8.72 (d, J=2.3 Hz, 1H), 8.10 (dd, J=2.0 Hz, 0.9 Hz, 1H), 8.06-8.00 (m, 1H), 7.75 (d, 2H), 6.61 (d, 2H), 5.82 (s, 2H), 2.29 (s, 3H).

Step 48-3: Preparation of (4-(5-methylpyridin-3-ylcarbamoyl)phenyl)carbonohydrazonoyl dicyanide 44 mg (yield: 46%) of the title compound was obtained in the same manner as in Step 1-3 of Example 1 above, except that 4-amino-N-(5-methylpyridin-3-yl)benzamide (71 mg, 0.31 mmol) obtained in Step 48-2 was used instead of N-(5-aminopyridin-2-yl)-5-methylpyrazine-2-carboxamide.

$^1H$ NMR (400 MHz, DMSO-$d_6$) δ 10.87 (s, 1H), 9.04 (d, J=2.2 Hz, 1H), 8.41 (dt, J=4.2 Hz, 1.8 Hz, 2H), 8.10 (d, 2H), 7.62 (d, 2H), 2.43 (s, 3H).

Example 49: Preparation of (4-(pyridin-3-ylcarbamoyl)phenyl)carbonohydrazonoyl dicyanide (Compound 49)

Step 49-1: Preparation of 4-nitro-N-(pyridin-3-yl)benzamide 272 mg (yield: 93%) of the title compound was obtained in the same manner as in Step 44-1 of Example 44 above, except that pyridine-3-amine (112 mg, 1.20 mmol) was used instead of p-anisidine.

$^1H$ NMR (400 MHz, DMSO-$d_6$) δ 10.78 (s, 1H), 8.94 (dd, J=2.6 Hz, 0.7 Hz, 1H), 8.40 (d, 2H), 8.36 (dd, J=4.7 Hz, 1.5 Hz, 1H), 8.26-8.17 (m, 3H), 7.44 (ddd, J=8.3 Hz, 4.7 Hz, 0.8 Hz, 1H).

Step 49-2: Preparation of 4-amino-N-(pyridin-3-yl)benzamide 145 mg (yield: 60%) of the title compound was obtained in the same manner as in Step 34-2 of Example 34 above, except that 4-nitro-N-(pyridin-3-yl)benzamide (272 mg, 1.12 mmol) obtained in Step 49-1 was used instead of 5-nitro-N-p-tolylpicolinamide.

$^1H$ NMR (400 MHz, DMSO-$d_6$) δ 9.95 (d, J=3.8 Hz, 1H), 8.91 (t, J=3.3 Hz, 1H), 8.26 (td, J=4.4 Hz, 1.6 Hz, 1H), 8.17 (dp, J=6.2 Hz, 1.8 Hz, 1H), 7.74 (ddd, J=8.0 Hz, 4.9 Hz, 2.9 Hz, 2H), 7.36 (dt, J=8.5 Hz, 4.2 Hz, 1H), 6.62 (ddd, J=8.1 Hz, 5.0 Hz, 2.9 Hz, 2H), 5.82 (d, J=3.9 Hz, 2H).

Step 49-3: Preparation of (4-(pyridin-3-ylcarbamoyl)phenyl)carbonohydrazonoyl dicyanide 42 mg (yield: 21%) of the title compound was obtained in the same manner as in Step 1-3 of Example 1 above, except that 4-amino-N-(pyridin-3-yl)benzamide (145 mg, 0.68 mmol) obtained in Step 49-2 was used instead of N-(5-aminopyridin-2-yl)-5-methylpyrazine-2-carboxamide.

$^1H$ NMR (400 MHz, DMSO-$d_6$) δ 10.50 (s, 1H), 8.99 (d, J=2.4 Hz, 1H), 8.36 (dd, J=4.8 Hz, 1.5 Hz, 1H), 8.26 (dt, J=8.4 Hz, 1.9 Hz, 1H), 8.04 (d, 2H), 7.58 (d, 2H), 7.49 (dd, J=8.4 Hz, 4.8 Hz, 1H).

Example 50: Preparation of (4-(pyrimidin-5-ylcarbamoyl)phenyl)carbonohydrazonoyl dicyanide (Compound 50)

Step 50-1: Preparation of 4-nitro-N-(pyrimidin-5-yl)benzamide 230 mg (yield: 112%) of the title compound was obtained in the same manner as in Step 34-1 of Example 34 above, except that 4-nitrobenzoic acid (200 mg, 1.20 mmol) was used instead of 5-nitrocholic acid, and 5-aminopyrimidine (114 mg, 1.20 mmol) was used instead of p-toluidine.

$^1H$ NMR (400 MHz, DMSO-$d_6$) δ 10.97 (s, 1H), 9.18 (s, 2H), 8.98 (s, 1H), 8.46-8.38 (m, 2H), 8.27-8.19 (m, 2H).

Step 50-2: Preparation of 4-amino-N-(pyrimidin-5-yl)benzamide 44 mg (yield: 17%) of the title compound was obtained in the same manner as in Step 34-2 of Example 34 above, except that 4-nitro-N-(pyrimidin-5-yl)benzamide (292 mg, 1.20 mmol) obtained in Step 50-1 was used instead of 5-nitro-N-p-tolylpicolinamide.

$^1H$ NMR (400 MHz, DMSO-$d_6$) δ 10.14 (s, 1H), 9.16 (s, 2H), 8.88 (s, 1H), 7.80-7.72 (m, 2H), 6.67-6.59 (m, 2H), 5.90 (s, 2H).

Step 50-3: Preparation of (4-(pyrimidin-5-ylcarbamoyl)phenyl)carbonohydrazonoyl dicyanide 51 mg (yield: 84%) of the title compound was obtained in the same manner as in Step 1-3 of Example 1 above, except that 4-amino-N-(pyrimidin-5-yl)benzamide (44 mg, 0.21 mmol) obtained in Step 50-2 was used instead of N-(5-aminopyridin-2-yl)-5-methylpyrazine-2-carboxamide.

$^1H$ NMR (400 MHz, DMSO-$d_6$) δ 13.20 (s, 1H), 10.64 (s, 1H), 9.18 (s, 2H), 8.95 (s, 1H), 8.12-8.04 (m, 2H), 7.67-7.59 (m, 2H).

Example 61: Preparation of (2-methoxy-4-(5-methylpyrazin-2-ylcarbamoyl)phenyl)carbonohydrazonoyl dicyanide (Compound 51)

Step 51-1: Preparation of 3-methoxy-N-(5-methylpyrazin-2-yl)-4-nitrobenzamide 174 mg (yield: 59%) of the title compound was obtained in the same manner as in Step 34-1 of Example 34 above, except that 3-methoxy-4-nitrobenzoic acid (200 mg, 1.01 mmol) was used instead of 5-nitrocholic acid, and 5-methylpyrazine-2-amine (111 mg, 1.01 mmol) was used instead of p-toluidine.

$^1H$ NMR (400 MHz, Chloroform-d) δ 9.56 (d, J=1.5 Hz, 1H), 8.40 (s, 1H), 8.19 (dd, J=1.5 Hz, 0.7 Hz, 1H), 7.93 (d, J=8.3 Hz, 1H), 7.74 (d, J=1.7 Hz, 1H), 7.48 (dd, J=8.3 Hz, 1.7 Hz, 1H), 4.06 (s, 3H), 2.59 (s, 3H).

Step 51-2: Preparation of 4-amino-3-methoxy-N-(6-methylpyrazin-2-yl)benzamide 132 mg (yield: 84%) of the title compound was obtained in the same manner as in Step 34-2 of Example 34 above, except that 3-methoxy-N-(5-methylpyrazin-2-yl)-4-nitrobenzamide (174 mg, 0.60 mmol) obtained in Step 51-1 was used instead of 5-nitro-N-p-tolylpicolinamide.

$^1$H NMR (400 MHz, DMSO-$d_6$) δ 10.55 (s, 1H), 9.28 (d, J=1.5 Hz, 1H), 8.34-8.29 (m, 1H), 7.55 (d, J=7.9 Hz, 2H), 6.66 (d, J=8.0 Hz, 1H), 5.51 (s, 2H), 3.86 (s, 3H), 2.47 (s, 3H).

Step 51-3: Preparation of (2-methoxy-4(5-methylpyrazin-2-ylcarbamoyl)phenyl)carbonohydrazonoyl dicyanide 35 mg (yield: 20%) of the title compound was obtained in the same manner as in Step 1-3 of Example 1 above, except that 4-amino-3-methoxy-N-(5-methylpyrazin-2-yl)benzamide (132 mg, 0.51 mmol) obtained in Step 51-2 was used instead of N-(5-aminopyridin-2-yl)-5-methylpyrazine-2-carboxamide.

$^1$H NMR (400 MHz, DMSO-$d_6$) δ 11.82 (s, 1H), 11.09 (s, 1H), 9.30 (d, J=1.5 Hz, 1H), 8.38 (d, J=1.5 Hz, 1H), 7.86 (d, J=1.8 Hz, 1H), 7.75 (dd, J=8.4 Hz, 1.8 Hz, 1H), 7.53 (d, J=8.4 Hz, 1H), 4.03 (s, 3H), 2.49 (s, 3H).

Example 52: Preparation of methyl-4-(5-methylpyrazin-2-ylcarbamoyl)phenyl)carbonohydrazonoyl dicyanide (Compound 52)

Step 52-1: Preparation of 2-methyl-N-(5-methylpyrazin-2-yl)-4-nitrobenzamide 105 mg (yield: 35%) of the title compound was obtained in the same manner as in Step 34-1 of Example 34 above, except that 2-methyl-4-nitrobenzoic acid (200 mg, 1.10 mmol) was used instead of 5-nitrocholic acid, and 5-methylpyrazine-2-amine (121 mg, 1.10 mmol) was used instead of p-toluidine.

$^1$H NMR (400 MHz, Chloroform-d) δ 9.53 (s, 1H), 8.32 (s, 1H), 8.19-8.08 (m, 2H), 8.04 (d, J=1.5 Hz, 1H), 7.69 (d, J=8.3 Hz, 1H), 2.63 (s, 3H), 2.55 (s, 3H).

Step 52-2: Preparation of 4-amino-2-methyl-N-(5-methylpyrazin-2-yl)benzamide 73 mg (yield: 78%) of the title compound was obtained in the same manner as in Step 34-2 of Example 34 above, except that 2-methyl-N-(5-methylpyrazin-2-yl)-4-nitrobenzamide (105 mg, 0.39 mmol) obtained in Step 52-1 was used instead of 5-nitro-N-p-tolylpicolinamide.

$^1$H NMR (400 MHz, DMSO-$d_6$) δ 10.41 (s, 1H), 9.23 (d, J=1.6 Hz, 1H), 8.29 (d, J=1.6 Hz, 1H), 7.37 (d, J=8.2 Hz, 1H), 6.45-6.37 (m, 2H), 5.58 (s, 2H), 2.46 (s, 3H), 2.35 (s, 3H).

Step 52-3: Preparation of (3-methyl-4-(5-methylpyrazin-2-ylcarbamoyl)phenyl)carbonohydrazonoyl dicyanide 82 mg (yield: 85%) of the title compound was obtained in the same manner as in Step 1-3 of Example 1 above, except that 4-amino-2-methyl-N-(5-methylpyrazin-2-yl)benzamide (73 mg, 0.30 mmol) obtained in Step 52-2 was used instead of N-(5-aminopyridin-2-yl)-5-methylpyrazine-2-carboxamide.

$^1$H NMR (400 MHz, DMSO-$d_6$) δ 13.06 (s, 1H), 10.97 (s, 1H), 9.28 (d, J=1.5 Hz, 1H), 8.33 (d, J=1.4 Hz, 1H), 7.59 (d, J=8.3 Hz, 1H), 7.41-7.32 (m, 2H), 2.48 (s, 3H), 2.43 (s, 3H).

Example 53: Preparation of (3-methyl-4-(6-methylpyridin-3-ylcarbamoyl)phenyl)carbonohydrazonoyl dicyanide (Compound 53)

Step 53-1: Preparation of 2-methyl-N-(6-methylpyridin-3-yl)-4-nitrobenzamide 270 mg (yield: 90%) of the title compound was obtained in the same manner as in Step 34-1 of Example 34 above, except that 2-methyl-4-nitrobenzoic acid (200 mg, 1.10 mmol) was used instead of 5-nitrocholic acid, and 5-amino-2-methylpyridine (119 mg, 1.10 mmol) was used instead of p-toluidine.

$^1$H NMR (400 MHz, Chloroform-d) δ 8.52 (d, J=2.6 Hz, 1H), 8.15-8.08 (m, 3H), 8.05 (dd, J=8.3 Hz, 2.3 Hz, 1H), 7.61 (d, J=8.3 Hz, 1H), 7.19 (d, J=8.4 Hz, 1H), 2.58 (s, 3H), 2.52 (s, 3H).

Step 53-2: Preparation of 4-amino-2-methyl-N-(6-methylpyridin-3-yl)benzamide 135 mg (yield: 56%) of the title compound was obtained in the same manner as in Step 34-2 of Example 34 above, except that 2-methyl-N-(6-methylpyridin-3-yl)-4-nitrobenzamide (270 mg, 1.00 mmol) obtained in Step 53-1 was used instead of 5-nitro-N-p-tolylpicolinamide.

$^1$H NMR (400 MHz, DMSO-$d_6$) δ 9.95 (s, 1H), 8.72 (dd, J=2.6 Hz, 0.7 Hz, 1H), 8.02 (dd, J=8.4 Hz, 2.6 Hz, 1H), 7.30 (d, J=8.9 Hz, 1H), 7.19 (d, J=8.4 Hz, 1H), 6.47-6.40 (m, 2H), 5.50 (s, 2H), 2.42 (s, 3H), 2.32 (s, 3H).

Step 53-3: Preparation of (3-methyl-4(6-methylpyridin-3-ylcarbamoyl)phenyl)carbonohydrazonoyl dicyanide 55 mg (yield: 31%) of the title compound was obtained in the same manner as in Step 1-3 of Example 1 above, except that 4-amino-2-methyl-N-(6-methylpyridin-3-yl)benzamide (135 mg, 0.56 mmol) obtained in Step 53-2 was used instead of N-(5-aminopyridin-2-yl)-5-methylpyrazine-2-carboxamide.

$^1$H NMR (400 MHz, DMSO-$d_6$) δ 10.54 (s, 1H), 8.85 (d, J=2.6 Hz, 1H), 8.15 (dd, J=8.5 Hz, 2.6 Hz, 1H), 7.58 (d, J=8.2 Hz, 1H), 7.43-7.33 (m, 3H), 2.50 (s, 3H), 2.44 (s, 3H).

Example 54: Preparation of (3-methyl-4-(6-methylpyrazin-2-ylcarbamoyl)phenyl)carbonohydrazonoyl dicyanide (Compound 54)

Step 54-1: Preparation of 2-methyl-N-(6-methylpyrazin-2-yl)-4-nitrobenzamide 97 mg (yield: 32%) of the title compound was obtained in the same manner as in Step 34-1 of Example 34 above, except that 2-methyl-4-nitrobenzoic acid (200 mg, 1.10 mmol) was used instead of 5-nitrocholic acid, and 6-methylpyrazine-2-amine (121 mg, 1.10 mmol) was used instead of p-toluidine.

$^1$H NMR (400 MHz, Chloroform-d) δ 9.44 (s, 1H), 8.32 (s, 1H), 8.20-8.11 (m, 3H), 7.70 (d, J=8.3 Hz, 1H), 2.63 (s, 3H), 2.50 (s, 3H).

Step 54-2: Preparation of 4-amino-2-methyl-N-(6-methylpyrazin-2-ylbenzamide 81 mg (yield: 94%) of the title compound was obtained in the same manner as in Step 34-2 of Example 34 above, except that 2-methyl-N-(6-methylpyrazin-2-yl)-4-nitrobenzamide (97 mg, 0.36 mmol) obtained in Step 54-1 was used instead of 5-nitro-N-p-tolylpicolinamide.

$^1$H NMR (400 MHz, DMSO-$d_6$) δ 10.44 (s, 1H), 9.19 (s, 1H), 8.23 (s, 1H), 7.38 (d, J=8.2 Hz, 1H), 6.45-6.36 (m, 2H), 5.59 (s, 2H), 2.45 (s, 3H), 2.35 (s, 3H).

Step 54-3: Preparation of (3-methyl-4-(6-methylpyrazin-2-ylcarbamoyl)phenyl)carbonohydrazonoyl dicyanide 90 mg (yield: 85%) of the title compound was obtained in the same manner as in Step 1-3 of Example 1 above, except that 4-amino-2-methyl-N-(6-methylpyrazin-2-yl)benzamide (80 mg, 0.33 mmol) obtained in Step 54-2 was used instead of N-(5-aminopyridin-2-yl)-5-methylpyrazine-2-carboxamide.

$^1$H NMR (400 MHz, DMSO-$d_6$) δ 13.05 (s, 1H), 11.04 (s, 1H), 9.24 (s, 1H), 8.31 (s, 1H), 7.60 (d, J=8.4 Hz, 1H), 7.41-7.32 (m, 2H), 2.47 (s, 3H), 2.44 (s, 3H).

Example 55: Preparation of (2-methyl-4-(6-methylpyridin-3-ylcarbamoyl)phenyl)carbonohydrazonoyl dicyanide (Compound 55)

Step 55-1: Preparation of 3-methyl-N-(6-methylpyridin-3-yl)-4-nitrobenzamide 166 mg (yield: 55%) of the title compound was obtained in the same manner as in Step 34-1 of Example 34 above, except that 3-methyl-4-nitrobenzoic acid (200 mg, 1.10 mmol) was used instead of 5-nitrocholic acid, and 5-amino-2-methylpyridine (119 mg, 1.10 mmol) was used instead of p-toluidine.

$^1$H NMR (400 MHz, DMSO-$d_6$) δ 10.59 (s, 1H), 8.79 (d, J=2.6 Hz, 1H), 8.12 (d, J=8.4 Hz, 1H), 8.09-8.03 (m, 2H), 7.98 (dd, J=8.4 Hz, 2.0 Hz, 1H), 7.27 (d, J=8.4 Hz, 1H), 2.59 (s, 3H), 2.45 (s, 3H).

Step 55-2: Preparation of 4-amino-3-methyl-N-(6-methylpyridin-3-yl)benzamide 78 mg (yield: 54%) of the title compound was obtained in the same manner as in Step 34-2 of Example 34 above, except that 3-methyl-N-(6-methylpyridin-3-yl)-4-nitrobenzamide (160 mg, 0.60 mmol) obtained in Step 55-1 was used instead of 5-nitro-N-p-tolylpicolinamide.

$^1$H NMR (400 MHz, DMSO-$d_6$) δ 9.86 (s, 1H), 8.79-8.74 (m, 1H), 8.05 (dd, J=8.4 Hz, 2.6 Hz, 1H), 7.67-7.58 (m, 2H), 7.20 (d, J=8.4 Hz, 1H), 6.65 (d, J=8.3 Hz, 1H), 5.56 (s, 2H), 2.43 (s, 3H), 2.13 (s, 3H).

Step 55-3: Preparation of (2-methyl-4-(6-methylpyridin-3-ylcarbamoyl)phenyl)carbonohydrazonoyl dicyanide 55 mg (yield: 26%) of the title compound was obtained in the same manner as in Step 1-3 of Example 1 above, except that 4-amino-3-methyl-N-(6-methylpyridin-3-yl)benzamide (78 mg, 0.32 mmol) obtained in Step 55-2 was used instead of N-(5-aminopyridin-2-yl)-5-methylpyrazine-2-carboxamide.

$^1$H NMR (400 MHz, DMSO-$d_6$) δ 11.11 (s, 1H), 9.23 (d, J=2.4 Hz, 1H), 8.68 (dd, J=8.9 Hz, 2.4 Hz, 1H), 7.99 (s, 1H), 7.94 (d, J=8.6 Hz, 1H), 7.89 (d, J=8.8 Hz, 1H), 7.53 (d, J=8.5 Hz, 1H), 2.70 (s, 3H), 2.48 (s, 3H).

Example 66: Preparation of (2-fluoro-4-(5-methylpyrazin-2-ylcarbamoyl)phenyl)carbonohydrazonoyl dicyanide (Compound 56)

Step 56-1: Preparation of 3-fluoro-N-(5-methylpyrazin-2-yl)-4-nitrobenzamide 232 mg (yield: 77%) of the title compound was obtained in the same manner as in Step 34-1 of Example 34 above, except that 3-fluoro-4-nitrobenzoic acid (200 mg, 1.08 mmol) was used instead of 5-nitrocholic acid, and 5-methylpyrazine-2-amine (118 mg, 1.08 mmol) was used instead of p-toluidine.

$^1$H NMR (400 MHz, Chloroform-d) δ 9.53 (d, J=1.5 Hz, 1H), 8.41 (s, 1H), 8.25-8.16 (m, 2H), 7.90 (dd, J=10.7 Hz, 1.9 Hz, 1H), 7.83 (ddd, J=8.4 Hz, 1.9 Hz, 1.0 Hz, 1H), 2.59 (s, 3H).

Step 56-2: Preparation of 4-amino-3-fluoro-N-(5-methylpyrazin-2-yl)benzamide 171 mg (yield: 83%) of the title compound was obtained in the same manner as in Step 34-2 of Example 34 above, except that 3-fluoro-N-(5-methylpyrazin-2-yl)-4-nitrobenzamide (230 mg, 0.83 mmol) obtained in Step 56-1 was used instead of 5-nitro-N-p-tolylpicolinamide.

$^1$H NMR (400 MHz, DMSO-$d_6$) δ 10.59 (s, 1H), 9.25 (d, J=1.5 Hz, 1H), 8.33 (d, J=1.5 Hz, 1H), 7.78 (dd, J=12.9 Hz, 2.0 Hz, 1H), 7.71 (dd, J=8.4 Hz, 2.1 Hz, 1H), 6.79 (t, J=8.7 Hz, 1H), 5.95 (s, 2H), 2.47 (s, 3H).

Step 56-3: Preparation of (2-fluoro-4-(5-methylpyrazin-2-ylcarbamoyl)phenyl)carbonohydrazonoyl dicyanide 19 mg (yield: 8%) of the title compound was obtained in the same manner as in Step 1-3 of Example 1 above, except that 4-amino-3-fluoro-N-(5-methylpyrazin-2-yl)benzamide (171 mg, 0.69 mmol) obtained in Step 56-2 was used instead of N-(5-aminopyridin-2-yl)-5-methylpyrazine-2-carboxamide.

$^1$H NMR (400 MHz, DMSO-$d_6$) δ 11.06 (s, 1H), 9.28 (d, J=1.5 Hz, 1H), 8.38 (d, J=1.5 Hz, 1H), 8.00 (dd, J=12.3 Hz, 2.0 Hz, 1H), 7.93 (dd, J=8.5 Hz, 1.9 Hz, 1H), 7.61 (t, J=8.3 Hz, 1H), 2.50 (s, 3H).

Example 57: Preparation of (2-methoxy-4-(6-methylpyridin-3-ylcarbamoyl)phenyl)carbonohydrazonoyl dicyanide (Compound 57)

Step 57-1: Preparation of 3-methoxy-N-(6-methylpyridin-3-yl)-4-nitrobenzamide 229 mg (yield: 78%) of the title compound was obtained in the same manner as in Step 34-1 of Example 34 above, except that 3-methoxy-4-nitrobenzoic acid (200 mg, 1.01 mmol) was used instead of 5-nitrocholic acid, and 5-amino-2-methylpyridine (110 mg, 1.01 mmol) was used instead of p-toluidine.

$^1$H NMR (400 MHz, DMSO-$d_6$) δ 10.59 (s, 1H), 8.79 (d, J=2.6 Hz, 1H), 8.10-8.02 (m, 2H), 7.84 (d, J=1.7 Hz, 1H), 7.68 (dd, J=8.4 Hz, 1.7 Hz, 1H), 7.29 (d, J=8.4 Hz, 1H), 4.04 (s, 3H), 2.47 (s, 3H).

Step 57-2: Preparation of 4-amino-3-methoxy-N-(6-methylpyridin-3-yl)benzamide 122 mg (yield: 59%) of the title compound was obtained in the same manner as in Step 34-2 of Example 34 above, except that 3-methoxy-N-(6-methylpyridin-3-yl)-4-nitrobenzamide (229 mg, 0.80 mmol) obtained in Step 57-1 was used instead of 5-nitro-N-p-tolylpicolinamide.

$^1H$ NMR (400 MHz, DMSO-$d_6$) δ 9.91 (s, 1H), 8.77 (d, J=2.6 Hz, 1H), 8.03 (dd, J=8.4, 2.6 Hz, 1H), 7.47 (dd, J=8.2, 1.9 Hz, 1H), 7.43 (d, J=1.9 Hz, 1H), 7.22 (d, J=8.4 Hz, 1H), 6.68 (d, J=8.2 Hz, 1H), 5.45 (s, 2H), 3.86 (s, 3H), 2.44 (s, 3H).

Step 57-3: Preparation of (2-methoxy-4-(6-methylpyridin-3-ylcarbamoyl)phenyl)carbonohydrazonoyl dicyanide 46 mg (yield: 59%) of the title compound was obtained in the same manner as in Step 1-3 of Example 1 above, except that 4-amino-3-methoxy-N-(6-methylpyridin-3-yl)benzamide (60 mg, 0.23 mmol) obtained in Step 57-2 was used instead of N-(5-aminopyridin-2-yl)-5-methylpyrazine-2-carboxamide.

$^1H$ NMR (400 MHz, DMSO-$d_6$) δ 11.35 (s, 1H), 9.27 (d, J=2.4 Hz, 1H), 8.76 (dd, J=8.8 Hz, 2.4 Hz, 1H), 7.93 (d, J=1.8 Hz, 1H), 7.88 (d, J=8.8 Hz, 1H), 7.78 (dd, J=8.4 Hz, 1.8 Hz, 1H), 7.59 (d, J=8.4 Hz, 1H), 4.07 (s, 3H), 2.70 (s, 3H).

Example 58: Preparation of (6-(phenylsulfonamido)pyridin-3-yl)carbonohydrazonoyl dicyanide (Compound 58)

Step 58-1: Preparation of N-(5-nitropyridin-2-yl)benzenesulfonamide

5-Nitropyridine-2-amine (100 mg, 0.72 mmol) was dissolved in THE (8 mL), and a reaction temperature was lowered to 0° C., and then sodium hydride (35 mg, 1.44 mmol) was added thereto. After the reaction mixture was stirred at 0° C. for 20 minutes, benzenesulfonyl chloride (111 μL, 0.86 mmol) was added thereto, and the reaction mixture was stirred at room temperature for 4.5 hours. Upon completion of the reaction, a reaction product was extracted dichloromethane and distilled water to obtain an organic layer, and the organic layer was dried over anhydrous magnesium sulfate and filtered. The filtrate was concentrated under reduced pressure, and the crude material was purified by column chromatography to obtain 105 mg (yield: 52%) of the title compound.

$^1H$ NMR (400 MHz, DMSO-$d_6$) δ 12.20 (s, 1H), 8.99 (d, J=2.7 Hz, 1H), 8.46 (dd, J=9.2 Hz, 2.8 Hz, 1H), 8.00 (dd, J=7.3 Hz, 1.9 Hz, 2H), 7.69-7.65 (m, 1H), 7.62 (d, 2H), 7.18 (d, J=9.2 Hz, 1H).

Step 58-2: Preparation of N-(5-aminopyridin-2-yl)benzenesulfonamide

N-(5-Nitropyridin-2-yl)benzenesulfonamide (105 mg, 0.37 mmol) obtained in Step 58-1 and 10% Pd/C (45 mg, 0.04 mmol) were dissolved in methanol (4 mL), and the reaction mixture was stirred at room temperature for 1 hour under a hydrogen atmosphere. Upon completion of the reaction, the reaction mixture was filtered using celite to remove the catalyst from the reaction mixture. The filtrate was concentrated under reduced pressure, and the crude material was purified by column chromatography to obtain 94 mg (yield: 52%) of the title compound.

$^1H$ NMR (400 MHz, DMSO-$d_6$) δ 10.40 (s, 1H), 7.80-7.73 (m, 2H), 7.62-7.54 (m, 1H), 7.57-7.48 (m, 2H), 7.47 (t, J=1.7 Hz, 1H), 6.98-6.88 (m, 2H), 5.08 (s, 2H).

Step 58-3: Preparation of (6-phenylsulfonamido)pyridin-3-yl)carbonohydrazonoyl dicyanide 24 mg (yield: 44%) of the title compound was obtained in the same manner as in Step 1-3 of Example 1 above, except that N-(5-aminopyridin-2-yl)benzenesulfonamide (42 mg, 0.17 mmol) obtained in Step 58-2 was used instead of N-(5-aminopyridin-2-yl)-5-methylpyrazine-2-carboxamide.

$^1H$ NMR (400 MHz, DMSO-$d_6$) δ 11.14 (s, 1H), 8.22 (s, 1H), 7.90 (d, 2H), 7.77 (dd, J=9.0 Hz, 2.8 Hz, 1H), 7.63 (d, 1H), 7.57 (d, 2H), 7.16 (d, J=9.0 Hz, 1H).

Example 59: Preparation of (6-(4-methoxyphenylsulfonamido)pyridin-3-yl)carbonohydrazonoyl dicyanide (Compound 59)

Step 59-1: Preparation of 4-methoxy-N-(5-nitropyridin-2-yl)benzenesulfonamide 191 mg (yield: 43%) of the title compound was obtained in the same manner as in Step 58-1 of Example 58 above, except that 4-methoxybenzene-1-sulfonyl chloride (411 mg, 2.15 mmol) was used instead of benzenesulfonyl chloride.

$^1H$ NMR (400 MHz, DMSO-$d_6$) δ 12.00 (s, 1H), 9.01 (dt, J=8.5 Hz, 3.5 Hz, 1H), 8.45 (td, J=8.8 Hz, 3.3 Hz, 1H), 7.95 (dt, J=14.1 Hz, 5.8 Hz, 2H), 7.14 (dt, J=14.5 Hz, 8.6 Hz, 3H), 3.84 (t, J=6.3 Hz, 3H).

Step 59-2: Preparation of N-(5-aminopyridin-2-yl)-4-methoxybenzenesulfonamide 193 mg (yield: 75%) of the title compound was obtained in the same manner as in Step 58-2 of Example 58 above, except that 4-methoxy-N-(5-nitropyridin-2-yl)benzenesulfonamide (285 mg, 0.92 mmol) obtained in Step 59-1 was used instead of N-(5-nitropyridin-2-yl)benzenesulfonamide.

$^1H$ NMR (400 MHz, DMSO-$d_6$) δ 10.15 (s, 1H), 7.69 (d, 2H), 7.50 (t, J=1.8 Hz, 1H), 7.04 (d, 2H), 6.91 (d, J=1.7 Hz, 2H), 5.06 (s, 2H), 3.80 (s, 3H).

Step 59-3: Preparation of (6-(4-methoxyphenylsulfonamido)pyridin-3-yl)carbonohydrazonoyl dicyanide 20 mg (yield: 9%) of the title compound was obtained in the same manner as in Step 1-3 of Example 1 above, except that N-(5-aminopyridin-2-yl)-4-methoxybenzenesulfonamide (176 mg, 0.63 mmol) obtained in Step 59-2 was used instead of N-(5-aminopyridin-2-yl)-5-methylpyrazine-2-carboxamide.

$^1H$ NMR (400 MHz, DMSO-$d_6$) δ 11.02 (s, 1H), 8.25 (d, J=2.7 Hz, 1H), 7.83 (d, 2H), 7.76 (dd, J=9.0 Hz, 2.8 Hz, 1H), 7.14 (d, J=9.0 Hz, 1H), 7.08 (d, 2H), 3.81 (s, 3H).

Example 60: Preparation of (6-(pyridin-3-sulfonamido)pyridin-3-yl)carbonohydrazonoyl dicyanide (Compound 60)

Step 60-1: Preparation of N(5-nitropyridin-2-yl)pyridin-3-sulfonamide 115 mg (yield: 40%) of the title compound was obtained in the same manner as in Step 58-1 of Example 58 above, except that pyridin-3-sulfonyl chloride (270 mg, 1.52 mmol) was used instead of benzenesulfonyl chloride.

$^1H$ NMR (400 MHz, DMSO-$d_6$) δ 12.50 (s, 2H), 9.14 (d, J=2.4 Hz, 2H), 9.00 (d, J=2.8 Hz, 2H), 8.83 (dd, J=4.9 Hz, 1.6 Hz, 2H), 8.45 (dd, J=9.2 Hz, 2.8 Hz, 2H), 8.38 (dt, J=8.2 Hz, 2.0 Hz, 2H), 7.65 (dd, J=8.1 Hz, 4.8 Hz, 2H), 7.15 (d, J=9.2 Hz, 2H).

Step 60-2: Preparation of N-(5-aminopyridin-2-yl)pyridin-3-sulfonamide 56 mg (yield: 54%) of the title compound was obtained in the same manner as in Step 58-2 of Example 58 above, except that 4-methoxy-N-(5-nitropyridin-2-yl)pyridin-3-sulfonamide (115 mg, 0.41 mmol) obtained in Step 60-1 was used instead of N-(5-nitropyridin-2-yl)benzenesulfonamide.

$^1$H NMR (400 MHz, DMSO-$d_6$) δ 10.94 (s, 1H), 8.89 (dd, J=2.4 Hz, 0.8 Hz, 1H), 8.74 (dd, J=4.8 Hz, 1.6 Hz, 1H), 8.13 (ddd, J=8.0 Hz, 2.3 Hz, 1.6 Hz, 1H), 7.58 (ddd, J=8.1 Hz, 4.8 Hz, 0.9 Hz, 1H), 7.43 (d, J=2.8 Hz, 1H), 7.02 (dd, J=8.8 Hz, 2.8 Hz, 1H), 6.96 (d, J=8.7 Hz, 1H), 5.15 (s, 2H).

Step 60-3: Preparation of (6-(pyridin-3-sulfonamido)pyridin-3-yl)carbonohydrazonoyl dicyanide 4 mg (yield: 5%) of the title compound was obtained in the same manner as in Step 1-3 of Example 1 above, except that N-(5-aminopyridin-2-yl)pyridin-3-sulfonamide (55 mg, 0.22 mmol) obtained in Step 60-2 was used instead of N-(5-aminopyridin-2-yl)-5-methylpyrazine-2-carboxamide.

$^1$H NMR (400 MHz, DMSO-$d_6$) δ 9.03 (d, J=2.4 Hz, 2H), 8.77 (dd, J=4.8 Hz, 1.6 Hz, 2H), 8.25 (dt, J=8.1 Hz, 2.1 Hz, 2H), 8.06 (s, 2H), 7.78 (dd, J=9.0 Hz, 2.7 Hz, 2H), 7.60 (dd, J=8.1 Hz, 4.8 Hz, 2H), 7.17 (d, J=9.1 Hz, 2H), 11.70 (s, 1H).

Example 61: Preparation of (6-(1-methyl-1H-pyrazole-4-sulfonamido)pyridin-3-yl)carbonohydrazonoyl dicyanide (Compound 61)

Step 61-1: Preparation of 1-methyl-N-(5-nitropyridin-2-yl)-1H-pyrazole-4-sulfonamide 187 mg (yield: 45%) of the title compound was obtained in the same manner as in Step 58-1 of Example 58 above, except that 1-methyl-1H-pyrazole-4-sulfonylchloride (390 mg, 2.16 mmol) was used instead of benzenesulfonyl chloride.

$^1$H NMR (400 MHz, DMSO-$d_6$) δ 11.98 (s, 1H), 9.12 (d, J=2.8 Hz, 1H), 8.51 (s, 1H), 8.46 (dd, J=9.2 Hz, 2.8 Hz, 1H), 7.95 (d, J=0.8 Hz, 1H), 7.15-7.09 (m, 1H), 3.87 (s, 3H).

Step 61-2: Preparation of N-(5-aminopyridin-2-yl)-1-methyl-1H-pyrazole-4-sulfonamide 125 mg (yield: 75%) of the title compound was obtained in the same manner as in Step 58-2 of Example 58 above, except that 1-methyl-N-(5-nitropyridin-2-yl)-1H-pyrazole-4-sulfonamide (185 mg, 0.65 mmol) obtained in Step 61-1 was used instead of N-(5-nitropyridin-2-yl)benzenesulfonamide.

$^1$H NMR (400 MHz, DMSO-$d_6$) δ 10.14 (s, 1H), 8.17 (s, 1H), 7.64 (d, J=0.7 Hz, 1H), 7.60-7.54 (m, 1H), 6.96 (dd, J=8.7 Hz, 2.7 Hz, 1H), 6.92 (dd, J=8.7 Hz, 0.8 Hz, 1H), 5.09 (s, 2H), 3.84 (s, 3H).

Step 61-3: Preparation of (6-(1-methyl-1H-pyrazole-4-sulfonamido)pyridin-3-yl)carbonohydrazonoyl dicyanide 27 mg (yield: 16%) of the title compound was obtained in the same manner as in Step 1-3 of Example 1 above, except that N-(5-aminopyridin-2-yl)-1-methyl-1H-pyrazole-4-sulfonamide (124 mg, 0.49 mmol) obtained in Step 61-2 was used instead of N-(5-aminopyridin-2-yl)-5-methylpyrazine-2-carboxamide.

$^1$H NMR (400 MHz, DMSO-$d_6$) δ13.05 (s, 1H), 11.00 (s, 1H), 8.36 (s, 1H), 8.33 (d, J=2.6 Hz, 1H), 7.81 (d, J=0.8 Hz, 1H), 7.78 (dd, J=9.0 Hz, 2.8 Hz, 1H), 7.12 (d, J=9.0 Hz, 1H), 3.85 (s, 3H).

Example 62: Preparation of (6-(thiophene-2-sulfonamido)pyridin-3-yl)carbonohydrazonoyl dicyanide (Compound 62)

Step 62-1: Preparation of N-(5-nitropyridin-2-yl)thiophene-2-sulfonamide 156 mg (yield: 38%) of the title compound was obtained in the same manner as in Step 58-1 of Example 58 above, except that 2-thiophenesulfonylchloride (341 mg, 1.87 mmol) was used instead of benzenesulfonyl chloride.

$^1$H NMR (400 MHz, DMSO-$d_6$) δ 12.47 (s, 1H), 9.09-9.04 (m, 1H), 8.50 (dd, J=9.2 Hz, 2.8 Hz, 1H), 7.99 (dd, J=5.0 Hz, 1.4 Hz, 1H), 7.86 (dd, J=3.8 Hz, 1.4 Hz, 1H), 7.26-7.20 (m, 1H), 7.18 (dd, J=5.0 Hz, 3.8 Hz, 1H).

Step 62-2: Preparation of N-(5(-aminopyridin-2-yl)thiophene-2-sulfonamide 49 mg (yield: 37%) of the title compound was obtained in the same manner as in Step 58-2 of Example 58 above, except that N-(5-nitropyidin-2-yl)thiophene-2-sulfonamide (148 mg, 0.52 mmol) obtained in Step 62-1 was used instead of N-(5-nitropyidin-2-yl)benzenesulfonamide.

$^1$H NMR (400 MHz, DMSO-$d_6$) δ 10.95 (s, 1H), 7.81 (dd, J=5.0 Hz, 1.4 Hz, 1H), 7.53-7.44 (m, 2H), 7.14-7.01 (m, 2H), 7.00 (d, J=8.7 Hz, 1H), 5.14 (s, 2H).

Step 62-3: Preparation of (6-(thiophene-2-sulfonamido)pyridin-3-yl)carbonohydrazonoyl dicyanide 6 mg (yield: 9%) of the title compound was obtained in the same manner as in Step 1-3 of Example 1 above, except that N-(5-aminopyridin-2-yl)thiophene-2-sulfonamide (49 mg, 0.19 mmol) obtained in Step 62-2 was used instead of N-(5-aminopyridin-2-yl)-5-methylpyrazine-2-carboxamide.

$^1$H NMR (400 MHz, DMSO-$d_6$) δ 11.37 (s, 1H), 8.26 (s, 1H), 7.91 (dd, J=5.0 Hz, 1.4 Hz, 1H), 7.84 (dd, J=9.1 Hz, 2.8 Hz, 1H), 7.70 (dd, J=3.8 Hz, 1.4 Hz, 1H), 7.22 (d, J=9.0 Hz, 1H), 7.14 (dd, J=5.0 Hz, 3.7 Hz, 1H).

Example 63: Preparation of (6-(4-methylphenylsulfonamido)pyridin-3-yl)carbonohydrazonoyl dicyanide (Compound 63)

Step 63-1: Preparation of 4-methyl-N-(5-nitropyridin-2-yl)benzenesulfonamide 121 mg (yield: 29%) of the title compound was obtained in the same manner as in Step 58-1 of Example 58 above, except that p-toluenesulfonyl chloride (356 mg, 1.87 mmol) was used instead of benzenesulfonyl chloride.

$^1$H NMR (400 MHz, DMSO-$d_6$) δ 12.10 (s, 1H), 8.99 (d, J=2.7 Hz, 1H), 8.45 (dd, J=9.2 Hz, 2.8 Hz, 1H), 7.92-7.84 (m, 2H), 7.45-7.38 (m, 2H), 7.17 (d, J=9.2 Hz, 1H), 2.37 (s, 3H).

Step 63-2: Preparation of N-(6-aminopyridin-2-yl)-4-methylbenzenesulfonamide 63 mg (yield: 58%) of the title compound was obtained in the same manner as in Step 58-2 of Example 58 above, except that 4-methyl-N-(5-nitropyridin-2-yl)benzenesulfonamide (121 mg, 0.41 mmol) obtained in Step 63-1 was used instead of N-(5-nitropyridin-2-yl)benzenesulfonamide.

$^1$H NMR (400 MHz, DMSO-$d_6$) δ 10.27 (s, 1H), 7.68-7.60 (m, 2H), 7.48 (t, J=1.8 Hz, 1H), 7.31 (d, J=8.1 Hz, 2H), 6.91 (d, J=1.7 Hz, 2H), 5.06 (s, 2H), 2.34 (s, 3H).

Step 63-3: Preparation of (6-(4-methylphenylsulfonamido)pyridin-3-yl)carbonohydrazonoyl dicyanide 2 mg (yield: 2%) of the title compound was obtained in the same manner as in Step 1-3 of Example 1 above, except that N-(5-aminopyridin-2-yl)-4-methylbenzenesulfonamide (60 mg, 0.27 mmol) obtained in Step 63-2 was used instead of N-(5-aminopyridin-2-yl)-5-methylpyrazine-2-carboxamide.

$^1$H NMR (400 MHz, DMSO-$d_6$) δ 11.11 (s, 1H), 8.22 (s, 1H), 7.77 (dd, J=12.2 Hz, 9.2 Hz, 3H), 7.37 (d, J=8.0 Hz, 2H), 7.15 (d, J=9.0 Hz, 1H), 2.36 (s, 3H).

Example 64: Preparation of (6-(4-fluorophenylsulfonamido)pyridin-3-yl)carbonohydrazonoyl dicyanide (Compound 64)

Step 64-1: Preparation of 4-fluoro-N-(5-nitropyridin-2-yl)benzenesulfonamide 204 mg (yield: 38%) of the title compound was obtained in the same manner as in Step 58-1 of Example 58 above, except that 4-fluorosulfonylchloride (420 mg, 2.16 mmol) was used instead of benzenesulfonyl chloride.

$^1$H NMR (400 MHz, DMSO-$d_6$) δ 12.26 (s, 1H), 9.01 (d, J=2.8 Hz, 1H), 8.47 (dd, J=9.2 Hz, 2.8 Hz, 1H), 8.13-8.02 (m, 2H), 7.51-7.41 (m, 2H), 7.17 (d, J=9.2 Hz, 1H).

Step 64-2: Preparation of N-(5-aminopyridin-2-yl)-4-fluorobenzenesulfonamide 153 mg (yield: 83%) of the title compound was obtained in the same manner as in Step 58-2 of Example 58 above, except that 4-fluoro-N-(5-nitropyridin-2-yl)benzenesulfonamide (204 mg, 0.69 mmol) obtained in Step 64-1 was used instead of N-(5-nitropyridin-2-yl)benzenesulfonamide.

$^1$H NMR (400 MHz, DMSO-$d_6$) δ 10.51 (s, 1H), 7.87-7.77 (m, 2H), 7.48 (d, J=2.6 Hz, 1H), 7.42-7.29 (m, 2H), 7.02-6.88 (m, 2H), 5.10 (s, 2H).

Step 64-3: Preparation of (6-(4-fluorophenylsulfonamido)pyridin-3-yl)carbonohydrazonoyl dicyanide 58 mg (yield: 29%) of the title compound was obtained in the same manner as in Step 1-3 of Example 1 above, except that N-(5-aminopyridin-2-yl)-4-fluorobenzenesulfonamide (150 mg, 0.56 mmol) obtained in Step 64-2 was used instead of N-(5-aminopyridin-2-yl)-5-methylpyrazine-2-carboxamide.

$^1$H NMR (400 MHz, DMSO-$d_6$) δ 13.02 (s, 1H), 11.30 (s, 3H), 8.25 (d, J=2.7 Hz, 2H), 8.03-7.91 (m, 4H), 7.79 (dd, J=9.0 Hz, 2.8 Hz, 2H), 7.47-7.37 (m, 4H), 7.15 (d, J=9.0 Hz, 2H).

Example 65: Preparation of (4-(N-(6-methylpyridin-3-yl)sulfamoyl)phenyl)carbonohydrazonoyl dicyanide (Compound 65)

Step 65-1: Preparation of N-(6-methylpyridin-3-yl)-4-nitrobenzenesulfonamide

5-Amino-2-methylpyridine (49 mg, 0.45 mmol) was dissolved in dichloromethane (5 mL), and a reaction temperature was lowered to 0° C., and then pyridine (55 μL, 0.68 mmol) was added thereto. After the reaction mixture was stirred at 0° C. for 5 minutes, 4-nitrobenzenesulfonyl chloride (100 mg, 0.45 mmol) was added thereto, and the reaction mixture was stirred at 0° C. for 1.5 hours. Upon completion of the reaction, a reaction product was extracted using dichloromethane and distilled water to obtain an organic layer, and the organic layer was dried over anhydrous magnesium sulfate and filtered. The filtrate was concentrated under reduced pressure, and the crude material was purified by column chromatography to obtain 70 mg (yield: 52%) of the title compound.

$^1$H NMR (400 MHz, DMSO-$d_6$) δ 10.70 (s, 1H), 8.42-8.35 (m, 2H), 8.14 (d, J=2.7 Hz, 1H), 8.01-7.94 (m, 2H), 7.40 (dd, J=8.4 Hz, 2.7 Hz, 1H), 7.17 (d, J=8.4 Hz, 1H), 2.37 (s, 3H).

Step 65-2: Preparation of 4-amino-N-(6-methylpyridin-3-yl)benzenesulfonamide

N-(6-Methylpyridin-3-yl)-4-nitrobenzenesulfonamide (142 mg, 0.48 mmol) obtained in Step 65-1 and 10% Pd/C (57 mg, 0.05 mmol) were dissolved in ethyl acetate (6 mL), and the reaction mixture was stirred at room temperature for 1 hour under a hydrogen atmosphere. Upon completion of the reaction, the reaction mixture was filtered using celite to remove the catalyst from the reaction mixture. The filtrate was concentrated under reduced pressure, and the crude material was purified by column chromatography to obtain 107 mg (yield: 84%) of the title compound.

$^1$H NMR (400 MHz, DMSO-$d_6$) δ 9.89 (s, 1H), 8.10 (dd, J=2.7 Hz, 0.7 Hz, 1H), 7.39-7.30 (m, 3H), 7.11 (d, J=8.3 Hz, 1H), 6.57-6.49 (m, 2H), 6.00 (s, 2H), 2.35 (s, 3H).

Step 65-3: Preparation of (4-(N-(6-methylpyridin-3-yl)sulfamoyl)phenyl)carbonohydrazonoyl dicyanide 115 mg (yield: 84%) of the title compound was obtained in the same manner as in Step 1-3 of Example 1 above, except that 4-amino-N-(6-methylpyridin-3-yl)benzenesulfonamide (105 mg, 0.40 mmol) obtained in Step 65-2 was used instead of N-(5-aminopyridin-2-yl)-5-methylpyrazine-2-carboxamide.

$^1$H NMR (400 MHz, DMSO-$d_6$) δ 10.45 (s, 1H), 8.16 (d, J=2.6 Hz, 1H), 7.78-7.70 (m, 2H), 7.59-7.51 (m, 2H), 7.48 (dd, J=8.4 Hz, 2.7 Hz, 1H), 7.25 (d, J=8.4 Hz, 1H), 2.40 (s, 3H).

Example 66: Preparation of (4-(N-(4-methoxyphenyl)sulfamoyl)phenyl)carbonohydrazonoyl dicyanide (Compound 66)

Step 66-1: Preparation of N-(4-methoxyphenyl)-4-nitrobenzenesulfonamide 182 mg (yield: 48%) of the title compound was obtained in the same manner as in Step 65-1 of Example 65 above, except that 4-methoxyaniline (150 mg, 1.22 mmol) was used instead of 5-amino-2-methylpyridine.

$^1$H NMR (400 MHz, DMSO-$d_6$) δ 10.25 (s, 1H), 8.42-8.34 (m, 2H), 7.96-7.88 (m, 2H), 7.03-6.95 (m, 2H), 6.88-6.79 (m, 2H), 3.69 (s, 3H).

Step 66-2: Preparation of 4-amino-N-(4-methoxyphenyl)benzenesulfonamide 149 mg (yield: 91%) of the title compound was obtained in the same manner as in Step 65-2 of Example 65 above, except that N-(4-methoxyphenyl)-4-nitrobenzenesulfonamide (180 mg, 0.58 mmol) obtained in Step 66-1 was used instead of N-(6-methylpyridin-3-yl)-4-nitrobenzenesulfonamide.

$^1$H NMR (400 MHz, DMSO-$d_6$) δ 9.45 (s, 1H), 7.34-7.26 (m, 2H), 6.99-6.91 (m, 2H), 6.82-6.73 (m, 2H), 6.55-6.47 (m, 2H), 5.91 (s, 2H), 3.66 (s, 3H).

Step 66-3: Preparation of (4-(N-(4-methoxyphenyl)sulfamoyl)phenyl)carbonohydrazonoyl dicyanide 42 mg (yield: 22%) of the title compound was obtained in the same manner as in Step 1-3 of Example 1 above, except that 4-amino-N-(4-methoxyphenyl)benzenesulfonamide (145 mg, 0.52 mmol) obtained in Step 66-2 was used instead of N-(5-aminopyridin-2-yl)-5-methylpyrazine-2-carboxamide.

$^1$H NMR (400 MHz, DMSO-$d_6$) δ 13.15 (s, 1H), 9.86 (s, 1H), 7.72-7.64 (m, 2H), 7.58-7.50 (m, 2H), 7.00-6.92 (m, 2H), 6.84-6.76 (m, 2H), 3.67 (s, 3H).

Example 67: Preparation of (4-(N-(5-methylpyrazin-2-yl)sulfamoyl)phenyl)carbonohydrazonoyl dicyanide (Compound 67)

Step 67-1: Preparation of N-(5-methylpyrazin-2-yl)-4-nitrobenzenesulfonamide 41 mg (yield: 20%) of the title compound was obtained in the same manner as in Step 65-1 of Example 65 above, except that 5-methylpyrazine-2-amine (74 mg, 0.68 mmol) was used instead of 5-amino-2-methylpyridine.

$^1$H NMR (400 MHz, DMSO-$d_6$) δ 11.73 (s, 1H), 8.44-8.36 (m, 2H), 8.29 (d, J=1.5 Hz, 1H), 8.22-8.14 (m, 2H), 8.12 (d, J=1.5 Hz, 1H), 2.37 (s, 3H).

Step 67-2: Preparation of 4-amino-N-(4-methylpyrazin-2-yl)benzenesulfonamide 66 mg (yield: 44%) of the title compound was obtained in the same manner as in Step 65-2 of Example 65 above, except that N-(5-methylpyrazin-2-yl)-4-nitrobenzenesulfonamide (166 mg, 0.56 mmol) obtained in Step 67-1 was used instead of N-(6-methylpyridin-3-yl)-4-nitrobenzenesulfonamide.

$^1$H NMR (400 MHz, DMSO-$d_6$) δ 10.85 (s, 1H), 8.25 (d, J=1.5 Hz, 1H), 8.12 (d, J=1.5 Hz, 1H), 7.57-7.49 (m, 2H), 6.61-6.53 (m, 2H), 6.05 (s, 2H), 2.36 (s, 3H).

Step 67-3: Preparation of (4-(N-(5-methylpyrazin-2-yl)sulfamoyl)phenyl)carbonohydrazonoyl dicyanide 5 mg (yield: 5%) of the title compound was obtained in the same manner as in Step 1-3 of Example 1 above, except that 4-amino-N-(4-methylpyrazin-2-yl)benzenesulfonamide (65 mg, 0.25 mmol) obtained in Step 67-2 was used instead of N-(5-aminopyridin-2-yl)-5-methylpyrazine-2-carboxamide.

$^1$H NMR (400 MHz, DMSO-$d_6$) δ 11.29 (s, 1H), 8.27 (d, J=1.5 Hz, 1H), 8.12 (d, J=1.5 Hz, 1H), 7.96-7.88 (m, 2H), 7.63-7.54 (m, 2H), 2.36 (s, 3H).

Example 68: Preparation of (6-phenoxypyridin-3-yl)carbonohydrazonoyl dicyanide (Compound 68)

Step 68-1: Preparation of 5-nitro-2-phenoxypyridine

2-Chloro-5-nitropyridine (200 mg, 1.26 mmol) was dissolved in DMF, and phenol (133 μL, 1.51 mmol) and potassium carbonate (698 mg, 1.84 mmol) were added thereto. The reaction mixture was stirred in a microwave at 150° C. for 1 hour. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 121 mg (yield: 44%) of the title compound.

$^1$H NMR (400 MHz, DMSO-$d_6$) δ 9.03 (d, J=2.8 Hz, 1H), 8.63 (dd, J=9.1 Hz, 2.9 Hz, 1H), 7.48 (dd, J=8.4 Hz, 7.3 Hz, 2H), 7.34-7.22 (m, 4H).

Step 68-2: Preparation of 6-phenoxypyridine-3-amine 64 mg (yield: 74%) of the title compound was obtained in the same manner as in Step 1-2 of Example 1 above, except that 5-nitro-2-phenoxypyridine (100 mg, 0.46 mmol) obtained in Step 68-1 was used instead of 5-methyl-N-(5-nitropyridin-2-yl)pyrazine-2-carboxamide.

1H NMR (400 MHz, DMSO-$d_6$) δ 9.03 (d, J=2.8 Hz, 1H), 8.63 (dd, J=9.1 Hz, 2.9 Hz, 1H), 7.48 (dd, J=8.4 Hz, 7.3 Hz, 2H), 7.34-7.20 (m, 4H).

Step 68-3: Preparation of (6-phenoxypyridin-3-yl)carbonohydrazonoyl Dicyanide 14 mg (yield: 19%) of the title compound was obtained in the same manner as in Step 1-3 of Example 1 above, except that 6-phenoxypyridine-3-amine (50 mg, 0.27 mmol) obtained in Step 68-2 was used instead of N-(5-aminopyridin-2-yl)-5-methylpyrazine-2-carboxamide.

$^1$H NMR (400 MHz, DMSO-$d_6$) δ 8.27 (d, J=2.8 Hz, 1H), 7.92 (dd, J=8.9 Hz, 2.8 Hz, 1H), 7.43 (t, J=7.9 Hz, 2H), 7.23 (t, J=7.4 Hz, 1H), 7.13 (d, J=8.2 Hz, 2H), 7.10 (d, J=8.9 Hz, 1H).

Example 69: Preparation of (6-(3-fluorophenoxy)pyridin-3-yl)carbonohydrazonoyl dicyanide (Compound 69)

Step 69-1: Preparation of 2-(3-fluorophenoxy)-5-nitropyridine 267 mg (yield: 90%) of the title compound was obtained in the same manner as in Step 68-1 of Example 68 above, except that 3-fluorophenol was used instead of phenol.

$^1$H NMR (400 MHz, DMSO-$d_6$) δ 9.05 (s, 1H), 8.65 (d, J=9.2 Hz, 1H), 7.52 (q, J=7.4 Hz, 6.5 Hz, 2H), 7.31 (d, J=9.1 Hz, 1H), 7.24-7.09 (m, 3H).

Step 69-2: Preparation of 6-(3-fluorophenoxy)pyridine-3-amine 172 mg (yield: 76%) of the title compound was obtained in the same manner as in Step 1-2 of Example 1 above, except that 2-(3-fluorophenoxy)-5-nitropyridine (260 mg, 1.11 mmol) obtained in Step 69-1 was used instead of 5-methyl-N-(5-nitropyridin-2-yl)pyrazine-2-carboxamide.

$^1$H NMR (400 MHz, DMSO-$d_6$) δ 7.58 (d, J=2.9 Hz, 1H), 7.41-7.31 (m, 1H), 7.10 (dd, J=8.6 Hz, 3.0 Hz, 1H), 6.96-6.88 (m, 1H), 6.85-6.73 (m, 3H), 5.18 (s, 2H).

Step 69-3: Preparation of (6-(3-fluorophenoxy)pyridin-3-yl)carbonohydrazonoyl dicyanide 92 mg (yield: 44%) of the title compound was obtained in the same manner as in Step 1-3 of Example 1 above, except that 6-(3-fluorophenoxy)pyridine-3-amine (150 mg, 0.73 mmol) obtained in Step 69-2 was used instead of N-(5-aminopyridin-2-yl)-5-methylpyrazine-2-carboxamide.

$^1$H NMR (400 MHz, DMSO-$d_6$) δ 8.29 (d, J=2.8 Hz, 1H), 7.94 (dd, J=8.9 Hz, 2.8 Hz, 1H), 7.51-7.39 (m, 1H), 7.15 (d, J=8.9 Hz, 1H), 7.11-7.03 (m, 2H), 7.02-6.95 (m, 1H).

Example 70: Preparation of (5-phenoxypyridin-2-yl)carbonohydrazonoyl dicyanide (Compound 70)

Step 70-1: Preparation of 2-nitro-5-phenoxypyridine 73 mg (yield: 18%) of the title compound was obtained in the same manner as in Step 68-1 of Example 68 above, except that 5-chloro-2-nitropyridine (300 mg, 1.89 mmol) was used instead of 2-chloro-5-nitropyridine.

$^1$H NMR (400 MHz, DMSO-$d_6$) δ 9.06-9.00 (m, 1H), 8.63 (dd, J=9.1 Hz, 2.9 Hz, 1H), 7.53-7.45 (m, 2H), 7.34-7.22 (m, 4H).

Step 70-2: Preparation of 5-phenoxypyridine-2-amine 73 mg (yield: 56%) of the title compound was obtained in the same manner as in Step 1-2 of Example 1 above, except that 2-nitro-5-phenoxypyridine (150 mg, 0.69 mmol) obtained in Step 70-1 was used instead of 5-methyl-N-(5-nitropyridin-2-yl)pyrazine-2-carboxamide.

$^1$H NMR (400 MHz, DMSO-$d_6$) δ 7.55 (d, J=2.7 Hz, 1H), 7.37-7.27 (m, 2H), 7.11-7.05 (m, 2H), 6.97-6.91 (m, 2H), 6.76 (d, J=8.6 Hz, 1H), 5.10 (s, 2H).

Step 70-3: Preparation of (6-phenoxypyridin-2-yl)carbonohydrazonoyl Dicyanide 132 mg (yield: 62%) of the title compound was obtained in the same manner as in Step 1-3 of Example 1 above, except that 5-phenoxypyridine-2-amine (150 mg, 0.80 mmol) obtained in Step 70-2 was used instead of N-(5-aminopyridin-2-yl)-5-methylpyrazine-2-carboxamide.

$^1$H NMR (400 MHz, DMSO-$d_6$) δ 8.26 (d, J=2.8 Hz, 1H), 7.91 (dd, J=8.9 Hz, 2.8 Hz, 1H), 7.46-7.38 (m, 2H), 7.22 (t, J=7.4 Hz, 1H), 7.16-7.07 (m, 3H).

Example 71: Preparation of (3-fluoro-4-phenoxyphenyl)carbonohydrazonoyl dicyanide (Compound 71)

Step 71-1: Preparation of 2-fluoro-4-nitro-1-phenoxybenzene 619 mg (yield: 98%) of the title compound was obtained in the same manner as in Step 68-1 of Example 68 above, except that 1,2-difluoro-4-nitrobenzene (0.30 mL, 2.71 mmol) was used instead of 2-chloro-5-nitrophenide.

$^1$H NMR (400 MHz, DMSO-$d_6$) δ 8.34 (dd, J=10.8 Hz, 2.8 Hz, 1H), 8.10 (dt, J=9.3 Hz, 1.5 Hz, 1H), 7.50 (t, J=7.7 Hz, 2H), 7.35-7.27 (m, 1H), 7.21 (d, J=8.7 Hz, 2H), 7.15 (t, J=8.7 Hz, 1H).

Step 71-2: Preparation of 3-fluoro-4-phenoxyaniline 536 mg (yield: 98%) of the title compound was obtained in the same manner as in Step 1-2 of Example 1 above, except that 2-fluoro-4-nitro-1-phenoxybenzene (630 mg, 2.70 mmol) obtained in Step 71-1 was used instead of 5-methyl-N-(5-nitropyidin-2-yl)pyrazine-2-carboxamide.

$^1$H NMR (400 MHz, DMSO-$d_6$) δ 7.34-7.26 (m, 2H), 7.01 (t, J=7.3 Hz, 1H), 6.91 (t, J=9.0 Hz, 1H), 6.84 (d, J=8.2 Hz, 2H), 6.49 (dd, J=13.3 Hz, 2.6 Hz, 1H), 6.40 (dd, J=8.7 Hz, 2.6 Hz, 1H), 5.34 (s, 2H).

Step 71-3: Preparation of (3-fluoro-4-phenoxyphenyl)carbonohydrazonoyl dicyanide 275 mg (yield: 66%) of the title compound was obtained in the same manner as in Step 1-3 of Example 1 above, except that 3-fluoro-4-phenoxyaniline (300 mg, 1.48 mmol) obtained in Step 71-2 was used instead of N-(5-aminopyridin-2-yl)-5-methylpyrazine-2-carboxamide.

$^1$H NMR (400 MHz, DMSO-$d_6$) δ 13.13 (s, 1H), 7.45 (dd, J=12.1 Hz, 2.5 Hz, 1H), 7.42-7.30 (m, 3H), 7.23 (t, J=8.8 Hz, 1H), 7.13 (t, J=7.4 Hz, 1H), 6.99 (d, J=7.6 Hz, 2H).

Example 72: Preparation of (3-fluoro-4-(pyridin-3-yloxy)phenyl)carbonohydrazonoyl dicyanide (Compound 72)

Step 72-1: Preparation of 3-(2-fluoro-4-nitrophenoxy)pyridine

The title compound was obtained in the same manner as in Step 68-1 of Example 68 above, except that 1,2-difluoro-4-nitrobenzene (0.20 mL, 1.81 mmol) was used instead of 2-chloro-5-nitropyridine, and 3-hydroxypyridine (206 mg, 2.17 mmol) was used instead of phenol and used in the next step without additional purification.

Step 72-1: Preparation of 3-(2-fluoro-4-nitrophenoxy)pyridine 295 mg (yield: 84%) of the title compound was obtained in the same manner as in Step 1-2 of Example 1 above, except that 3-(2-fluoro-4-nitrophenoxy)pyridine (400 mg, 1.71 mmol) obtained in Step 72-1 was used instead of 5-methyl-N-(5-nitropyidin-2-yl)pyrazine-2-carboxamide.

$^1$H NMR (400 MHz, DMSO-$d_6$) δ 8.34-8.21 (m, 2H), 7.34 (dd, J=8.5 Hz, 4.6 Hz, 1H), 7.25-7.17 (m, 1H), 6.98 (t,

J=9.1 Hz, 1H), 6.51 (dd, J=13.3 Hz, 2.6 Hz, 1H), 6.41 (dd. J=8.6 Hz, 2.5 Hz, 1H), 5.41 (s, 2H).

Step 72-3: Preparation of (3-fluoro-4-(pyridin-3-yloxy)phenyl)carbonohydrazonoyl dicyanide 361 mg (yield: 94%) of the title compound was obtained in the same manner as in Step 1-3 of Example 1 above, except that 3-fluoro-4-(pyridin-3-yloxy)aniline (280 mg, 1.37 mmol) obtained in Step 72-2 was used instead of N-(5-aminopyridin-2-yl)-5-methylpyrazine-2-carboxamide.

$^1$H NMR (400 MHz, DMSO-$d_6$) δ 8.42 (t, J=1.9 Hz, 1H), 8.38 (t, J=3.0 Hz, 1H), 7.50-7.43 (m, 3H), 7.33 (dd, J=4.2 Hz, 2.2 Hz, 2H).

Example 73: Preparation of (4-phenoxy-3-(trifluoromethyl)phenyl)carbonohydrazonoyl dicyanide (Compound 73)

Step 73-1: Preparation of 4-nitro-1-phenoxy-2-(trifluoromethyl)benzene 404 mg (yield: 98%) of the title compound was obtained in the same manner as in Step 68-1 of Example 68 above, except that 1-fluoro-4-nitro-2-(trifluoromethyl)benzene (0.20 mL, 1.46 mmol) was used instead of 2-chloro-5-nitropyridine.

$^1$H NMR (400 MHz, DMSO-$d_6$) δ 8.55-8.44 (m, 2H), 7.55 (t, J=7.9 Hz, 2H), 7.37 (t, J=7.2 Hz, 1H), 7.25 (d, J=8.6 Hz, 1H), 7.09 (d, J=9.2 Hz, 1H).

Step 73-2: Preparation of 4-phenoxy-3-(trifluoromethyl)aniline 305 mg (yield: 97%) of the title compound was obtained in the same manner as in Step 1-2 of Example 1 above, except that 4-nitro-1-phenoxy-2-(trifluoromethyl)benzene (350 mg, 1.24 mmol) obtained in Step 73-1 was used instead of 5-methyl-N-(5-nitropyridin-2-yl)pyrazine-2-carboxamide.

$^1$H NMR (400 MHz, DMSO-$d_6$) δ 7.32 (t, J=7.9 Hz, 2H), 7.04 (t, J=7.3 Hz, 1H), 6.93 (d, J=2.6 Hz, 1H), 6.89-6.80 (m, 4H), 5.46 (s, 2H).

Step 73-3: Preparation of (4-phenoxy-3-(trifluoromethyl)phenyl)carbonohydrazonoyl dicyanide 206 mg (yield: 79%) of the title compound was obtained in the same manner as in Step 1-3 of Example 1 above, except that 4-phenoxy-3-(trifluoromethyl)aniline (200 mg, 0.79 mmol) obtained in Step 73-2 was used instead of N-(5-aminopyridin-2-yl)-5-methylpyrazine-2-carboxamide.

$^1$H NMR (400 MHz, DMSO-$d_6$) δ 7.84 (d, J=2.7 Hz, 1H), 7.71 (dd, J=9.0 Hz, 2.7 Hz, 1H), 7.50-7.38 (m, 2H), 7.22 (t, J=7.4 Hz, 1H), 7.13-7.04 (m, 3H).

Example 74: Preparation of (3-methyl-4-(pyridin-3-yloxy)phenyl)carbonohydrazonoyl dicyanide (Compound 74)

Step 74-1: Preparation of 3-(2-methyl-4-nitro phenoxy) pyridine

The title compound was obtained in the same manner as in Step 68-1 of Example 68 above, except that 2-fluoro-5-nitrotoluene (200 mg, 1.29 mmol) was used instead of 2-chloro-5-nitropyridine, and 3-hydroxypyrimidine (147 mg, 1.55 mmol) was used instead of phenol and used in the next step without additional purification.

Step 74-2: Preparation of 3-methyl-4-(pyridin-3-yloxy)aniline 215 mg (yield: 99%) of the title compound was obtained in the same manner as in Step 1-2 of Example 1 above, except that 3-(2-methyl-4-nitrophenoxy)pyridine (250 mg, 1.09 mmol) obtained in Step 74-1 was used instead of 5-methyl-N-(5-nitropyidin-2-yl)pyrazine-2-carboxamide.

$^1$H NMR (400 MHz, DMSO-$d_6$) δ 8.21 (s, 2H), 7.31 (dd, J=8.5 Hz, 4.6 Hz, 1H), 7.09 (dd, J=8.5 Hz, 1.5 Hz, 1H), 6.73 (d, J=8.5 Hz, 1H), 6.53-6.42 (m, 2H), 5.00 (s, 2H), 1.98 (s, 3H).

Step 74-3: Preparation of (3-methyl-4-(pyridin-3-yloxy)phenyl)carbonohydrazonoyl dicyanide 226 mg (yield: 82%) of the title compound was obtained in the same manner as in Step 1-3 of Example 1 above, except that 3-methyl-4-(pyridin-3-yloxy)aniline (200 mg, 0.10 mmol) obtained in Step 74-2 was used instead of N-(5-aminopyridin-2-yl)-5-methylpyrazine-2-carboxamide.

$^1$H NMR (400 MHz, DMSO-$d_6$) δ 8.39-8.30 (m, 2H), 7.51-7.39 (m, 2H), 7.37-7.29 (m, 2H), 7.02 (d, J=8.7 Hz, 1H).

Example 75: Preparation of methyl(5-phenoxypyridin-2-yl)carbonohydrazonoyl dicyanide (Compound 75)

(5-Phenoxypyridin-2-yl)carbonohydrazonoyl dicyanide (50 mg, 0.19 mmol) prepared in Example 70 was dissolved in DMF under a nitrogen atmosphere. potassium tert-butoxide (28 mg, 0.25 mmol) was added to the reaction solution at room temperature, and iodomethane (24 μL, 0.38 mmol) was added thereto, and then the reaction mixture was stirred at 60° C. for 12 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 8 mg (yield: 15%) of the title compound.

$^1$H NMR (400 MHz, DMSO-$d_6$) δ 8.70 (d, J=2.6 Hz, 1H), 8.22 (dd, J=9.3 Hz, 2.6 Hz, 1H), 7.60 (t, J=7.9 Hz, 2H), 7.44 (dd, J=12.1 Hz, 7.7 Hz, 3H), 7.01 (d, J=9.3 Hz, 1H), 4.19 (s, 3H).

Example 76: Preparation of (6-(3-fluorophenoxy) pyridin-3-yl(methyl)carbonohydrazonoyl dicyanide (Compound 76)

7 mg (yield: 13%) of the title compound was obtained in the same manner as in Example 75 above, except that (6-(3-fluorophenoxy)pyridin-3-yl)carbonohydrazonoyl dicyanide (50 mg, 0.18 mmol) obtained in Example 69 was used instead of (5-phenoxypyridin-2-yl)carbonohydrazonoyl dicyanide.

$^1$H NMR (400 MHz, DMSO-$d_6$) δ 8.72 (d, J=2.6 Hz, 1H), 8.22 (dd, J=9.3 Hz, 2.6 Hz, 1H), 7.69-7.59 (m, 1H), 7.43 (dt, J=9.7 Hz, 2.4 Hz, 1H), 7.36-7.28 (m, 2H), 7.15 (d, J=9.3 Hz, 1H), 4.18 (s, 3H).

Example 77: Preparation of (3-fluoro-4-phenoxyphenyl)(methyl)carbonohydrazonoyl dicyanide (Compound 77)

66 mg (yield: 63%) of the title compound was obtained in the same manner as in Example 75 above, except that (3-fluoro-4-phenoxyphenyl)carbonohydrazonoyl dicyanide (100 mg, 0.36 mmol) prepared in Example 71 was used instead of (5-phenoxypyridin-2-yl)carbonohydrazonoyl dicyanide.

$^1$H NMR (400 MHz, DMSO-$d_6$) δ 7.65 (d, J=12.0 Hz, 1H), 7.40 (t, J=7.9 Hz, 3H), 7.27 (t, J=8.8 Hz, 1H), 7.16 (t, J=7.4 Hz, 1H), 7.01 (d, J=8.0 Hz, 2H), 4.02 (s, 3H).

Example 78: Preparation of methyl(4-phenoxy-3-(trifluoromethyl)phenyl)carbonohydrazonoyl dicyanide (Compound 78)

52 mg (yield: 50%) of the title compound was obtained in the same manner as in Example 75 above, except that (4-phenoxy-3-(trifluoromethyl)phenyl)carbonohydrazonoyl dicyanide (100 mg, 0.30 mmol) prepared in Example 73 was used instead of (5-phenoxypyridin-2-yl)carbonohydrazonoyl dicyanide.

$^1$H NMR (400 MHz, DMSO-$d_6$) δ 7.94-7.72 (m, 2H), 7.45 (t, J=8.0 Hz, 2H), 7.24 (t, J=7.4 Hz, 1H), 7.16-7.06 (m, 3H), 4.04 (s, 3H).

Example 79: Preparation of (3-methyl-4-(pyridin-4-yloxy)phenyl)carbonohydrazonoyl dicyanide (Compound 79)

Step 79-1: Preparation of 4-(2-methyl-4-nitrophenoxy)pyridine 61 mg (yield: 20%) of the title compound was obtained in the same manner as in Step 68-1 of Example 68 above, except that 2-fluoro-5-nitrotoluene (200 mg, 1.29 mmol) was used instead of 2-chloro-5-nitropyridine and 4-hydroxypyrimidine (147 mg, 1.55 mmol) was used instead of phenol.

$^1$H NMR (400 MHz, DMSO-$d_6$) δ 8.36 (d, J=2.7 Hz, 1H), 8.21 (dd, J=8.6 Hz, 2.7 Hz, 1H), 7.81-7.76 (m, 2H), 7.70 (d, J=8.7 Hz, 1H), 6.23 (d, J=7.8 Hz, 2H), 2.32 (s, 3H).

Step 79-2: Preparation of 3-methyl-4-(pyridin-4-yloxy)aniline 31 mg (yield: 72%) of the title compound was obtained in the same manner as in Step 1-2 of Example 1 above, except that 4-(2-methyl-4-nitrophenoxy)pyridine (50 mg, 0.202 mmol) obtained in Step 79-1 was used instead of 5-methyl-N-(5-nitropyidin-2-yl)pyrazine-2-carboxamide.

$^1$H NMR (400 MHz, DMSO-$d_6$) δ 7.59-7.52 (m, 2H), 6.96 (d, J=8.3 Hz, 1H), 6.52-6.42 (m, 2H), 6.15-6.09 (m, 2H).

Step 79-3: Preparation of (3-methyl-4-(pyridin-4-yloxy)phenyl)carbonohydrazonic Dicyanide 22 mg (yield: 46%) of the title compound was obtained in the same manner as in Step 1-3 of Example 1 above, except that 3-methyl-4-(pyridin-4-yloxy)aniline (30 mg, 0.15 mmol) obtained in Step 79-2 was used instead of N-(5-aminopyridin-2-yl)-5-methylpyrazine-2-carboxamide.

$^1$H NMR (400 MHz, DMSO-$d_6$) δ 8.01 (d, J=7.1 Hz, 2H), 7.51-7.35 (m, 3H), 6.55 (d, J=7.1 Hz, 2H), 2.16 (s, 3H).

Example 80: Preparation of (3-fluoro-4-(pyridin-4-yloxy)phenyl)carbonohydrazonoyl dicyanide (Compound 80)

Step 80-1: Preparation of 4-(2-fluoro-4-nitrophenoxy)pyridine 353 mg (yield: 42%) of the title compound was obtained in the same manner as in Step 68-1 of Example 68 above, except that 1,2-difluoro-4-nitrobenzene (0.20 mL, 1.81 mmol) was used instead of 2-chloro-5-nitropyridine, and 4-hydroxypyrimidine (206 mg, 2.17 mmol) was used instead of phenol.

$^1$H NMR (400 MHz, DMSO-$d_6$) δ 8.46 (dd, J=10.6 Hz, 2.5 Hz, 1H), 8.29-8.22 (m, 1H), 7.99-7.89 (m, 3H), 6.28 (d, J=7.9 Hz, 2H).

Step 80-2: Preparation of 3-fluoro-4-(pyridin-4-yloxy)aniline 94 mg (yield: 32%) of the title compound was obtained in the same manner as in Step 1-2 of Example 1 above, except that 4-(2-fluoro-4-nitrophenoxy)pyridine (340 mg, 1.45 mmol) obtained in Step 80-1 was used instead of 5-methyl-N-(5-nitropyridin-2-yl)pyrazine-2-carboxamide.

$^1$H NMR (400 MHz, DMSO-$d_6$) δ 7.69-7.61 (m, 2H), 7.18 (t, J=8.9 Hz, 1H), 6.56-6.39 (m, 2H), 6.15 (d, J=7.6 Hz, 2H), 5.78 (s, 2H).

Step 80-3: Preparation of (3-fluoro-4-(pyridin-5-yloxy)phenyl)carbonohydrazonoyl dicyanide 105 mg (yield: 95%) of the title compound was obtained in the same manner as in Step 1-3 of Example 1 above, except that 3-fluoro-4-(pyridin-4-yloxy)aniline (80 mg, 0.39 mmol) obtained in Step 80-2 was used instead of N-(5-aminopyridin-2-yl)-5-methylpyrazine-2-carboxamide.

$^1$H NMR (400 MHz, DMSO-$d_6$) δ 8.20 (d, J=7.1 Hz, 2H), 7.67 (t, J=8.6 Hz, 1H), 7.50-7.30 (m, 2H), 6.67 (d, J=7.1 Hz, 2H).

Example 81: Preparation of (3-methyl-4-(pyrimidin-5-yloxy)phenyl)carbonohydrazonoyl dicyanide (Compound 81)

Step 81-1: Preparation of 5-(2-methyl-4-nitrophenoxy)pyrimidine 121 mg (yield: 41%) of the title compound was obtained in the same manner as in Step 68-1 of Example 68 above, except that 2-fluoro-5-nitrotoluene (200 mg, 1.29 mmol) was used instead of 2-chloro-5-nitropyridine, and 5-hydroxypyrimidine (149 mg, 1.55 mmol) was used instead of phenol.

$^1$H NMR (400 MHz, DMSO-$d_6$) δ 9.11 (s, 1H), 8.76 (s, 2H), 8.30 (dd, J=2.8 Hz, 0.9 Hz, 1H), 8.08 (dd, J=9.0 Hz, 2.7 Hz, 1H), 7.11 (d, J=9.0 Hz, 1H), 2.41 (s, 3H).

Step 81-2: Preparation of 3-methyl-4-pyrimidin-5-yloxy)aniline 80 mg (yield: 92%) of the title compound was obtained in the same manner as in Step 1-2 of Example 1 above, except that 5-(2-methyl-4-nitrophenoxy)pyrimidine (100 mg, 0.43 mmol) obtained in Step 81-1 was used instead of 5-methyl-N-(5-nitropyidin-2-yl)pyrazine-2-carboxamide.

$^1$H NMR (400 MHz, DMSO-$d_6$) δ 8.91-8.76 (m, 1H), 8.35 (s, 1H), 6.78 (d, J=8.4 Hz, 1H), 6.47 (dd, J=24.4 Hz, 5.5 Hz, 2H), 5.04 (s, 2H), 1.99 (s, 3H).

Step 81-3: Preparation of (3-fluoro-4-(pyrimidin-5-yloxy)phenyl)carbonohydrazonoyl dicyanide 65 mg (yield: 67%) of the title compound was obtained in the same manner as in Step 1-3 of Example 1 above, except that 3-fluoro-4-(pyrimidin-5-yloxy)aniline (150 mg, 0.73 mmol) obtained in Step 81-2 was used instead of N-(5-aminopyridin-2-yl)-5-methylpyrazine-2-carboxamide.

$^1$H NMR (400 MHz, DMSO-$d_6$) δ 13.05 (s, 1H), 8.97 (s, 1H), 8.53 (s, 2H), 7.48 (d, J=2.7 Hz, 1H), 7.36 (dd, J=8.8 Hz, 2.7 Hz, 1H), 7.11 (d, J=8.8 Hz, 1H), 2.24 (s, 3H).

Example 82: Preparation of (3-fluoro-4-(pyrimidin-5-yloxy)phenyl)carbonohydrazonoyl dicyanide (Compound 82)

Step 82-1: Preparation of 5-(2-fluoro-4-nitrophenoxy)pyrimidine 346 mg (yield: 81%) of the title compound was obtained in the same manner as in Step 68-1 of Example 68 above, except that 1,2-difluoro-4-nitrobenzene (0.20 mL, 1.81 mmol) was used instead of 2-chloro-5-nitropyridine, and 5-hydroxypyrimidine (208 mg, 2.17 mmol) was used instead of phenol.

$^1$H NMR (400 MHz, DMSO-$d_6$) δ 9.13 (s, 1H), 8.86 (s, 2H), 8.41 (dd, J=10.7 Hz, 2.7 Hz, 1H), 8.12 (ddd, J=9.2 Hz, 2.7 Hz, 1.5 Hz, 1H), 7.46 (dd, J=9.1 Hz, 8.2 Hz, 1H).

Step 82-2: Preparation of 3-fluoro-4-(pyrimidin-6-yloxy)aniline 180 mg (yield: 69%) of the title compound was obtained in the same manner as in Step 1-2 of Example 1 above, except that 5-(2-fluoro-4-nitrophenoxy)pyrimidine (300 mg, 1.28 mmol) obtained in Step 82-1 was used instead of 5-methyl-N-(5-nitropyidin-2-yl)pyrazine-2-carboxamide.

$^1$H NMR (400 MHz, DMSO-$d_6$) δ 8.91 (s, 1H), 8.48 (s, 2H), 7.05 (t, J=9.1 Hz, 1H), 6.52 (dd, J=13.4 Hz, 2.6 Hz, 1H), 6.42 (ddd, J=8.7 Hz, 2.6 Hz, 1.1 Hz, 1H), 5.46 (s, 2H).

Step 82-3: Preparation of (3-fluoro-4-(pyrimidin-5-yloxy)phenyl)carbonohydrazonoyl dicyanide 93 mg (yield: 45%) of the title compound was obtained in the same manner as in Step 1-3 of Example 1 above, except that 3-fluoro-4-(pyrimidin-5-yloxy)aniline (150 mg, 0.73 mmol) obtained in Step 82-2 was used instead of N-(5-aminopyridin-2-yl)-5-methylpyrazine-2-carboxamide.

$^1$H NMR (400 MHz, DMSO-$d_6$) δ 9.01 (s, 1H), 8.65 (s, 2H), 7.49 (dd, J=12.2 Hz, 2.5 Hz, 1H), 7.42 (t, J=8.7 Hz, 1H), 7.35 (dd, J=9.0 Hz, 1.5 Hz, 1H).

Example 83: Preparation of (4-(pyridin-2-yloxy)phenyl)carbonohydrazonoyl dicyanide (Compound 83)

Step 83-1: Preparation of 4-(pyridin-2-yloxy)aniline

After 4-aminophenol (200 mg, 1.83 mmol) was dissolved in dimethyl sulfoxide, 2-fluoropyridine (158 μL, 1.83 mmol) and cesium carbonate (716 mg, 2.20 mmol) were added thereto, and the reaction mixture was stirred at 80° C. for 12 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 113 mg (yield: 33%) of the title compound.

$^1$H NMR (400 MHz, DMSO-$d_6$) δ 8.11 (ddd, J=4.9 Hz, 2.1 Hz, 0.8 Hz, 1H), 7.76 (ddd, J=8.3 Hz, 7.2 Hz, 2.0 Hz, 1H), 7.03 (ddd, J=7.2 Hz, 4.9 Hz, 1.0 Hz, 1H), 6.84 (d, J=8.3 Hz, 1H), 6.81-6.76 (m, 2H), 6.63-6.53 (m, 2H), 4.97 (s, 2H).

Step 83-2: Preparation of (4-(pyridin-2-yloxy)phenyl)carbonohydrazonoyl dicyanide 67 mg (yield: 48%) of the title compound was obtained in the same manner as in Step 1-3 of Example 1 above, except that 4-(pyridin-2-yloxy)aniline (100 mg, 0.54 mmol) obtained in Step 83-1 was used instead of N-(5-aminopyridin-2-yl)-5-methylpyrazine-2-carboxamide.

$^1$H NMR (400 MHz, DMSO-$d_6$) δ 13.08 (s, 1H), 8.15 (d, J=4.9 Hz, 1H), 7.91-7.82 (m, 1H), 7.51 (d, J=9.1 Hz, 1H), 7.21-7.12 (m, 3H), 7.05 (d, J=8.3 Hz, 1H).

Example 84: Preparation of (4-(pyrazin-2-yloxy)phenyl)carbonohydrazonoyl dicyanide (Compound 84)

Step 84-1: Preparation of 4-(pyrazin-2-yloxy)aniline 268 mg (yield: 78%) of the title compound was obtained in the same manner as in Step 83-1 of Example 83 above, except that 2-fluoropyrazine (148 μL, 1.83 mmol) was used instead of 2-fluoropyridine.

$^1$H NMR (400 MHz, DMSO-$d_6$) δ 8.39 (d, J=1.4 Hz, 1H), 8.29 (d, J=2.7 Hz, 1H), 8.16 (dd, J=2.7 Hz, 1.4 Hz, 1H), 6.85 (d, J=8.7 Hz, 2H), 6.59 (d, J=8.7 Hz, 2H), 5.04 (s, 2H).

Step 84-2: Preparation of (4-(pyrazin-2-yloxy)phenyl)carbonohydrazonoyl dicyanide 66 mg (yield: 23%) of the title compound was obtained in the same manner as in Step 1-3 of Example 1 above, except that 4-(pyrazin-2-yloxy)aniline (200 mg, 1.07 mmol) obtained in Step 84-1 was used instead of N-(5-aminopyridin-2-yl)-5-methylpyrazine-2-carboxamide.

$^1$H NMR (400 MHz, DMSO-$d_6$) δ 13.09 (s, 1H), 8.56 (d, J=1.4 Hz, 1H), 8.39 (d, J=2.7 Hz, 1H), 8.21 (dd, J=2.8 Hz, 1.4 Hz, 1H), 7.53 (d, J=9.0 Hz, 2H), 7.28 (d, J=8.9 Hz, 2H).

Example 85: Preparation of (4-(pyridin-3-yloxy)phenyl)carbonohydrazonoyl dicyanide (Compound 85)

Step 85-1: Preparation of 4-pyridin-3-yloxy)aniline 62 mg (yield: 18%) of the title compound was obtained in the same manner as in Step 83-1 of Example 83 above, except that 3-fluoropyridine (158 μL, 1.83 mmol) was used instead of 2-fluoropyridine.

$^1$H NMR (400 MHz, DMSO-$d_6$) δ 8.32-8.18 (m, 2H), 7.33 (ddd, J=8.5 Hz, 4.6 Hz, 0.7 Hz, 1H), 7.21 (ddd, J=8.5 Hz, 2.9 Hz, 1.4 Hz, 1H), 6.81 (d, J=8.8 Hz, 2H), 6.60 (d, J=8.8 Hz, 2H), 5.04 (s, 2H).

Step 85-2: Preparation of (4-(pyridin-3-yloxy)phenyl)carbonohydrazonoyl dicyanide 18 mg (yield: 25%) of the title compound was obtained in the same manner as in Step 1-3 of Example 1 above, except that 4-(pyridin-3-yloxy)aniline (50 mg, 0.27 mmol) obtained in Step 85-1 was used instead of N-(5-aminopyridin-2-yl)-5-methylpyrazine-2-carboxamide.

$^1$H NMR (400 MHz, DMSO-$d_6$) δ 8.48-8.34 (m, 2H), 7.60-7.42 (m, 4H), 7.15 (d, J=9.0 Hz, 2H).

Example 86: Preparation of (4-(2-cyanophenoxy)phenyl)carbonohydrazonoyl dicyanide (Compound 86)

Step 86-1: Preparation of 2-(4-aminophenoxy)benzonitrile 308 mg (yield: 80%) of the title compound was obtained in the same manner as in Step 83-1 of Example 83 above, except that 2-fluorobenzonitrile (195 μL, 1.83 mmol) was used instead of 2-fluoropyridine.

$^1$H NMR (400 MHz, DMSO-$d_6$) δ 7.82 (dd, J=7.7 Hz, 1.7 Hz, 1H), 7.59 (ddd, J=8.8 Hz, 7.4 Hz, 1.7 Hz, 1H), 7.17 (td, J=7.6 Hz, 1.0 Hz, 1H), 6.87 (d, J=8.7 Hz, 2H), 6.77 (d, J=8.6 Hz, 1H), 6.64 (d, J=8.8 Hz, 2H), 5.15 (s, 2H).

Step 86-2: Preparation of (4-(2-cyanophenoxy)phenyl)carbonohydrazonoyl dicyanide 246 mg (yield: 72%) of the title compound was obtained in the same manner as in Step 1-3 of Example 1 above, except that 2-(4-aminophenoxy)benzonitrile (250 mg, 1.19 mmol) obtained in Step 86-1 was used instead of N-(5-aminopyridin-2-yl)-5-methylpyrazine-2-carboxamide.

$^1$H NMR (400 MHz, DMSO-$d_6$) δ 13.08 (s, 1H), 7.91 (dd, J=7.8 Hz, 1.7 Hz, 1H), 7.69 (ddd, J=8.7 Hz, 7.5 Hz, 1.7 Hz, 1H), 7.60-7.52 (m, 2H), 7.31 (t, J=7.6 Hz, 1H), 7.26-7.18 (m, 2H), 7.00 (d, J=8.5 Hz, 1H).

Example 87: Preparation of (4(4-cyanophenoxy)phenyl)carbonohydrazonoyl dicyanide (Compound 87)

Step 87-1: Preparation of 4-(4-aminophenoxy)benzonitrile 295 mg (yield: 76%) of the title compound was obtained in the same manner as in Step 83-1 of Example 83 above, except that 4-fluorobenzonitrile (222 mg, 1.83 mmol) was used instead of 2-fluoropyridine.

$^1$H NMR (400 MHz, DMSO-$d_6$) δ 7.77 (d, J=8.7 Hz, 2H), 6.98 (d, J=8.7 Hz, 2H), 6.83 (d, J=8.7 Hz, 2H), 6.63 (d, J=8.7 Hz, 2H), 5.12 (s, 2H).

Step 87-2: Preparation of (4-(4-cyanophenoxy)phenyl)carbonohydrazonoyl dicyanide 196 mg (yield: 57%) of the title compound was obtained in the same manner as in Step 1-3 of Example 1 above, except that 4-(4-aminophenoxy)benzonitrile (250 mg, 1.19 mmol) obtained in Step 87-1 was used instead of N-(5-aminopyridin-2-yl)-5-methylpyrazine-2-carboxamide.

$^1$H NMR (400 MHz, DMSO-$d_6$) δ 13.10 (s, 1H), 7.85 (d, J=8.6 Hz, 2H), 7.55 (d, J=8.9 Hz, 2H), 7.21 (d, J=8.7 Hz, 2H), 7.12 (d, J=8.5 Hz, 2H).

Example 88: Preparation of (4(3-cyanophenoxy)phenyl)carbonohydrazonoyl dicyanide (Compound 88)

Step 88-1: Preparation of 3(4-aminophenoxy)benzonitrile 46 mg (yield: 12%) of the title compound was obtained in the same manner as in Step 83-1 of Example 83 above, except that 3-chlorobenzonitrile (252 mg, 1.83 mmol) was used instead of 2-fluoropyridine.

$^1$H NMR (400 MHz, DMSO-$d_6$) δ 7.55-7.45 (m, 2H), 7.27 (s, 1H), 7.20 (d, J=8.3 Hz, 1H), 6.82 (d, J=8.5 Hz, 2H), 6.62 (d, J=8.5 Hz, 2H), 5.10 (s, 2H).

Step 88-2: Preparation of (4-(3-cyanophenoxy)phenyl)carbonohydrazonoyl dicyanide 25 mg (yield: 40%) of the title compound was obtained in the same manner as in Step 1-3 of Example 1 above, except that 3-(4-aminophenoxy)benzonitrile (46 mg, 0.22 mmol) obtained in Step 88-1 was used instead of N-(5-aminopyridin-2-yl)-5-methylpyrazine-2-carboxamide.

$^1$H NMR (400 MHz, DMSO-$d_6$) δ 7.66-7.57 (m, 2H), 7.54 (d, J=9.0 Hz, 3H), 7.37 (dt, J=7.3 Hz, 2.4 Hz, 1H), 7.17 (d, J=8.9 Hz, 2H).

Example 89: Preparation of (4-(6-(trifluoromethyl) pyridin-3-yloxy)phenyl)carbonohydrazonoyl dicyanide (Compound 89)

Step 89-1: Preparation of 4(6-(trifluoromethyl)pyridin-3-yloxy)aniline 250 mg (yield: 54%) of the title compound was obtained in the same manner as in Step 83-1 of Example 83 above, except that 5-fluoro-2-(trifluoromethyl)pyridine (221 μL, 1.83 mmol) was used instead of 2-fluoropyridine.

$^1$H NMR (400 MHz, DMSO-$d_6$) δ 8.44 (d, J=2.8 Hz, 1H), 7.83 (d, J=8.7 Hz, 1H), 7.36 (dd, J=8.7 Hz, 2.9 Hz, 1H), 6.89 (d, J=8.8 Hz, 2H), 6.64 (d, J=8.7 Hz, 2H), 5.15 (s, 2H).

Step 89-2: Preparation of (4-(6-(trifluoromethyl) pyridin-3-yloxy)phenyl)carbohydrazonoyl Dicyanide 51 mg (yield: 19%) of the title compound was obtained in the same manner as in Step 1-3 of Example 1 above, except that 4-(6-(trifluoromethyl)pyridin-3-yloxy)aniline (200 mg, 0.79 mmol) obtained in Step 89-1 was used instead of N-(5-aminopyridin-2-yl)-5-methylpyrazine-2-carboxamide.

$^1$H NMR (400 MHz, DMSO-$d_6$) δ 13.11 (s, 1H), 8.56 (d, J=2.8 Hz, 1H), 7.91 (d, J=8.7 Hz, 1H), 7.63-7.51 (m, 3H), 7.28 (d, J=9.0 Hz, 2H).

Example 90: Preparation of (4-(5-(trifluoromethyl) pyridin-2-yloxy)phenyl)carbonohydrazonoyl dicyanide (Compound 90)

Step 90-1: Preparation of 4-(5-(trifluoromethyl)pyridin-2-yloxy)aniline 396 mg (yield: 85%) of the title compound was obtained in the same manner as in Step 83-1 of Example 83 above, except that 2-fluoro-5-(trifluoromethyl)pyridine (221 μL, 1.83 mmol) was used instead of 2-fluoropyridine.

$^1$H NMR (400 MHz, DMSO-$d_6$) δ 8.54 (dd. J=1.7 Hz, 0.9 Hz, 1H), 8.15 (dd, J=8.8 Hz, 2.6 Hz, 1H), 7.06 (d, J=8.6 Hz, 1H), 6.90-6.78 (m, 2H), 6.69-6.56 (m, 2H), 5.06 (s, 2H).

Step 90-2: Preparation of (4-(5-(trifluoromethyl) pyridin-2-yloxy)phenyl)carbohydrazonoyl Dicyanide 241 mg (yield: 62%) of the title compound was obtained in the same manner as in Step 1-3 of Example 1 above, except that 4-(5-(trifluoromethyl)pyridin-2-yloxy)aniline (300 mg, 1.18 mmol) obtained in Step 90-1 was used instead of N-(5-aminopyridin-2-yl)-5-methylpyrazine-2-carboxamide.

$^1$H NMR (400 MHz, DMSO-$d_6$) δ 13.01 (s, 1H), 8.57 (d, J=1.9 Hz, 0H), 8.25 (dd, J=8.8 Hz, 2.7 Hz, 1H), 7.61-7.50 (m, 2H), 7.33-7.16 (m, 3H).

Example 91: Preparation of (4-(pyrimidin-2-yloxy)phenyl)carbonohydrazonoyl dicyanide (Compound 91)

Step 91-1: Preparation of 4-pyrimidin-2-yloxy)aniline 142 mg (yield: 41%) of the title compound was obtained in the same manner as in Step 83-1 of Example 83 above, except that 2-fluoropyrimidine (115 μL, 1.83 mmol) was used instead of 2-fluoropyridine.

$^1$H NMR (400 MHz, DMSO-$d_6$) δ 8.59 (d, J=4.7 Hz, 2H), 7.19 (t, J=4.7 Hz, 1H), 6.90-6.76 (m, 2H), 6.64-6.53 (m, 2H), 5.00 (s, 2H).

Step 91-2: Preparation of (4-(pyrimidin-2-yloxy)phenyl)carbonohydrazonoyl dicyanide 118 mg (yield: 84%) of the title compound was obtained in the same manner as in Step 1-3 of Example 1 above, except that 4-(pyrimidin-2-yloxy)aniline (100 mg, 0.53 mmol) obtained in Step 91-1 was used instead of N-(5-aminopyridin-2-yl)-5-methylpyrazine-2-carboxamide.

$^1$H NMR (400 MHz, DMSO-$d_6$) δ 13.10 (s, 1H), 8.66 (d, J=4.8 Hz, 2H), 7.61-7.47 (m, 2H), 7.33-7.22 (m, 3H).

Example 92: Preparation of (4-(pyridazin-3-yloxy)phenyl)carbonohydrazonoyl dicyanide (Compound 92)

Step 92-1: Preparation of 4-(pyridazin-3-yloxy)anillne 120 mg (yield: 35%) of the title compound was obtained in the same manner as in Step 83-1 of Example 83 above, except that 2-chloropyridazine (161 μL, 1.83 mmol) was used instead of 2-fluoropyridine.

$^1$H NMR (400 MHz, DMSO-$d_6$) δ 8.99-8.91 (m, 1H), 7.69 (dd, J=9.0 Hz, 4.5 Hz, 1H), 7.27 (dd, J=9.0 Hz, 1.3 Hz, 1H), 6.87 (d, J=8.7 Hz, 2H), 6.61 (d, J=8.7 Hz, 2H), 5.06 (s, 2H).

Step 92-2: Preparation of (4-(pyridazin-3-yloxy)phenyl)carbonohydrazonoyl dicyanide 79 mg (yield: 56%) of the title compound was obtained in the same manner as in Step 1-3 of Example 1 above, except that 4-(pyridazin-3-yloxy)aniline (100 mg, 0.53 mmol) obtained in Step 92-1 was used instead of N-(5-aminopyridin-2-yl)-5-methylpyrazine-2-carboxamide.

$^1$H NMR (400 MHz, DMSO-$d_6$) δ 13.16 (s, 1H), 9.08 (dd, J=4.6 Hz, 1.3 Hz, 1H), 7.88 (dd, J=9.0 Hz, 4.6 Hz, 1H), 7.63-7.53 (m, 3H), 7.31 (d, J=9.0 Hz, 2H).

Example 93: Preparation of (4-(2-fluorophenoxy)phenyl)carbonohydrazonoyl dicyanide (Compound 93)

Step 93-1: Preparation of 4-(2-fluorophenoxy)aniline 113 mg (yield: 30%) of the title compound was obtained in the same manner as in Step 83-1 of Example 83 above, except that 1,2-difluorobenzene (181 μL, 1.83 mmol) was used instead of 2-fluoropyridine.

$^1$H NMR (400 MHz, DMSO-$d_6$) δ 7.31 (ddd, J=11.5 Hz, 7.8 Hz, 1.9 Hz, 1H), 7.15-7.04 (m, 2H), 6.89 (td, J=8.2 Hz, 2.0 Hz, 1H), 6.77 (d, J=8.7 Hz, 1H), 6.59 (d, J=8.6 Hz, 1H), 4.99 (s, 2H).

Step 93-2: Preparation of (4-(2-fluorophenoxy)phenyl)carbonohydrazonoyl dicyanide 38 mg (yield: 25%) of the title compound was obtained in the same manner as in Step 1-3 of Example 1 above, except that 4-(2-fluorophenoxy)aniline (110 mg, 0.54 mmol) obtained in Step 93-1 was used instead of N-(5-aminopyridin-2-yl)-5-methylpyrazine-2-carboxamide.

$^1$H NMR (400 MHz, DMSO-$d_6$) δ 13.07 (s, 1H), 7.49 (d, J=9.1 Hz, 2H), 7.45-7.39 (m, 1H), 7.32-7.19 (m, 3H), 7.05 (d, J=9.0 Hz, 2H).

Example 94: Preparation of (4(3-fluorophenoxy)phenyl)carbonohydrazonoyl dicyanide (Compound 94)

Step 94-1: Preparation of 4-(3-fluorophenoxy)anillne 175 mg (yield: 47%) of the title compound was obtained in the same manner as in Step 83-1 of Example 83 above, except that 1,3-difluorobenzene (180 μL, 1.83 mmol) was used instead of 2-fluoropyridine.

$^1$H NMR (400 MHz, DMSO-$d_6$) δ 7.38-7.28 (m, 1H), 6.88-6.76 (m, 3H), 6.73-6.58 (m, 4H), 5.06 (s, 2H).

Step 94-2: Preparation of (4-(3-fluorophenoxy)phenyl)carbonohydrazonoyl dicyanide 45 mg (yield: 19%) of the title compound was obtained in the same manner as in Step 1-3 of Example 1 above, except that 4-(3-fluorophenoxy)aniline (170 mg, 0.84 mmol) obtained in Step 94-1 was used instead of N-(5-aminopyridin-2-yl)-5-methylpyrazine-2-carboxamide.

$^1$H NMR (400 MHz, DMSO-$d_6$) δ 13.09 (s, 1H), 7.53 (d, J=9.0 Hz, 2H), 7.49-7.37 (m, 1H), 7.15 (d, J=9.0 Hz, 2H), 7.00 (td, J=8.5 Hz, 2.5 Hz, 1H), 6.90 (dt, J=10.4 Hz, 2.4 Hz, 1H), 6.85 (dd, J=8.2 Hz, 2.3 Hz, 1H).

Example 95: Preparation of (6-(benzyloxy)pyridin-3-yl)carbonohydrazonoyl dicyanide (Compound 95)

Step 95-1: Preparation of 2-(benzyloxy)-5-nitropyridine

Phenylmethanol (300 mg, 2.77 mmol) was dissolved in THE under a nitrogen atmosphere, 60% NaH (133 mg, 3.32 mmol) was added thereto, and the reaction mixture was stirred at 0° C. for 1 hour. Then, 2-chloro-5-nitropyridine (439 mg, 2.77 mmol) was added thereto, and the reaction mixture was further stirred for 2 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, solidified using ether, and filtered to obtain 217 mg (yield: 34%) of the title compound in a solid state.

$^1$H NMR (400 MHz, DMSO-$d_6$) δ 9.106-9.114 (d, J=3.2 Hz, 1H), 8.491-8.521 (dd, J=9.2 Hz, 2.8 Hz, 1H), 7.354-7.490 (m, 5H), 7.097-7.120 (d, J=9.2 Hz, 1H), 5.496 (s, 2H).

Step 95-2: Preparation of 5-(benzyloxy)uridine-3-amine

After 2-(benzyloxy)-5-nitropyridine (100 mg, 0.43 mmol) obtained in Step 95-1 was dissolved in THF, $NH_4Cl$ (92 mg, 1.72 mmol) was added thereto, and the reaction mixture was refluxed at 75° C. for 30 minutes. Thereafter, Fe (96.06 mg, 1.72 mmol) was added thereto, and the reaction mixture was further refluxed at 75° C. for 4 hours. Upon completion of the reaction, a reaction product was filtered using celite and extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 61 mg (yield: 71%) of the title compound.

$^1$H NMR (400 MHz, $CDCl_3$) δ 7.666-7.659 (d, J=2.8 Hz, 1H), 7.452-7.277 (m, 5H), 7.046-7.017 (dd, J=8.8 Hz, 2.8 Hz, 1H), 6.674-6.652 (d, J=8.8 Hz, 1H), 5.288 (s, 2H), 3.378 (s, 2H).

Step 95-3: Preparation of (6-(benzyloxy)pyridin-3-yl)carbonohydrazonoyl dicyanide 21 mg (yield: 15%) of the title compound was obtained in the same manner as in Step 1-3 of Example 1 above, except that 6-(benzyloxy)pyridine-3-amine (100 mg, 0.5 mmol) obtained in Step 95-2 was used instead of N-(5-aminopyridin-2-yl)-5-methylpyrazine-2-carboxamide.

$^1$H NMR (400 MHz, $CDCl_3$) δ 9.708 (s, 1H), 8.149-8.143 (d, J=2.4 Hz, 1H), 7.694-7.664 (dd, J=8.8 Hz, 2.8 Hz, 1H), 7.462-7.335 (m, 5H), 6.910-6.888 (d, J=8.8 Hz, 1H), 5.393 (s, 1H).

Example 96: Preparation of (6-(4-(trifluoromethyl) benzyloxy)pyridin-3-yl)carbonohydrazonoyl dicyanide (Compound 96)

Step 96-1: Preparation of 5-nitro-2-(4-(trifluoromethyl)benzyloxy)pyridine 253.7 mg (yield: 60%) of the title compound was obtained in the same manner as in Step 95-1 of Example 95 above, except that (4-(trifluoromethyl)phenyl)methanol (300 mg, 1.7 mmol) was used instead of phenylmethanol.

$^1$H NMR (400 MHz, DMSO-$d_6$) δ 9.103-9.096 (d, J=2.8 Hz, 1H), 8.546-8.516 (dd, J=9.2 Hz, 2.8 Hz, 1H), 7.781-7.760 (d, J=8.4 Hz, 2H), 7.708-7.688 (d, J=8 Hz, 2H), 7.173-7.150 (d, J=9.2 Hz, 1H), 5.607 (s, 2H).

Step 96-2: Preparation of 6-(4-(trifluoromethyl)benzyloxy)pyridine-3-amine 158 mg (yield: 88%) of the title compound was obtained in the same manner as in Step 95-2 of Example 95 above, except that 5-nitro-2-(4-(trifluoromethyl)benzyloxy)pyridine (200 mg, 0.67 mmol) obtained in Step 96-1 was used instead of 2-(benzyloxy)-5-nitropyridine.

$^1$H NMR (400 MHz, $CDCl_3$) δ 7.651-7.644 (d, J=2.8 Hz, 1H), 7.622-7.602 (d, J=8.0 Hz, 2H), 7.557-7.536 (d, J=8.4 Hz, 2H), 7.074-7.045 (dd, J=8.8 Hz, 2.8 Hz, 1H), 6.697-6.675 (d, J=8.8 Hz, 1H), 5.357, 2H), 3.389 (s, 2H).

Step 96-3: Preparation of (6-(4-(trifluoromethyl) benzyloxy)pyridin-3-yl)carbonohydrazonoyl dicyanide 12 mg (yield: 24%) of the title compound was obtained in the same manner as in Step 1-3 of Example 1 above, except that 6-(4-(trifluoromethyl)benzyloxy)pyridine-3-amine (40 mg, 0.15 mmol) obtained in Step 96-2 was used instead of N-(5-aminopyridin-2-yl)-5-methylpyrazine-2-carboxamide.

$^1$H NMR (400 MHz, $CDCl_3$) δ 9.828 (s, 1H), 8.149-8.142 (d, J=2.8 Hz, 1H), 7.718-7.688 (dd, J=9.2 Hz, 2.8 Hz, 1H), 7.648-7.627 (d, J=8.4 Hz, 2H), 7.570-7.550 (d, J=8 Hz, 2H), 6.936-6.913 (d, J=9.2 Hz, 1H), 5.456 (s, 2H).

Example 97: Preparation of (4-(benzyloxy)-3-(trifluoromethyl)phenyl)carbonohydrazonoyl dicyanide (Compound 97)

Step 97-1: Preparation of 1-(benzyloxy)-4-nitro2-(trifluoromethyl)benzene

In the same manner as in Step 68-1 of Example 68 above, 1-fluoro-4-nitro-2-(trifluoromethyl)benzene (0.2 mL, 1.4 mmol) was dissolved in dimethyl formamide, phenylmethanol (174 μL, 1.68 mmol) and potassium carbonate (290 mg, 2.1 mmol) were added thereto, and the reaction mixture was stirred using a microwave at 150° C. for 1 hour. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 305 mg (yield: 73%) of the title compound.

$^1$H NMR (400 MHz, $CDCl_3$) δ 8.533-8.526 (d, J=2.8 Hz 1H), 8.394-8.364 (dd, J=9.2 Hz, 2.8 Hz, 1H), 7.424-7.350 (m, 5H), 7.143-7.120 (d, J=9.2 Hz, 1H), 5.327 (s, 2H).

Step 97-2: Preparation of 4-(benzyloxy)-3-(trifluoromethyl)aniline

In the same manner as in Step 96-2 of Example 96 above, 1-(benzyloxy)-4-nitro-2-(trifluoromethyl)benzene (150 mg, 0.5 mmol) was dissolved in THF, and $NH_4Cl$ (216 mg, 4.04 mmol) was added thereto. The reaction mixture was refluxed at 75° C. for 1 hour. After 1 hour, Fe (226 mg, 4.04 mmol) was added thereto, and the reaction mixture was refluxed at 75° C. for 15 hours. Upon completion of the reaction, a reaction product was filtered using celite and extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 71 mg (yield: 53%) of the title compound.

1H NMR (400 MHz, $CDCl_3$) δ 7.412-7.275 (m, 5H), 6.911-6.904 (d, J=2.8 Hz 1H), 6.862-6.840 (d, J=8.8 Hz, 1H), 6.749-6.721 (dd, J=8.8 Hz, 2.4 Hz, 1H), 5.065 (s, 2H), 3.515 (s, 2H).

Step 97-3: Preparation of (4-(benzyloxy)-3-(trifluoromethyl)phenyl)carbonohydrazonoyl dicyanide In the same manner as in Step 34-3 of Example 34 above, 4-(benzyloxy)-3-(trifluoromethyl)aniline (50 mg, 0.19 mmol) and sodium nitrite (19 mg, 0.28 mmol) were dissolved in ethanol, and a diazonium salt was formed using a 1.0 M aqueous hydrochloric acid solution (0.56 mL, 0.56 mmol). After the diazonium salt was formed, malononitrile (25 mg, 0.38 mmol) was added thereto to obtain 37 mg (yield: 56%) of the title compound.

$^1$H NMR (400 MHz, DMSO-$d_6$) δ 13.025 (s, 1H), 7.749-7.742 (d, J=2.8 Hz, 1H), 7.909-7.681 (dd, J=9.0 Hz, 2.5 Hz, 1H), 7.452-7.392 (m, 5H), 7.357-7.340 (d, J=6.8 Hz, 1H), 5.284 (s, 2H).

Example 98: Preparation of (3-(trifluoromethyl)-4-(4-(trifluoromethyl)benzyloxy)phenyl)carbonohydrazonoyl dicyanide (Compound 98)

Step 98-1: Preparation of 4-nitro-2-(trifluoromethyl)-1-4(4-(trifluoromethyl)benzil)ox)benzene In the same manner as in Step 95-1 of Example 95 above, (4-(trifluoromethyl)phenyl)methanol (164 μL, 1.2 mmol) was dissolved in a THE solution under a nitrogen atmosphere, and 60% NaH (72 mg, 1.8 mmol) was added thereto. The reaction mixture was stirred at 0° C. for 30 minutes. After 30 minutes, 1-fluoro-4-nitro-2-(trifluoromethyl)benzene (137 μL, 1 mmol) was added thereto, and the reaction mixture was stirred for 2 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 266 mg (yield: 73%) of the title compound.

$^1$H NMR (400 MHz, DMSO-$d_6$) δ 8.580-8.550 (dd, J=9.2 Hz, 2.8 Hz, 1H), 8.431-8.425 (d, J=2.4 Hz, 1H), 7.836-7.816 (d, J=8.0 Hz, 2H), 7.690-7.670 (d, J=8.0 Hz, 2H), 7.608-7.585 (d, J=9.2 Hz, 1H), 5.586 (s, 2H).

Step 98-2: Preparation of 3-(trifluoromethyl)-4-(4-(trifluoromethyl)benzil)ox)aniline In the same manner as in Step 1-2 of Example 1 above, 4-nitro-2-(trifluoromethyl)-1-((4-(trifluoromethyl)benzyl)oxy)benzene (183 mg, 0.5 mmol) and 10% Pd/C (10.6 mg, 0.1 mmol) were dissolved in 1,4-dioxane, and 86.4 mg (yield: 52%) of the title compound was obtained under a hydrogen atmosphere.

$^1$H NMR (400 MHz, DMSO-$d_6$) δ 7.783-7.762 (d, J=8.4 Hz, 2H), 7.640-7.620 (d, J=8.0 Hz, 2H), 7.057-7.035 (d, J=8.8 Hz, 1H), 6.864-6.857 (d, J=2.8 Hz, 1H), 6.789-6.760 (dd, J=8.8 Hz, 2.8 Hz, 1H), 5.190 (s, 2H), 5.119 (s, 2H).

Step 98-3: Preparation of (3-(trifluoromethyl)-4-(4-(trifluoromethyl)benzyl)oxy)phenyl)carbonohydrazonoyl dicyanide In the same manner as in Step 34-3 of Example 34 above, 3-(trifluoromethyl)-4-((4-(trifluoromethyl)benzyl)oxy)aniline (60 mg, 0.18 mmol) and sodium nitrite (19 mg, 0.28 mmol) were dissolved in ethanol, and a diazonium salt was formed using a 1.0 M aqueous hydrochloric acid solution (0.54 mL, 0.54 mmol). After the diazonium salt was formed, malononitrile (24 mg, 0.36 mmol) was added thereto to obtain 30 mg (yield: 41%) of the title compound.

$^1$H NMR (400 MHz, DMSO-$d_6$) δ 13.118 (s, 1H), 7.812-7.792 (d, J=8.0 Hz, 2H), 7.758-7.752 (d, J=2.4 Hz, 1H), 7.718-7.689 (dd, J=9.0 Hz, 2.6 Hz, 1H), 7.666-7.646 (d, J=8.0 Hz, 2H), 7.431-7.408 (d, J=9.2 Hz, 1H), 5.403 (s, 2H).

Example 99: Preparation of (6-(4-methylbenzyloxy)pyridin-3-yl)carbonohydrazonoyl dicyanide (Compound 99)

Step 99-1: Preparation of 2-4(4-methylbenzyloxy)-5-nitropyridine

In the same manner as in Step 85-1 of Example 85 above, p-tolylmethanol (160 mg, 1.3 mmol) was dissolved in a THF solution under a nitrogen atmosphere, and 60% NaH (72 mg, 1.8 mmol) was added thereto. The reaction mixture was stirred at 0° C. for 30 minutes. After 30 minutes, 2-chloro-5-nitropyridine (160 mg, 1 mmol) was added thereto, and the reaction mixture was stirred for 2 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 140 mg (yield: 57%) of the title compound.

$^1$H NMR (400 MHz, DMSO-$d_6$) δ 9.105-9.098 (d, J=2.8 Hz, 1H), 8.506-8.476 (dd, J=3.0 Hz, 8.6 Hz, 1H), 7.374-7.354 (d, J=8 Hz, 2H), 7.213-7.193 (d, J=8 Hz, 2H), 7.091-7.068 (d, J=9.2 Hz, 1H), 5.443 (s, 2H), 2.307 (s, 3H).

Step 99-2: Preparation of 6-(4-methylbenzyloxy)pyridine-3-amine

In the same manner as in Step 1-2 of Example 1 above, 2-((4-methylbenzyl)oxy)-5-nitropyridine (100 mg, 0.41 mmol) and 10% Pd/C (8.71 mg, 0.08 mmol) were dissolved in 1,4-dioxane, and 60 mg (yield: 68%) of the title compound was obtained under a hydrogen atmosphere.

$^1$H NMR (400 MHz, $CDCl_3$) δ 7.669-7.662 (d, J=2.8 Hz, 1H), 7.344-7.324 (d, J=8 Hz, 2H), 7.179-7.159 (d, J=8 Hz, 2H), 7.043-7.014 (dd, J=3.0 Hz, 8.6 Hz, 1H), 6.657-6.636 (d, J=8.4 Hz, 1H), 3.342 (s, 2H), 2.347 (s, 3H).

Step 99-3: Preparation of (6-(4-methylbenzyloxy)pyridin-3-yl)carbonohydrazonoyl dicyanide In the same manner as in Step 34-3 of Example 34 above, 6-((4-methylbenzyl)oxy)pyridine-3-amine (54 mg, 0.25 mmol) and sodium nitrite (26 mg, 0.38 mmol) were dissolved in ethanol, and a diazonium salt was formed using a 1.0 M aqueous hydrochloric acid solution (0.76 mL, 0.76 mmol). After the diazonium salt was formed, malononitrile (33 mg, 0.5 mmol) was added thereto to obtain 19 mg (yield: 26%) of the title compound.

$^1$H NMR (400 MHz, Acetone-$d_6$) δ 11.874 (s, 1H), 8.337-8.330 (d, J=2.8 Hz, 1H), 7.909-7.879 (dd, J=9.0 Hz, 3.0 Hz, 1H), 7.369-7.350 (d, J=7.6 Hz, 2H), 7.201-7.183 (d, J=7.2 Hz, 2H), 6.941-6.919 (d, J=8.8 Hz, 1H), 5.351 (s, 2H), 2.323 (s, 3H).

Example 100: Preparation of (6-phenethoxypyridin-3-yl)carbonohydrazonoyl dicyanide (Compound 100)

Step 100-1: Preparation of 5-nitro-2-phenethylpyridine

In the same manner as in Step 95-1 of Example 95, 2-phenylethan-1-ol (144 μL, 1.20 mmol) was dissolved in a THE solution under a nitrogen atmosphere, and 60% NaH (72 mg, 1.8 mmol) was added thereto. The reaction mixture was stirred at 0° C. for 30 minutes. After 30 minutes, 2-chloro-5-nitro-pyridine (158 mg, 1.0 mmol) was added thereto, and the reaction mixture was further stirred for 4 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 112 mg (yield: 50%) of the title compound.

$^1$H NMR (400 MHz, DMSO-$d_6$) δ 9.081-9.075 (d, J=2.4 Hz, 1H), 8.476-8.446 (dd, J=9.2 Hz, 2.8 Hz, 1H), 7.317-7.213 (m, 5H), 7.016-6.993 (d, J=9.2 Hz, 1H), 4.640-4.606 (t, J=6.8 Hz, 2H), 3.093-3.059 (t, J=6.8 Hz, 2H).

Step 100-2: Preparation of 6-phenethoxypyridine-3-amine

In the same manner as in Step 1-2 of Example 1 above, 5-nitro-2-phenethylpyridine (50 mg, 0.2 mmol) and 10% Pd/C (4.5 mg, 0.04 mmol) were dissolved in 1,4-dioxane, and 34 mg (yield: 80%) of the title compound was obtained under a hydrogen atmosphere.

$^1$H NMR (400 MHz, Acetone-$d_6$) δ 7.525-7.519 (d, J=2.4 Hz, 1H), 7.324-7.193 (m, 5H), 7.086-7.058 (dd, J=8.4 Hz, 2.8 Hz, 1H), 7.710-7.688 (d, J=8.8 Hz, 1H), 4.486-4.451 (t, J=7.0 Hz, 2H), 3.076-3.041 (t, J=7.0 Hz, 2H), 2.818 (s, 2H).

Step 100-3: Preparation of (6-phenethoxypyridin-3-yl)carbonohydrazonoyl dicyanide In the same manner as in Step 34-3 of Example 34 above, 6-phenethoxypyridine-3-amine (30 mg, 0.14 mmol) and sodium nitrite (15 mg, 0.21 mmol) were dissolved in ethanol, and a diazonium salt was formed using a 1.0 M aqueous hydrochloric acid solution (0.42 mL, 0.42 mmol). After the diazonium salt was formed, malononitrile (19 mg, 0.28 mmol) was added thereto to obtain 18 mg (yield: 44%) of the title compound.

$^1$H NMR (400 MHz, Acetone-$d_6$) δ 11.868 (s, 1H), 8.316-8.310 (d, J=2.4 Hz, 1H), 7.884-7.855 (dd, J=9.0 Hz, 2.6 Hz, 1H), 7.341-7.201 (m, 5H), 6.879-6.856 (d, J=9.2 Hz, 1H), 4.548-4.513 (t, J=7.0 Hz, 2H), 3.098-3.063 (t, J=7.0 Hz, 2H).

Example 101: Preparation of (4-phenethoxy-3-(trifluoromethyl)phenyl)carbonohydrazonoyl dicyanide (Compound 101)

Step 101-1: Preparation of 4-nitro-1-phenethoxy-2-(trifluoromethyl)benzene

In the same manner as in Step 85-1 of Example 85 above, 2-phenylethan-1-ol (258 μL, 2.15 mmol) was dissolved in a THE solution under a nitrogen atmosphere, and 60% NaH (115 mg, 2.87 mmol) was added thereto. The reaction mixture was stirred at 0° C. for 30 minutes. After 30 minutes, 1-fluoro-4-nitro-2-(trifluoromethyl)benzene (0.2 mL, 1.43 mmol) was added thereto, and the reaction mixture was stirred for 4 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 332 mg (yield: 74%) of the title compound.

$^1$H NMR (400 MHz, DMSO-$d_6$) δ 8.518-8.488 (dd, J=9.2 Hz, 2.8 Hz, 1H), 8.374-8.367 (d, J=2.8 Hz, 1H), 7.543-7.520 (d, J=9.2 Hz, 1H), 7.355-7.236 (m, 5H), 4.526-4.493 (t, J=6.6 Hz, 2H), 3.120-3.087 (t, J=6.6 Hz, 2H).

Step 101-2: Preparation of 4-phenethoxy-3-(trifluoromethyl)aniline

In the same manner as in Step 1-2 of Example 1 above, 4-nitro-1-phenethoxy-2-(trifluoromethyl)benzene (250 mg, 0.8 mmol) and 10% Pd/C (17 mg, 0.16 mmol) were dissolved in 1,4-dioxane, and 194 mg (yield: 86%) of the title compound was obtained under a hydrogen atmosphere.

$^1$H NMR (400 MHz, DMSO-$d_6$) δ 7.321-7.209 (m, 5H), 6.971-6.949 (d, J=8.8 Hz, 1H), 6.832-6.825 (d, J=2.8 Hz, 1H), 6.783-6.755 (dd, J=8.6 Hz, 2.6 Hz, 1H), 5.021 (s, 2H), 4.143-4.109 (t, J=6.8 Hz, 2H), 3.001-2.967 (t, J=6.8 Hz, 2H).

Step 101-3: Preparation of (4-phenethoxy-3-(trifluoromethyl)phenyl)carbonohydrazonoyl dicyanide In the same manner as in Step 34-3 of Example 34 above, 4-phenethoxy-3-(trifluoromethyl)aniline (50 mg, 0.18 mmol) and sodium nitrite (19 mg, 0.27 mmol) were dissolved in ethanol, and a diazonium salt was formed using a 1.0 M aqueous hydrochloric acid solution (0.53 mL, 0.53 mmol). After the diazonium salt was formed, malononitrile (24 mg, 0.36 mmol) was added thereto to obtain 55 mg (yield: 85%) of the title compound.

1H NMR (400 MHz, $CDCl_3$) δ 9.566 (s, 1H), 7.534-7.527 (d, J=2.8 Hz, 1H), 7.430-7.401 (dd, J=9.0 Hz, 2.6 Hz, 1H), 7.348-7.233 (m, 5H), 7.026-7.004 (d, J=8.8 Hz, 1H), 4.278-4.244 (t, J=6.8 Hz, 2H), 3.163-3.130 (t, J=6.6 Hz, 2H).

Example 102: Preparation of (6-(4-methoxyphenethoxy)pyridin-3-yl)carbonohydrazonoyl dicyanide (Compound 102)

Step 102-1: Preparation of 2-(4-methoxyphenethoxy)-5-nitropyridine

In the same manner as in Step 95-1 of Example 95 above, 2-(4-methoxyphenyl)ethan-1-ol (183 mg, 1.20 mmol) was dissolved in a THF solution under a nitrogen atmosphere, and 60% NaH (72 mg, 1.8 mmol) was added thereto. The reaction mixture was stirred at 0° C. for 30 minutes. After 30 minutes, 2-chloro-5-nitro-pyridine (160 mg, 1.0 mmol) was added thereto, and the reaction mixture was stirred for 3 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 184 mg (yield: 67%) of the title compound.

$^1$H NMR (400 MHz, DMSO-$d_6$) δ 9.082-9.074 (d, J=3.2 Hz, 1H), 8.479-8.449 (dd, J=9.2 Hz, 2.8 Hz, 1H), 7.233-7.212 (d, J=8.4 Hz, 2H), 7.014-6.991 (d, J=9.2 Hz, 1H), 6.882-6.861 (d, J=8.4 Hz, 2H), 4.589-4.555 (t, J=6.8 Hz, 2H), 3.723 (s, 3H), 3.023-2.989 (t, J=6.8 Hz, 2H).

Step 102-2: Preparation of 6-(4-methoxyphenethoxy)pyridine-3-amine

In the same manner as in Step 1-2 of Example 1 above, 2-(4-methoxyphenethoxy)-5-nitropyridine (140 mg, 0.51 mmol) and 10% Pd/C (11 mg, 0.1 mmol) were dissolved in 1,4-dioxane, and 62 mg (yield: 50%) of the title compound was obtained under a hydrogen atmosphere.

$^1$H NMR (400 MHz, DMSO-$d_6$) δ 7.490-7.484 (d, J=2.4 Hz, 1H), 7.197-7.176 (d, J=8.4 Hz, 2H), 7.005-6.976 (dd, J=8.8 Hz, 2.8 Hz, 1H), 6.866-6.844 (d, J=8.8 Hz, 2H), 6.517-6.496 (d, J=8.4 Hz, 1H), 4.726 (s, 2H), 4.261-4.226 (t, J=7.0 Hz, 2H), 3.719 (s, 3H), 2.906-2.871 (t, J=7.0 Hz, 2H).

Step 102-3: Preparation of (6-(4-methoxyphenethoxy)pyridin-3-yl)carbonohydrazonoyl dicyanide In the same manner as in Step 34-3 of Example 34 above, 6-(4-methoxyphenethoxy)pyridine-3-amine (50 mg, 0.18 mmol) and sodium nitrite (19 mg, 0.27 mmol) were dissolved in ethanol, and a diazonium salt was formed using a 1.0 M aqueous hydrochloric acid solution (0.55 mL, 0.55 mmol). After the diazonium salt was formed, malononitrile (24 mg, 0.36 mmol) was added thereto to obtain 24 mg (yield: 41%) of the title compound.

$^1$H NMR (400 MHz, Acetone-$d_6$) δ 11.866 (s, 1H), 8.313-8.306 (d, J=2.8 Hz, 1H), 7.883-7.853 (dd, J=9.2 Hz, 2.8 Hz, 1H), 7.249-7.228 (d, J=8.4 Hz, 2H), 6.880-6.854 (m, 3H), 4.499-4.463 (t, J=7.2 Hz, 2H), 3.767 (s, 3H), 3.026-2.991 (t, J=7.0 Hz, 2H).

Example 103: Preparation of (6-(4-(trifluoromethyl)phenethoxy)pyridin-3-yl)carbonohydrazonoyl dicyanide (Compound 103)

Step 103-1: Preparation of 5-nitro-2-(4-(trifluoromethyl)phenethoxy)pyridine In the same manner as in Step 95-1 above, 2-(4-(trifluoromethyl)phenyl)ethan-1-ol (0.18 mL, 1.20 mmol) was dissolved in a THE solution under a nitrogen atmosphere, and 60% NaH (72 mg, 1.8 mmol) was added thereto. The reaction mixture was stirred at 0° C. for 30 minutes. After 30 minutes, 2-chloro-5-nitro-pyridine (160 mg, 1.0 mmol) was added thereto, and the reaction mixture was stirred for 3 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 215 mg (yield: 69%) of the title compound.

$^1$H NMR (400 MHz, $CDCl_3$-$d_6$) δ 9.058-9.052 (d, J=2.4 Hz, 1H), 8.358-8.329 (dd, J=8.8 Hz, 2.8 Hz, 1H), 7.584-7.564 (d, J=8.0 Hz, 2H), 7.411-7.391 (d, J=8.0 Hz, 2H), 6.816-6.794 (d, J=8.8 Hz, 1H), 4.692-4.658 (t, J=6.8 Hz, 2H), 3.196-3.162 (t, J=6.8 Hz, 2H).

Step 103-2: Preparation of 6-(4-(trifluoromethyl)phenethoxy)pyridine-3-amine In the same manner as in Step 1-2 of Example 1 above 5-nitro-2-(4-(trifluoromethyl)phenethoxy)pyridine (160 mg, 0.51 mmol) and 10% Pd/C (11 mg, 0.1 mmol) were dissolved in 1,4-dioxane, and 94 mg (yield: 67%) of the title compound was obtained under a hydrogen atmosphere.

$^1$H NMR (400 MHz, DMSO-$d_6$) δ 7.674-7.654 (d, J=8.0 Hz, 2H), 7.531-7.496 (m, 3H), 7.013-6.984 (dd, J=8.6 Hz, 3.0 Hz, 1H), 6.524-6.502 (d, J=8.8 Hz, 1H), 4.753 (s, 2H), 4.368-4.334 (t, J=6.8 Hz, 2H), 3.092-3.059 (t, J=6.6 Hz, 2H).

Step 103-3: Preparation of (6-(4-(trifluoromethyl)phenethoxy)pyridin-3-yl)carbonohydrazonic Dicyanide In the same manner as in Step 34-3 of Example 34 above, 6-(4-(trifluoromethyl)phenethoxy)pyridine-3-amine (70 mg, 0.25 mmol) and sodium nitrite (26 mg, 0.37 mmol) were dissolved in ethanol, and a diazonium salt was formed using a 1.0 M aqueous hydrochloric acid solution (0.74 mL, 0.74 mmol). After the diazonium salt was formed, malononitrile (33 mg, 0.5 mmol) was added thereto to obtain 91 mg (yield: 100%) of the title compound.

$^1$H NMR (400 MHz, Acetone-$d_6$) δ 11.947 (s, 1H), 8.320-8.314 (d, J=2.4 Hz, 1H), 7.884-7.855 (dd, J=8.8 Hz, 2.8 Hz, 1H), 7.668-7.647 (d, J=8.4 Hz, 2H), 7.585-7.565 (d, J=8.0 Hz, 2H), 6.879-6.857 (d, J=8.8 Hz, 1H), 4.606-4.573 (t, J=6.6 Hz, 2H), 3.218-3.184 (t, J=6.8 Hz, 2H).

Example 104: Preparation of (3-methoxy-4-(5-methylpyrazin-2-ylcarbamoyl)phenyl)carbonohydrazonoyl dicyanide (Compound 104)

Step 104-1: Preparation of 2-methoxy-N-(5-methylpyrazin-2-yl)-4-nitrobenzamide 185 mg (yield: 63%) of the title compound was obtained in the same manner as in Step 34-1 of Example 34 above, except that 2-methoxy-4-nitrobenzoic acid (200 mg, 1.01 mmol) was used instead of 5-nitrocholic acid, and 5-methylpyrazine-2-amine (111 mg, 1.01 mmol) was used instead of p-toluidine.

$^1$H NMR (400 MHz, DMSO-$d_6$) δ 10.95 (s, 1H), 9.33 (s, 1H), 8.35 (d, J=1.5 Hz, 1H), 7.94 (dq, J=3.9 Hz, 2.0 Hz, 2H), 7.89 (d, J=8.9 Hz, 1H), 4.03 (s, 3H), 2.50 (s, 3H).

Step 104-2: Preparation of 4-amino-2-methoxy-N-(5-methylpyrazin-2-yl)benzamide 135 mg (yield: 82%) of the title compound was obtained in the same manner as in Step 34-2 of Example 34 above, except that 2-methoxy-N-(5-methylpyrazin-2-yl)-4-nitrobenzamide (183 mg, 0.63 mmol) obtained in Step 104-1 was used instead of 5-nitro-N-p-tolylpicolinamide.

$^1$H NMR (400 MHz, DMSO-$d_6$) δ 10.95 (s, 1H), 9.33 (s, 1H), 8.35 (d, J=1.5 Hz, 1H), 7.94 (dq, J=3.9 Hz, 2.0 Hz, 2H), 7.89 (d, J=8.9 Hz, 1H), 4.03 (s, 3H), 2.50 (s, 3H).

Step 104-3: Preparation of (3-methoxy-4-(5-methylpyrazin-2-ylcarbamoyl)phenyl)carbonohydrazonoyl dicyanide 18 mg (yield: 19%) of the title compound was obtained in the same manner as in Step 1-3 of Example 1 above, except that 4-amino-2-methoxy-N-(5-methylpyrazin-2-yl)benzamide (70 mg, 0.27 mmol) obtained in Step 104-2 was used instead of N-(5-aminopyridin-2-yl)-5-methylpyrazine-2-carboxamide.

$^1$H NMR (400 MHz, DMSO-$d_6$) δ 10.95 (s, 1H), 9.33 (s, 1H), 8.35 (d, J=1.5 Hz, 1H), 7.94 (dq, J=3.9 Hz, 2.0 Hz, 2H), 7.89 (d, J=8.9 Hz, 1H), 4.03 (s, 3H), 2.50 (s, 3H).

Example 106: Preparation of (3-methoxy-4-(6-methylpyrazin-2-ylcarbamoyl)phenyl)carbonohydrazonoyl dicyanide (Compound 106)

Step 105-1: Preparation of 2-methoxy-N-(6-methylpyrazin-2-yl)-4-nitrobenzamide 113 mg (yield: 38%) of the title compound was obtained in the same manner as in Step 34-1 of Example 34 above, except that 2-methoxy-4-nitrobenzoic acid (200 mg, 1.01 mmol) was used instead of 5-nitrocholic acid, and 6-methylpyrazine-2-amine (111 mg, 1.01 mmol) was used instead of p-toluidine.

$^1$H NMR (400 MHz, DMSO-$d_6$) δ 13.11 (s, 1H), 9.28 (s, 1H), 8.36 (s, 1H), 7.94-7.92 (m, 2H), 4.02 (s, 3H), 2.48 (s, 3H).

Step 105-2: Preparation of 4-amino-2-methoxy-N-(6-methylpyrazin-2-yl)benzamide 29 mg (yield: 26%) of the title compound was obtained in the same manner as in Step 34-2 of Example 34 above, except that 2-methoxy-N-(6-methylpyrazin-2-yl)-4-nitrobenzamide (124 mg, 0.43 mmol) obtained in Step 105-1 was used instead of 5-nitro-N-p-tolylpicolinamide.

$^1$H NMR (400 MHz, DMSO-$d_6$) δ 10.14 (s, 1H), 9.32 (s, 1H), 8.25 (s, 1H), 7.78 (d, J=8.4 Hz, 1H), 6.33 (d, J=1.6 Hz, 1H), 6.31 (dd, J=8.4 Hz, 1.6 Hz, 1H), 6.09 (s, 2H), 3.96 (s, 3H), 2.45 (s, 3H).

Step 105-3: Preparation of (3-methoxy-4-(6-methylpyrazin-2-ylcarbamoyl)phenyl)carbonohydrazonoyl dicyanide 8 mg (yield: 24%) of the title compound was obtained in the same manner as in Step 1-3 of Example 1 above, except that 4-amino-2-methoxy-N-(6-methylpyrazin-2-yl)benzamide (27 mg, 0.11 mmol) obtained in Step 105-2 was used instead of N-(5-aminopyridin-2-yl)-5-methylpyrazine-2-carboxamide.

1H NMR (400 MHz, DMSO-$d_6$) δ 10.42 (s, 1H), 9.30 (s, 1H), 8.32 (s, 1H), 7.93 (d, J=8.6 Hz, 1H), 7.27 (d, J=2.0 Hz, 1H), 7.19 (dd, J=8.6 Hz, 1.9 Hz, 1H), 4.01 (s, 3H), 2.47 (s, 3H).

Example 106: Preparation of (3-chloro-4-(6-methylpyrazin-2-ylcarbamoyl)phenyl)carbonohydrazonoyl dicyanide (Compound 106)

Step 106-1: Preparation of 2-chloro-N-(5-methylpyrazin-2-yl)-4-nitrobenzamide 174 mg (yield: 59%) of the title compound was obtained in the same manner as in Step 34-1 of Example 34 above, except that 2-methoxy-4-nitrobenzoic acid (200 mg, 1.01 mmol) was used instead of 5-nitrocholic acid, and 6-methylpyrazine-2-amine (111 mg, 1.01 mmol) was used instead of p-toluidine.

$^1$H NMR (400 MHz, DMSO-$d_6$) δ 11.52 (s, 1H), 9.31 (s, 1H), 8.42 (d, J=2.2 Hz, 1H), 8.37 (s, 1H), 8.30 (dd, J=8.4 Hz, 2.2 Hz, 1H), 7.93 (d, J=8.4 Hz, 1H), 2.52 (s, 3H).

Step 106-2: Preparation of 4-amino-2-chloro-N-(5-methylpyrazin-2-ylbenzamide

2-Chloro-N-(5-methylpyrazin-2-yl)-4-nitrobenzamide (165 mg, 0.56 mmol) obtained in Step 106-1 was dissolved in acetic acid (6 mL) under a nitrogen atmosphere, and the reaction mixture was stirred at room temperature for 2 hours. Upon completion of the reaction, iron was filtered using ethyl acetate and the filtrate was extracted using an aqueous sodium hydrogen carbonate solution and ethyl acetate. An organic layer was dried over anhydrous magnesium sulfate and purified by column chromatography to obtain 60 mg (yield: 40%) of the title compound.

$^1$H NMR (400 MHz, DMSO-$d_6$) δ 10.68 (s, 2H), 9.25 (d, J=1.5 Hz, 2H), 8.31 (d, J=1.5 Hz, 2H), 7.35 (d, J=8.4 Hz, 2H), 6.65 (d, J=2.1 Hz, 2H), 6.54 (dd, J=8.4 Hz, 2.2 Hz, 2H), 5.90 (s, 2H), 2.47 (s, 3H).

Step 106-3: Preparation of (3-chloro-4-(5-methylpyrazin-2-ylcarbamoyl)phenyl)carbonohydrazonoyl dicyanide 40 mg (yield: 51%) of the title compound was obtained in the same manner as in Step 1-3 of Example 1 above, except that 4-amino-2-chloro-N-(5-methylpyrazin-2-yl)benzamide (60 mg, 0.23 mmol) obtained in Step 106-2 was used instead of N-(5-aminopyridin-2-yl)-5-methylpyrazine-2-carboxamide.

$^1$H NMR (400 MHz, DMSO-$d_6$) δ 12.98 (s, 1H), 11.23 (s, 1H), 9.29 (s, 1H), 8.35 (s, 1H), 7.68 (d, J=8.4 Hz, 1H), 7.58 (d, J=2.1 Hz, 1H), 7.50 (dd, J=8.5 Hz, 2.1 Hz, 1H), 2.52 (s, 3H).

Example 107: Preparation of (3-methoxy-4-(5-methylpyridin-3-ylcarbamoyl)phenyl)carbonohydrazonoyl dicyanide (Compound 107)

Step 107-1: Preparation of 2-methoxy-N-(5-methylpyridin-3-yl)-4-nitrobenzamide 246 mg (yield: 84%) of the title compound was obtained in the same manner as in Step 34-1 of Example 34 above, except that 2-methoxy-4-nitrobenzoic acid (200 mg, 1.01 mmol) was used instead of 5-nitrocholic acid, and 3-amino-5-methylpyridine (110 mg, 1.01 mmol) was used instead of p-toluidine.

$^1$H NMR (400 MHz, DMSO-$d_6$) δ 10.86 (s, 1H), 8.95-8.90 (m, 1H), 8.40 (s, 1H), 8.23 (d, J=2.1 Hz, 1H), 7.96 (dt, J=3.9 Hz, 2.5 Hz, 2H), 7.84 (d, J=8.9 Hz, 1H), 4.02 (s, 3H), 2.42 (s, 3H).

Step 107-2: Preparation of 4-amino-2-methoxy-N-(5-methylpyridin-3-yl)benzamide 83 mg (yield: 38%) of the title compound was obtained in the same manner as in Step 34-2 of Example 34 above, except that 2-methoxy-N-(5-methylpyridin-3-yl)-4-nitrobenzamide (240 mg, 0.84 mmol) obtained in Step 107-1 was used instead of 5-nitro-N-p-tolylpicolinamide.

$^1$H NMR (400 MHz, DMSO-$d_6$) δ 9.81 (s, 1H), 8.69 (d, J=2.4 Hz, 1H), 8.11 (d, J=1.9 Hz, 1H), 8.04 (s, 1H), 7.66 (d, J=8.5 Hz, 1H), 6.33-6.23 (m, 2H), 5.93 (s, 2H), 3.94 (s, 3H), 2.31 (s, 3H).

Step 107-3: Preparation of (3-methoxy-4-(5-methylpyridin-3-ylcarbamoyl)phenyl)carbonohydrazonoyl dicyanide 54 mg (yield: 55%) of the title compound was obtained in the same manner as in Step 1-3 of Example 1 above, except that 4-amino-2-methoxy-N-(5-methylpyridin-3-yl)benzamide (74 mg, 0.29 mmol) obtained in Step 107-2 was used instead of N-(5-aminopyridin-2-yl)-5-methylpyrazine-2-carboxamide.

$^1$H NMR (400 MHz, DMSO-$d_6$) δ 10.24 (s, 1H), 8.84-8.79 (m, 1H), 8.24 (s, 1H), 8.14 (t, J=2.2 Hz, 1H), 7.77 (d, J=8.4 Hz, 1H), 7.21 (d, J=1.9 Hz, 1H), 7.13 (dd, J=8.4 Hz, 1.9 Hz, 1H), 3.96 (s, 3H), 2.35 (s, 3H).

Example 108: Preparation of (3-methoxy-4-(p-tolylcarbamoyl)phenyl)carbonohydrazonoyl Dicyanide (Compound 108)

Step 108-1: Preparation of 2-methoxy-4-nitro-N-(p-tolyl)benzamide 150 mg (yield: 68%) of the title compound was obtained in the same manner as in Step 34-1 of Example 34 above, except that 2-methoxy-4-nitrobenzoic acid (150 mg, 0.76 mmol) was used instead of 5-nitrocholic acid.

$^1$H NMR (400 MHz, DMSO-$d_6$) δ 10.29 (s, 1H), 7.96-7.89 (m, 2H), 7.81 (d, J=8.8 Hz, 1H), 7.62 (d, J=8.4 Hz, 2H), 7.17 (d, J=8.4 Hz, 2H), 4.00 (s, 3H), 2.30 (s, 3H).

Step 108-2: Preparation of 4-amino-2-methoxy-N-(p-toll)benzamide 121 mg (yield: 99%) of the title compound was obtained in the same manner as in Step 34-2 of Example 34 above, except that 2-methoxy-4-nitro-N-(p-tolyl)benzamide (135 mg, 0.47 mmol) obtained in Step 108-1 was used instead of 5-nitro-N-p-tolylpicolinamide.

$^1$H NMR (400 MHz, DMSO-$d_6$) δ 9.70 (s, 1H), 7.66 (d, J=8.5 Hz, 1H), 7.64-7.57 (m, 2H), 7.13 (d, J=8.2 Hz, 2H), 6.30 (d, J=1.9 Hz, 1H), 6.26 (dd, J=8.5 Hz, 2.0 Hz, 1H), 5.86 (s, 2H), 3.93 (s, 3H), 2.28 (s, 3H), 2.28 (s, 3H).

Step 108-3: Preparation of (3-methoxy-4-(p-tolylcarbamoyl)phenyl)carbonohydrazonoyl Dicyanide 95 mg (yield: 60%) of the title compound was obtained in the same manner as in Step 1-3 of Example 1 above, except that 4-amino-2-methoxy-N-(p-tolyl)benzamide (121 mg, 0.47 mmol) obtained in Step 108-2 was used instead of N-(5-aminopyridin-2-yl)-5-methylpyrazine-2-carboxamide.

$^1$H NMR (400 MHz, DMSO-$d_6$) δ 13.19 (s, 1H), 9.97 (s, 1H), 7.77 (d, J=8.4 Hz, 1H), 7.63 (d, J=8.1 Hz, 2H), 7.27 (d, J=2.0 Hz, 1H), 7.17 (dd, J=10.5 Hz, 8.3 Hz, 3H), 3.95 (s, 3H), 2.29 (s, 3H).

Example 109: Preparation of (3-methoxy-4-(4-methoxyphenylcarbamoyl)phenyl)carbonohydrazonoyl Dicyanide (Compound 109)

Step 109-1: Preparation of 2-methoxy-N-(4-methoxyphenyl)-4-nitrobenzamide 225 mg (yield: 73%) of the title compound was obtained in the same manner as in Step 34-1 of Example 34 above, except that 2-methoxy-4-nitrobenzoic acid (200 mg, 1.01 mmol) was used instead of 5-nitrocholic acid, and p-anisidine (125 mg, 1.01 mmol) was used instead of p-toluidine.

$^1$H NMR (400 MHz, DMSO-$d_6$) δ 10.24 (s, 1H), 7.97-7.90 (m, 2H), 7.81 (d, J=8.8 Hz, 1H), 7.65 (d, J=8.8. Hz, 2H), 6.96 (d, J=8.8 Hz, 2H), 4.01 (s, 3H), 3.76 (s, 3H).

Step 109-2: Preparation of 4-amino-2-methoxy-N-(p-tolyl)benzamide 173 mg (yield: 85%) of the title compound was obtained in the same manner as in Step 34-2 of Example 34 above, except that 2-methoxy-N-(4-methoxyphenyl)-4-nitrobenzamide (225 mg, 0.74 mmol) obtained in Step 109-1 was used instead of 5-nitro-N-p-tolylpicolinamide.

$^1$H NMR (400 MHz, DMSO-$d_6$) δ 9.63 (s, 1H), 7.68-7.57 (m, 3H), 6.93-6.85 (m, 2H), 6.29 (d, J=1.9 Hz, 1H), 6.25 (dd, J=8.5 Hz, 1.9 Hz, 1H), 5.83 (s, 2H), 3.91 (s, 3H), 3.33 (s, 1H).

Step 109-3: Preparation of (3-methoxy-4-(4-methoxyphenylcarbamoyl)phenyl)carbonohydrazonoyl dicyanide 90 mg (yield: 44%) of the title compound was obtained in the same manner as in Step 1-3 of Example 1 above, except that 4-amino-2-methoxy-N-(4-methoxyphenyl)benzamide (158 mg, 0.58 mmol) obtained in Step 109-2 was used instead of N-(5-aminopyridin-2-yl)-5-methylpyrazine-2-carboxamide.

$^1$H NMR (400 MHz, DMSO-$d_6$) δ 13.11 (s, 1H), 9.91 (s, 1H), 7.78 (d, J=8.4 Hz, 1H), 7.65 (d, J=8.7 Hz, 2H), 7.25 (d, J=2.0 Hz, 1H), 7.17 (dd, J=8.5 Hz, 1.9 Hz, 1H), 6.93 (d, J=8.6 Hz, 2H), 3.96 (s, 3H), 3.76 (s, 3H).

Example 110: Preparation of (6-(furan-3-carboxamido)pyridin-3-yl)carbonohydrazonoyl dicyanide (Compound 110)

Step 110-1: Preparation of N-(5-nitropyridin-2-yl)furan-3-carboxamide 444 mg (yield: 71%) of the title compound was obtained in the same manner as in Step 11-1 of Example 11 above, except that furan-3-carboxylic acid (300 mg, 2.68 mmol) was used instead of 5-methylpyrazine-2-carboxylic acid, and 2-amino-5-nitroaniline (372 mg, 2.68 mmol) was used instead of 2-chloro-4-nitroaniline.

$^1$H NMR (400 MHz, DMSO-$d_6$) δ 11.36 (s, 1H), 9.22 (d, J=2.8 Hz, 1H), 8.65 (td, J=5.2 Hz, 4.7 Hz, 2.8 Hz, 2H), 8.42 (d, J=9.3 Hz, 1H), 7.83 (s, 1H), 7.10 (s, 1H).

Step 110-2: Preparation of N-(5-aminopyridin-2-yl)furan-3-carboxamide 174 mg (yield: 50%) of the title compound was obtained in the same manner as in Step 1-2 of Example 1 above, except that N-(5-nitropyridin-2-yl)furan-3-carboxamide (400 mg, 1.71 mmol) obtained in Step 110-1 was used instead of 5-methyl-N-(5-nitropyidin-2-yl)pyrazine-2-carboxamide.

$^1$H NMR (400 MHz, DMSO-$d_6$) δ 10.14 (s, 1H), 8.48-8.34 (m, 1H), 7.87-7.67 (m, 3H), 7.11-6.95 (m, 2H), 5.14 (s, 2H).

Step 110-3: Preparation of (6-(furan-3-carboxamido)pyridin-3-yl)carbonohydrazonoyl dicyanide 183 mg (yield: 89%) of the title compound was obtained in the same manner as in Step 1-3 of Example 1 above, except that N-(5-aminopyridin-2-yl)furan-3-carboxamide (150 mg, 0.74 mmol) obtained in Step 110-2 was used instead of N-(5-aminopyridin-2-yl)-5-methylpyrazine-2-carboxamide.

$^1$H NMR (400 MHz, DMSO-$d_6$) δ 10.78 (s, 1H), 8.55 (s, 1H), 8.50 (d, J=2.7 Hz, 1H), 8.22 (d, J=9.1 Hz, 1H), 7.90 (dd, J=9.1 Hz, 2.8 Hz, 1H), 7.79 (s, 1H).

Example 111: Preparation of (3-methyl-4-(thiazole-4-carboxamido)phenyl)carbonohydrazonoyl dicyanide (Compound 111)

Step 111-1: Preparation of N-(2-methyl-4-nitrophenyl)thiazole-4-carboxamide 204 mg (yield: 33%) of the title compound was obtained in the same manner as in Step 11-1 of Example 11 above, except that thiazole-4-carboxylic acid (300 mg, 2.32 mmol) was used instead of 5-methylpyrazine-2-carboxylic acid, and 2-methyl-4-nitroaniline (354 mg, 2.32 mmol) was used instead of 2-chloro-4-nitroaniline.

$^1$H NMR (400 MHz, DMSO-$d_6$) δ 10.03 (s, 1H), 9.32 (d, J=2.0 Hz, 1H), 8.61 (d, J=1.9 Hz, 1H), 8.24-8.18 (m, 2H), 8.15 (dd, J=9.0 Hz, 2.6 Hz, 1H), 2.44 (s, 3H).

Step 111-2: Preparation of N-(4-amino-2-methylphenyl)thiazole-4-carboxamide 129 mg (yield: 97%) of the title compound was obtained in the same manner as in Step 1-2 of Example 1 above, except that N-(2-methyl-4-nitrophenyl)thiazole-4-carboxamide (150 mg, 0.57 mmol) obtained in Step 111-1 was used instead of 5-methyl-N-(5-nitropyridin-2-yl)pyrazine-2-carboxamide.

$^1$H NMR (400 MHz, DMSO-$d_6$) δ 9.49 (s, 1H), 9.23 (d, J=2.0 Hz, 1H), 8.39 (d, J=2.0 Hz, 1H), 7.13 (d, J=8.4 Hz, 1H), 6.52-6.33 (m, 2H), 4.95 (s, 2H), 2.09 (s, 3H).

Step 111-3: Preparation of (3-methyl-4-(thiazole-4-carboxamido)phenovis)carbonohydrazonoyl dicyanide 121 mg (yield: 82%) of the title compound was obtained in the same manner as in Step 1-3 of Example 1 above, except that N-(4-amino-2-methylphenyl)thiazole-4-carboxamide (110 mg, 0.47 mmol) obtained in Step 111-2 was used instead of N-(5-aminopyridin-2-yl)-5-methylpyrazine-2-carboxamide.

$^1$H NMR (400 MHz, DMSO-$d_6$) δ 13.02 (s, 1H), 9.85 (s, 1H), 9.28 (d, J=2.0 Hz, 1H), 8.49 (d, J=2.0 Hz, 1H), 7.72 (d, J=8.7 Hz, 1H), 7.48-7.11 (m, 2H), 2.30 (s, 3H).

Example 112: Preparation of (6-(thiazole-4-carboxamido)pyridin-3-yl)carbonohydrazonoyl dicyanide (Compound 112)

Step 112-1: Preparation of N-(5-nitropyridin-2-yl)thiazole-4-carboxamide 108 mg (yield: 19%) of the title compound was obtained in the same manner as in Step 11-1 of Example 11 above, except that thiazole-4-carboxylic acid (300 mg, 2.32 mmol) was used instead of 5-methylpyrazine-2-carboxylic acid, and 2-amino-5-nitroaniline (324 mg, 2.32 mmol) was used instead of 2-chloro-4-nitroaniline.

$^1$H NMR (400 MHz, DMSO-$d_6$) δ 10.56 (s, 1H), 9.31 (d, J=2.0 Hz, 1H), 9.23 (dd, J=2.8 Hz, 0.7 Hz, 1H), 8.75 (d, J=1.9 Hz, 1H), 8.71 (dd, J=9.2 Hz, 2.8 Hz, 1H), 8.43 (dd, J=9.2 Hz, 0.7 Hz, 1H).

Step 112-2: Preparation of N-(5-aminopyridin-2-yl)thiazole-4-carboxamide 48 mg (yield: 55%) of the title compound was obtained in the same manner as in Step 1-2 of Example 1 above, except that N-(5-nitropyridin-2-yl)thiazole-4-carboxamide (100 mg, 0.40 mmol) obtained in Step 112-1 was used instead of 5-methyl-N-(5-nitropyidin-2-yl)pyrazine-2-carboxamide.

$^1$H NMR (400 MHz, DMSO-$d_6$) δ 9.57 (s, 1H), 9.25 (d, J=2.0 Hz, 1H), 8.50 (d, J=1.9 Hz, 1H), 7.88 (d, J=8.7 Hz, 1H), 7.73 (d, J=2.8 Hz, 1H), 7.05 (dd, J=8.7 Hz, 2.8 Hz, 1H), 5.21 (s, 2H).

Step 112-3: Preparation of (6-(thiazole-4-carboxamido)pyridin-3-yl)carbonohydrazonoyl dicyanide 60 mg (yield: 99%) of the title compound was obtained in the same manner as in Step 1-3 of Example 1 above, except that N-(5-aminopyridin-2-yl)thiazole-4-carboxamide (45 mg, 0.20 mmol) obtained in Step 112-2 was used instead of N-(5-aminopyridin-2-yl)-5-methylpyrazine-2-carboxamide.

$^1$H NMR (400 MHz, DMSO-$d_6$) δ 10.09 (s, 1H), 9.29 (d, J=2.0 Hz, 1H), 8.63 (d, J=2.0 Hz, 1H), 8.49 (d, J=2.7 Hz, 1H), 8.26 (d, J=9.0 Hz, 1H), 7.95 (dd, J=9.0 Hz, 2.7 Hz, 1H).

Example 113: Preparation of (6-(oxazole-4-carboxamido)pyridin-3-yl)carbonohydrazonoyl dicyanide (Compound 113)

Step 113-1: Preparation of N-(6-nitropyridin-2-yl)oxazole-4-carboxamide 76 mg (yield: 12%) of the title compound was obtained in the same manner as in Step 11-1 of Example 11 above, except that oxazole-4-carboxylic acid (300 mg, 2.65 mmol) was used instead of 5-methylpyrazine-2-carboxylic acid, and 2-amino-5-nitroaniline (369 mg, 2.65 mmol) was used instead of 2-chloro-4-nitroaniline.

$^1$H NMR (400 MHz, DMSO-$d_6$) δ 10.71 (s, 1H), 9.23 (d, J=2.8 Hz, 1H), 9.05 (s, 1H), 8.80-8.56 (m, 2H), 8.39 (d, J=9.2 Hz, 1H).

Step 113-2: Preparation of N-(6-aminopyridin-2-yl)oxazole-4-carboxamide 58 mg (yield: 95%) of the title compound was obtained in the same manner as in Step 1-2 of Example 1 above, except that N-(5-nitropyridin-2-yl)oxazole-4-carboxamide (70 mg, 0.30 mmol) obtained in Step 113-1 was used instead of 5-methyl-N-(5-nitropyridin-2-yl)pyrazine-2-carboxamide.

$^1$H NMR (400 MHz, DMSO-$d_6$) δ 9.41 (s, 1H), 8.84 (d, J=1.0 Hz, 1H), 8.59 (d, J=1.0 Hz, 1H), 7.82 (d, J=8.7 Hz, 1H), 7.73 (d, J=2.8 Hz, 1H), 7.04 (dd, J=8.7 Hz, 2.9 Hz, 1H), 5.22 (s, 2H).

Step 113-3: Preparation of (6-(oxazole-4-carboxamido)pyridin-3-yl)carbonohydrazonoyl dicyanide 183 mg (yield: 89%) of the title compound was obtained in the same manner as in Step 1-3 of Example 1 above, except that N-(5-aminopyridin-2-yl)oxazole-4-carboxamide (70 mg, 0.30 mmol) obtained in Step 113-2 was used instead of N-(5-aminopyridin-2-yl)-5-methylpyrazine-2-carboxamide.

$^1$H NMR (400 MHz, DMSO-$d_6$) δ 10.05 (s, 1H), 8.95 (s, 1H), 8.63 (s, 1H), 8.49 (s, 1H), 8.21 (d, J=9.0 Hz, 1H), 7.93 (dd, J=9.0 Hz, 2.7 Hz, 1H).

Example 114: Preparation of (6-(oxazole-5-carboxamido)pyridin-3-yl)carbonohydrazonoyl dicyanide (Compound 114)

Step 114-1: Preparation of N-(5-nitropyridin-2-yl)oxazole-5-carboxamide 95 mg (yield: 15%) of the title compound was obtained in the same manner as in Step 11-1 of Example 11 above, except that oxazole-5-carboxylic acid (300 mg, 2.65 mmol) was used instead of 5-methylpyrazine-2-carboxylic acid, and 2-amino-5-nitroaniline (369 mg, 2.65 mmol) was used instead of 2-chloro-4-nitroaniline.

$^1$H NMR (400 MHz, DMSO-$d_6$) δ 11.79 (s, 1H), 9.25 (d, J=2.8 Hz, 1H), 8.82-8.61 (m, 2H), 8.45-8.27 (m, 2H).

Step 114-2: Preparation of N-(5-aminopyridin-2-yl)oxazole-5-carboxamide 45 mg (yield: 58%) of the title compound was obtained in the same manner as in Step 1-2 of Example 1 above, except that N-(5-nitropyridin-2-yl)oxazole-5-carboxamide (400 mg, 1.71 mmol) obtained in Step 114-1 was used instead of 5-methyl-N-(5-nitropyidin-2-yl)pyrazine-2-carboxamide.

$^1$H NMR (400 MHz, DMSO-$d_6$) δ 10.53 (s, 1H), 8.59 (s, 1H), 8.09 (s, 1H), 7.82-7.68 (m, 2H), 7.02 (dd, J=8.7 Hz, 2.9 Hz, 1H), 5.23 (s, 2H).

Step 114-3: Preparation of (6-(oxazole-5-carboxamido)pyridin-3-yl)carbonohydrazonoyl dicyanide 31 mg (yield: 55%) of the title compound was obtained in the same manner as in Step 1-3 of Example 1 above, except that N-(5-aminopyridin-2-yl)oxazole-5-carboxamide (40 mg, 0.20 mmol) obtained in Step 114-2 was used instead of N-(5-aminopyridin-2-yl)-5-methylpyrazine-2-carboxamide.

$^1$H NMR (400 MHz, DMSO-$d_6$) δ 11.17 (s, 1H), 8.66 (s, 1H), 8.51 (d, J=2.7 Hz, 1H), 8.22 (s, 1H), 8.18 (d, J=9.1 Hz, 1H), 7.91 (dd, J=9.1 Hz, 2.8 Hz, 1H).

Example 115: Preparation of (6-(isoxazole-3-carboxamido)pyridin-3-yl)carbonohydrazonoyl dicyanide (Compound 115)

Step 115-1: Preparation of N-(5-nitropyridin-2-yl)isoxazole-3-carboxamide 222 mg (yield: 36%) of the title compound was obtained in the same manner as in Step 11-1 of Example 11 above, except that isoxazole-3-carboxylic acid (300 mg, 2.65 mmol) was used instead of 5-methylpyrazine-2-carboxylic acid, and 2-amino-5-nitroaniline (369 mg, 2.65 mmol) was used instead of 2-chloro-4-nitroaniline.

$^1$H NMR (400 MHz, DMSO-$d_6$) δ 11.60 (s, 1H), 9.25 (d, J=2.8 Hz, 1H), 9.20 (d, J=1.7 Hz, 1H), 8.71 (dd, J=9.2 Hz, 2.8 Hz, 1H), 8.36 (d, J=9.2 Hz, 1H), 7.18 (d, J=1.7 Hz, 1H).

Step 115-2: Preparation of N-(6-aminopyridin-2-yl)furan-3-carboxamide

The title compound was obtained in the same manner as in Step 1-2 of Example 1 above, except that N-(5-nitropyridin-2-yl)isoxazole-3-carboxamide (200 mg, 0.85 mmol) obtained in Step 115-1 was used instead of 5-methyl-N-(5-nitropyridin-2-yl)pyrazine-2-carboxamide and used in the next step without additional purification.

Step 115-3: Preparation of (6-(Isoxazole-3-carboxamido)pyridin-3-yl)carbonohydrazonoyl dicyanide 28 mg (yield: 34%) of the title compound was obtained in the same manner as in Step 1-3 of Example 1 above, except that N-(5-aminopyridin-2-yl)isoxazole-3-carboxamide (60 mg, 0.29 mmol) obtained in Step 115-2 was used instead of N-(5-aminopyridin-2-yl)-5-methylpyrazine-2-carboxamide.

$^1$H NMR (400 MHz, DMSO-$d_6$) δ 10.94 (s, 1H), 9.16 (s, 1H), 8.52 (s, 1H), 8.17 (d, J=9.0 Hz, 1H), 8.01-7.87 (m, 1H), 7.12 (s, 1H).

Example 116: Preparation of (4-(thiazol-2-yloxy)phenyl)carbonohydrazonoyl dicyanide (Compound 116)

Step 116-1: Preparation of 4-(thiazol-2-yloxy)aniline

After 4-aminophenyl (200 mg, 1.83 mmol) was dissolved in DMSO, 2-chlorothiazole (157 μL, 1.83 mmol) and cesium carbonate (716 mg, 2.20 mmol) were added thereto, and the reaction mixture was stirred at 80° C. for 12 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 224 mg (yield: 64%) of the title compound.

$^1$H NMR (400 MHz, DMSO-$d_6$) δ 7.24 (d, J=3.8 Hz, 1H), 7.08 (d, J=3.7 Hz, 1H), 6.99 (d, J=8.8 Hz, 2H), 6.60 (d, J=8.8 Hz, 2H), 5.21 (s, 2H).

Step 116-2: Preparation of (4-(thiazol-2-yloxy)phenyl)carbonohydrazonoyl dicyanide 116 mg (yield: 41%) of the title compound was obtained in the same manner as in Step 1-3 of Example 1 above, except that 4-(thiazol-2-yloxy)aniline (200 mg, 1.04 mmol) obtained in Step 116-1 was used instead of N-(5-aminopyridin-2-yl)-5-methylpyrazine-2-carboxamide.

$^1$H NMR (400 MHz, DMSO-$d_6$) δ 13.09 (s, 1H), 7.55 (d, J=9.0 Hz, 2H), 7.41 (d, J=9.0 Hz, 2H), 7.30 (d, J=3.8 Hz, 1H), 7.25 (d, J=3.7 Hz, 1H).

Example 117: Preparation of (4-(benzyloxy)phenyl)carbonohydrazonoyl Dicyanide (Compound 117)

Step 117-1: Preparation of 1-(benzyloxy)-4-nitrobenzene

After phenylmethanol (0.31 mL, 2.98 mmol) was dissolved in DMSO under a nitrogen atmosphere, 60% NaH (159 mg, 3.97 mmol) was added thereto, and the reaction mixture was stirred at room temperature for 30 minutes. Thereafter, 1-fluoro-4-nitrobenzene (0.21 mL, 1.98 mmol) was added thereto, and the reaction mixture was further stirred for 3 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure and solidified to obtain 296 mg (yield: 65%) of the title compound.

$^1$H NMR (400 MHz, DMSO-$d_6$) δ 8.243-8.219 (d, J=9.3 Hz, 2H), 7.496-7.371 (m, 5H), 7.256-7.233 (d, J=9.3 Hz, 2H), 5.278 (s, 1H).

Step 117-2: Preparation of 4-benzyloxy)aniline 28 mg (yield: 14%) of the title compound was obtained in the same manner as in Step 1-2 of Example 1 above, except that 1-(benzyloxy)-4-nitrobenzene (230 mg, 1 mmol) obtained in Step 117-1 was used instead of 5-methyl-N-(5-nitropyridin-2-yl)pyrazine-2-carboxamide.

$^1$H NMR (400 MHz, $CDCl_3$) δ 7.395-7.273 (m, 5H), 6.810-6.788 (d, J=8.8 Hz, 2H), 6.622-6.600 (d, J=8.8 Hz, 2H), 4.968 (s, 2H), 3.402 (s, 2H).

Step 117-3: Preparation of (4-(benzyloxy)phenyl)carbonohydrazonoyl Dicyanide 31 mg (yield: 86%) of the title compound was obtained in the same manner as in Step 1-3 of Example 1 above, except that 4-(benzyloxy)aniline (25 mg, 0.13 mmol) obtained in Step 117-2 was used instead of N-(5-aminopyridin-2-yl)-5-methylpyrazine-2-carboxamide.

$^1$H NMR (400 MHz, Acetone-$d_6$) δ 11.786 (s, 1H), 7.491-7.468 (d, J=9.2 Hz, 2H), 7.485-7.319 (m, 5H), 7.124-7.102 (d, J=9.2 Hz, 2H), 5.164 (s, 2H).

Example 118: Preparation of (4-(4-(trifluoromethyl) benzyloxy)phenyl)carbonohydrazonoyl dicyanide (Compound 118)

Step 118-1: Preparation of 1-nitro-4-(4-trifluoromethyl)benzyloxy)benzene 135 mg (yield: 46%) of the title compound was obtained in the same manner as in Step 95-1 of Example 95 above, except that (4-(trifluoromethyl)phenyl)methanol (262 mg, 1.49 mmol) was used instead of phenylmethanol, and 1-fluoro-4-nitrobenzene (0.11 mL, 0.99 mmol) was used instead of 2-chloro-4-nitropyridine.

$^1$H NMR (400 MHz, $CDCl_3$) δ 8.202-8.179 (d, J=9.2 Hz, 2H), 7.682-7.661 (d, J=8.4 Hz, 2H), 7.607-7.587 (d, J=8.0 Hz, 2H), 7.085-7.062 (d, J=9.2 Hz, 2H), 5.271 (s, 2H).

Step 118-2: Preparation of 4-(4-(trifluoromethyl)benzyloxy)aniline 78 mg (yield: 67%) of the title compound was obtained in the same manner as in Step 1-2 of Example 1 above, except that 1-nitro-4-((4-trifluoromethyl)benzyl)oxy)benzene (400 mg, 1.71 mmol) obtained in Step 118-1 was used instead of 5-methyl-N-(5-nitropyidin-2-yl)pyrazine-2-carboxamide.

$^1$H NMR (400 MHz, DMSO-d %) δ 7.749-7.729 (d, J=8.0 Hz, 2H), 7.640-7.620 (d, J=8.0 Hz, 2H), 6.743-6.721 (d, J=8.8 Hz, 2H), 6.521-6.499 (d, J=8.8 Hz, 2H), 5.065 (s, 2H), 4.647 (s, 2H).

Step 118-3: Preparation of (4-(4-(trifluoromethyl) benzyloxy)phenyl)carbonohydrazonoyl dicyanide 56 mg (yield: 62%) of the title compound was obtained in the same manner as in Step 1-3 of Example 1 above, except that 4-(4-(trifluoromethyl)benzyloxy)aniline (70 mg, 0.26 mmol) obtained in Step 118-2 was used instead of N-(5-aminopyridin-2-yl)-5-methylpyrazine-2-carboxamide.

$^1$H NMR (400 MHz, Acetone-$d_6$) δ 12.007 (s, 1H), 7.774-7.753 (d, J=8.4 Hz, 2H), 7.739-7.718 (d, J=8.4 Hz, 2H), 7.503-7.480 (d, J=9.2 Hz, 2H), 7.152-7.129 (d, J=9.2 Hz, 2H), 5.297 (s, 2H).

Example 119: Preparation of (4-(4-methylbenzyloxy)phenyl)carbonohydrazonoyl dicyanide (Compound 119)

Step 119-1: Preparation of 1-methyl-4-((4-nitrophenoxy)methyl)benzene 512 mg (yield: 71%) of the title compound was obtained in the same manner as in Step 117-1 of Example 117 above, except that (4-(trifluoromethyl)phenyl)methanol (262 mg, 1.49 mmol) was used instead of phenylmethanol, and 1-fluoro-4-nitrobenzene (0.11 mL, 0.99 mmol) was used instead of 2-chloro-4-nitropyridine.

$^1$H NMR (400 MHz, DMSO-$d_6$) δ 8.231-8.207 (d, J=9.6 Hz, 2H), 7.376-7.357 (d, J=7.6 Hz, 2H), 7.235-7.212 (m, 4H), 5.222 (s, 2H), 2.320 (s, 3H).

Step 119-2: Preparation of 4-(4-methylbenzyloxy)aniline 68 mg (yield: 32%) of the title compound was obtained in the same manner as in Step 95-2 of Example 95 above, except that 1-methyl-4-((4-nitrophenoxy)methyl)benzene (240 mg, 0.99 mmol) obtained in Step 119-1 was used instead of 2-(benzyloxy)-5-nitropyridine, and a reaction temperature was adjusted to 60° C.

$^1$H NMR (400 MHz, DMSO-$d_6$) δ 7.296-7.276 (d, J=8.0 Hz, 2H), 7.183-7.163 (d, J=8.0 Hz, 2H), 6.712-6.690 (d, J=8.8 Hz, 2H), 6.506-6.484 (d, J=8.8 Hz, 2H), 4.887 (s, 2H), 4.598 (s, 2H), 2.301 (s, 3H).

Step 119-3: Preparation of (4-(4-methylbenzyloxy)phenyl)carbonohydrazonoyl dicyanide 25 mg (yield: 31%) of the title compound was obtained in the same manner as in Step 1-3 of Example 1 above, except that 4-(4-methylbenzyloxy)aniline (60 mg, 0.28 mmol) obtained in Step 119-2 was used instead of N-(5-aminopyridin-2-yl)-5-methylpyrazine-2-carboxamide.

$^1$H NMR (400 MHz, DMSO-$d_6$) δ 12.982 (s, 1H), 7.419-7.397 (d, J=8.8 Hz, 2H), 7.336-7.317 (d, J=7.6 Hz, 2H), 7.208-7.188 (d, J=8.0 Hz, 2H), 7.068-7.046 (d, J=8.8 Hz, 1H), 5.059 (s, 2H), 2.307 (s, 3H).

Example 120: Preparation of (4-(4-methoxyphenethoxy)phenyl)carbonohydrazonoyl dicyanide (Compound 120)

Step 120-1: Preparation of 1-methoxy-4-(2-(4-nitrophenoxy)ethyl)benzene 431 mg (yield: 80%) of the title compound was obtained in the same manner as in Step 117-1 of Example 117 above, except that 2-(4-methoxyphenyl)ethan-1-ol (453 mg, 2.98 mmol) was used instead of phenylmethanol.

$^1$H NMR (400 MHz, DMSO-$d_6$) δ 8.204-8.180 (d, J=9.6 Hz, 2H), 7.259-7.238 (d, J=8.4 Hz, 2H), 7.158-7.134 (d, J=9.6 Hz, 2H), 6.889-6.868 (d, J=8.4 Hz, 2H), 4.317-4.282 (t, J=6.4 Hz, 2H), 3.726 (s, 3H), 3.027-2.993 (t, J=6.8 Hz, 2H).

Step 120-2: Preparation of 4-(4-methoxyphenethoxy)aniline 197 mg (yield: 82%) of the title compound was obtained in the same manner as in Step 1-2 of Example 1 above, except that 1-methoxy-4-(2-(4-nitrophenoxy)ethyl)benzene (270 mg, 0.99 mmol) obtained in Step 120-1 was used instead of 5-methyl-N-(5-nitropyridin-2-yl)pyrazine-2-carboxamide.

$^1$H NMR (400 MHz, DMSO-$d_6$) δ 7.217-7.196 (d, J=8.4 Hz, 2H), 6.871-6.849 (d, J=8.8 Hz, 2H), 6.644-6.623 (d, J=8.4 Hz, 2H), 6.506-6.485 (d, J=8.4 Hz, 2H), 4.584 (s, 2H), 3.994-3.960 (t, J=6.8 Hz, 2H), 3.721 (s, 3H), 2.905-2.871 (t, J=6.8 Hz, 2H).

Step 120-3: Preparation of (4-(4-methoxyphenethoxy)phenyl)carbonohydrazonoyl dicyanide 88 mg (yield: 44%) of the title compound was obtained in the same manner as in Step 1-3 of Example 1 above, except that 4-(4-methoxyphenethoxy)aniline (150 mg, 0.62 mmol) obtained in Step 120-2 was used instead of N-(5-aminopyridin-2-yl)-5-methylpyrazine-2-carboxamide.

$^1$H NMR (400 MHz, DMSO-$d_6$) δ 11.681 (s, 2H), 7.394-7.371 (d, J=9.2 Hz, 2H), 7.247-7.226 (d, J=8.4 Hz, 2H), 6.988-6.966 (d, J=8.8 Hz, 2H), 6.885-6.864 (d, J=8.4 Hz, 2H), 4.158-4.124 (t, J=6.8 Hz, 2H), 3.728 (s, 3H), 2.978-2.944 (t, J=6.8 Hz, 2H).

Example 121: Preparation of (4-(4-(trifluoromethyl) phenethoxy)phenyl)carbonohydrazonoyl dicyanide (Compound 121)

Step 121-1: Preparation of 1-nitro-4-(4-(trifluoromethyl)phenethoxy)benzene 155 mg (yield: 25%) of the title compound was obtained in the same manner as in Step 117-1 of Example 117 above, except that 2-(4-(trifluoromethyl)phenyl)ethan-1-ol (0.45 mL, 2.98 mmol) was used instead of phenylmethanol.

$^1$H NMR (400 MHz, $CDCl_3$) δ 8.177-8.154 (d, J=9.2 Hz, 2H), 7.593-7.573 (d, J=8.0 Hz, 2H), 7.429-7.409 (d, J=8.0 Hz, 2H), 6.951-6.928 (d, J=9.2 Hz, 2H), 4.315-4.282 (t, J=6.6 Hz, 2H), 3.220-3.187 (t, J=6.6 Hz, 2H).

Step 121-2: Preparation of 4-(4-(trifluoromethyl)phenethoxy)aniline 94 mg (yield: 70%) of the title compound was obtained in the same manner as in Step 1-2 of Example 1 above, except that 1-nitro-4-(4-(trifluoromethyl)phenethoxy)benzene (150 mg, 0.48 mmol) obtained in Step 121-2 was used instead of 5-methyl-N-(5-nitropyidin-2-yl)pyrazine-2-carboxamide.

$^1$H NMR (400 MHz, DMSO-$d_6$) δ 7.669-7.649 (d, J=8.0 Hz, 2H), 7.544-7.524 (d, J=8.0 Hz, 2H), 6.650-6.628 (d, J=8.8 Hz, 2H), 6.507-6.485 (d, J=8.8 Hz, 2H), 4.600 (s, 2H), 4.094-4.061 (t, J=6.6 Hz, 2H), 3.075-3.042 (t, J=6.6 Hz, 2H).

Step 121-3: Preparation of (4-(4-(trifluoromethyl) phenethoxy)phenyl)carbonohydrazonoyl dicyanide 94 mg (yield: 93%) in the same manner as in Step 1-3 of Example 1 above, except that 4-(4-(trifluoromethyl) phenethoxy)aniline (80 mg, 0.28 mmol) obtained in Step 121-2 was used instead of N-(5-aminopyridin-2-yl)-5-methylpyrazine-2-carboxamide.

$^1$H NMR (400 MHz, DMSO-$d_6$) δ 12.980 (s, 1H), 7.689-7.669 (d, J=8.0 Hz, 2H), 7.574-7.554 (d, J=8.0 Hz, 2H), 7.413-7.390 (d, J=9.2 Hz, 2H), 7.010-6.988 (d, J=8.8 Hz, 2H), 4.264-4.232 (t, J=6.4 Hz, 2H), 3.155-3.122 (t, J=6.6 Hz, 2H).

Example 122: Preparation of (4-phenethoxyphenyl)carbonohydrazonoyl Dicyanide (Compound 122)

Step 122-1: Preparation of 1-nitro-4-phenethoxybenzene 132 mg (yield: 28%) of the title compound was obtained in the same manner as in Step 117-1 of Example 117 above, except that 2-phenylethan-1-ol (0.36 mL, 2.98 mmol) was used instead of phenylmethanol.

$^1$H NMR (400 MHz, DMSO-$d_6$) δ 8.203-8.180 (d, J=9.2 Hz, 2H), 7.370-7.218 (m, 5H), 7.164-7.141 (d, J=9.2 Hz, 2H), 4.372-4.338 (t, J=6.8 Hz, 2H), 3.098-3.064 (t, J=6.8 Hz, 2H).

Step 122-2: Preparation of 4-phenethoxyaniline 85 mg (yield: 82%) of the title compound was obtained in the same manner as in Step 1-2 of Example 1 above, except that 1-nitro-4-phenethoxybenzene (120 mg, 0.49 mmol) obtained in Step 122-1 was used instead of 5-methyl-N-(5-nitropyridin-2-yl)pyrazine-2-carboxamide.

$^1$H NMR (400 MHz, DMSO-$d_6$) δ 7.324-7.191 (m, 5H), 6.652-6.630 (d, J=8.8 Hz, 2H) 6.652-6.630 (d, J=8.8 Hz, 2H), 4.586 (s, 2H), 4.046-4.014 (t, J=7.0 Hz, 2H), 2.976-2.941 (t, J=7.0 Hz, 2H).

Step 122-3: Preparation of (4-phenethoxyphenyl)carbonohydrazonoyl Dicyanide 83 mg (yield: 75%) of the title compound was obtained in the same manner as in Step 1-3 of Example 1 above, except that 4-phenethoxyaniline (80 mg, 0.38 mmol) obtained in Step 122-2 was used instead of N-(5-aminopyridin-2-yl)-5-methylpyrazine-2-carboxamide.

$^1$H NMR (400 MHz, DMSO-$d_6$) δ 12.977 (s, 1H), 7.412-7.390 (d, J=8.8 Hz, 2H), 7.327-7.214 (m, 5H), 7.010-6.987 (d, J=9.2 Hz, 2H), 4.217-4.183 (t, J=6.8 Hz, 2H), 3.051-3.017 (t, J=6.8 Hz, 2H).

Example 123: Preparation of (4-(4-chlorophenethoxy)phenyl)carbonohydrazonoyl dicyanide (Compound 123)

Step 123-1: Preparation of 1-chloro-4-(2-(4-nitrophenoxyethyl)benzene 423 mg (yield: 77%) of the title compound was obtained in the same manner as in Step 117-1 of Example 117 above, except that 2-(4-chlorophenyl)ethan-1-ol (0.4 mL, 2.98 mmol) was used instead of phenylmethanol.

$^1$H NMR (400 MHz, DMSO-$d_6$) δ 8.201-8.178 (d, J=9.2 Hz, 2H), 7.368 (s, 4H), 7.154-7.130 (d, J=9.6 Hz, 2H), 4.360-4.326 (t, J=6.8 Hz, 2H), 3.093-3.059 (t, J=6.8 Hz, 2H).

Step 123-2: Preparation of 4-(4-chlorophenethoxy)anillne 169 mg (yield: 67%) in the same manner as in Step 1-2 of Example 1 above, except that 1-chloro-4-(2-(4-nitrophenoxy)ethyl)benzene (280 mg, 1.01 mmol) obtained in Step 123-1 was used instead of 5-methyl-N-(5-nitropyridin-2-yl) pyrazine-2-carboxamide.

$^1$H NMR (400 MHz, DMSO-$d_6$) δ 7.363-7.292 (m, 4H), 6.645-6.623 (d, J=8.8 Hz, 2H), 6.512-6.490 (d, J=8.8 Hz, 2H), 4.595 (s, 2H), 4.037-4.004 (t, J=6.6 Hz, 2H), 2.967-2.934 (t, J=6.6 Hz, 2H).

Step 123-3: Preparation of (4-(4-chlorophenethoxy)phenyl)carbonohydrazonoyl dicyanide 59 mg (yield: 30%) of the title compound was obtained in the same manner as in Step 1-3 of Example 1 above, except that 4-(4-chlorophenethoxy)aniline (150 mg, 0.61 mmol) obtained in Step 123-2 was used instead of N-(5-aminopyridin-2-yl)-5-methylpyrazine-2-carboxamide.

$^1$H NMR (400 MHz, Acetone-$d_6$) δ 11.767 (s, 1H), 7.469-7.446 (d, J=9.2 Hz, 2H), 7.394-7.327 (m, 4H), 7.038-7.015 (d, J=9.2 Hz, 2H), 4.270-4.236 (t, J=6.8 Hz, 2H), 3.117-3.083 (t, J=6.8 Hz, 2H).

Example 124: Preparation of (4-(pyridin-3-ylmethoxy)phenyl)carbonohydrazonoyl dicyanide (Compound 124)

Step 124-1: Preparation of 3-(4-nitrophenoxy)methyl)pyridine 236 mg (yield: 52%) of the title compound was obtained in the same manner as in Step 117-1 of Example 117 above, except that pyridin-3-ylmethanol (0.29 mL, 2.98 mmol) was used instead of phenylmethanol.

$^1$H NMR (400 MHz, DMSO-$d_6$) δ 8.727-8.723 (d, J=1.6 Hz, 1H), 8.602-8.586 (dd, J=4.8 Hz, 1.6 Hz, 1H), 8.263-8.240 (d, J=9.2 Hz, 2H), 7.938-7.910 (dt, J=7.7 Hz, 1.8 Hz, 1H), 7.484-7.453 (dd, J=7.6 Hz, 4.8 Hz, 1H), 7.288-7.265 (d, J=9.2 Hz, 2H), 5.336 (s, 2H).

Step 124-2: Preparation of 4-(pyridin-3-ylmethoxy)aniline 76 mg (yield: 44%) of the title compound was obtained in the same manner as in Step 1-2 of Example 1 above, except that 3-((4-nitrophenoxy)methyl)pyridine (200 mg, 0.87 mmol) obtained in Step 124-1 was used instead of 5-methyl-N-(5-nitropyridin-2-yl)pyrazine-2-carboxamide.

$^1$H NMR (400 MHz, DMSO-$d_6$) δ 8.631 (s, 1H), 8.540-8.528 (d, J=4.8 Hz, 1H), 7.845-7.826 (d, J=7.6 Hz, 1H), 7.433-7.402 (dd. J=7.6 Hz, 4.8 Hz, 1H), 6.762-6.740 (d, J=8.8 Hz, 2H), 6.533-6.512 (d, J=8.4 Hz, 2H), 5.004 (s, 2H), 4.657 (s, 2H).

Step 124-3: Preparation of (4-(pyridin-3-ylmethoxy)phenyl)carbonohydrazonoyl dicyanide 54 mg (yield: 56%) of the title compound was obtained in the same manner as in Step 1-3 of Example 1 above, except that 4-(pyridin-3-ylmethoxy)aniline (70 mg, 0.35 mmol) obtained in Step 124-2 was used instead of N-(5-aminopyridin-2-yl)-5-methylpyrazine-2-carboxamide.

$^1$H NMR (400 MHz, Acetone-$d_6$) δ 11.824 (s, 1H), 8.715 (s, 1H), 8.568-8.559 (d, J=3.6 Hz, 1H), 7.906-7.887 (d, J=7.6 Hz, 1H), 7.508-7.485 (d, J=9.2 Hz, 2H), 8.430-8.398 (dd, J=7.8 Hz, 5.0 Hz, 1H), 7.156-7.133 (d, J=9.2 Hz, 2H), 5.225 (s, 2H).

Example 125: Preparation of (4-(pyrazin-2-ylmethoxy)phenyl)carbonohydrazonoyl dicyanide (Compound 125)

Step 125-1: Preparation of 2-((4-nitrophenoxy)methyl)pyrazine $PPh_3$ (629 mg, 2.40 mmol) and DIAD (0.47 mL, 2.40 mmol) were dissolved in THF under a nitrogen atmosphere, and the reaction mixture was stirred at 0° C. for 30 minutes. Pyrazin-2-ylmethanol (220 mg, 2 mmol) and 4-nitrophenol (334 mg, 2.40 mmol) were added to the reaction mixture, and the reaction mixture was stirred at room temperature for one day. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 147 mg (yield: 26%) of the title compound.

$^1$H NMR (400 MHz, Acetone-$d_6$) δ 8.876 (s, 1H), 8.659-8.630 (m, 2H), 8.280-8.257 (dd, J=7.0 Hz, 2.2 Hz, 2H), 7.331-7.308 (dd, J=7.2 Hz, 2.0 Hz, 2H), 5.468 (s, 2H).

Step 125-2: Preparation of 4-(pyrazin-2-ylmethoxy)aniline 64 mg (yield: 36%) of the title compound was obtained in the same manner as in Step 1-2 of Example 1 above, except that 2-((4-nitrophenoxy)methyl)pyrazine (200 mg, 0.87 mmol) obtained in Step 125-1 was used instead of 5-methyl-N-(5-nitropyridin-2-yl)pyrazine-2-carboxamide.

$^1$H NMR (400 MHz, DMSO-$d_6$) δ 8.764 (s, 1H), 8.651-8.614 (d, J=14.8 Hz, 2H), 6.777-6.756 (d, J=8.4 Hz, 2H), 6.527-6.505 (d, J=8.8 Hz, 2H), 5.104 (s, 2H), 4.669 (s, 2H).

Step 125-3: Preparation of (4-(pyrazin-2-ylmethoxy)phenyl)carbonohydrazonoyl dicyanide 60 mg (yield: 86%) of the title compound was obtained in the same manner as in Step 1-3 of Example 1 above, except that 4-(pyrazin-2-ylmethoxy)aniline (50 mg, 0.25 mmol)

obtained in Step 125-2 was used instead of N-(5-aminopyridin-2-yl)-5-methylpyrazine-2-carboxamide.

$^1$H NMR (400 MHz, DMSO-$d_6$) δ 11.807 (s, 1H), 8.834 (s, 1H), 8.629-8.598 (m, 2H), 7.522-7.499 (d, J=9.2 Hz, 2H), 7.194-7.171 (d, J=9.2 Hz, 2H), 5.317 (s, 2H).

Example 126: Preparation of (4-((1H-benzo[d]imidazol-2-yl)methoxy)phenyl)carbonohydrazonoyl dicyanide (Compound 126)

Step 126-1: Preparation of 2-4(4-nitrophenoxy) methyl)-1H-benzo[d]imidazole 152 mg (yield: 28%) of the title compound was obtained in the same manner as in Step 117-1 of Example 117 above, except that (1H-benzo[d]imidazol-2-yl)methanol (300 mg, 2.02 mmol) was used instead of phenylmethanol.

$^1$H NMR (400 MHz, DMSO-$d_6$) δ 12.745 (s, 1H), 8.264-8.241 (d, J=9.2 Hz, 2H), 7.648-7.629 (d, J=7.6 Hz, 1H), 7.515-7.497 (d, J=7.2 Hz, 1H), 7.333-7.310 (d, J=9.2 Hz, 2H), 7.247-7.170 (m, 2H), 5.506 (s, 2H).

Step 126-2: Preparation of 4-((1H-benzo[d]imidazol-2-yl)methoxy)aniline 78 mg (yield: 80%) of the title compound was obtained in the same manner as in Step 1-2 of Example 1 above, except that 2-((4-nitrophenoxy)methyl)-1H-benzo[d]imidazole (110 mg, 0.41 mmol) obtained in Step 126-1 was used instead of 5-methyl-N-(5-nitropyridin-2-yl)pyrazine-2-carboxamide.

$^1$H NMR (400 MHz, DMSO-$d_6$) δ 12.587 (s, 1H), 7.609-7.589 (d, J=8.0 Hz, 1H), 7.481-7.461 (d, J=8.0 Hz, 1H), 7.213-7.142 (m, 2H), 6.805-6.784 (d, J=8.4 Hz, 2H), 6.524-6.503 (d, J=8.4 Hz, 2H), 5.144 (s, 2H), 4.666 (s, 2H).

Step 126-3: Preparation of (4-((1H-benzo[d]imidazol-2-yl)methoxy)phenyl)carbonohydrazonic Dicyanide 56 mg (yield: 71%) of the title compound was obtained in the same manner as in Step 1-3 of Example 1 above, except that 4-((1H-benzo[d]imidazol-2-yl)methoxy)aniline (60 mg, 0.25 mmol) obtained in Step 126-2 was used instead of N-(5-aminopyridin-2-yl)-5-methylpyrazine-2-carboxamide.

$^1$H NMR (400 MHz, DMSO-$d_6$) δ 7.695-7.672 (dd, J=6.0 Hz, 3.2 Hz, 2H), 7.476-7.453 (d, J=9.2 Hz, 2H), 7.379-7.356 (dd, J=6.0 Hz, 3.2 Hz, 2H), 7.197-7.174 (d, J=9.2 Hz, 2H), 5.488 (s, 2H).

Example 127: Preparation of (4-(pyridazin-3-ylmethoxy)phenyl)carbonohydrazonoyl dicyanide (Compound 127)

Step 127-1: Preparation of 3-((4-nitrophenoxy)methyl)pyridazine 177 mg (yield: 38%) of the title compound was obtained in the same manner as in Step 117-1 of Example 117 above, except that pyridazin-3-ylmethanol (220 mg, 2.0 mmol) was used instead of phenylmethanol.

$^1$H NMR (400 MHz, DMSO-$d_6$) δ 9.269-9.258 (m, 1H), 8.274-8.252 (d, J=9.2 Hz, 2H), 7.901-7.879 (d, J=8.8 Hz, 1H), 7.821-7.788 (m, 1H), 7.331-7.308 (d, J=9.2 Hz, 2H), 5.597 (s, 2H).

Step 127-2: Preparation of 4-(pyridazin-3-ylmethoxy)aniline 62 mg (yield: 51%) of the title compound was obtained in the same manner as in Step 1-2 of Example 1 above, except that 3-((4-nitrophenoxy)methyl)pyridazine (140 mg, 0.61 mmol) obtained in Step 127-1 was used instead of 5-methyl-N-(5-nitropyridin-2-yl)pyrazine-2-carboxamide.

1H NMR (400 MHz, DMSO-$d_6$) δ 9.196-9.180 (dd, J=4.8 Hz, 1.6 Hz, 1H), 7.789-7.710 (m, 2H), 6.771-6.749 (d, J=8.8 Hz, 2H), 6.519-6.497 (d, J=8.8 Hz, 2H), 5.243 (s, 2H), 4.668 (s, 2H).

Step 127-3: Preparation of (4-(pyridazin-3-ylmethoxy)phenyl)carbonohydrazonoyl dicyanide 36 mg (yield: 52%) of the title compound was obtained in the same manner as in Step 1-3 of Example 1 above, except that 4-(pyridazin-3-ylmethoxy)aniline (50 mg, 0.25 mmol) obtained in Step 127-2 was used instead of N-(5-aminopyridin-2-yl)-5-methylpyrazine-2-carboxamide.

$^1$H NMR (400 MHz, DMSO-$d_6$) δ 12.983 (s, 1H), 9.223-9.207 (dd, J=4.8 Hz, 1.6 Hz, 1H), 7.837-7.736 (m, 2H), 7.335-7.313 (d, J=8.8 Hz, 2H), 7.058-7.035 (d, J=8.8 Hz, 2H), 5.393 (s, 2H).

Example 128: Preparation of (4-(benzo[d]oxazol-2-ylmethoxy)phenyl)carbonohydrazonoyl dicyanide (Compound 128)

Step 128-1: Preparation of 2-(4-nitrophenoxy)methyl)benzo[d]oxazole 131 mg (yield: 26%) of the title compound was obtained in the same manner as in Step 117-1 of Example 117 above, except that 4-nitrophenol (394 mg, 2.83 mmol) was used instead of phenylmethanol, and 2-(bromomethyl)benzo[d]oxazole (400 mg, 1.89 mmol) was used instead of 1-fluoro-4-nitrobenzene.

$^1$H NMR (400 MHz, DMSO-$d_6$) δ 8.260-8.237 (d, J=9.2 Hz, 2H), 7.804-7.769 (t, J=7.0 Hz, 2H), 7.476-7.396 (m, 2H), 7.340-7.317 (d, J=9.2 Hz, 2H), 5.682 (s, 2H).

Step 128-2: Preparation of 4-(benzo[d]oxazol-2-ylmethoxy)aniline 87 mg (yield: 76%) of the title compound was obtained in the same manner as in Step 1-2 of Example 1 above, except that 2-((4-nitrophenoxy)methyl)benzo[d]oxazole (130 mg, 0.48 mmol) obtained in Step 128-1 was used instead of 5-methyl-N-(5-nitropyridin-2-yl)pyrazine-2-carboxamide.

$^1$H NMR (400 MHz, DMSO-$d_6$) δ 7.777-7.743 (t, J=6.8 Hz, 2H), 7.452-7.372 (m, 2H), 6.793-6.771 (d, J=8.8 Hz, 2H), 6.512-6.490 (d, J=8.8 Hz, 2H), 5.263 (s, 2H), 4.696 (s, 2H).

Step 128-3: Preparation of (4-(benzo[d]oxazol-2-ylmethoxy)phenyl)carbonohydrazonoyl dicyanide 62 mg (yield: 59%) of the title compound was obtained in the same manner as in Step 1-3 of Example 1 above, except that 4-(benzo[d]oxazol-2-ylmethoxy)aniline (80 mg, 0.33 mmol) obtained in Step 128-2 was used instead of N-(5-aminopyridin-2-yl)-5-methylpyrazine-2-carboxamide.

$^1$H NMR (400 MHz, DMSO-$d_6$) δ 13.001 (s, 1H), 7.794-7.755 (t, J=7.8 Hz, 2H), 7.462-7.388 (m, 4H), 7.167-7.145 (d, J=8.8 Hz, 2H), 5.488 (s, 2H).

Example 129: Preparation of (4-(benzo[d]thiazol-2-ylmethoxy)phenyl)carbonohydrazonoyl dicyanide (Compound 129)

Step 129-1: Preparation of 2-(4-nitrophenoxy)methyl)benzo[d]thiazole 154 mg (yield: 31%) of the title compound was obtained in the same manner as in Step 117-1 of Example 117 above, except that 4-nitrophenol (366 mg, 2.63 mmol) was used instead of phenylmethanol, and 2-(bromomethyl)benzo[d]thiazole (400 mg, 1.75 mmol) was used instead of 1-fluoro-4-nitrobenzene.

$^1$H NMR (400 MHz, DMSO-$d_6$) δ 8.265-8.242 (d, J=9.2 Hz, 2H), 8.153-8.133 (d, J=8.0 Hz, 1H), 8.052-8.032 (d, J=8.0 Hz, 1H), 7.575-7.539 (t, J=7.2 Hz, 1H), 7.499-7.464 (t, J=7.0 Hz, 1H), 7.342-7.319 (d, J=9.2 Hz, 2H), 5.797 (s, 2H).

Step 129-2: Preparation of 4-(benzo[d]thiazol-2-ylmethoxy)aniline 80 mg (yield: 60%) of the title compound was obtained in the same manner as in Step 1-2 of Example 1 above, except that 2-((4-nitrophenoxy)methyl)benzo[d]thiazole (150 mg, 0.52 mmol) obtained in Step 129-1 was used instead of 5-methyl-N-(5-nitropyridin-2-yl)pyrazine-2-carboxamide.

$^1$H NMR (400 MHz, DMSO-$d_6$) δ 8.118-8.099 (d, J=7.6 Hz, 1H), 8.005-7.985 (d, J=8.0 Hz, 1H), 7.544-7.509 (t, J=7.0 Hz, 1H), 7.466-7.431 (t, J=7.0 Hz, 1H), 6.817-6.794 (d, J=9.2 Hz, 2H), 6.528-6.505 (d, J=9.2 Hz, 2H), 5.414 (s, 2H), 4.710 (s, 2H).

Step 129-3: Preparation of (4-(benzo[d]thiazol-2-ylmethoxy)phenyl)carbonohydrazonoyl dicyanide 74 mg (yield: 72%) of the title compound was obtained in the same manner as in Step 1-3 of Example 1 above, except that 4-(benzo[d]thiazol-2-ylmethoxy)aniline (80 mg, 0.31 mmol) obtained in Step 129-2 was used instead of N-(5-aminopyridin-2-yl)-5-methylpyrazine-2-carboxamide.

$^1$H NMR (400 MHz, DMSO-$d_6$) δ 13.005 (s, 1H), 8.134-8.115 (d, J=7.6 Hz, 1H), 8.033-8.013 (d, J=8.0 Hz, 1H), 7.562-7.527 (t, J=7.0 Hz, 1H), 7.487-7.426 (m, 3H), 7.178-7.155 (d, J=9.2 Hz, 2H), 5.619 (s, 2H).

Example 130: Preparation of (4-(benzo[b]thiophen-2-ylmethoxy)phenyl)carbonohydrazonoyl dicyanide (Compound 130)

Step 130-1: Preparation of 2-((4-nitrophenoxy)benzo[b]thiophene 500 mg (yield: 96%) of the title compound was obtained in the same manner as in Step 117-1 of Example 117 above, except that benzo[b]thiophen-2-ylmethanol (300 mg, 1.83 mmol) was used instead of phenylmethanol.

$^1$H NMR (400 MHz, DMSO-$d_6$) δ 8.240-8.218 (d, J=8.8 Hz, 2H), 7.972-7.953 (d, J=7.6 Hz, 1H), 7.867-7.849 (d, J=7.2 Hz, 1H), 7.587 (s, 2H), 7.412-7.351 (m, 2H), 7.303-7.280 (d, J=9.2 Hz, 2H), 5.616 (s, 2H).

Step 130-2: Preparation of 4-(benzo[b]thiophen-2-ylmethoxy)aniline 51 mg (yield: 14%) of the title compound was obtained in the same manner as in Step 1-2 of Example 1 above, except that 2-((4-nitrophenoxy)benzo[b]thiophene (400 mg, 1.40 mmol) obtained in Step 130-1 was used instead of 5-methyl-N-(5-nitropyridin-2-yl)pyrazine-2-carboxamide.

1H NMR (400 MHz, DMSO-$d_6$) δ 7.942-7.924 (d, J=7.2 Hz, 1H), 7.820-7.801 (d, J=7.6 Hz, 1H), 7.432 (s, 1H), 7.382-7.315 (m, 2H), 6.771-6.750 (d, J=8.4 Hz, 2H), 6.508-6.487 (d, J=8.4 Hz, 2H), 5.251 (s, 2H), 4.652 (s, 2H).

Step 130-3: Preparation of (4-(benzo[b]thiophen-2-ylmethoxy)phenyl)carbonohydrazonoyl dicyanide 42 mg (yield: 54%) of the title compound was obtained in the same manner as in Step 1-3 of Example 1 above, except that 4-(benzo[b]thiophen-2-ylmethoxy)aniline (60 mg, 0.24 mmol) obtained in Step 130-2 was used instead of N-(5-aminopyridin-2-yl)-5-methylpyrazine-2-carboxamide.

$^1$H NMR (400 MHz, DMSO-$d_6$) δ 12.791 (s, 1H), 7.959-7.940 (d, J=7.6 Hz, 1H), 7.843-7.827 (d, J=6.4 Hz, 1H), 7.519 (s, 1H), 7.426-7.404 (d, J=8.8 Hz, 2H), 7.378-7.351 (m, 2H), 7.133-7.110 (d, J=9.2 Hz, 2H), 5.447 (s, 2H).

Example 131: Preparation of (6-(4-chlorophenethoxy)pyridin-3-yl)carbonohydrazonoyl dicyanide (Compound 131)

Step 131-1: Preparation of 2-(4-chlorophenethoxy)-5-nitropyridine 205 mg (yield: 49%) of the title compound was obtained in the same manner as in Step 95-1 of Example 95 above, except that 2-(4-chlorophenyl)ethanol (0.25 mL, 1.80 mmol) was used instead of phenylmethanol.

$^1$H NMR (400 MHz, DMSO-$d_6$) δ 9.08 (dd, J=2.9 Hz, 0.6 Hz, 1H), 8.47 (dd, J=9.2 Hz, 2.9 Hz, 1H), 7.41-7.31 (m, 4H), 7.01 (dd, J=9.2 Hz, 0.6 Hz, 1H), 4.62 (t, J=6.7 Hz, 2H), 3.08 (t, J=6.7 Hz, 2H).

Step 131-2: Preparation of 6-(4-chlorophenethoxy)pyridine-3-amine 86 mg (yield: 51%) of the title compound was obtained in the same manner as in Step 1-2 of Example 1 above, except that 2-(4-chlorophenethoxy)-5-nitropyridine obtained in Step 131-1 was used instead of 5-methyl-N-(5-nitropyridin-2-yl)pyrazine-2-carboxamide.

$^1$H NMR (400 MHz, DMSO-$d_6$) δ 7.50 (d, J=2.3 Hz, 1H), 7.33 (q, J=8.6 Hz, 4H), 7.00 (dd, J=8.7 Hz, 2.9 Hz, 1H), 6.51 (d, J=9.3 Hz, 1H), 4.75 (s, 2H), 4.30 (t, J=6.7 Hz, 2H), 2.97 (t, J=6.7 Hz, 2H).

Step 131-3: Preparation of (6-(4-chlorophenethoxy)pyridin-3-yl)carbonohydrazonoyl dicyanide 67 mg (yield: 73%) of the title compound was obtained in the same manner as in Step 1-3 of Example 1 above, except that 6-(4-chlorophenethoxy)pyridine-3-amine obtained in Step 131-2 was used instead of N-(5-aminopyridin-2-yl)-5-methylpyrazine-2-carboxamide.

$^1$H NMR (400 MHz, Acetone-$d_6$) δ 11.96 (s, 1H), 8.31 (d, J=2.8 Hz, 1H), 7.87 (dd, J=9.0 Hz, 2.9 Hz, 1H), 7.41-7.24 (m, 4H), 6.86 (d, J=9.0 Hz, 1H), 4.53 (t, J=6.8 Hz, 2H), 3.09 (t, J=6.8 Hz, 2H).

Example 132: Preparation of (4-(4-methylbenzyloxy)-3-(trifluoromethyl)phenyl)carbonohydrazonoyl dicyanide (Compound 132)

Step 132-1: Preparation of 1-(4-methylbenzyloxy)-4-nitro-2-(trifluoromethyl)benzene 416 mg (yield: 93%) of the title compound was obtained in the same manner as in Step 95-1 of Example 95 above, except that p-tolylmethanol (263 mg, 2.15 mmol) was used instead of phenylmethanol, and 1-fluoro-4-nitro-2-(trifluoromethyl)benzene (0.2 mL, 1.43 mmol) was used instead of 2-chloro-5-nitropyridine.

$^1$H NMR (400 MHz, DMSO-$d_6$) δ 8.53 (dd, J=9.2 Hz, 2.9 Hz, 1H), 8.40 (d, J=2.9 Hz, 1H), 7.59 (d, J=9.3 Hz, 1H), 7.36 (d, J=7.9 Hz, 2H), 7.24 (d, J=7.8 Hz, 2H), 5.41 (s, 2H), 2.32 (s, 3H).

Step 132-2: Preparation of 4-(4-methylbenzyloxy)-3-(trifluoromethyl)aniline 34 mg (yield: 19%) of the title compound was obtained in the same manner as in Step 95-2 of Example 95 above, except that 1-(4-methylbenzyloxy)-4-nitro-2-(trifluoromethyl)benzene obtained in Step 132-1 was used instead of 2-(benzyloxy)-5-nitropyridine.

$^1$H NMR (400 MHz, DMSO-$d_6$) δ 7.30 (d, J=8.0 Hz, 2H), 7.20 (d, J=7.8 Hz, 2H), 7.04 (d, J=8.8 Hz, 1H), 6.84 (d, J=2.8 Hz, 1H), 6.77 (dd, J=8.7 Hz, 2.7 Hz, 1H), 5.05 (s, 2H), 5.02 (s, 2H), 2.31 (s, 3H).

Step 132-3: Preparation of (4-(4-methylbenzyloxy)-3-(trifluoromethyl)phenyl)carbonohydrazonoyl dicyanide 29 mg (yield: 74%) of the title compound was obtained in the same manner as in Step 1-3 of Example 1 above, except that 4-(4-methylbenzyloxy)-3-(trifluoromethyl)aniline obtained in Step 132-2 was used instead of N-(5-aminopyridin-2-yl)-5-methylpyrazine-2-carboxamide.

$^1$H NMR (400 MHz, Acetone-$d_6$) δ 11.83 (s, 1H), 7.81 (d, J=2.8 Hz, 1H), 7.75 (dd, J=9.0 Hz, 2.8 Hz, 1H), 7.43 (d, J=9.0 Hz, 1H), 7.38 (d, J=7.7 Hz, 32), 7.22 (d, J=7.9 Hz, 2H), 5.29 (s, 2H), 2.33 (s, 3H).

Example 133: Preparation of (4-(4-chlorophenethoxy)-3-(trifluoromethyl)phenyl)carbonohydrazonoyl dicyanide (Compound 133)

Step 133-1: Preparation of 1-(4-chlorophenethoxy)-4-nitro-2-(trifluoromethyl)benzene 144 mg (yield: 29%) of the title compound was obtained in the same manner as in Step 95-1 of Example 95 above, except that 2-(4-chlorophenyl)ethanol (0.3 mL, 2.15 mmol) was used instead of phenylmethanol, and 1-fluoro-4-nitro-2-(trifluoromethyl)benzene (0.2 mL, 1.43 mmol) was used instead of 2-chloro-5-nitropyridine.

$^1$H NMR (400 MHz, Acetone-$d_6$) δ 8.50 (dd, J=9.2 Hz, 2.9 Hz, 1H), 8.43 (d, J=2.8 Hz, 1H), 7.52 (d, J=9.2 Hz, 1H), 7.40 (d, J=8.6 Hz, 2H), 7.35 (d, J=8.5 Hz, 2H), 4.58 (t, J=6.5 Hz, 2H), 3.21 (t, J=6.5 Hz, 2H).

Step 133-2: Preparation of 4-(4-chlorophenethoxy)-3-(trifluoromethyl)aniline 28 mg (yield: 25%) of the title compound was obtained in the same manner as in Step 1-2 of Example 1 above, except that 1-(4-chlorophenethoxy)-4-nitro-2-(trifluoromethyl)benzene obtained in Step 133-1 was used instead of 5-methyl-N-(5-nitropyridin-2-yl)pyrazine-2-carboxamide $^1$H NMR (400 MHz, DMSO-$d_6$) δ 7.37-7.31 (m, 4H), 6.96 (d, J=8.7 Hz, 1H), 6.81 (d, J=2.8 Hz, 1H), 6.76 (dd, J=8.8 Hz, 2.8 Hz, 1H), 5.02 (s, 2H), 4.12 (t, J=6.6 Hz, 2H), 2.98 (t, J=6.5 Hz, 2H).

Step 133-3: Preparation of (4-(4-chlorophenethoxy)-3-(trifluoromethyl)phenyl)carbonohydrazonoyl dicyanide 15 mg (yield: 47%) of the title compound was obtained in the same manner as in Step 1-3 of Example 1 above, except that 4-(4-chlorophenethoxy)-3-(trifluoromethyl)aniline obtained in Step 133-2 was used instead of N-(5-aminopyridin-2-yl)-5-methylpyrazine-2-carboxamide.

$^1$H NMR (400 MHz, Acetone-$d_6$) δ 11.86 (s, 1H), 7.78 (d, J=2.7 Hz, 1H), 7.74 (dd, J=9.0 Hz, 2.8 Hz, 1H), 7.44-7.26 (m, 5H), 4.39 (t, J=6.5 Hz, 2H), 3.14 (t, J=6.5 Hz, 2H).

Example 134: Preparation of (4-(4-methoxyphenethoxy)-3-(trifluoromethyl)phenyl)carbonohydrazonoyl dicyanide (Compound 134)

Step 134-1: Preparation of 1-(4-methoxyphenethoxy)-4-nitro-2-(trifluoromethyl)benzene 165 mg (yield: 95%) of the title compound was obtained in the same manner as in Step 95-1 of Example 95 above, except that 2-(4-methoxyphenyl)ethanol (328 mg, 2.15 mmol) was used instead of phenylmethanol, and 1-fluoro-4-nitro-2-(trifluoromethyl)benzene (0.2 mL, 1.43 mmol) was used instead of 2-chloro-5-nitropyridine.

$^1$H NMR (400 MHz, DMSO-$d_6$) δ 8.50 (dd, J=9.2 Hz, 2.9 Hz, 1H), 8.37 (d, J=2.9 Hz, 1H), 7.52 (d, J=9.3 Hz, 1H), 7.25 (d, J=8.6 Hz, 2H), 6.87 (d, J=8.6 Hz, 2H), 4.45 (t, J=6.6 Hz, 2H), 3.73 (s, 3H), 3.03 (t, J=6.6 Hz, 2H).

Step 134-2: Preparation of 4-(4-methoxyphenethoxy)-3-(trifluoromethyl)aniline 226 mg (yield: 73%) of the title compound was obtained in the same manner as in Step 1-2 of Example 1 above, except that 1-(4-methoxyphenethoxy)-4-nitro-2-(trifluoromethyl)benzene obtained in Step 134-1 was used instead of 5-methyl-N-(5-nitropyridin-2-yl)pyrazine-2-carboxamide.

$^1$H NMR (400 MHz, DMSO-$d_6$) δ 7.22 (d, J=8.6 Hz, 2H), 6.95 (d, J=8.8 Hz, 1H), 6.89-6.84 (m, 2H), 6.82 (d, J=2.8 Hz, 1H), 6.76 (dd, J=8.8 Hz, 2.8 Hz, 1H), 5.02 (s, 2H), 4.07 (t, J=6.8 Hz, 2H), 3.73 (s, 3H), 2.92 (t, J=6.8 Hz, 2H).

Step 134-3: Preparation of (4-(4-methoxyphenethoxy)-3-(trifluoromethyl)phenyl)carbonohydrazonoyl dicyanide 156 mg (yield: 84%) of the title compound was obtained in the same manner as in Step 1-3 of Example 1 above, except that 4-(4-methoxyphenethoxy)-3-(trifluoromethyl)aniline obtained in Step 134-2 was used instead of N-(5-aminopyridin-2-yl)-5-methylpyrazine-2-carboxamide.

$^1$H NMR (400 MHz, Chloroform-d) δ 9.83 (s, 1H), 7.54 (d, J=2.8 Hz, 1H), 7.42 (dd, J=9.0 Hz, 2.8 Hz, 1H), 7.22 (d, J=8.6 Hz, 2H), 7.01 (d, J=9.0 Hz, 1H), 6.86 (d, J=8.6 Hz, 2H), 4.21 (t, J=6.7 Hz, 2H), 3.80 (s, 3H), 3.08 (t, J=6.7 Hz, 2H).

Example 135: Preparation of (3-(trifluoromethyl)-4-(4-(trifluoromethyl)phenethoxy)phenyl)carbonohydrazonoyl dicyanide (Compound 135)

Step 135-1: Preparation of 4-nitro-2-(trifluoromethyl-1-(4-(trifluoromethyl)phenethoxy)benzene 298 mg (yield: 53%) of the title compound was obtained in the same manner as in Step 95-1 of Example 95 above, except that 2-(4-(trifluoromethyl)phenyl)ethanol (0.33 mL, 2.15 mmol) was used instead of phenylmethanol, and 1-fluoro-4-nitro-2-(trifluoromethyl)benzene (0.2 mL, 1.43 mmol) was used instead of 2-chloro-5-nitropyridine.

$^1$H NMR (400 MHz, DMSO-$d_6$) δ 8.52 (dd, J=9.3 Hz, 2.9 Hz, 1H), 8.37 (d, J=2.8 Hz, 1H), 7.68 (d, J=8.0 Hz, 2H), 7.55 (dd, J=11.8 Hz, 8.6 Hz, 3H), 4.57 (t, J=6.4 Hz, 2H), 3.21 (t, J=6.3 Hz, 2H).

Step 135-2: Preparation of 3-(trifluoromethyl)-4-(4-(trifluoromethyl)phenethoxy)aniline 176 mg (yield: 73%) of the title compound was obtained in the same manner as in Step 1-2 of Example 1 above, except that 4-nitro-2-(trifluoromethyl)-1-(4-(trifluoromethyl)phenethoxy)benzene obtained in Step 135-1 was used instead of 5-methyl-N-(5-nitropyridin-2-yl)pyrazine-2-carboxamide.

$^1$H NMR (400 MHz, DMSO-$d_6$) δ 7.66 (d, J=8.0 Hz, 2H), 7.54 (d, J=7.9 Hz, 2H), 6.97 (d, J=8.7 Hz, 1H), 6.81 (d, J=2.7 Hz, 1H), 6.77 (dd, J=8.9 Hz, 2.7 Hz, 1H), 5.03 (s, 2H), 4.18 (t, J=6.4 Hz, 2H), 3.09 (t, J=6.5 Hz, 2H).

Step 135-3: Preparation of (3-(trifluoromethyl)-4-(4-(trifluoromethyl)phenethoxy)phenyl)carbonohydrazonoyl dicyanide 158 mg (yield: 86%) of the title compound was obtained in the same manner as in Step 1-3 of Example 1 above, except that 3-(trifluoromethyl)-4-(4-(trifluoromethyl)phenethoxy)aniline obtained in Step 135-2 was used instead of N-(5-aminopyridin-2-yl)-5-methylpyrazine-2-carboxamide.

$^1$H NMR (400 MHz, Acetone-$d_6$) δ 12.09 (s, 1H), 7.79-7.71 (m, 2H), 7.66 (d, J=8.2 Hz, 2H), 7.60 (d, J=8.2 Hz, 2H), 7.37 (d, J=8.9 Hz, 1H), 4.45 (t, J=6.4 Hz, 2H), 3.26 (t, J=6.3 Hz, 2H).

Example 136: Preparation of (4-(pyrimidin-2-ylmethoxy)phenyl)carbonohydrazonoyl dicyanide (Compound 136)

Step 136-1: Preparation of 2-((4-nitrophenoxy)methyl)pvrimidine

Triphenylphosphine ($PPh_3$, 1.26 g, 4.80 mmol) and diisopropyl azodicarboxylate (DIAD, 0.95 mL, 4.80 mmol) were dissolved in a THF solution under a nitrogen atmosphere, and the reaction mixture was stirred at 0° C. for 30 minutes. Pyrimidin-2-ylmethanol (0.36 mL, 4 mmol) and 4-nitrophenol (667 mg, 4.80 mmol) were added to the reaction mixture, and the reaction mixture was stirred at room temperature for one day. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 365 mg (yield: 39%) of the title compound.

$^1$H NMR (400 MHz, DMSO-$d_6$) δ 8.861-8.849 (d, J=4.8 Hz, 2H), 8.219-8.196 (d, J=9.2 Hz, 2H), 7.516-7.491 (t, J=5.0 Hz, 1H), 7.215-7.192 (d, J=9.2 Hz, 2H), 5.492 (s, 2H).

Step 136-2: Preparation of 4-(pyrimidin-2-ylmethoxy)aniline 98 mg (yield: 49%) of the title compound was obtained in the same manner as in Step 1-2 of Example 1 above, except that 2-((4-nitrophenoxy)methyl)pyrimidine obtained in Step 136-1 was used instead of 5-methyl-N-(5-nitropyridin-2-yl)pyrazine-2-carboxamide.

$^1$H NMR (400 MHz, DMSO-$d_6$) δ 8.840-8.828 (d, J=4.8 Hz, 2H), 7.478-7.454 (t, J=4.8 Hz, 1H), 6.708-6.687 (d, J=8.4 Hz, 2H), 6.503-6.482 (d, J=8.4 Hz, 2H), 5.095 (s, 2H), 4.619 (s, 2H).

Step 136-3: Preparation of (4-(pyrimidin-2-ylmethoxy)phenyl)carbonohydrazonoyl dicyanide 70 mg (yield: 63%) of the title compound was obtained in the same manner as in Step 1-3 of Example 1 above, except that 4-(pyrimidin-2-ylmethoxy)aniline obtained in Step 136-2 was used instead of N-(5-aminopyridin-2-yl)-5-methylpyrazine-2-carboxamide.

$^1$H NMR (400 MHz, DMSO-$d_6$) δ 12.980 (s, 1H), 8.853-8.841 (d, J=4.8 Hz, 2H), 7.499-7.474 (t, J=5.0 Hz, 1H), 7.421-7.398 (d, J=9.2 Hz, 2H), 7.060-7.037 (d, J=9.2 Hz, 2H), 5.301 (s, 2H).

Example 137: Preparation of (4-((1H-pyrazol-4-yl)methoxy)phenyl)carbonohydrazonoyl dicyanide (Compound 137)

Step 137-1: Preparation of 2-((4-nitrophenoxy)methyl)pyrimidine $Cs_2CO_3$ (2.45 g, 7.55 mmol), 4-nitrophenol (420 mg, 3.02 mmol), and 4-(chloromethyl)-1H-pyrazole (577 mg, 3.77 mmol) were dissolved in DMF under a nitrogen atmosphere, and the reaction mixture was stirred at room temperature for 12 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 186 mg (yield: 28%) of the title compound.

$^1$H NMR (400 MHz, DMSO-$d_6$) δ 12.90 (s, 1H), 8.21 (d, J=8.8 Hz, 2H), 7.74 (s, 1H), 7.24 (d, J=9.3 Hz, 2H), 6.38 (s, 1H), 5.22 (s, 2H).

Step 137-2: Preparation of 4-41H-Pyrazol-4-ylmethoxy)aniline 151 mg (yield: 97%) of the title compound was obtained in the same manner as in Step 1-2 of Example 1 above, except that 4-((4-nitrophenoxy)methyl)-1H-pyrazole obtained in Step 137-1 was used instead of 5-methyl-N-(5-nitropyridin-2-yl)pyrazine-2-carboxamide.

$^1H$ NMR (400 MHz, DMSO-$d_6$) δ 12.73 (s, 1H), 7.68 (s, 1H), 6.71 (d, J=8.8 Hz, 2H), 6.49 (d, J=8.8 Hz, 2H), 6.28 (d, J=2.1 Hz, 1H), 4.87 (s, 2H), 4.59 (s, 2H).

Step 137-3: Preparation of (4-((1H-pyrazol-4-yl) methoxy)phenovis)carbonohydrazonoyl dicyanide 33 mg (yield: 33%) of the title compound was obtained in the same manner as in Step 1-3 of Example 1 above, except that 4-((1H-pyrazol-4-ylmethoxy)aniline obtained in Step 137-2 was used instead of N-(5-aminopyridin-2-yl)-5-methylpyrazine-2-carboxamide.

$^1H$ NMR (400 MHz, DMSO-$d_6$) δ 13.00 (s, 1H), 7.67 (s, 1H), 7.42 (d, J=7.1 Hz, 2H), 7.08 (d, J=7.2 Hz, 2H), 6.34 (s, 1H), 5.07 (s, 2H).

Example 138: Preparation of (4-((5-methylpyrazin-2-yl)methoxy)phenyl)carbonohydrazonoyl dicyanide (Compound 138)

Step 138-1: Preparation of 2-methyl-5-4(4-nitrophenoxy)methyl)pyrazine 258 mg (yield: 33%) of the title compound was obtained in the same manner as in Step 95-1 of Example 95 above, except that (5-methylpyrazin-2-yl)methanol (400 mg, 3.22 mmol) was used instead of phenylmethanol, and 1-fluoro-4-nitrobenzene (0.84 mL, 4.83 mmol) was used instead of 2-chloro-5-nitropyridine.

$^1H$ NMR (400 MHz, DMSO-$d_6$) δ 8.71 (s, 1H), 8.58 (s, 1H), 8.23 (d, J=9.3 Hz, 2H), 7.28 (d, J=9.3 Hz, 2H), 5.38 (s, 2H), 2.52 (s, 3H).

Step 138-2: Preparation of 4-((5-methylpyrazin-2-yl)methoxy)aniline 108 mg (yield: 61%) of the title compound was obtained in the same manner as in Step 1-2 of Example 1 above, except that 2-methyl-5-((4-nitrophenoxy)methyl)pyrazine obtained in Step 138-1 was used instead of 5-methyl-N-(5-nitropyridin-2-yl)pyrazine-2-carboxamide.

$^1H$ NMR (400 MHz, DMSO-$d_6$) δ 8.61 (s, 1H), 8.53 (s, 1H), 6.75 (d, J=7.3 Hz, 2H), 6.51 (d, J=7.1 Hz, 2H), 5.05 (s, 2H), 4.65 (s, 2H), 1.99 (s, 3H).

Step 138-3: Preparation of (4-4(6-methylpyrazin-2-yl)methoxy)phenyl)carbonohydrazonic Dicyanide 93 mg (yield: 69%) of the title compound was obtained in the same manner as in Step 1-3 of Example 1 above, except that 4-((5-methylpyrazin-2-yl)methoxy)aniline obtained in Step 138-2 was used instead of N-(5-aminopyridin-2-yl)-5-methylpyrazine-2-carboxamide.

$^1H$ NMR (400 MHz, DMSO-$d_6$) δ 12.99 (s, 1H), 8.66 (s, 1H), 8.56 (s, 1H), 7.43 (d, J=9.1 Hz, 2H), 7.11 (d, J=9.1 Hz, 2H), 5.22 (s, 2H).

Example 139: Preparation of (4-(1-(4-(trifluoromethyl)phenyl)ethoxy)phenyl)carbonohydrazonoyl dicyanide (Compound 139)

Step 139-1: Preparation of 1-nitro-4-(1-(4-(trifluoromethyl)phenyl)ethoxy)benzene 495 mg (yield: 79%) of the title compound was obtained in the same manner as in Step 136-1 of Example 136 above, except that 1-(4-(trifluoromethyl)phenyl)ethanol (0.31 mL, 2 mmol) was used instead of pyrimidin-2-ylmethanol.

$^1H$ NMR (400 MHz, DMSO-$d_6$) δ 8.15 (d, J=9.1 Hz, 2H), 7.75 (d, J=8.1 Hz, 2H), 7.66 (d, J=8.0 Hz, 2H), 7.13 (d, J=9.2 Hz, 2H), 5.86 (q, J=6.3 Hz, 1H), 1.62 (d, J=6.3 Hz, 3H).

Step 139-2: Preparation of 4-(1-(4-(trifluoromethyl)phenyl)ethoxy)aniline 159 mg (yield: 59%) of the title compound was obtained in the same manner as in Step 1-2 of Example 1 above, except that 1-nitro-4-(1-(4-(trifluoromethyl)phenyl)ethoxy) benzene obtained in Step 139-1 was used instead of 5-methyl-N-(5-nitropyridin-2-yl)pyrazine-2-carboxamide.

$^1H$ NMR (400 MHz, DMSO-$d_6$) δ 7.69 (d, J=8.1 Hz, 2H), 7.59 (d, J=8.1 Hz, 2H), 6.61 (d, J=8.8 Hz, 2H), 6.41 (d, J=8.8 Hz, 2H), 5.36 (q, J=6.4 Hz, 1H), 4.59 (s, 2H), 1.49 (d, J=6.4 Hz, 3H).

Step 139-3: Preparation of (4-(1-(4-(trifluoromethyl)phenyl)ethoxy)phenyl)carbonohydrazonoyl dicyanide 137 mg (yield: 72%) of the title compound was obtained in the same manner as in Step 1-3 of Example 1 above, except that 4-(1-(4-(trifluoromethyl)phenyl)ethoxy)aniline obtained in Step 139-2 was used instead of N-(5-aminopyridin-2-yl)-5-methylpyrazine-2-carboxamide.

$^1H$ NMR (400 MHz, DMSO-$d_6$) δ 12.96 (s, 1H), 7.72 (d, J=8.2 Hz, 2H), 7.63 (d, J=8.1 Hz, 2H), 7.38-7.29 (m, 2H), 7.05-6.94 (m, 2H), 5.64 (q, J=6.3 Hz, 1H), 1.57 (d, J=6.3 Hz, 3H).

Example 140: Preparation of (4-(1-(pyridin-3-yl) ethoxy)phenyl)carbonohydrazonoyl Dicyanide (Compound 140)

Step 140-1: Preparation of 4-(1-(pyridin-3-yl)ethoxy)aniline 277 mg (yield: 39%) of the title compound was obtained in the same manner as in Step 136-1 of Example 136 above, except that 1-(pyridin-3-yl)ethanol (0.33 mL, 2.92 mmol) was used instead of pyrimidin-2-ylmethanol.

$^1H$ NMR (400 MHz, DMSO-$d_6$) δ 8.68 (d, J=2.1 Hz, 1H), 8.51 (dd, J=4.8 Hz, 1.7 Hz, 1H), 8.15 (d, J=9.3 Hz, 2H), 7.84 (dt, J=7.9 Hz, 2.0 Hz, 1H), 7.40 (ddd, J=7.9 Hz, 4.8 Hz, 0.9 Hz, 1H), 7.16 (d, J=9.3 Hz, 2H), 5.83 (q, J=6.4 Hz, 1H), 1.64 (d, J=6.4 Hz, 3H).

Step 140-2: Preparation of 4-(1-pyridin-3-yl)ethoxy)aniline 98 mg (yield: 41%) of the title compound was obtained in the same manner as in Step 1-2 of Example 1 above, except that 4-(1-(pyridin-3-yl)ethoxy)aniline obtained in Step 140-1 was used instead of 5-methyl-N-(5-nitropyridin-2-yl) pyrazine-2-carboxamide.

$^1H$ NMR (400 MHz, DMSO-$d_6$) δ 8.57 (d, J=2.3 Hz, 1H), 8.45 (dd, J=4.8 Hz, 1.6 Hz, 1H), 7.77 (d, J=7.9 Hz, 1H), 7.35 (dd, J=7.9 Hz, 4.8 Hz, 1H), 6.63 (d, J=8.7 Hz, 2H), 6.42 (d, J=8.7 Hz, 2H), 5.32 (q, J=6.4 Hz, 1H), 4.63-4.52 (m, 2H), 1.51 (d, J=6.4 Hz, 3H).

Step 140-3: Preparation of (4-(1-(pyridin-3-yl) ethoxy)phenyl)carbonohydrazonoyl dicyanide 41 mg (yield: 34%) of the title compound was obtained in the same manner as in Step 1-3 of Example 1 above, except that 4-(1-pyridin-3-yl)ethoxy)aniline obtained in Step 140-2 was used instead of N-(5-aminopyridin-2-yl)-5-methylpyrazine-2-carboxamide.

$^1$H NMR (400 MHz, DMSO-$d_6$) δ 12.95 (s, 1H), 8.65 (d, J=2.3 Hz, 1H), 8.49 (dd, J=4.8 Hz, 1.7 Hz, 1H), 7.84 (dt, J=7.9 Hz, 2.0 Hz, 1H), 7.40 (ddd, J=7.8 Hz, 4.8 Hz, 0.8 Hz, 1H), 7.33 (d, J=9.1 Hz, 2H), 6.99 (d, J=9.1 Hz, 2H), 5.61 (q, J=6.4 Hz, 1H), 1.58 (d, J=6.4 Hz, 3H).

Example 141: Preparation of (4-(benzyloxy)-3-methylphenyl)carbonohydrazonoyl dicyanide (Compound 141)

Step 141-1: Preparation of 1-(benzyloxy)-2-methyl-4-nitrobenzene 551 mg (yield: 74%) of the title compound was obtained in the same manner as in Step 136-1 of Example 136 above, except that phenylmethanol (0.32 mL, 3.05 mmol) was used instead of pyrimidin-2-ylmethanol and 2-methyl-4-nitrophenol (561 mg, 3.66 mmol) was used instead of 4-nitrophenol.

$^1$H NMR (400 MHz, DMSO-$d_6$) δ 8.14-8.01 (m, 2H), 7.51-7.47 (m, 2H), 7.42 (td, J=7.2 Hz, 1.3 Hz, 2H), 7.36 (d, J=6.4 Hz, 1H), 7.24 (d, J=9.9 Hz, 1H), 5.29 (s, 2H), 2.28 (s, 3H).

Step 141-2: Preparation of 4-(benzyloxy)-3-methylaniline 320 mg (yield: 73%) of the title compound was obtained in the same manner as in Step 95-2 of Example 95 above, except that 1-(benzyloxy)-2-methyl-4-nitrobenzene obtained in Step 141-1 was used instead of 2-(benzyloxy)-5-nitropyridine.

$^1$H NMR (400 MHz, DMSO-$d_6$) δ 7.46-7.27 (m, 5H), 6.70 (d, J=8.5 Hz, 1H), 6.40 (d, J=2.0 Hz, 1H), 6.33 (dd, J=8.5 Hz, 2.8 Hz, 1H), 4.93 (s, 2H), 4.53 (s, 1H), 2.08 (s, 3H).

Step 141-3: Preparation of (4-(benzyloxy)-3-methylphenyl)carbonohydrazonoyl dicyanide 180 mg (yield: 44%) of the title compound was obtained in the same manner as in Step 1-3 of Example 1 above, except that 4-(benzyloxy)-3-methylaniline obtained in Step 141-2 was used instead of N-(5-aminopyridin-2-yl)-5-methylpyrazine-2-carboxamide.

$^1$H NMR (400 MHz, DMSO-$d_6$) δ 12.95 (s, 1H), 7.46 (d, J=6.7 Hz, 2H), 7.40 (t, J=7.4 Hz, 2H), 7.36-7.31 (m, 2H), 7.27 (dd, J=8.6 Hz, 2.2 Hz, 1H), 7.06 (d, J=8.9 Hz, 1H), 5.13 (s, 2H), 2.22 (s, 3H).

Example 142: Preparation of (3-methyl-4-(4-methylbenzyloxy)phenyl)carbonohydrazonoyl dicyanide (Compound 142)

Step 142-1: Preparation of 2-methyl-1-(4-methylbenzyloxy)-4-nitrobenzene 360 mg (yield: 47%) of the title compound was obtained in the same manner as in Step 136-1 of Example 136 above, except that p-tolylmethanol (360 mg, 2.95 mmol) was used instead of pyrimidin-2-ylmethanol, and 2-methyl-4-nitrophenol (541 mg, 3.54 mmol) was used instead of 4-nitrophenol.

$^1$H NMR (400 MHz, DMSO-$d_6$) δ 8.15-8.03 (m, 2H), 7.37 (d, J=8.1 Hz, 2H), 7.26-7.19 (m, 3H), 5.24 (s, 2H), 2.31 (s, 3H), 2.26 (s, 3H).

Step 142-2: Preparation of 3-methyl-4-(4-methylbenzyloxy)aniline 360 mg (yield: 47%) of the title compound was obtained in the same manner as in Step 95-2 of Example 95 above, except that 2-methyl-1-(4-methylbenzyloxy)-4-nitrobenzene obtained in Step 142-1 was used instead of 2-(benzyloxy)-5-nitropyridine.

$^1$H NMR (400 MHz, DMSO-$d_6$) δ 7.29 (d, J=8.0 Hz, 2H), 7.17 (d, J=7.8 Hz, 2H), 6.69 (d, J=8.5 Hz, 1H), 6.39 (dd, J=2.8 Hz, 0.9 Hz, 1H), 6.32 (dd, J=8.5 Hz, 2.8 Hz, 1H), 4.87 (s, 2H), 4.52 (s, 2H), 2.30 (s, 3H), 2.05 (s, 3H).

Step 142-3: Preparation of (3-methyl-4-(4-methylbenzyloxy)phenyl)carbonohydrazonoyl Dicyanide 207 mg (yield: 77%) of the title compound was obtained in the same manner as in Step 1-3 of Example 1 above, except that 3-methyl-4-(4-methylbenzyloxy)aniline obtained in Step 142-2 was used instead of N-(5-aminopyridin-2-yl)-5-methylpyrazine-2-carboxamide.

$^1$H NMR (400 MHz, DMSO-$d_6$) δ 12.94 (s, 1H), 7.36-7.29 (m, 3H), 7.26 (dd, J=8.8 Hz, 2.8 Hz, 1H), 7.20 (d, J=7.8 Hz, 2H), 7.05 (d, J=8.8 Hz, 1H), 5.07 (s, 2H), 2.31 (s, 3H), 2.19 (s, 3H).

Example 143: Preparation of (3-methyl-4-(pyrimidin-2-ylmethoxy)phenyl)carbonohydrazonoyl dicyanide (Compound 143)

Step 143-1: Preparation of 2-((2-methyl-4-nitrophenoxy)methyl)pvrimidine 516 mg (yield: 70%) of the title compound was obtained in the same manner as in Step 136-1 of Example 136 above, except that 2-methyl-4-nitrophenol (551 mg, 3.60 mmol) was used instead of 4-nitrophenol.

$^1$H NMR (400 MHz, DMSO-$d_6$) δ 8.85 (d, J=4.9 Hz, 2H), 8.11 (d, J=2.9 Hz, 1H), 8.05 (dd, J=9.1 Hz, 3.0 Hz, 1H), 7.49 (t, J=4.9 Hz, 1H), 7.11 (d, J=9.0 Hz, 1H), 5.51 (s, 2H), 2.31 (s, 3H).

Step 143-2: Preparation of 3-methyl-4-(pyrimidin-2-ylmethoxy)aniline 154 mg (yield: 70%) of the title compound was obtained in the same manner as in Step 1-2 of Example 1 above, except that 2-((2-methyl-4-nitrophenoxy)methyl)pyrimidine obtained in Step 143-1 was used instead of 5-methyl-N-(5-nitropyridin-2-yl)pyrazine-2-carboxamide.

$^1$H NMR (400 MHz, DMSO-$d_6$) δ 8.82 (d, J=4.9 Hz, 2H), 7.45 (t, J=4.9 Hz, 1H), 6.62 (d, J=8.5 Hz, 1H), 6.39 (dd, J=2.8 Hz, 0.9 Hz, 1H), 6.28 (dd, J=8.6 Hz, 2.7 Hz, 1H), 5.08 (s, 2H), 4.52 (s, 2H), 2.08 (s, 3H).

Step 143-3: Preparation of (3-methyl-4-(pyrimidin-2-ylmethoxy)phenyl)carbonohydrazonoyl dicyanide 130 mg (yield: 63%) of the title compound was obtained in the same manner as in Step 1-3 of Example 1 above, except that 3-methyl-4-(pyrimidin-2-ylmethoxy)aniline obtained in Step 143-2 was used instead of N-(5-aminopyridin-2-yl)-5-methylpyrazine-2-carboxamide.

$^1$H NMR (400 MHz, DMSO-$d_6$) δ 12.94 (s, 1H), 8.84 (d, J=4.9 Hz, 2H), 7.47 (t, J=4.9 Hz, 1H), 7.31 (d, J=2.7 Hz, 1H), 7.22 (dd, J=8.8 Hz, 2.8 Hz, 1H), 6.95 (d, J=8.9 Hz, 1H), 5.31 (s, 2H), 2.23 (s, 3H).

Example 144: Preparation of (3-methyl-4-(pyrazin-2-ylmethoxy)phenyl)carbonohydrazonoyl dicyanide (Compound 144)

Step 144-1: Preparation of 2-((2-meth-4-nitrophenoxy)methyl)pyrazine 500 mg (yield: 68%) of the title compound was obtained in the same manner as in Step 136-1 of Example 136 above, except that pyrazin-2-ylmethanol (330 mg, 3.0 mmol) was used instead of pyrimidin-2-ylmethanol, and 2-methyl-4-nitrophenol (551 mg, 3.60 mmol) was used instead of 4-nitrophenol.

$^1$H NMR (400 MHz, DMSO-$d_6$) δ 8.87 (d, J=1.5 Hz, 1H), 8.70 (dd, J=2.6 Hz, 1.5 Hz, 1H), 8.67 (d, J=2.6 Hz, 1H), 8.13 (d, J=7.6 Hz, 2H), 7.30 (d, J=9.4 Hz, 1H), 5.46 (s, 2H), 2.32 (s, 3H).

Step 144-2: Preparation of 3-methyl-4-(pyrazin-2-ylmethoxy)aniline 133 mg (yield: 63%) of the title compound was obtained in the same manner as in Step 95-2 of Example 95 above, except that 2-((2-methyl-4-nitrophenoxy)methyl)pyrazine obtained in Step 144-1 was used instead of 2-(benzyloxy)-5-nitropyridine.

$^1$H NMR (400 MHz, DMSO-$d_6$) δ 8.77 (d, J=1.5 Hz, 1H), 8.65 (dd, J=2.6 Hz, 1.5 Hz, 1H), 8.61 (d, J=2.6 Hz, 1H), 6.73 (d, J=8.6 Hz, 1H), 6.42 (d, J=2.7 Hz, 1H), 6.34 (dd, J=8.5 Hz, 2.8 Hz, 1H), 5.09 (s, 2H), 4.59 (s, 2H), 2.10 (s, 3H).

Step 144-3: Preparation of (3-methyl-4-(pyrazin-2-ylmethoxy)phenyl)carbonohydrazonoyl dicyanide 88 mg (yield: 50%) of the title compound was obtained in the same manner as in Step 1-3 of Example 1 above, except that 3-methyl-4-(pyrazin-2-ylmethoxy)aniline obtained in Step 144-2 was used instead of N-(5-aminopyridin-2-yl)-5-methylpyrazine-2-carboxamide.

$^1$H NMR (400 MHz, DMSO-$d_6$) δ12.96 (s, 1H), 8.83 (d, J=1.5 Hz, 1H), 8.71-8.57 (m, 2H), 7.34 (d, J=2.7 Hz, 1H), 7.29 (dd, J=8.8 Hz, 2.8 Hz, 1H), 7.11 (d, J=8.9 Hz, 1H), 5.29 (s, 2H), 2.25 (s, 3H).

Example 145: Preparation of (3-methyl-4-(pyridin-3-ylmethoxy)phenyl)carbonohydrazonoyl dicyanide (Compound 145)

Step 145-1: Preparation of 3-((2-methyl-4-nitrophenoxy)methyl)pyridine 130 mg (yield: 13%) of the title compound was obtained in the same manner as in Step 136-1 of Example 136 above, except that pyridin-3-ylmethanol (0.39 mL, 4.03 mmol) was used instead of pyrimidin-2-ylmethanol, and 2-methyl-4-nitrophenol (741 mg, 4.84 mmol) was used instead of 4-nitrophenol.

$^1$H NMR (400 MHz, DMSO-$d_6$) δ 8.72 (d, J=1.4 Hz, 1H), 8.58 (dd, J=4.8 Hz, 1.6 Hz, 1H), 8.19-8.07 (m, 2H), 7.92 (dt, J=7.9 Hz, 1.9 Hz, 1H), 7.46 (ddd, J=7.8 Hz, 4.8 Hz, 0.9 Hz, 1H), 7.28 (d, J=8.6 Hz, 1H), 5.35 (s, 2H), 2.28 (s, 3H).

Step 145-2: Preparation of 3-methyl-4-(pyridin-3-ylmethoxy)aniline 55 mg (yield: 48%) of the title compound was obtained in the same manner as in Step 95-2 of Example 95 above, except that 3-((2-methyl-4-nitrophenoxy)methyl)pyridine obtained in Step 145-1 was used instead of 2-(benzyloxy)-5-nitropyridine.

$^1$H NMR (400 MHz, DMSO-$d_6$) δ 8.65-8.57 (m, 1H), 8.52 (dd, J=4.8 Hz, 1.7 Hz, 1H), 7.88-7.77 (m, 1H), 7.41 (ddd, J=7.7 Hz, 4.8 Hz, 0.9 Hz, 1H), 6.73 (d, J=8.5 Hz, 1H), 6.47-6.35 (m, 1H), 6.34 (dd, J=8.5 Hz, 2.8 Hz, 1H), 4.98 (s, 2H), 4.56 (s, 2H), 2.06 (s, 3H).

Step 145-3: Preparation of (3-methyl-4-(pyridin-3-ylmethoxy)phenyl)carbonohydrazonoyl dicyanide 32 mg (yield: 48%) of the title compound was obtained in the same manner as in Step 1-3 of Example 1 above, except that 3-methyl-4-(pyridin-3-ylmethoxy)aniline obtained in Step 145-2 was used instead of N-(5-aminopyridin-2-yl)-5-methylpyrazine-2-carboxamide.

$^1$H NMR (400 MHz, Acetone-$d_6$) δ 11.72 (s, 1H), 8.73 (d, J=2.3 Hz, 1H), 8.56 (dd, J=4.8 Hz, 1.7 Hz, 1H), 7.91 (dt, J=7.9 Hz, 2.0 Hz, 1H), 7.47-7.38 (m, 2H), 7.34 (dd, J=8.8 Hz, 2.8 Hz, 1H), 7.13 (d, J=8.8 Hz, 1H), 5.24 (s, 2H), 2.28 (s, 3H).

Example 146: Preparation of (4-((1H-benzo[d]imidazol-2-yl)methoxy)-3-methylphenyl)carbonohydrazonoyl dicyanide (Compound 146)

Step 146-1: Preparation of 2-((2-methyl-4-nitrophenoxy)methyl)-1H-benzo[d]imidazole 119 mg (yield: 18%) of the title compound was obtained in the same manner as in Step 136-1 of Example 136 above, except that (1H-benzo[d]imidazol-2-yl)methanol (350 mg, 2.36 mmol) was used instead of pyrimidin-2-ylmethanol, and 2-methyl-4-nitrophenol (434 mg, 2.83 mmol) was used instead of 4-nitrophenol.

$^1$H NMR (400 MHz, DMSO-$d_6$) δ 8.17-8.07 (m, 2H), 7.64 (d, J=8.1 Hz, 1H), 7.51 (d, J=7.4 Hz, 1H), 7.35 (d, J=9.8 Hz, 1H), 7.27-7.14 (m, 2H), 5.52 (s, 2H), 2.32 (s, 3H).

Step 146-2: Preparation of 4-4(1H-benzo[d]imidazol-2-yl)methoxy)-3-methylaniline 80 mg (yield: 81%) of the title compound was obtained in the same manner as in Step 1-2 of Example 1 above, except that 2-((2-methyl-4-nitrophenoxy)methyl)-1H-benzo[d]imidazole obtained in Step 146-1 was used instead of 5-methyl-N-(5-nitropyridin-2-yl)pyrazine-2-carboxamide.

$^1$H NMR (400 MHz, DMSO-$d_6$) δ 7.54 (dd, J=6.0 Hz, 3.2 Hz, 2H), 7.17 (dd, J=6.0 Hz, 3.2 Hz, 2H), 6.77 (d, J=8.5 Hz, 1H), 6.41 (d, J=2.7 Hz, 1H), 6.33 (dd, J=8.5 Hz, 2.8 Hz, 1H), 5.11 (s, 2H), 4.58 (s, 2H), 2.11 (s, 3H).

Step 146-3: Preparation of (4-((1H-benzo[d]imidazol-2-yl)methoxy)-3-methylphenyl)carbonohydrazonoyl dicyanide 42 mg (yield: 46%) of the title compound was obtained in the same manner as in Step 1-3 of Example 1 above, except that 4-((1H-benzo[d]imidazol-2-yl)methoxy)-3-methylaniline obtained in Step 146-2 was used instead of N-(5-aminopyridin-2-yl)-5-methylpyrazine-2-carboxamide.

$^1$H NMR (400 MHz, Acetone-$d_6$) δ 7.59 (dd, J=6.0 Hz, 3.2 Hz, 2H), 7.38 (d, J=2.8 Hz, 1H), 7.31 (dd, J=8.9 Hz, 2.8 Hz, 1H), 7.25-7.16 (m, 3H), 5.45 (s, 2H), 2.30 (s, 3H).

Example 147: Preparation of (3-methyl-4-((6-methylpyrazin-2-yl)methoxy)phenyl)carbonohydrazonoyl dicyanide (Compound 147)

Step 147-1: Preparation of 2-methyl-4-((2-methyl-4-nitrophenoxy)methyl)pyrazine 171 mg (yield: 33%) of the title compound was obtained in the same manner as in Step 136-1 of Example 136 above, except that (5-methylpyrazin-2-yl)methanol (250 mg, 2.01 mmol) was used instead of pyrimidin-2-ylmethanol, and 2-methyl-4-nitrophenol (370 mg, 2.42 mmol) was used instead of 4-nitrophenol.

$^1$H NMR (400 MHz, DMSO-$d_6$) δ 8.71 (s, 1H), 8.58 (s, 1H), 8.17-8.04 (m, 2H), 7.29 (d, J=9.9 Hz, 1H), 5.40 (s, 2H), 2.52 (s, 3H), 2.29 (s, 3H).

Step 147-2: Preparation of 3-methyl-4-((5-methylpyrazin-2-yl)methoxyaniline 54 mg (yield: 36%) of the title compound was obtained in the same manner as in Step 1-2 of Example 1 above, except that 2-methyl-5-((2-methyl-4-nitrophenoxy)methyl)pyrazine obtained in Step 147-1 was used instead of 5-methyl-N-(5-nitropyridin-2-yl)pyrazine-2-carboxamide.

$^1$H NMR (400 MHz, Chloroform-d) δ 8.71 (s, 1H), 8.42 (s, 1H), 6.72 (d, J=8.5 Hz, 1H), 6.57 (d, J=2.9 Hz, 1H), 6.48 (dd, J=8.5 Hz, 2.9 Hz, 1H), 5.12 (s, 2H), 3.41 (s, 2H), 2.58 (s, 3H), 2.24 (s, 3H).

Step 147-3: Preparation of (3-methyl-4-((5-methylpyrazin-2-yl)methoxy)phenyl)carbonohydrazonoyl dicyanide 33 mg (yield: 48%) of the title compound was obtained in the same manner as in Step 1-3 of Example 1 above, except that 3-methyl-4-((5-methylpyrazin-2-yl)methoxy)aniline obtained in Step 147-2 was used instead of N-(5-aminopyridin-2-yl)-5-methylpyrazine-2-carboxamide.

$^1$H NMR (400 MHz, DMSO-$d_6$) δ 12.94 (s, 1H), 8.67 (s, 1H), 8.56 (s, 1H), 7.33 (s, 1H), 7.28 (dd, J=8.7 Hz, 2.7 Hz, 1H), 7.10 (d, J=8.8 Hz, 1H), 5.23 (s, 2H), 2.50 (s, 3H), 2.22 (s, 3H).

Example 148: Preparation of (3-methyl-4-(4-(trifluoromethyl)benzyloxy)phenyl)carbonohydrazonoyl dicyanide (Compound 148)

Step 148-1: Preparation of 2-methyl-4-nitro-1-(4-(trifluoromethyl)benzyloxy)benzene 217 mg (yield: 28%) of the title compound was obtained in the same manner as in Step 136-1 of Example 136 above, except that (4-(trifluoromethyl)phenyl)methanol (0.34 mL, 2.50 mmol) was used instead of pyrimidin-2-ylmethanol, and 2-methyl-4-nitrophenol (460 mg, 3.00 mmol) was used instead of 4-nitrophenol.

$^1$H NMR (400 MHz, DMSO-$d_6$) δ 8.17-8.09 (m, 2H), 7.80 (d, J=8.1 Hz, 2H), 7.71 (d, J=8.0 Hz, 2H), 7.23 (d, J=9.9 Hz, 1H), 5.42 (s, 2H), 2.32 (s, 3H).

Step 148-2: Preparation of 3-methyl-4-(4-(trifluoromethyl)benzyloxy)aniline 83 mg (yield: 46%) of the title compound was obtained in the same manner as in Step 95-2 of Example 95 above, except that 2-methyl-4-nitro-1-(4-(trifluoromethyl)benzyloxy)benzene obtained in Step 148-1 was used instead of 2-(benzyloxy)-5-nitropyridine.

$^1$H NMR (400 MHz, DMSO-$d_6$) δ 7.75 (d, J=8.0 Hz, 2H), 7.64 (d, J=8.0 Hz, 2H), 6.69 (d, J=8.5 Hz, 1H), 6.46-6.38 (m, 1H), 6.33 (dd, J=8.5 Hz, 2.8 Hz, 1H), 5.05 (s, 2H), 4.56 (s, 2H), 2.10 (s, 3H).

Step 148-3: Preparation of (3-methyl-4-(4-(trifluoromethyl)benzyloxy)phenyl)carbonohydrazonoyl dicyanide 51 mg (yield: 50%) of the title compound was obtained in the same manner as in Step 1-3 of Example 1 above, except that 3-methyl-4-(4-(trifluoromethyl)benzyloxy)aniline obtained in Step 148-2 was used instead of N-(5-aminopyridin-2-yl)-5-methylpyrazine-2-carboxamide.

$^1$H NMR (400 MHz, DMSO-$d_6$) δ 12.95 (s, 1H), 7.78 (d, J=8.1 Hz, 2H), 7.68 (d, J=8.1 Hz, 2H), 7.34 (d, J=2.7 Hz, 1H), 7.28 (dd, J=8.8 Hz, 2.8 Hz, 1H), 7.05 (d, J=8.9 Hz, 1H), 5.26 (s, 2H), 2.25 (s, 3H).

Example 149: Preparation of (3-methyl-4-(pyridazin-3-ylmethoxy)phenyl)carbonohydrazonoyl dicyanide (Compound 149)

Step 149-1: Preparation of 3-((2-methyl-4-nitrophenoxy)methyl)pyridazine 264 mg (yield: 28%) of the title compound was obtained in the same manner as in Step 95-1 of Example 95 above, except that pyridazin-3-ylmethanol (426 mg, 3.87 mmol) was used instead of phenylmethanol, and 1-fluoro-2-methyl-4-nitrobenzene (400 mg, 2.58 mmol) was used instead of 2-chloro-5-nitropyridine.

$^1$H NMR (400 MHz, DMSO-$d_6$) δ 9.25 (dd, J=4.9 Hz, 1.7 Hz, 1H), 8.19-8.06 (m, 2H), 7.88 (dd, J=8.5 Hz, 1.7 Hz, 1H), 7.79 (dd, J=8.5 Hz, 4.9 Hz, 1H), 7.31 (d, J=9.6 Hz, 1H), 5.60 (s, 2H), 2.31 (s, 3H).

Step 149-2: Preparation of 3-methyl-4-(pyridazin-3-ylmethoxy)aniline 63 mg (yield: 36%) of the title compound was obtained in the same manner as in Step 1-2 of Example 1 above, except that 3-((2-methyl-4-nitrophenoxy)methyl)pyridazine obtained in Step 149-1 was used instead of 5-methyl-N-(5-nitropyridin-2-yl)pyrazine-2-carboxamide.

$^1$H NMR (400 MHz, DMSO-$d_6$) δ 9.19 (dd, J=4.8 Hz, 1.9 Hz, 1H), 7.89-7.55 (m, 2H), 6.73 (d, J=8.5 Hz, 1H), 6.42 (dd, J=2.8 Hz, 0.8 Hz, 1H), 6.38-6.26 (m, 1H), 5.23 (s, 2H), 4.59 (s, 2H), 2.10 (s, 3H).

Step 149-3: Preparation of (3-methyl-4-(pyridazin-3-ylmethoxy)phenyl)carbonohydrazonoyl dicyanide 38 mg (yield: 46%) of the title compound was obtained in the same manner as in Step 1-3 of Example 1 above, except that 3-methyl-4-(pyridazin-3-ylmethoxy)aniline obtained in Step 149-2 was used instead of N-(5-aminopyridin-2-yl)-5-methylpyrazine-2-carboxamide.

$^1$H NMR (400 MHz, DMSO-$d_6$) δ 12.97 (s, 1H), 9.23 (dd, J=4.8 Hz, 1.7 Hz, 1H), 7.85 (dd, J=8.4 Hz, 1.7 Hz, 1H), 7.78 (dd, J=8.5 Hz, 4.9 Hz, 1H), 7.34 (d, J=2.7 Hz, 1H), 7.29 (dd, J=8.8 Hz, 2.8 Hz, 1H), 7.13 (d, J=8.9 Hz, 1H), 5.44 (s, 2H), 2.25 (s, 3H).

Example 150: Preparation of (4-(benzo[b]thiophen-2-ylmethoxy)-3-methylphenyl)carbonohydrazonoyl dicyanide (Compound 150)

Step 150-1: Preparation of 2-((2-methyl-4-nitrophenoxy)methyl)benzo[b]thiophene 100 mg (yield: 12%) of the title compound was obtained in the same manner as in Step 95-1 of Example 95 above, except that benzo[b]thiophen-2-ylmethanol (476 mg, 2.90 mmol) was used instead of phenylmethanol, and 1-fluoro-2-methyl-4-nitrobenzene (300 mg, 1.93 mmol) was used instead of 2-chloro-5-nitropyridine.

$^1$H NMR (400 MHz, DMSO-$d_6$) δ 8.16-8.07 (m, 2H), 7.97 (d, J=6.4 Hz, 1H), 7.86 (d, J=6.8 Hz, 1H), 7.57 (s, 1H), 7.44-7.28 (m, 3H), 5.64 (s, 2H), 2.29 (s, 3H).

Step 150-2: Preparation of 4-(benzo[b]thiophen-2-ylmethoxy)-3-methylaniline 60 mg (yield: 68%) of the title compound was obtained in the same manner as in Step 1-2 of Example 1 above, except that 2-((2-methyl-4-nitrophenoxy)methyl)benzo[b]thiophene obtained in Step 150-1 was used instead of 5-methyl-N-(5-nitropyridin-2-yl)pyrazine-2-carboxamide.

$^1$H NMR (400 MHz, DMSO-$d_6$) δ 7.94 (dd, J=8.1 Hz, 1.1 Hz, 1H), 7.82 (dd, J=6.9 Hz, 2.1 Hz, 1H), 7.43 (s, 1H), 7.41-7.23 (m, 2H), 6.78 (d, J=8.5 Hz, 1H), 6.40 (d, J=2.5 Hz, 1H), 6.34 (dd, J=8.5 Hz, 2.8 Hz, 1H), 5.24 (d, J=1.1 Hz, 2H), 4.57 (s, 2H), 2.09 (s, 3H).

Step 150-3: Preparation of (4-(benzo[b]thiophen-2-ylmethoxy)-3-methylphenyl)carbonohydrazonoyl dicyanide 41 mg (yield: 54%) of the title compound was obtained in the same manner as in Step 1-3 of Example 1 above, except that 4-(benzo[b]thiophen-2-ylmethoxy)-3-methylaniline obtained in Step 150-2 was used instead of N-(5-aminopyridin-2-yl)-5-methylpyrazine-2-carboxamide.

$^1$H NMR (400 MHz, DMSO-$d_6$) δ 12.95 (s, 1H), 7.96 (d, J=7.0 Hz, 1H), 7.84 (d, J=7.0 Hz, 1H), 7.51 (s, 1H), 7.45-7.24 (m, 4H), 7.16 (d, J=8.9 Hz, 1H), 5.46 (s, 2H), 2.22 (s, 3H).

Example 151: Preparation of (4-((1H-pyrazol-3-yl)methoxy)-3-methylphenyl)carbonohydrazonoyl dicyanide (Compound 151)

Step 151-1: Preparation of 3-((2-methyl-4-nitrophenoxy)methyl)-1H-pyrazole 300 mg (yield: 66%) of the title compound was obtained in the same manner as in Step 137-1 of Example 137 above, except that 2-methyl-4-nitrophenol (300 mg, 1.96 mmol) was used instead of 4-nitrophenol, and 3-(chloromethyl)-1H-pyrazole hydrochloride (375 mg, 2.45 mmol) was used instead of 4-(chloromethyl)-1H-pyrazole.

$^1$H NMR (400 MHz, DMSO-$d_6$) δ 12.88 (s, 1H), 8.29-7.96 (m, 2H), 7.74 (s, 1H), 7.34 (d, J=8.8 Hz, 1H), 6.38 (s, 1H), 5.25 (s, 2H), 2.22 (s, 3H).

Step 151-2: Preparation of 4-(1H-pyrazol-3-yl)methoxy-3-methylaniline 65 mg (yield: 32%) of the title compound was obtained in the same manner as in Step 1-2 of Example 1 above, except that 3-((2-methyl-4-nitrophenoxy)methyl)-1H-pyrazole obtained in Step 151-1 was used instead of 5-methyl-N-(5-nitropyridin-2-yl)pyrazine-2-carboxamide.

$^1$H NMR (400 MHz, DMSO-d %) δ 12.71 (s, 1H), 7.68 (s, 1H), 6.74 (d, J=8.5 Hz, 1H), 6.48-6.31 (m, 1H), 6.33 (dd, J=8.5 Hz, 2.8 Hz, 1H), 6.28 (s, 1H), 4.86 (s, 2H), 4.51 (s, 2H), 2.02 (s, 3H).

Step 151-3: Preparation of (4-((1H-pyrazol-3-yl)methoxy)-3-methylphenyl)carbonohydrazonoyl dicyanide 35 mg (yield: 42%) of the title compound was obtained in the same manner as in Step 1-3 of Example 1 above, except that 4-((1H-pyrazol-3-yl)methoxy)-3-methylaniline obtained in Step 151-2 was used instead of N-(5-aminopyridin-2-yl)-5-methylpyrazine-2-carboxamide.

$^1$H NMR (400 MHz, Acetone-$d_6$) δ 12.13 (s, 1H), 11.77 (s, 1H), 7.68 (s, 1H), 7.35 (d, J=2.8 Hz, 1H), 7.31 (dd, J=8.8 Hz, 2.8 Hz, 1H), 7.17 (d, J=8.8 Hz, 1H), 6.40 (d, J=2.2 Hz, 1H), 5.17 (s, 2H), 2.05 (s, 3H).

Example 152: Preparation of (3-methyl-4-(thiazol-4-ylmethoxy)phenyl)carbonohydrazonoyl dicyanide (Compound 152)

Step 152-1: Preparation of 4-((2-methyl-4-nitrophenoxy)methyl)thiazole 138 mg (yield: 28%) of the title compound was obtained in the same manner as in Step 137-1 of Example 137 above, except that 2-methyl-4-nitrophenol (300 mg, 1.96 mmol) was used instead of 4-nitrophenol, and 4-(chloromethyl)thiazole hydrochloride (417 mg, 2.45 mmol) was used instead of 4-(chloromethyl)-1H-pyrazole.

$^1$H NMR (400 MHz, DMSO-$d_6$) δ 9.16 (d, J=2.0 Hz, 1H), 8.19-7.99 (m, 2H), 7.85 (d, J=2.0 Hz, 1H), 7.34 (d, J=9.8 Hz, 1H), 5.42 (s, 2H), 2.26 (s, 3H).

Step 152-2: Preparation of 3-methyl-4-(thiazol-4-ylmethoxy)aniline 87 mg (yield: 76%) of the title compound was obtained in the same manner as in Step 1-2 of Example 1 above, except that 4-((2-methyl-4-nitrophenoxy)methyl)thiazole obtained in Step 152-1 was used instead of 5-methyl-N-(5-nitropyridin-2-yl)pyrazine-2-carboxamide.

$^1$H NMR (400 MHz, DMSO-$d_6$) δ 9.10 (d, J=2.0 Hz, 1H), 7.67 (d, J=2.0 Hz, 1H), 6.75 (d, J=8.5 Hz, 1H), 6.40 (dd, J=2.8 Hz, 0.9 Hz, 1H), 6.34 (dd, J=8.4 Hz, 2.8 Hz, 1H), 5.04 (s, 2H), 4.55 (s, 2H), 2.06 (s, 3H).

Step 152-3: Preparation of (3-methyl-4-(thiazol-4-ylmethoxy)phenovis)carbonohydrazonoyl dicyanide 51 mg (yield: 48%) of the title compound was obtained in the same manner as in Step 1-3 of Example 1 above, except that 3-methyl-4-(thiazol-4-ylmethoxy)aniline obtained in Step 152-2 was used instead of N-(5-aminopyridin-2-yl)-5-methylpyrazine-2-carboxamide.

$^1$H NMR (400 MHz, DMSO-$d_6$) δ 12.95 (s, 1H), 9.13 (d, J=2.0 Hz, 1H), 7.77 (d, J=2.0 Hz, 1H), 7.41-7.25 (m, 2H), 7.14 (d, J=8.8 Hz, 1H), 5.24 (s, 2H), 2.19 (s, 3H).

Example 153: Preparation of (4-(benzyloxy)-3-methoxyphenyl)carbonohydrazonoyl dicyanide (Compound 153)

Step 153-1: Preparation of 1-(benzyloxy)-2-methoxy-4-nitrobenzene 447 mg (yield: 85%) of the title compound was obtained in the same manner as in Step 136-1 of Example 136 above, except that phenylmethanol (0.21 mL, 2.03 mmol) was used instead of pyrimidin-2-ylmethanol, and 2-methoxy-4-nitrophenol (413 mg, 2.44 mmol) was used instead of 4-nitrophenol.

$^1$H NMR (400 MHz, DMSO-$d_6$) δ 7.90 (dd, J=9.0 Hz, 2.7 Hz, 1H), 7.76 (d, J=2.7 Hz, 1H), 7.51-7.33 (m, 5H), 7.28 (d, J=9.0 Hz, 1H), 5.26 (s, 2H), 3.89 (s, 3H).

Step 153-2: Preparation of 4-(benzyloxy)-3-methoxyaniline 42 mg (yield: 16%) of the title compound was obtained in the same manner as in Step 95-2 of Example 95 above, except that 1-(benzyloxy)-2-methoxy-4-nitrobenzene obtained in Step 153-1 was used instead of 2-(benzyloxy)-5-nitropyridine.

$^1$H NMR (400 MHz, DMSO-$d_6$) δ 7.50-7.14 (m, 5H), 6.70 (dd, J=8.5 Hz, 2.0 Hz, 1H), 6.30 (s, 1H), 6.05 (d, J=8.4 Hz, 1H), 4.90 (s, 2H), 4.72 (s, 2H), 3.71 (s, 3H).

Step 153-3: Preparation of (4-(benzyloxy)-3-methoxyphenyl)carbonohydrazonoyl dicyanide 25 mg (yield: 48%) of the title compound was obtained in the same manner as in Step 1-3 of Example 1 above, except that 4-(benzyloxy)-3-methoxyaniline obtained in Step 153-2 was used instead of N-(5-aminopyridin-2-yl)-5-methylpyrazine-2-carboxamide.

$^1$H NMR (400 MHz, DMSO-$d_6$) δ 12.97 (s, 1H), 7.49-7.30 (m, 5H), 7.14 (d, J=2.4 Hz, 1H), 7.09 (d, J=8.8 Hz, 1H), 7.01 (dd, J=8.7 Hz, 2.5 Hz, 1H), 5.10 (s, 2H), 3.81 (s, 3H).

Example 164: Preparation of (3-methoxy-4-(4-methylbenzyloxy)phenyl)carbonohydrazonoyl dicyanide (Compound 154)

Step 154-1: Preparation of 2-methoxy-1-(4-methylbenzyloxy-4-nitrobenzene 410 mg (yield: 77%) of the title compound was obtained in the same manner as in Step 136-1 of Example 136 above, except that p-tolylmethanol (240 mg, 1.96 mmol) was used instead of pyrimidin-2-ylmethanol, and 2-methoxy-4-nitrophenol (399 mg, 2.36 mmol) was used instead of 4-nitrophenol.

$^1$H NMR (400 MHz, DMSO-$d_6$) δ 7.89 (dd, J=9.0 Hz, 2.7 Hz, 1H), 7.75 (d, J=2.7 Hz, 1H), 7.35 (d, J=8.0 Hz, 2H), 7.26 (d, J=9.0 Hz, 1H), 7.22 (d, J=7.8 Hz, 2H), 5.20 (s, 2H), 3.88 (s, 3H), 2.31 (s, 3H).

Step 154-2: Preparation of 3-methoxy-4-(4-methylbenzyloxy)aniline 216 mg (yield: 81%) of the title compound was obtained in the same manner as in Step 95-2 of Example 95 above, except that 2-methoxy-1-(4-methylbenzyloxy)-4-nitrobenzene obtained in Step 153-1 was used instead of 2-(benzyloxy)-5-nitropyridine.

$^1$H NMR (400 MHz, DMSO-$d_6$) δ 7.27 (d, J=8.0 Hz, 2H), 7.16 (d, J=7.5 Hz, 2H), 6.66 (d, J=8.4 Hz, 1H), 6.27 (d, J=2.5 Hz, 1H), 6.02 (dd, J=8.4 Hz, 2.5 Hz, 1H), 4.82 (s, 2H), 4.69 (s, 2H), 3.68 (s, 3H), 2.29 (s, 3H).

Step 154-3: Preparation of (3-methoxy-4-(4-methylbenzyloxy)phenyl)carbonohydrazonoyl dicyanide 119 mg (yield: 60%) of the title compound was obtained in the same manner as in Step 1-3 of Example 1 above, except that 3-methoxy-4-(4-methylbenzyloxy)aniline obtained in Step 154-2 was used instead of N-(5-aminopyridin-2-yl)-5-methylpyrazine-2-carboxamide.

$^1$H NMR (400 MHz, DMSO-$d_6$) δ 12.96 (s, 1H), 7.33 (d, J=7.8 Hz, 2H), 7.21 (d, J=7.8 Hz, 2H), 7.13 (d, J=2.4 Hz, 1H), 7.07 (d, J=8.8 Hz, 1H), 7.00 (dd, J=8.7 Hz, 2.4 Hz, 1H), 5.04 (s, 2H), 3.80 (s, 3H), 2.32 (s, 3H).

Example 165: Preparation of (3-methoxy-4-(4-(trifluoromethyl)benzyloxy)phenyl)carbonohydrazonoyl dicyanide (Compound 155)

Step 166-1: Preparation of 2-methoxy-4-nitro-1-(4-(trifluoromethyl)benzyloxy)benzene 520 mg (yield: 80%) of the title compound was obtained in the same manner as in Step 136-1 of Example 136 above, except that (4-(trifluoromethyl)phenyl)methanol (0.27 mL, 1.99 mmol) was used instead of pyrimidin-2-ylmethanol, and 2-methoxy-4-nitrophenol (403 mg, 2.38 mmol) was used instead of 4-nitrophenol.

$^1$H NMR (400 MHz, DMSO-$d_6$) δ 7.91 (dd, J=9.0 Hz, 2.7 Hz, 1H), 7.83-7.75 (m, 3H), 7.69 (d, J=8.0 Hz, 2H), 7.26 (d, J=9.0 Hz, 1H), 5.39 (s, 2H), 3.91 (s, 3H).

Step 155-2: Preparation of 3-methoxy-4-(4-(trifluoromethyl)benzyloxy)aniline 187 mg (yield: 62%) of the title compound was obtained in the same manner as in Step 95-2 of Example 95 above, except that 2-methoxy-4-nitro-1-(4-(trifluoromethyl)benzyloxy)benzene obtained in Step 155-1 was used instead of 2-(benzyloxy)-5-nitropyridine.

$^1$H NMR (400 MHz, DMSO-$d_6$) δ 7.73 (d, J=8.1 Hz, 2H), 7.63 (d, J=8.5 Hz, 2H), 6.69 (d, J=8.4 Hz, 1H), 6.29 (d, J=2.5 Hz, 1H), 6.03 (dd, J=8.4 Hz, 2.5 Hz, 1H), 4.99 (s, 2H), 4.73 (s, 2H), 3.70 (s, 3H).

Step 155-3: Preparation of (3-methoxy-4-(4-(trifluoromethyl)benzyloxy)phenyl)carbonohydrazonoyl dicyanide 127 mg (yield: 68%) of the title compound was obtained in the same manner as in Step 1-3 of Example 1 above, except that 3-methoxy-4-(4-(trifluoromethyl)benzyloxy)aniline obtained in Step 155-2 was used instead of N-(5-aminopyridin-2-yl)-5-methylpyrazine-2-carboxamide.

1H NMR (400 MHz, DMSO-$d_6$) δ 12.97 (s, 1H), 7.78 (d, J=8.1 Hz, 2H), 7.67 (d, J=8.0 Hz, 2H), 7.15 (d, J=2.4 Hz, 1H), 7.08 (d, J=8.7 Hz, 1H), 7.01 (dd, J=8.7 Hz, 2.4 Hz, 1H), 5.22 (s, 2H), 3.83 (s, 3H).

Example 156: Preparation of (4-(benzo[d]oxazol-2-ylmethoxy)-3-methylphenyl)carbonohydrazonoyl dicyanide (Compound 156)

Step 156-1: Preparation of 2-((2-methyl-4-nitrophenoxy)methyl)benzo[d]oxazole 186 mg (yield: 28%) of the title compound was obtained in the same manner as in Step 137-1 of Example 137 above, except that 2-methyl-4-nitrophenol (300 mg, 1.96 mmol) was used instead of 4-nitrophenol, and 2-(bromomethyl)benzo[d]oxazole (520 mg, 2.45 mmol) was used instead of 4-(chloromethyl)-1H-pyrazole.

$^1$H NMR (400 MHz, DMSO-$d_6$) δ 8.16-8.07 (m, 2H), 7.83-7.74 (m, 2H), 7.49-7.39 (m, 2H), 7.38-7.31 (m, 1H), 5.70 (s, 2H), 2.31 (s, 3H).

Step 156-2: Preparation of 4-(benzo[d]oxazol-2-ylmethoxy)aniline 133 mg (yield: 94%) of the title compound was obtained in the same manner as in Step 1-2 of Example 1 above, except that 2-((2-methyl-4-nitrophenoxy)methyl)benzo[d]oxazole obtained in Step 156-1 was used instead of 5-methyl-N-(5-nitropyridin-2-yl)pyrazine-2-carboxamide.

$^1$H NMR (400 MHz, DMSO-$d_6$) δ 7.80-7.75 (m, 2H), 7.55-7.16 (m, 2H), 6.80 (d, J=8.5 Hz, 1H), 6.41 (d, J=2.0 Hz, 1H), 6.34 (dd, J=8.5 Hz, 2.8 Hz, 1H), 5.26 (s, 2H), 4.65 (s, 2H), 2.00 (s, 3H).

Step 156-3: Preparation of (4-benzo[d]oxazol-2-ylmethoxy)-3-methylphenyl)carbonohydrazonoyl dicyanide 41 mg (yield: 24%) of the title compound was obtained in the same manner as in Step 1-3 of Example 1 above, except that 4-(benzo[d]oxazol-2-ylmethoxy)-3-methylaniline obtained in Step 156-2 was used instead of N-(5-aminopyridin-2-yl)-5-methylpyrazine-2-carboxamide.

$^1$H NMR (400 MHz, DMSO-$d_6$) δ 12.99 (s, 1H), 7.79 (d, J=10.4 Hz, 2H), 7.54-7.38 (m, 2H), 7.32 (d, J=25.0 Hz, 2H), 7.18 (d, J=8.8 Hz, 1H), 5.52 (s, 2H), 2.25 (s, 3H).

Example 157: Preparation of (4-(benzo[d]thiazol-2-ylmethoxy)-3-methylphenyl)carbonohydrazonoyl dicyanide (Compound 157)

Step 157-1: Preparation of 2-((2-methyl-4-nitrophenoxy)methyl)benzo[d]thiazole 50 mg (yield: 16%) of the title compound was obtained in the same manner as in Step 95-1 of Example 95 above, except that 2-methyl-4-nitrophenol (232 mg, 1.51 mmol) was used instead of phenylmethanol, 2-(bromomethyl)benzo[d]thiazole (230 mg, 1.01 mmol) was used instead of 2-chloro-5-nitropyridine, and DMSO was used as a solvent.

$^1$H NMR (400 MHz, DMSO-$d_6$) δ 8.20-8.10 (m, 3H), 8.04 (d, J=7.8 Hz, 1H), 7.52 (dddd, J=30.6 Hz, 8.3 Hz, 7.2 Hz, 1.3 Hz, 2H), 7.34 (d, J=9.0 Hz, 1H), 5.80 (s, 2H), 2.38 (s, 3H).

Step 157-2: Preparation of 4-(benzo[d]thiazol-2-ylmethoxy)-3-methylaniline 48 mg (yield: 89%) of the title compound was obtained in the same manner as in Step 1-2 of Example 1 above, except that 2-((2-methyl-4-nitrophenoxy)methyl)benzo[d]thiazole obtained in Step 157-1 was used instead of 5-methyl-N-(5-nitropyridin-2-yl)pyrazine-2-carboxamide.

$^1$H NMR (400 MHz, DMSO-$d_6$) δ 8.14 (d, J=7.1 Hz, 1H), 8.01 (d, J=7.8 Hz, 1H), 7.54 (ddd, J=8.2 Hz, 7.2 Hz, 1.3 Hz, 1H), 7.47 (ddd, J=8.3 Hz, 7.2 Hz, 1.2 Hz, 1H), 6.80 (d, J=8.6 Hz, 1H), 6.45 (d, J=2.7 Hz, 1H), 6.36 (dd, J=8.5 Hz, 2.8 Hz, 1H), 5.41 (s, 2H), 4.64 (s, 2H), 2.18 (s, 3H).

Step 157-3: Preparation of (4-(benzo[d]thiazol-2-ylmethoxy)-3-methylphenyl)carbonohydrazonoyl dicyanide 19 mg (yield: 32%) of the title compound was obtained in the same manner as in Step 1-3 of Example 1 above, except that 4-(benzo[d]thiazol-2-ylmethoxy)-3-methylaniline obtained in Step 157-2 was used instead of N-(5-aminopyridin-2-yl)-5-methylpyrazine-2-carboxamide.

$^1$H NMR (400 MHz, DMSO-$d_6$) δ 8.14 (d, J=7.4 Hz, 1H), 8.03 (d, J=8.1 Hz, 1H), 7.55 (t, J=7.0 Hz, 1H), 7.47 (t, J=7.0 Hz, 1H), 7.35 (d, J=2.7 Hz, 1H), 7.28 (dd, J=8.8 Hz, 2.7 Hz, 1H), 7.15 (d, J=8.9 Hz, 1H), 5.61 (s, 2H), 2.31 (s, 3H).

Example 158: Preparation of (4-(benzo[b]thiophen-2-ylmethoxy)-3-methoxyphenyl)carbonohydrazonoyl dicyanide (Compound 168)

Step 158-1: Preparation of 2-((methoxy-4-nitrophenoxy)methyl)benzo[b]thiophene 173 mg (yield: 28%) of the title compound was obtained in the same manner as in Step 95-1 of Example 95 above, except that benzo[b]thiophen-2-ylmethanol (489 mL, 2.98 mmol) was used instead of phenylmethanol, and 1-fluoro-2-methoxy-4-nitrobenzene (340 mg, 1.99 mmol) was used instead of 2-chloro-5-nitropyridine.

$^1$H NMR (400 MHz, DMSO-$d_6$) δ 8.02-7.95 (m, 1H), 7.91 (dd, J=9.0 Hz, 2.7 Hz, 1H), 7.88 (dd, J=6.5 Hz, 2.8 Hz, 1H), 7.79 (d, J=2.7 Hz, 1H), 7.59 (s, 1H), 7.46-7.29 (m, 3H), 5.62 (s, 2H), 3.92 (s, 3H).

Step 158-2: Preparation of 4-(benzo[b]thiophen-2-ylmethoxy)-3-methoxyaniline 31 mg (yield: 34%) of the title compound was obtained in the same manner as in Step 1-2 of Example 1 above, except that 2-((methoxy-4-nitrophenoxy)methyl)benzo[b]thiophene obtained in Step 158-1 was used instead of 5-methyl-N-(5-nitropyridin-2-yl)pyrazine-2-carboxamide.

$^1$H NMR (400 MHz, DMSO-$d_6$) δ 7.94 (d, J=6.9 Hz, 1H), 7.80 (d, J=6.5 Hz, 1H), 7.47-7.19 (m, 3H), 6.72 (d, J=8.4 Hz, 1H), 6.28 (d, J=2.4 Hz, 1H), 6.01 (dd, J=8.5 Hz, 2.5 Hz, 1H), 5.17 (s, 2H), 4.76 (s, 2H), 3.71 (s, 3H).

Step 158-3: Preparation of (4-(benzo[b]thiophen-2-ylmethoxy)-3-methoxyphenyl)carbonohydrazonoyl dicyanide 20 mg (yield: 51%) of the title compound was obtained in the same manner as in Step 1-2 of Example 1 above, except that 4-(benzo[b]thiophen-2-ylmethoxy)-3-methoxyaniline obtained in Step 158-2 was used instead of N-(5-aminopyridin-2-yl)-5-methylpyrazine-2-carboxamide.

$^1$H NMR (400 MHz, DMSO-$d_6$) δ 12.96 (s, 1H), 7.97-7.90 (m, 1H), 7.83 (dd, J=6.7 Hz, 2.7 Hz, 1H), 7.49 (s, 1H), 7.46-7.28 (m, 2H), 7.19-7.06 (m, 2H), 6.99 (dd, J=8.7 Hz, 2.5 Hz, 1H), 5.41 (s, 2H), 3.81 (s, 3H).

Example 159: Preparation of (3-methoxy-4-(pyrazin-2-ylmethoxy)phenyl)carbonohydrazonoyl dicyanide (Compound 159)

Step 159-1: Preparation of 2-((2-methoxy-4-nitrophenoxy)methylpyrazine 482 mg (yield: 93%) of the title compound was obtained in the same manner as in Step 95-1 of Example 95 above, except that pyrazin-2-ylmethanol (328 mg, 2.98 mmol) was used instead of phenylmethanol, and 1-fluoro-2-methoxy-4-nitrobenzene (340 mg, 1.99 mmol) was used instead of 2-chloro-5-nitropyridine.

$^1$H NMR (400 MHz, DMSO-$d_6$) δ 8.83 (d, J=1.5 Hz, 1H), 8.74-8.58 (m, 2H), 7.91 (dd, J=8.9 Hz, 2.7 Hz, 1H), 7.79 (d, J=2.7 Hz, 1H), 7.34 (d, J=9.0 Hz, 1H), 5.42 (s, 2H), 3.91 (s, 3H).

Step 159-2: Preparation of 3-methoxy-4-(pyrazin-2-ylmethoxy)aniline 47 mg (yield: 20%) of the title compound was obtained in the same manner as in Step 95-2 of Example 95 above, except that 2-((2-methoxy-4-nitrophenoxy)methylpyrazine obtained in Step 159-1 was used instead of 2-(benzyloxy)-5-nitropyridine.

$^1$H NMR (400 MHz, DMSO-$d_6$) δ 8.77 (s, 1H), 8.67-8.47 (m, 2H), 6.72 (d, J=8.5 Hz, 1H), 6.29 (d, J=2.5 Hz, 1H), 6.03 (dd. J=8.4 Hz, 2.5 Hz, 1H), 5.04 (s, 2H), 4.76 (s, 2H), 3.69 (s, 3H).

Step 159-3: Preparation of (3-methoxy-4-(pyrazin-2-ylmethoxy)phenyl)carbonohydrazonoyl dicyanide 34 mg (yield: 58%) of the title compound was obtained in the same manner as in Step 1-3 of Example 1 above, except that 3-methoxy-4-(pyrazin-2-ylmethoxy)aniline obtained in Step 159-2 was used instead of N-(5-aminopyridin-2-yl)-5-methylpyrazine-2-carboxamide.

$^1$H NMR (400 MHz, DMSO-$d_6$) δ 12.97 (s, 1H), 8.79 (s, 1H), 8.72-8.47 (m, 2H), 7.22-7.03 (m, 2H), 7.01 (dd, J=8.7 Hz, 2.5 Hz, 1H), 5.24 (s, 2H), 3.81 (s, 3H).

Example 160: Preparation of (3-methoxy-4-(pyridin-3-ylmethoxy)phenyl)carbonohydrazonoyl dicyanide (Compound 160)

Step 160-1: Preparation of 3-((2-methoxy-4-nitrophenoxy)methyl)pyridine 234 mg (yield: 44%) of the title compound was obtained in the same manner as in Step 95-1 of Example 95 above, except that pyridin-3-ylmethanol (0.3 mL, 3.07 mmol) was used instead of phenylmethanol, and 1-fluoro-2-methoxy-4-nitrobenzene (350 mg, 2.05 mmol) was used instead of 2-chloro-5-nitropyridine.

$^1$H NMR (400 MHz, DMSO-$d_6$) δ 8.69 (d, J=1.5 Hz, 1H), 8.58 (dd, J=4.9 Hz, 1.7 Hz, 1H), 8.01-7.85 (m, 2H), 7.77 (d, J=2.7 Hz, 1H), 7.46 (ddd, J=7.8 Hz, 4.8 Hz, 0.9 Hz, 1H), 7.32 (d, J=9.0 Hz, 1H), 5.31 (s, 2H), 3.89 (s, 3H).

Step 160-2: Preparation of 3-methoxy-4-(pyridin-3-dimethoxy)aniline 64 mg (yield: 73%) title compound in the same manner as in Step 95-2 of Example 95 above, except that 3-((2-methoxy-4-nitrophenoxy)methyl)pyridine obtained in Step 160-1 was used instead of 2-(benzyloxy)-5-nitropyridine.

$^1$H NMR (400 MHz, DMSO-$d_6$) δ 8.59 (d, J=1.4 Hz, 1H), 8.51 (dd, J=4.8 Hz, 1.7 Hz, 1H), 7.81 (d, J=7.8 Hz, 1H), 7.48-7.12 (m, 1H), 6.70 (d, J=8.5 Hz, 1H), 6.28 (d, J=2.5 Hz, 1H), 6.03 (dd, J=8.4 Hz, 2.5 Hz, 1H), 4.92 (s, 2H), 4.74 (s, 2H), 3.69 (s, 3H).

Step 160-3: Preparation of (3-methoxy-4-(pyridin-3-ylmethoxy)phenyl)carbonohydrazonoyl dicyanide 39 mg (yield: 49%) of the title compound was obtained in the same manner as in Step 1-3 of Example 1 above, except that 3-methoxy-4-(pyridin-3-ylmethoxy)aniline obtained in Step 160-2 was used instead of N-(5-aminopyridin-2-yl)-5-methylpyrazine-2-carboxamide.

$^1$H NMR (400 MHz, Acetone-$d_6$) δ 11.72 (s, 1H), 8.71 (d, J=2.3 Hz, 1H), 8.56 (dd, J=4.9 Hz, 1.7 Hz, 1H), 7.90 (d, J=7.8 Hz, 1H), 7.41 (dd, J=7.8 Hz, 4.9 Hz, 1H), 7.23 (d, J=2.5 Hz, 1H), 7.13 (d, J=8.7 Hz, 1H), 7.05 (dd, J=8.7 Hz, 2.5 Hz, 1H), 5.20 (s, 2H), 3.88 (s, 3H).

Example 161: Preparation of (3-methoxy-4-(pyrimidin-2-ylmethoxy)phenyl)carbonohydrazonoyl dicyanide (Compound 161)

Step 161-1: Preparation of 2-((2-methoxy-4-nitrophenoxy)methyl)pvrimidine 290 mg (yield: 56%) of the title compound was obtained in the same manner as in Step 95-1 of Example 95 above, except that pyrimidin-2-ylmethanol (0.27 mL, 2.98 mmol) was used instead of phenylmethanol, and 1-fluoro-2-methoxy-4-nitrobenzene (340 mg, 1.99 mmol) was used instead of 2-chloro-5-nitropyridine.

$^1$H NMR (400 MHz, DMSO-$d_6$) δ 8.84 (d, J=4.9 Hz, 2H), 7.84 (dd, J=9.0 Hz, 2.7 Hz, 1H), 7.77 (d, J=2.7 Hz, 1H), 7.49 (t, J=4.9 Hz, 1H), 7.13 (d, J=9.0 Hz, 1H), 5.46 (s, 2H), 3.91 (s, 3H).

Step 161-2: Preparation of 3-methoxy-4-(pyrimidin-2-ylmethoxy)aniline 153 mg (yield: 66%) of the title compound was obtained in the same manner as in Step 1-2 of Example 1 above, except that 2-((2-methoxy-4-nitrophenoxy)methyl)pyrimidine obtained in Step 161-1 was used instead of 5-methyl-N-(5-nitropyridin-2-yl)pyrazine-2-carboxamide.

$^1$H NMR (400 MHz, DMSO-dB) δ 8.82 (d, J=4.9 Hz, 2H), 7.45 (t, J=4.9 Hz, 1H), 6.61 (d, J=8.4 Hz, 1H), 6.27 (d, J=2.5 Hz, 1H), 5.99 (dd, J=8.4 Hz, 2.5 Hz, 1H), 5.02 (s, 2H), 4.69 (s, 2H), 3.68 (s, 3H).

Step 161-3: Preparation of (3-methoxy-4-(pyrimidin-2-ylmethoxy)phenyl)carbonohydrazonoyl dicyanide 49 mg (yield: 24%) of the title compound was obtained in the same manner as in Step 1-3 of Example 1 above, except that 3-methoxy-4-(pyrimidin-2-ylmethoxy)aniline obtained in Step 161-2 was used instead of N-(5-aminopyridin-2-yl)-5-methylpyrazine-2-carboxamide.

$^1$H NMR (400 MHz, DMSO-$d_6$) δ 12.94 (s, 1H), 8.84 (d, J=4.9 Hz, 2H), 7.47 (t, J=4.9 Hz, 1H), 7.12 (s, 1H), 6.95 (s, 2H), 5.25 (d, J=1.8 Hz, 2H), 3.80 (s, 3H).

Example 162: Preparation of (3-methoxy-4-((5-methylpyrazin-2-yl)methoxy)phenyl)carbonohydrazonoyl dicyanide (Compound 162)

Step 162-1: Preparation of 2-((2-methoxy-4-nitrophenoxy)methyl-5-methylpyrazine 178 mg (yield: 32%) of the title compound was obtained in the same manner as in Step 95-1 of Example 95 above, except that (5-methylpyrazin-2-yl)methanol (370 mg, 2.98 mmol) was used instead of phenylmethanol, and 1-fluoro-2-methoxy-4-nitrobenzene (340 mg, 1.99 mmol) was used instead of 2-chloro-5-nitropyridine.

$^1$H NMR (400 MHz, DMSO-$d_6$) δ 8.68 (d, J=1.5 Hz, 1H), 8.58 (s, 1H), 7.90 (dd, J=8.9 Hz, 2.7 Hz, 1H), 7.77 (d, J=2.7 Hz, 1H), 7.33 (d, J=9.0 Hz, 1H), 5.36 (s, 2H), 3.90 (s, 3H), 2.52 (s, 3H).

Step 162-2: Preparation of 3-methoxy-4-((5-methylpyrazin-2-yl)methoxy)anillne 114 mg (yield: 75%) of the title compound was obtained in the same manner as in Step 1-2 of Example 1 above, except that 2-((2-methoxy-4-nitrophenoxy)methyl)-5-methylpyrazine obtained in Step 162-1 was used instead of 5-methyl-N-(5-nitropyidin-2-yl)pyrazine-2-carboxamide.

$^1$H NMR (400 MHz, DMSO-$d_6$) δ 8.61 (d, J=1.5 Hz, 1H), 8.51 (d, J=1.0 Hz, 1H), 6.70 (d, J=8.4 Hz, 1H), 6.28 (d, J=2.5 Hz, 1H), 6.03 (dd, J=8.4 Hz, 2.5 Hz, 1H), 4.99 (s, 2H), 4.75 (s, 2H), 3.69 (s, 3H), 2.50 (s, 3H).

Step 162-3: Preparation of (3-methoxy-4-((5-methylpyrazin-2-yl)methoxy)phenyl)carbonohydrazonoyl dicyanide 74 mg (yield: 51%) of the title compound was obtained in the same manner as in Step 1-3 of Example 1 above, except that 3-methoxy-4-((5-methylpyrazin-2-yl)methoxy)aniline obtained in Step 162-2 was used instead of N-(5-aminopyridin-2-yl)-5-methylpyrazine-2-carboxamide.

$^1$H NMR (400 MHz, DMSO-$d_6$) δ 12.97 (s, 1H), 8.64 (d, J=1.5 Hz, 1H), 8.55 (s, 1H), 7.31-7.02 (m, 2H), 7.00 (dd, J=8.7 Hz, 2.5 Hz, 1H), 5.19 (s, 2H), 3.80 (s, 3H), 2.51 (s, 3H).

Example 163: Preparation of (4-((1H-benzo[d]imidazol-2-yl)methoxy)-3-methoxyphenyl)carbonohydrazonoyl dicyanide (Compound 163)

Step 163-1: Preparation of 2-((2-methoxy-4-nitrophenoxy)methyl)-1H-benzo[d]imidazole 84 mg (yield: 14%) of the title compound was obtained in the same manner as in Step 136-1 of Example 136 above, except that (1H-benzo[d]imidazol-2-yl)methanol (300 mg, 2.02 mmol) was used instead of pyrimidin-2-ylmethanol, and 2-methoxy-4-nitrophenol (411 mg, 2.43 mmol) was used instead of 4-nitrophenol.

$^1$H NMR (400 MHz, DMSO-$d_6$) δ 12.78 (s, 1H), 7.92 (dd, J=9.0 Hz, 2.7 Hz, 1H), 7.79 (d, J=2.7 Hz, 1H), 7.54 (dd, J=3.1 Hz, 1.6 Hz, 2H), 7.42 (d, J=9.0 Hz, 1H), 7.27-7.13 (m, 2H), 5.49 (s, 2H), 3.90 (s, 3H).

Step 163-2: Preparation of 4-((1H-benzo[d]imidazol-2-yl)methoxy)-3-methoxyaniline 46 mg (yield: 52%) of the title compound was obtained in the same manner as in Step 1-2 of Example 1 above, except that 2-((2-methoxy-4-nitrophenoxy)methyl)-1H-benzo[d]imidazole obtained in Step 163-1 was used instead of 5-methyl-N-(5-nitropyidin-2-yl)pyrazine-2-carboxamide.

$^1$H NMR (400 MHz, DMSO-$d_6$) δ 12.56 (s, 1H), 7.53 (s, 2H), 7.17 (dd, J=6.2 Hz, 3.1 Hz, 2H), 6.76 (d, J=8.5 Hz, 1H), 6.29 (d, J=2.4 Hz, 1H), 6.01 (dd, J=8.4 Hz, 2.5 Hz, 1H), 5.07 (s, 2H), 4.76 (s, 2H), 3.70 (s, 3H).

Step 163-3: Preparation of (44(1H-benzo[d]imidazol-2-yl)methoxy)-3-methoxyphenyl)carbonohydrazonoyl dicyanide 7 mg (yield: 13%) of the title compound was obtained in the same manner as in Step 1-3 of Example 1 above, except that 4-((1H-benzo[d]imidazol-2-yl)methoxy)-3-methoxyaniline obtained in Step 163-2 was used instead of N-(5-aminopyridin-2-yl)-5-methylpyrazine-2-carboxamide.

$^1$H NMR (400 MHz, Acetone-$d_6$) δ 11.806 (s, 1H), 7.59 (dd, J=5.9 Hz, 3.3 Hz, 2H), 7.35-7.09 (m, 4H), 7.02 (dd, J=8.7 Hz, 2.5 Hz, 1H), 5.38 (s, 2H), 3.89 (s, 3H).

Example 164: Preparation of (3-methoxy-4-(pyridazin-3-ylmethoxy)phenyl)carbonohydrazonoyl dicyanide (Compound 164)

Step 164-1: Preparation of 3-((2-methoxy-4-nitrophenoxy)methyl)pyridazine 296 mg (yield: 57%) of the title compound was obtained in the same manner as in Step 95-1 of Example 95 above, except that pyridazin-3-ylmethanol (328 mg, 2.98 mmol) was used instead of phenylmethanol, and 1-fluoro-2-methoxy-4-nitrobenzene (340 mg, 1.99 mmol) was used instead of 2-chloro-5-nitropyridine.

$^1$H NMR (400 MHz, DMSO-$d_6$) δ 9.25 (dd, J=4.8 Hz, 1.8 Hz, 1H), 7.91 (dd, J=8.9 Hz, 2.7 Hz, 1H), 7.84 (dd, J=8.5 Hz, 1.9 Hz, 1H), 7.81-7.76 (m, 2H), 7.35 (d, J=9.0 Hz, 1H), 5.56 (s, 2H), 3.91 (s, 3H).

Step 164-2: Preparation of 3-methoxy-4-(pyridazin-3-ylmethoxy)aniline 75 mg (yield: 42%) of the title compound was obtained in the same manner as in Step 1-2 of Example 1 above, except that 3-((2-methoxy-4-nitrophenoxy)methyl)pyridazine obtained in Step 164-1 was used instead of 5-methyl-N-(5-nitropyidin-2-yl)pyrazine-2-carboxamide.

$^1$H NMR (400 MHz, DMSO-$d_6$) δ 9.18 (dd, J=4.9 Hz, 1.8 Hz, 1H), 7.81 (dd, J=8.4 Hz, 1.8 Hz, 1H), 7.74 (dd, J=8.4 Hz, 4.9 Hz, 1H), 6.73 (d, J=8.4 Hz, 1H), 6.29 (d, J=2.5 Hz, 1H), 6.03 (dd, J=8.4 Hz, 2.5 Hz, 1H), 5.18 (s, 2H), 4.77 (s, 2H), 3.70 (s, 3H).

Step 164-3: Preparation of (3-methoxy-4-(pyridazin-3-ylmethoxy)phenyl)carbonohydrazonoyl dicyanide 24 mg (yield: 26%) of the title compound was obtained in the same manner as in Step 1-3 of Example 1 above, except that 3-methoxy-4-(pyridazin-3-ylmethoxy)aniline obtained in Step 164-2 was used instead of N-(5-aminopyridin-2-yl)-5-methylpyrazine-2-carboxamide.

$^1$H NMR (400 MHz, DMSO-$d_6$) δ 12.97 (s, 1H), 9.22 (dd, J=4.8 Hz, 1.9 Hz, 1H), 8.06-7.54 (m, 2H), 7.34-7.10 (m, 2H), 7.01 (dd, J=8.8 Hz, 2.5 Hz, 1H), 5.38 (s, 2H), 3.81 (s, 3H).

Example 165: Preparation of (4-(benzo[d]thiazol-2-ylmethoxy)-3-methoxyphenyl)carbonohydrazonoyl dicyanide (Compound 165)

Step 165-1: Preparation of 24(2-methoxy-4-nitrophenoxy)methyl)benzo[d]thiazole 100 mg (yield: 22%) of the title compound was obtained in the same manner as in Step 95-1 of Example 95 above, except that 2-methoxy-4-nitrophenol (367 mg, 2.17 mmol) was used instead of phenylmethanol, 2-(bromomethyl) benzo[d]thiazole (330 mg, 1.45 mmol) was used instead of 2-chloro-5-nitropyridine, and DMSO was used as a solvent.

$^1$H NMR (400 MHz, DMSO-$d_6$) δ 8.14 (d, J=8.6 Hz, 1H), 8.04 (d, J=7.7 Hz, 1H), 7.91 (dd. J=9.0 Hz, 2.7 Hz, 1H), 7.82 (d, J=2.7 Hz, 1H), 7.55 (ddd, J=8.2 Hz, 7.2 Hz, 1.3 Hz, 1H), 7.50-7.42 (m, 1H), 7.35 (d, J=9.0 Hz, 1H), 5.77 (s, 2H), 3.95 (s, 3H).

Step 165-2: Preparation of 4-benzo[d]thiazol-2-ylmethoxy)-3-methoxyaniline 70 mg (yield: 78%) of the title compound was obtained in the same manner as in Step 1-2 of Example 1 above, except that 2-((2-methoxy-4-nitrophenoxy)methyl)benzo[d]thiazole obtained in Step 165-1 was used instead of 5-methyl-N-(5-nitropyidin-2-yl)pyrazine-2-carboxamide.

$^1$H NMR (400 MHz, DMSO-$d_6$) δ 8.12 (d, J=7.5 Hz, 1H), 7.98 (d, J=8.1 Hz, 1H), 7.52 (ddd, J=8.3 Hz, 7.2 Hz, 1.4 Hz, 1H), 7.45 (td, J=7.6 Hz, 1.3 Hz, 1H), 6.78 (d, J=8.5 Hz, 1H), 6.31 (d, J=2.5 Hz, 1H), 6.03 (dd, J=8.5 Hz, 2.4 Hz, 1H), 5.32 (s, 2H), 4.82 (s, 2H), 3.73 (s, 3H).

Step 165-3: Preparation of (4-(benzo[d]thiazol-2-ylmethoxy)-3-methoxyphenyl)carbonohydrazonoyl dicyanide 27 mg (yield: 32%) of the title compound was obtained in the same manner as in Step 1-3 of Example 1 above, except that 4-(benzo[d]thiazol-2-ylmethoxy)-3-methoxyaniline obtained in Step 165-2 was used instead of N-(5-aminopyridin-2-yl)-5-methylpyrazine-2-carboxamide.

$^1$H NMR (400 MHz, DMSO-$d_6$) δ 12.97 (s, 1H), 8.13 (d, J=8.0 Hz, 1H), 8.01 (d, J=7.5 Hz, 1H), 7.54 (ddd, J=8.3 Hz, 7.2 Hz, 1.3 Hz, 1H), 7.46 (td, J=7.6 Hz, 7.2 Hz, 1.3 Hz, 1H), 7.22-7.10 (m, 2H), 7.01 (dd, J=8.7 Hz, 2.4 Hz, 1H), 5.57 (s, 2H), 3.85 (s, 3H).

Example 166: Preparation of (4-(benzo[d]oxazol-2-ylmethoxy)-3-methoxyphenyl)carbonohydrazonoyl dicyanide (Compound 166)

Step 166-1: Preparation of 2-4(2-methoxy-4-nitrophenoxy)methyl benzo[d]oxazole 221 mg (yield: 47%) of the title compound was obtained in the same manner as in Step 95-1 of Example 95 above, except that 2-methoxy-4-nitrophenol (398 mg, 2.36 mmol) was used instead of phenylmethanol, 2-(bromomethyl) benzo[d]oxazole (330 mg, 1.57 mmol) was used instead of 2-chloro-5-nitropyridine, and DMSO was used as a solvent.

$^1$H NMR (400 MHz, DMSO-$d_6$) δ 7.91 (dd, J=8.9 Hz, 2.7 Hz, 1H), 7.82-7.72 (m, 3H), 7.56-7.39 (m, 2H), 7.37 (d, J=9.0 Hz, 1H), 5.65 (s, 2H), 3.92 (s, 3H).

Step 166-2: Preparation of 4-(benzo[d]oxazol-2-ylmethoxy)-3-methoxyaniline 126 mg (yield: 82%) of the title compound was obtained in the same manner as in Step 1-2 of Example 1 above, except that 2-((2-methoxy-4-nitrophenoxy)methyl)benzo[d] oxazole obtained in Step 166-1 was used instead of 5-methyl-N-(5-nitropyidin-2-yl)pyrazine-2-carboxamide.

$^1$H NMR (400 MHz, DMSO-$d_6$) δ 7.88-7.68 (m, 2H), 7.50-7.25 (m, 2H), 6.70 (d, J=8.4 Hz, 1H), 6.27 (d, J=2.5 Hz, 1H), 6.00 (dd, J=8.4 Hz, 2.5 Hz, 1H), 5.15 (s, 2H), 4.81 (s, 2H), 3.66 (s, 3H).

Step 166-3: Preparation of (4-(benzo[d]oxazol-2-ylmethoxy)-3-methoxyphenyl)carbonohydrazonoyl dicyanide 19 mg (yield: 13%) of the title compound was obtained in the same manner as in Step 1-3 of Example 1 above, except that 4-(benzo[d]oxazol-2-ylmethoxy)-3-methoxyaniline obtained in Step 166-2 was used instead of N-(5-aminopyridin-2-yl)-5-methylpyrazine-2-carboxamide.

$^1$H NMR (400 MHz, DMSO-$d_6$) δ 12.95 (s, 1H), 7.78 (ddd, J=7.5 Hz, 3.5 Hz, 1.6 Hz, 2H), 7.55-7.30 (m, 2H), 7.15 (d, J=8.6 Hz, 2H), 7.00 (dd, J=8.7 Hz, 2.4 Hz, 1H), 5.42 (s, 2H), 3.80 (s, 3H).

Example 167: Preparation of (3-methoxy-4-(thiazol-4-ylmethoxy)phenyl)carbonohydrazonoyl dicyanide (Compound 167)

Step 167-1: Preparation of 4-((2-methoxy-4-nitrophenoxy)methyl)thiazole 55 mg (yield: 10%) of the title compound was obtained in the same manner as in Step 137-1 of Example 137 above, except that 2-methoxy-4-nitrophenol (340 mg, 2.01 mmol) was used instead of 4-nitrophenol, and 4-(chloromethyl) thiazole hydrochloride (428 mg, 2.51 mmol) was used instead of 4-(chloromethyl)-1H-pyrazole $^1$H NMR (400 MHz, DMSO-$d_6$) δ 9.16 (d, J=2.0 Hz, 1H), 7.92 (dd, J=9.0 Hz, 2.7 Hz, 1H), 7.87 (d, J=2.0 Hz, 1H), 7.77 (d, J=2.7 Hz, 1H), 7.39 (d, J=9.0 Hz, 1H), 5.38 (s, 2H), 3.89 (s, 3H).

Step 167-2: Preparation of 3-methoxy-4-(thiazol-4-ylmethoxy)aniline 54 mg (yield: 67%) of the title compound was obtained in the same manner as in Step 1-2 of Example 1 above, except that 4-((2-methoxy-4-nitrophenoxy)methyl)thiazole obtained in Step 167-1 was used instead of 5-methyl-N-(5-nitropyidin-2-yl)pyrazine-2-carboxamide.

1H NMR (400 MHz, DMSO-$d_6$) δ 9.10 (d, J=2.0 Hz, 1H), 7.67 (d, J=2.0 Hz, 1H), 6.72 (d, J=8.4 Hz, 1H), 6.29 (d, J=2.5 Hz, 1H), 6.05 (dd, J=8.4 Hz, 2.6 Hz, 1H), 5.01 (s, 2H), 4.73 (s, 2H), 3.70 (s, 3H).

Step 167-3: Preparation of (3-methoxy-4-(thiazol-4-ylmethoxy)phenyl)carbonohydrazonoyl dicyanide 39 mg (yield: 59%) of the title compound was obtained in the same manner as in Step 1-3 of Example 1 above, except that 3-methoxy-4-(thiazol-4-ylmethoxy)aniline obtained in Step 167-2 was used instead of N-(5-aminopyridin-2-yl)-5-methylpyrazine-2-carboxamide.

$^1$H NMR (400 MHz, DMSO-$d_6$) δ 12.98 (s, 1H), 9.14 (d, J=2.0 Hz, 1H), 7.79 (d, J=2.0 Hz, 1H), 7.36-7.06 (m, 2H), 7.02 (dd, J=8.7 Hz, 2.5 Hz, 1H), 5.21 (s, 2H), 3.80 (s, 3H).

Example 168: Preparation of (4-((1H-pyrazol-3-yl)methoxy)-3-methoxyphenyl)carbonohydrazonoyl dicyanide (Compound 168)

Step 168-1: Preparation of 3-((2-methoxy-4-nitrophenoxy)methyl)-1H-pyrazole 85 mg (yield: 17%) of the title compound was obtained in the same manner as in Step 137-1 of Example 137 above, except that 2-methoxy-4-nitrophenol (340 mg, 2.01 mmol) was used instead of 4-nitrophenol.

$^1$H NMR (400 MHz, DMSO-$d_6$) δ 12.91 (s, 1H), 7.91 (dd, J=9.1 Hz, 2.6 Hz, 1H), 7.75 (s, 2H), 7.38 (d, J=9.0 Hz, 1H), 6.39 (s, 1H), 5.22 (s, 2H), 3.88 (s, 3H).

Step 168-2: Preparation of 4-4(1H-pyrazol-3-ylmethoxy)-3-methoxyaniline 63 mg (yield: 90%) of the title compound was obtained in the same manner as in Step 1-2 of Example 1 above, except that 3-((2-methoxy-4-nitrophenoxy)methyl)-1H-pyrazole obtained in Step 168-1 was used instead of 5-methyl-N-(5-nitropyridin-2-yl)pyrazine-2-carboxamide.

$^1$H NMR (400 MHz, DMSO-$d_6$) δ 12.72 (s, 1H), 7.68 (s, 1H), 6.71 (d, J=8.4 Hz, 1H), 6.28 (d, J=2.5 Hz, 2H), 6.04 (dd, J=8.4 Hz, 2.5 Hz, 1H), 4.84 (s, 2H), 4.70 (s, 2H), 3.68 (s, 3H).

Step 168-3: Preparation of (4-((1H-pyrazol-3-yl)methoxy)-3-methoxyphenyl)carbonohydrazonoyl dicyanide 54 mg (yield: 67%) of the title compound was obtained in the same manner as in Step 1-3 of Example 1 above, except that 4-((1H-pyrazol-3-yl)methoxy)-3-methoxyaniline obtained in Step 168-2 was used instead of N-(5-aminopyridin-2-yl)-5-methylpyrazine-2-carboxamide.

$^1$H NMR (400 MHz, DMSO-$d_6$) δ 12.99 (s, 1H), 7.71-7.55 (m, 1H), 7.28-7.09 (m, 2H), 7.02 (dd, J=8.7 Hz, 2.5 Hz, 1H), 6.35 (d, J=2.1 Hz, 1H), 5.05 (s, 2H), 3.78 (s, 3H).

Example 169: Preparation of (3-methoxy-4-(pyridin-2-ylmethoxy)phenyl)carbonohydrazonoyl dicyanide (Compound 169)

Step 169-1: 2-((2-methoxy-4-nitrophenoxy)methyl)pyridine 223 mg (yield: 43%) of the title compound was obtained in the same manner as in Step 95-1 of Example 95 above, except that pyridin-2-ylmethanol (0.29 mL, 2.98 mmol) was used instead of phenylmethanol, and 1-fluoro-2-methoxy-4-nitrobenzene (340 mg, 1.99 mmol) was used instead of 2-chloro-5-nitropyridine.

$^1$H NMR (400 MHz, DMSO-$d_6$) δ 8.60 (ddd, J=4.8 Hz, 1.8 Hz, 1.0 Hz, 1H), 7.97-7.83 (m, 2H), 7.78 (d, J=2.7 Hz, 1H), 7.53 (d, J=7.8 Hz, 1H), 7.38 (ddd, J=7.6 Hz, 4.8 Hz, 1.2 Hz, 1H), 7.27 (d, J=8.9 Hz, 1H), 5.33 (s, 2H), 3.92 (s, 3H).

Step 169-2: Preparation of 3-methoxy-4-(pyridin-2-ylmethoxy)aniline 150 mg (yield: 84%) of the title compound was obtained in the same manner as in Step 95-2 of Example 95 above, except that 2-((2-methoxy-4-nitrophenoxy)methyl)pyridine obtained in Step 169-1 was used instead of 2-(benzyloxy)-5-nitropyridine.

$^1$H NMR (400 MHz, DMSO-$d_6$) δ 8.53 (d, J=4.4 Hz, 1H), 7.82 (td, J=7.7 Hz, 1.8 Hz, 1H), 7.52 (d, J=7.8 Hz, 1H), 7.31 (ddd, J=7.8 Hz, 4.8 Hz, 1.1 Hz, 1H), 6.69 (d, J=8.5 Hz, 1H), 6.29 (d, J=2.5 Hz, 1H), 6.02 (dd, J=8.5 Hz, 2.5 Hz, 1H), 4.96 (s, 2H), 4.72 (s, 2H), 3.70 (s, 3H).

Step 169-3: Preparation of (3-methoxy-4-(pyridin-2-ylmethoxy)phenyl)carbonohydrazonoyl dicyanide 89 mg (yield: 47%) of the title compound was obtained in the same manner as in Step 1-3 of Example 1 above, except that 3-methoxy-4-(pyridin-2-ylmethoxy)aniline obtained in Step 169-2 was used instead of N-(5-aminopyridin-2-yl)-5-methylpyrazine-2-carboxamide.

$^1$H NMR (400 MHz, DMSO-$d_6$) δ 12.97 (s, 1H), 8.58 (d, J=4.3 Hz, 1H), 7.85 (td, J=7.7 Hz, 1.8 Hz, 1H), 7.52 (d, J=7.8 Hz, 1H), 7.36 (ddd, J=7.5 Hz, 4.9 Hz, 1.2 Hz, 1H), 7.14 (d, J=2.5 Hz, 1H), 7.07 (d, J=8.8 Hz, 1H), 6.99 (dd, J=8.8 Hz, 2.4 Hz, 1H), 5.16 (s, 2H), 3.82 (s, 3H).

Example 170: Preparation of (3-methoxy-4-((6-methylpyridin-3-yl)methoxy)phenyl)carbonohydrazonoyl dicyanide (Compound 170)

Step 170-1: Preparation of 5-((2-methoxy-4-nitrophenoxy)methyl)-2-methylpyridine 206 mg (yield: 38%) of the title compound was obtained in the same manner as in Step 95-1 of Example 95 above, except that (46-methylpyridin-3-yl)methanol (367 mg, 2.98 mmol) was used instead of phenylmethanol, and 1-fluoro-2-methoxy-4-nitrobenzene (340 mg, 1.99 mmol) was used instead of 2-chloro-5-nitropyridine.

$^1$H NMR (400 MHz, DMSO-$d_6$) δ 8.55 (d, J=2.3 Hz, 1H), 7.91 (dd, J=8.9 Hz, 2.7 Hz, 1H), 7.77 (dd, J=6.5 Hz, 2.5 Hz, 2H), 7.31 (dd, J=8.4 Hz, 3.3 Hz, 2H), 5.25 (s, 2H), 3.88 (s, 3H), 2.48 (s, 3H).

Step 170-2: Preparation of 3-methoxy-4-((-methylpyridin-3-yl)methoxy)aniline 128 mg (yield: 85%) of the title compound was obtained in the same manner as in Step 95-2 of Example 95 above, except that 5-((2-methoxy-4-nitrophenoxy)methyl)-2-methylpyridine obtained in Step 170-1 was used instead of 2-(benzyloxy)-5-nitropyridine.

$^1$H NMR (400 MHz, DMSO-$d_6$) δ 8.43 (d, J=2.2 Hz, 1H), 7.68 (dd, J=7.9 Hz, 2.3 Hz, 1H), 7.24 (d, J=7.9 Hz, 1H), 6.68 (d, J=8.4 Hz, 1H), 6.27 (d, J=2.5 Hz, 1H), 6.02 (dd, J=8.4 Hz, 2.5 Hz, 1H), 4.87 (s, 2H), 4.72 (s, 2H), 3.68 (s, 3H), 2.46 (s, 3H).

Step 170-3: Preparation of (3-methoxy-4-((6-methylpyridin-3-yl)methoxy)phenyl)carbonohydrazonoyl dicyanide 107 mg (yield: 68%) of the title compound was obtained in the same manner as in Step 1-3 of Example 1 above, except that 3-methoxy-4-((6-methylpyridin-3-yl)methoxy)aniline obtained in Step 170-2 was used instead of N-(5-aminopyridin-2-yl)-5-methylpyrazine-2-carboxamide.

$^1$H NMR (400 MHz, DMSO-$d_6$) δ 13.20 (s, 1H), 8.54 (d, J=2.2 Hz, 1H), 7.81 (dd, J=8.0 Hz, 2.3 Hz, 1H), 7.35 (d,

J=8.0 Hz, 1H), 7.21-7.05 (m, 2H), 6.99 (dd, J=8.7 Hz, 2.4 Hz, 1H), 5.09 (s, 2H), 3.78 (s, 3H), 2.50 (s, 3H).

Example 171: Preparation of (3-methoxy-4-((2-methylthiazol-4-yl)methoxy)phenyl)carbonohydrazonoyl dicyanide (Compound 171)

Step 171-1: Preparation of 4-((2-methoxy-4-nitrophenoxy)methyl)-2-methylthiazole 235 mg (yield: 42%) of the title compound was obtained in the same manner as in Step 95-1 of Example 95 above, except that (2-methylthiazol-4-yl)methanol (385 mg, 2.98 mmol) was used instead of phenylmethanol, 1-fluoro-2-methoxy-4-nitrobenzene (340 mg, 1.99 mmol) was used instead of 2-chloro-5-nitropyridine, and DMSO was used as a solvent.

$^1$H NMR (400 MHz, DMSO-$d_6$) δ 7.90 (dd, J=9.0 Hz, 2.8 Hz, 1H), 7.76 (d, J=2.8 Hz, 1H), 7.61 (s, 1H), 7.35 (d, J=9.0 Hz, 1H), 5.25 (s, 2H), 3.88 (s, 3H), 2.67 (s, 3H).

Step 171-2: Preparation of 3-methoxy-4-((2-methylthiazol-4-yl)methoxy)aniline 126 mg (yield: 71%) of the title compound was obtained in the same manner as in Step 1-2 of Example 1 above, except that 4-((2-methoxy-4-nitrophenoxy)methyl)-2-methylthiazole obtained in Step 171-1 was used instead of 5-methyl-N-(5-nitropyridin-2-yl)pyrazine-2-carboxamide.

$^1$H NMR (400 MHz, DMSO-$d_6$) δ 7.41 (s, 1H), 6.70 (d, J=8.4 Hz, 1H), 6.28 (d, J=2.5 Hz, 1H), 6.04 (dd, J=8.5 Hz, 2.5 Hz, 1H), 4.88 (s, 2H), 4.79 (s, 2H), 3.68 (s, 3H), 2.64 (s, 3H).

Step 171-3: Preparation of (3-methoxy-4-((2-methylthiazol-4-yl)methoxy)phenyl)carbonohydrazonoyl dicyanide 84 mg (yield: 53%) of the title compound was obtained in the same manner as in Step 1-3 of Example 1 above, except that 3-methoxy-4-((2-methylthiazol-4-yl)methoxy)aniline obtained in Step 171-2 was used instead of N-(5-aminopyridin-2-yl)-5-methylpyrazine-2-carboxamide.

$^1$H NMR (400 MHz, DMSO-$d_6$) δ 12.96 (s, 1H), 7.52 (s, 1H), 7.29-7.08 (m, 2H), 7.01 (dd, J=8.7 Hz, 2.5 Hz, 1H), 5.07 (s, 2H), 3.78 (s, 3H), 2.66 (s, 3H).

Example 172: Preparation of (3-methoxy-4-(thiophen-2-ylmethoxy)phenyl)carbonohydrazonoyl dicyanide (Compound 172)

Step 172-1: Preparation of 2-((2-methoxy-4-nitrophenoxy)methyl)thiophene 164 mg (yield: 31%) of the title compound was obtained in the same manner as in Step 95-1 of Example 95 above, except that thiophen-2-ylmethanol (0.28 mL, 2.98 mmol) was used instead of phenylmethanol, and 1-fluoro-2-methoxy-4-nitrobenzene (340 mg, 1.99 mmol) was used instead of 2-chloro-5-nitropyridine.

$^1$H NMR (400 MHz, DMSO-$d_6$) δ 7.90 (dd, J=9.0 Hz, 2.7 Hz, 1H), 7.75 (d, J=2.7 Hz, 1H), 7.60 (dd, J=5.1 Hz, 1.3 Hz, 1H), 7.34 (d, J=9.0 Hz, 1H), 7.27 (dd, J=3.5 Hz, 1.2 Hz, 1H), 7.06 (dd, J=5.1 Hz, 3.5 Hz, 1H), 5.45 (s, 2H), 3.88 (s, 3H).

Step 172-2: Preparation of 3-methoxy-4-(thiophen-2-ylmethoxy)aniline 105 mg (yield: 74%) of the title compound was obtained in the same manner as in Step 95-2 of Example 95 above, except that 2-((2-methoxy-4-nitrophenoxy)methyl)thiophene obtained in Step 172-1 was used instead of 2-(benzyloxy)-5-nitropyridine.

$^1$H NMR (400 MHz, DMSO-$d_6$) δ 7.51 (dd, J=5.1 Hz, 1.3 Hz, 1H), 7.07 (dd, J=3.4 Hz, 1.2 Hz, 1H), 6.99 (dd. J=5.1 Hz, 3.4 Hz, 1H), 6.67 (d, J=8.4 Hz, 1H), 6.27 (d, J=2.5 Hz, 1H), 6.02 (dd, J=8.4 Hz, 2.5 Hz, 1H), 5.03 (s, 2H), 4.73 (s, 2H), 3.68 (s, 3H).

Step 172-3: Preparation of (3-methoxy-4-(thiophen-2-ylmethoxy)phenyl)carbonohydrazonoyl dicyanide 58 mg (yield: 44%) of the title compound was obtained in the same manner as in Step 1-3 of Example 1 above, except that 3-methoxy-4-(thiophen-2-ylmethoxy)aniline obtained in Step 172-2 was used instead of N-(5-aminopyridin-2-yl)-5-methylpyrazine-2-carboxamide.

$^1$H NMR (400 MHz, DMSO-$d_6$) δ 12.96 (s, 1H), 7.55 (d, J=5.0 Hz, 1H), 7.19 (d, J=3.5 Hz, 1H), 7.15-7.08 (m, 2H), 7.06-6.87 (m, 2H), 5.26 (s, 2H), 3.78 (s, 3H).

Example 173: Preparation of (3-methoxy-4-(thiophen-3-ylmethoxy)phenyl)carbonohydrazonoyl dicyanide (Compound 173)

Step 173-1: Preparation of 3-((2-methoxy-4-nitrophenoxy)methyl)thiophene 216 mg (yield: 41%) of the title compound was obtained in the same manner as in Step 95-1 of Example 95 above, except that thiophen-3-ylmethanol (0.28 mL, 2.98 mmol) was used instead of phenylmethanol, and 1-fluoro-2-methoxy-4-nitrobenzene (340 mg, 1.99 mmol) was used instead of 2-chloro-5-nitropyridine.

$^1$H NMR (400 MHz, DMSO-$d_6$) δ 7.90 (dd, J=8.9 Hz, 2.7 Hz, 1H), 7.75 (d, J=2.7 Hz, 1H), 7.68-7.62 (m, 1H), 7.58 (dd, J=4.9 Hz, 3.0 Hz, 1H), 7.30 (d, J=9.0 Hz, 1H), 7.20 (dd, J=5.0 Hz, 1.3 Hz, 1H), 5.24 (s, 2H), 3.88 (s, 3H).

Step 173-2: Preparation of 3-methoxy-4-(thiophen-3-ylmethoxy)aniline 153 mg (yield: 87%) of the title compound was obtained in the same manner as in Step 95-2 of Example 95 above, except that 3-((2-methoxy-4-nitrophenoxy)methyl)thiophene obtained in Step 173-1 was used instead of 2-(benzyloxy)-5-nitropyridine.

$^1$H NMR (400 MHz, DMSO-$d_6$) δ 7.51 (dd, J=4.9 Hz, 2.9 Hz, 1H), 7.47-7.42 (m, 1H), 7.13 (dd, J=4.9 Hz, 1.3 Hz, 1H), 6.68 (d, J=8.4 Hz, 1H), 6.26 (d, J=2.5 Hz, 1H), 6.02 (dd, J=8.4 Hz, 2.5 Hz, 1H), 4.86 (s, 2H), 4.70 (s, 2H), 3.68 (s, 3H).

Step 173-3: Preparation of (3-methoxy-4-(thiophen-3-ylmethoxy)phenyl)carbonohydrazonoyl dicyanide 60 mg (yield: 38%) of the title compound was obtained in the same manner as in Step 1-3 of Example 1 above, except that 3-methoxy-4-(thiophen-3-ylmethoxy)aniline obtained in Step 173-2 was used instead of N-(5-aminopyridin-2-yl)-5-methylpyrazine-2-carboxamide.

$^1$H NMR (400 MHz, DMSO-$d_6$) δ 12.96 (s, 1H), 7.61-7.47 (m, 2H), 7.17 (dd, J=4.6 Hz, 1.6 Hz, 1H), 7.16-7.04 (m, 2H), 7.01 (dd, J=8.7 Hz, 2.4 Hz, 1H), 5.07 (s, 2H), 3.79 (s, 3H).

Example 174: Preparation of (3-methoxy-4-((1-methyl-1H-pyrazol-4-yl)methoxy)phenyl)carbonohydrazonoyl dicyanide (Compound 174)

Step 174-1: Preparation of 4-((2-methoxy-4-nitrophenoxy)methyl)-1-methyl-1H-pyrazole 347 mg (yield: 66%) of the title compound was obtained in the same manner as in Step 95-1 of Example 95 above, except that (1-methyl-1H-pyrazol-4-yl)methanol (0.29 mL, 4 mmol) was used instead of phenylmethanol, 1-fluoro-2-methoxy-4-nitrobenzene (340 mg, 1.99 mmol) was used instead of 2-chloro-5-nitropyridine, and DMSO was used as a solvent.

$^1$H NMR (400 MHz, DMSO-$d_6$) δ 7.89 (dd, J=9.0 Hz, 2.7 Hz, 1H), 7.83 (s, 1H), 7.73 (d, J=2.7 Hz, 1H), 7.53 (d, J=0.8 Hz, 1H), 7.32 (d, J=9.0 Hz, 1H), 5.10 (s, 2H), 3.85 (s, 3H), 3.83 (s, 3H).

Step 174-2: Preparation of 3-methoxy-4-4(1-methyl-1H-pyrazol-4-yl)methoxyaniline 130 mg (yield: 73%) of the title compound was obtained in the same manner as in Step 1-2 of Example 1 above, except that 4-((2-methoxy-4-nitrophenoxy)methyl)-1-methyl-1H-pyrazole obtained in Step 174-1 was used instead of 5-methyl-N-(5-nitropyidin-2-yl)pyrazine-2-carboxamide.

$^1$H NMR (400 MHz, DMSO-$d_6$) δ 7.67 (s, 1H), 7.39 (s, 1H), 6.66 (d, J=8.4 Hz, 1H), 6.25 (d, J=2.4 Hz, 1H), 6.03 (dd, J=8.4 Hz, 2.5 Hz, 1H), 4.71 (s, 2H), 4.67 (s, 2H), 3.80 (s, 3H), 3.66 (s, 3H).

Step 174-3: Preparation of (3-methoxy-4-((1-methyl-1H-pyrazol-4-yl)methoxy)phenyl)carbonohydrazonoyl dicyanide 30 mg (yield: 23%) of the title compound was obtained in the same manner as in Step 1-3 of Example 1 above, except that 3-methoxy-4-((1-methyl-1H-pyrazol-4-yl)methoxy) aniline obtained in Step 174-2 was used instead of N-(5-aminopyridin-2-yl)-5-methylpyrazine-2-carboxamide.

$^1$H NMR (400 MHz, DMSO-$d_6$) δ 12.95 (s, 1H), 7.77 (s, 1H), 7.47 (s, 1H), 7.22-7.06 (m, 2H), 7.00 (dd, J=8.7 Hz, 2.5 Hz, 1H), 4.92 (s, 2H), 3.81 (s, 3H), 3.76 (s, 3H).

Example 175: Preparation of acetyl(3-methyl-4-(4-methylbenzyloxy)phenyl)carbonohydrazonoyl dicyanide (Compound 175)

(3-Methyl-4-(4-methylbenzyloxy)phenyl)carbonohydrazonoyl dicyanide (100 mg, 0.33 mmol) prepared in Example 142 and KOH (20 mg, 0.36 mmol) were dissolved in methanol, and the reaction mixture was stirred at room temperature for 3 hours. Upon completion of the reaction, the reaction mixture was concentrated under reduced pressure to remove the solvent and solidified using ether. A produced solid (68 mg, 0.20 mmol) and triethylamine (14 μL, 0.10 mmol) were dissolved in acetonitrile, and acetyl chloride (35 μL, 0.50 mmol) was added thereto, and then the reaction mixture was stirred at room temperature for 4 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, solidified using ether, and filtered. The filtrate was re-concentrated under reduced pressure and solidified using hexane to obtain 16 mg (yield: 23%) of the title compound.

$^1$H NMR (400 MHz, DMSO-$d_6$) δ 7.376-7.357 (d, J=8.0 Hz, 2H), 7.229-7.203 (m, 4H), 7.151-7.127 (d, J=9.5 Hz, 1H), 5.156 (s, 2H), 2.472 (s, 3H), 2.323 (s, 3H), 2.194 (s, 3H).

Preparation Examples

Meanwhile, the novel compound represented by Formula 1 according to the present invention may be formulated in various forms. The following examples exemplarily describe several methods of preparing formulations including the compound represented by Formula 1 according to the present invention as an active ingredient, and the present invention is not limited thereto.

Preparation Example 1: Preparation of Tablet by Direct Pressing 5.0 mg of each of the active ingredients prepared in Examples 1 to 175 was sieved, mixed with 14.1 mg of lactose, 0.8 mg of crospovidone USNF, and 0.1 mg of magnesium stearate, and then pressed into tablets.

Preparation Example 2: Preparation of Tablet by Wet Granulation 5.0 mg of each of the active ingredients prepared in Examples 1 to 175 was sieved and mixed with 16.0 mg of lactose and 4.0 mg of starch. 0.3 mg of polysorbate 80 was dissolved in pure water, and this solution was added to the mixture in a suitable amount, followed by atomizing to obtain fine particles. After drying, the fine particles were sieved, mixed with 2.7 mg of colloidal silicon dioxide and 2.0 mg of magnesium stearate, and pressed into tablets.

Preparation Example 3: Preparation of Powder and Capsule 5.0 mg of each of the active ingredients prepared in Examples 1 to 175 was sieved and then mixed with 14.8 mg of lactose, 10.0 mg of polyvinylpyrrolidone, and 0.2 mg of magnesium stearate. The mixture was filled into hard No. 5 gelatin capsules using a suitable apparatus to prepare capsules.

Preparation Example 4: Preparation of Injection Drug 100 mg of each of the active ingredients prepared in Examples 1 to 175 was mixed with 180 mg of mannitol, 26 mg of $Na_2HPO_4 \cdot 12H_2O$, and 2974 mg of distilled water to prepare injection drugs.

Experimental Example 1: Selection of Tau Protein Aggregation-Inhibiting Substance Using Cell Model In order to select novel tau protein aggregation-inhibiting substances, tau-BiFC cell model, in which formation of tau oligomers in living cells is easily observed, was used. Tau-BiFC cells were aliquoted into a 384-well plate. On the next day, the cells were treated with each of the compounds prepared according to Examples 1 to 175 at concentrations of 1 μM, 3 μM, and 10 μM, together with Forskolin (at a treatment concentration of 30 μM), which is a compound inducing tau protein aggregation by activating tau phosphorylase PKA. After 48 hours, nuclei in the cells were stained using Hoechst (at a treatment concentration of 2 μg/mL), and BiFC fluorescence intensity was automatically measured using Operetta (PerkinElmer) to count stained nuclei in each well out of the entire well plate. The group treated only with Forskolin, which induces tau protein aggregation, was set to a reference point of a 100% tau protein-aggregated state, and the effects of the compounds were confirmed using the equation "BiFC fluorescence intensity due to compound synthesized according to embodiment of present invention/(fluorescence intensity of control group treated only with Forskolin inducing tau protein aggregation−fluorescence intensity of untreated control group)×100". Furthermore, the degree of cytotoxicity induced by the newly synthesized compound was also measured based on the 100% cell viability of the group treated only with Forskolin as a reference, and the cytotoxicity value of each compound was calculated using the equation "(number of stained nuclei in group treated with compound/number of stained nuclei in group treated with Forskolin)×100". Based on the treatment results, substances inhibiting intracellular tau protein aggregation were selected from a series of candidate groups showing a tau protein aggregation inhibition rate of 70% or more and cell viability of 100% at a compound treatment concentration of 10 μM or more.

Experimental Example 2: Confirmation of Concentration-Dependent Inhibitory Effect of Novel Compound on Tau Protein Aggregation In order to evaluate dose-dependent tau protein aggregation inhibition effects of the compounds selected according to Experimental Example 1 on tau protein aggregation, tau-BiFC cells were treated with the selected compounds at concentrations of 0.03 μM, 0.01 μM, 0.3 μM, 1 μM, 3 μM, 10 μM, and 30 μM, respectively, together with Forskolin (at a treatment concentration of 30 μM), which is a tau protein aggregation inducing substance. After 48 hours, tau protein aggregation reaction and degrees of cytotoxicity were analyzed by observing images of the cells. $IC_{50}$ and toxicity of the compounds were analyzed by way of nonlinear regression analysis of prism software (Graph Pad). Calculated results of representative compounds are shown in Table 2 below.

TABLE 2

| | Tau BiFC in cells | | |
|---|---|---|---|
| Compound # | $IC_{50}$ (μM) | Response (% @10 μM) | Cell viability (% @10 μM) |
| 1 | 0.4 | 0 | 94.3 |
| 2 | 1.4 | 0 | 71.5 |
| 3 | 0.03 | 0 | 62.1 |
| 4 | — | 30.7 | 67 |
| 5 | — | 14.5 | 61.2 |
| 6 | — | 43.9 | 61.3 |
| 7 | — | 0 | 30.6 |
| 8 | 0.04 | 0 | 88 |
| 10 | — | 0 | 21.7 |
| 11 | 0.11 | 0 | 82.5 |
| 12 | 0.64 | 17.9 | 122.1 |
| 13 | 0.55 | 30 | 110 |
| 14 | — | 147.4 | 102 |
| 15 | 0.09 | 0 | 79.9 |
| 16 | 0.11 | 0 | 66.2 |
| 17 | 0.31 | 0 | 102.7 |
| 18 | 0.66 | 0 | 113 |

TABLE 2-continued

| | Tau BiFC in cells | | |
|---|---|---|---|
| Compound # | $IC_{50}$ (μM) | Response (% @10 μM) | Cell viability (% @10 μM) |
| 19 | 0.27 | 0 | 119.1 |
| 20 | 0.18 | 0 | 110.4 |
| 21 | 0.75 | 0 | 104.3 |
| 22 | 0.32 | 0 | 105.8 |
| 23 | 0.13 | 0 | 114.2 |
| 24 | <0.30 | 0 | 103.9 |
| 25 | 0.39 | 0 | 122.4 |
| 26 | 0.71 | 0 | 109.8 |
| 27 | 0.37 | 0 | 122 |
| 28 | 0.54 | 0 | 125.8 |
| 29 | 1.04 | 0 | 139.9 |
| 30 | 0.08 | 0 | 145 |
| 31 | 0.54 | 0 | 114.3 |
| 32 | 0.31 | 0 | 145.3 |
| 33 | — | 63.9 | 125 |
| 34 | 9 | 76 | 88.1 |
| 35 | — | 34.2 | 97.9 |
| 36 | — | 35.9 | 86.9 |
| 37 | — | 62.7 | 117.8 |
| 38 | 0.99 | 0 | 110.6 |
| 39 | 0.63 | 0 | 131.1 |
| 40 | — | 7.9 | 130.7 |
| 41 | — | 0 | 115.2 |
| 42 | — | 0 | 123.1 |
| 43 | — | 3 | 168.6 |
| 44 | — | 0 | 70.4 |
| 45 | 1.18 | 0 | 140.5 |
| 46 | 0.86 | 0 | 155 |
| 47 | 2.58 | 0 | 122.7 |
| 48 | — | 0 | 122.3 |
| 49 | — | 75.9 | 117.2 |
| 50 | — | 86.6 | 116.4 |
| 51 | — | 45.4 | 107.1 |
| 52 | — | 24 | 120.2 |
| 53 | — | 22.9 | 116.1 |
| 54 | — | 8.3 | 116 |
| 55 | — | 65.6 | 116.1 |
| 56 | 1.85 | 0 | 129.9 |
| 57 | — | 51.7 | 108.6 |
| 58 | — | 51.4 | 113.5 |
| 59 | — | 74.3 | 128.2 |
| 60 | — | 90.2 | 116.9 |
| 61 | — | 108.8 | 112.7 |
| 62 | — | 87.3 | 116.5 |
| 63 | — | 11.5 | 136.7 |
| 64 | — | 56 | 114.2 |
| 65 | — | 72.6 | 111.4 |
| 66 | — | 61.2 | 123.9 |
| 67 | — | 68.2 | 108.4 |
| 68 | 0.11 | 0 | 117 |
| 69 | 0.26 | 0 | 119.4 |
| 70 | 0.31 | 0 | 94.5 |
| 71 | — | 0 | 46 |
| 72 | 1.99 | 0 | 129.5 |
| 73 | — | 0 | 49.6 |
| 74 | 0.44 | 0 | 92.7 |
| 75 | — | 102.3 | 131.4 |
| 76 | — | 79.9 | 121.7 |
| 77 | — | 84.8 | 91.6 |
| 78 | — | 69.6 | 74 |
| 79 | — | 65.9 | 115.7 |
| 80 | — | 68 | 112.3 |
| 81 | 0.55 | 0 | 116.2 |
| 82 | 2.96 | 0 | 126.4 |
| 83 | 1.14 | 0 | 104 |
| 84 | 2.12 | 0 | 111.4 |
| 85 | 1.58 | 0 | 99.1 |
| 86 | 2.12 | 0 | 72.6 |
| 87 | 1.22 | 0 | 39.4 |
| 88 | 3.06 | 0 | 44.4 |
| 89 | 2.4 | 0 | 32.5 |
| 90 | 1.29 | 0 | 43.7 |
| 91 | 3.12 | 0 | 117 |
| 92 | 0.55 | 0 | 116.8 |
| 93 | 1.29 | 0 | 66.5 |

TABLE 2-continued

| | Tau BiFC in cells | | |
|---|---|---|---|
| Compound # | $IC_{50}$ (μM) | Response (% @10 μM) | Cell viability (% @10 μM) |
| 94 | 1.28 | 0 | 33.6 |
| 95 | — | 0 | 71.9 |
| 96 | 0.4 | 0 | 27.5 |
| 97 | 0.1 | 0 | 27.1 |
| 98 | 0.25 | 0 | 26.9 |
| 99 | 0.24 | 0 | 29.2 |
| 100 | 0.78 | 0 | 39.4 |
| 101 | 0.95 | 0 | 30.1 |
| 102 | 0.96 | 0 | 54.5 |
| 103 | 2.35 | 0 | 37.9 |
| 104 | 0.26 | 0 | 142 |
| 105 | 0.4 | 0 | 142.9 |
| 106 | — | 0 | 184.9 |
| 107 | 0.6 | 0 | 137.9 |
| 108 | 1.4 | 0 | 121.8 |
| 109 | 1.4 | 0 | 141.8 |
| 110 | 0.79 | 0 | 160.5 |
| 111 | 0.5 | 0 | 136.4 |
| 112 | 0.2 | 0 | 158.2 |
| 113 | 0.2 | 0 | 147 |
| 114 | 1.5 | 0 | 149.5 |
| 115 | 0.6 | 0 | 157.6 |
| 116 | 1.4 | 0 | 124 |
| 117 | 1.24 | 16.6 | 126.0 |
| 118 | 5.75 | 25.7 | 82.6 |
| 119 | 3.55 | 38.9 | 112.5 |
| 120 | 1.45 | 0.0 | 66.2 |
| 121 | 4.61 | 3.4 | 72.7 |
| 122 | 1.86 | 11.7 | 92.9 |
| 123 | 0.78 | 0.0 | 34.6 |
| 124 | 0.62 | 0.0 | 140.9 |
| 125 | 2.3 | 0.0 | 140.5 |
| 126 | 0.1 | 0.0 | 133.2 |
| 127 | 1.2 | 0.0 | 134.9 |
| 128 | 0.3 | 0.0 | 108.5 |
| 129 | 0.2 | 0.0 | 106.9 |
| 130 | — | 0.0 | 113 |
| 131 | — | 10.6 | 33.4 |
| 132 | — | 0.0 | 39.2 |
| 133 | — | 0.0 | 39.7 |
| 134 | — | 0.0 | 38.1 |
| 135 | — | 0.0 | 41.7 |
| 136 | 1.44 | 0.0 | 95.7 |
| 137* | — | 31 | 129 |
| 138* | — | 15 | 133 |
| 139* | — | 39 | 123 |
| 140* | — | 18 | 135 |
| 141* | 0.866 | −25 | 109 |
| 142* | 1.606 | −5 | 111 |
| 143* | — | 11 | 125 |
| 144* | 1.279 | −20 | 111 |
| 145* | 0.126 | −49 | 95 |
| 146* | 0.444 | −35 | 133 |
| 147* | 0.147 | −19 | 98 |
| 148* | — | 22 | 114 |
| 149* | 0.185 | −8 | 124 |
| 150* | — | 11 | 118 |
| 151* | 0.022 | −32 | 126 |
| 152* | 0.054 | −37 | 117 |
| 153* | 0.037 | −43 | 122 |
| 154* | 0.032 | −52 | 106 |
| 155* | — | −43 | 80 |
| 156* | 0.05 | −29 | 124 |
| 157* | — | 8 | 124 |
| 158* | 0.268 | −33 | 96 |
| 159* | 0.007 | −40 | 114 |
| 160* | 0.007 | −33 | 111 |
| 161* | 0.109 | −17 | 119 |
| 162* | 0.049 | −25 | 115 |
| 163* | — | 91 | 106 |
| 164* | 0.096 | −1 | 109 |
| 165* | — | −40 | 113 |
| 166* | 0.214 | −43 | 121 |
| 167* | 0.01 | −38 | 118 |
| 168* | 0.132 | −17 | 123 |

TABLE 2-continued

| | Tau BiFC in cells | | |
|---|---|---|---|
| Compound # | $IC_{50}$ (μM) | Response (% @10 μM) | Cell viability (% @10 μM) |
| 169 | | | |
| 170 | | | |
| 171 | | | |
| 172 | | | |
| 173 | | | |
| 174 | | | |

*: response and cell viability measured at 3 μM.

Experimental Example 3: Inhibitory Effect of Novel Compound on CYP Coenzyme Activity The inhibitory effects of the compounds prepared according to Examples 1 to 175 on CYP coenzyme activity were identified. Specifically, human liver microsomes (0.25 mg/mL), a 0.1 M phosphate buffer solution (pH 7.4), a substrate drug cocktail of five types of drug metabolism enzymes (50 μM phenacetin, 10 μM diclofenac, 100 μM S-mephenytoin, 5 μM dextromethorphan, and 2.5 μM midazolam), and the compound at a concentration of 0 μM or 10 μM were mixed and pre-cultured at 37° C. for 5 minutes, and then further cultured at 37° C. for 15 minutes together with an NADPH generation system solution added thereto. Thereafter, the reaction was terminated by adding an acetonitrile solution containing an internal standard material (terfenadine) and centrifuged for 5 minutes (14,000 rpm, 4° C.), and then a supernatant was injected into an LC-MS/MS system for simultaneous analysis of metabolites of the substrate drugs to thereby evaluate the inhibitory effects on drug metabolism.

Metabolites of each CYP coenzyme indicator drug generated through the reaction were analyzed using the Shimadzu Nexera XR system and TSQ Vantage (Thermo). In an HPLC column, Kinetex C18 (2.1 mm×100 mm, 2.6 μm, particle size; Phenomenex, USA) was used, and mobile phases were (A) distilled water containing 0.1% formic acid and (B) acetonitrile containing 0.1% formic acid, and a gradient program shown in Table 3 was applied thereto.

TABLE 3

| Time (min) | Flow rate (mL/min) | % A | % B |
|---|---|---|---|
| 0 | 0.3 | 100 | 0 |
| 1.0 | 0.3 | 60 | 40 |
| 4.0 | 0.3 | 50 | 50 |
| 4.1 | 0.3 | 100 | 0 |
| 7.0 | 0.3 | 100 | 0 |

The generated metabolites were quantified using a multiple reaction monitoring (MRM) quantification mode, and Xcalibur (version 1.6.1) was used for data analysis. Inhibitory effects of the novel compound prepared according to the examples of the present invention on CYP coenzyme activity are shown in Table 4 below.

TABLE 4

| Compound # | CYP1A2 | CYP2C9 | CYP2C19 | CYP2D6 | CYP3A4 |
|---|---|---|---|---|---|
| 1 | 80.7 | 71.1 | 74.6 | 93.1 | 85 |
| 3 | 85.6 | 61.9 | 78.2 | 83.6 | 80.8 |
| 6 | 85.2 | 38 | 64.8 | 75.7 | 62.2 |

TABLE 4-continued

| Compound # | CYP1A2 | CYP2C9 | CYP2C19 | CYP2D6 | CYP3A4 |
|---|---|---|---|---|---|
| 16 | 71.4 | 40.3 | 78.6 | 80.8 | 86.9 |
| 19 | 55.1 | 14.6 | 73.1 | 73 | 76.5 |
| 20 | 69.4 | 22.3 | 72 | 75.8 | 76.1 |
| 23 | 85 | 40.6 | 82.5 | >100 | 83.3 |
| 27 | 76.8 | 23.7 | 78.3 | 76 | >100 |
| 30 | 83.9 | 62.9 | 81.5 | 89.9 | 95.2 |
| 38 | 92.5 | 49.1 | 83.0 | >100 | 92.4 |
| 45 | 95.5 | 80.8 | 83.4 | >100 | 96.7 |
| 46 | 97.8 | 70.4 | 83.1 | >100 | 85.5 |
| 104 | 78.4 | 48.6 | 82.4 | >100 | 66.1 |
| 110 | 88.3 | 77.1 | 88.4 | 91.3 | 98.9 |
| 124 | 23.4 | 4.4 | 69.9 | 46.6 | 37.5 |
| 136 | 80.3 | 70 | 76.5 | 94.4 | 88.9 |
| 137 | >100 | 37 | >100 | >100 | 84.8 |
| 138 | 97.4 | 92.5 | >100 | 92.7 | 89.4 |
| 140 | 96.7 | 11.7 | >100 | 69.6 | 30.8 |
| 143 | 95.9 | >100 | >100 | >100 | 90.3 |
| 144 | 37.7 | 24.5 | >100 | >100 | 89.2 |
| 145 | 5.3 | 2.2 | 46.5 | 39.1 | 22 |
| 146 | >100 | 47.2 | 88.4 | >100 | 82.7 |
| 151 | 51.8 | 19.4 | >100 | 94.8 | 88 |
| 152 | 75.5 | 17.2 | 95 | 96.1 | >100 |
| 153 | 67.9 | 44.1 | 100 | 90.7 | 98.9 |
| 154 | 79.1 | 26.6 | 76.3 | 81.7 | 72.5 |
| 156 | 95.9 | 54 | 83.7 | 96 | 92.6 |
| 159 | 42.4 | 54.7 | 88 | 86.1 | 82.1 |
| 160 | 5.8 | 6.5 | 68.5 | 59.7 | 17.9 |
| 162 | 79.8 | 73.5 | 75.9 | 70.3 | 73.3 |

Experimental Example 4: Identification of Stability of Liver Microsome Due to Novel Compound The stability of liver microsomes due to the compounds prepared according to Examples 1 to 175 was confirmed. Specifically, four types of liver microsomes (human, dog, rat, and mouse, each 0.25 mg/mL), a 0.1 M phosphate buffer solution (pH 7.4), and each of the compounds at a concentration of 1 μM were mixed and pre-cultured at 37° C. for 5 minutes and further cultured at 37° C. for 30 minutes together with an NADPH generation system solution added thereto. Thereafter, the reaction was terminated by adding an acetonitrile solution containing an internal standard material (chloropropamide) and centrifuged for 5 minutes (14,000 rpm, 4° C.), and then a supernatant was injected into an LC-MS/MS system for analysis of substrate drugs to thereby evaluate metabolic stability due to 8 types of compounds.

The amount of the substrate remaining after the reaction was analyzed using the Shimadzu Nexera XR system and TSQ Vantage (Thermo). In an HPLC column, Kinetex XB-C18 (2.1 mm×100 mm, particle size of 2.6 μm; Phenomenex, USA) was used, and mobile phases were (A) distilled water containing 0.1% formic acid and (B) acetonitrile containing 0.1% formic acid. Analyst software (version 1.6.3) and Xcalibur (version 1.6.1) were used for data analysis. The calculated results are shown in Table 5 below.

TABLE 5

| Compound # | Human (%) | Dog (%) | Rat (%) | Mouse (%) |
|---|---|---|---|---|
| 1 | 86.5 | 66.9 | 56.7 | 21.2 |
| 3 | 95.7 | 75.4 | 72.6 | 46.1 |
| 6 | 77.5 | >100 | 88.4 | 74.8 |
| 16 | 91.6 | 59.5 | 61 | 67.3 |
| 19 | 84.8 | 78.8 | 51.4 | 62.3 |
| 20 | 91.9 | >100 | 33.7 | 68.3 |
| 26 | 72.5 | 29.8 | 19.8 | 7.1 |
| 27 | 86.9 | 3.6 | 8.8 | 5.4 |
| 30 | 94.8 | 84.7 | 72.4 | 70.7 |

TABLE 5-continued

| Compound # | Human (%) | Dog (%) | Rat (%) | Mouse (%) |
|---|---|---|---|---|
| 31 | 28.7 | ND | ND | ND |
| 38 | 99.1 | 98.8 | >100 | 96.4 |
| 45 | 96.8 | >100 | >100 | >100 |
| 46 | >100 | >100 | 86.3 | >100 |
| 68 | 6.7 | 87.8 | 63 | 93.6 |
| 69 | 8.4 | 94.8 | 75.6 | 81.6 |
| 104 | 84.1 | — | 87.5 | 97.2 |
| 110 | 89.7 | — | 81.8 | 92.4 |
| 143 | 78.3 | — | 57.6 | 50 |
| 144 | 74.9 | — | 92.4 | 80.9 |
| 145 | 93.7 | — | 91.2 | 93.3 |
| 146 | 64.6 | — | 31.1 | 70.5 |
| 147 | 86.4 | — | 89 | 91.3 |
| 148 | 77.4 | — | 86.3 | >100 |
| 149 | 93.7 | — | 82.2 | 87.9 |
| 150 | 80.7 | — | 78.7 | 99.5 |
| 152 | 73.2 | — | 72.3 | 56.6 |
| 155 | 95.4 | — | 82 | 90.8 |
| 156 | 49.3 | — | 55.5 | 41.3 |
| 157 | 69.1 | — | 46 | 33.2 |
| 158 | 36.9 | — | 48.2 | 73.7 |
| 163 | 86.9 | — | 71.3 | 59.5 |
| 164 | 96.8 | — | 29.1 | 24.6 |
| 165 | 42.4 | — | 42.4 | 69.6 |
| 166 | 6.6 | — | 6.5 | 68.1 |
| 168 | 54.8 | — | 44 | 77.8 |
| 171 | 79.2 | — | 80.3 | 70.3 |
| 172 | 73.3 | — | 65.3 | 57.3 |
| 174 | 72 | — | 54.3 | >100 |

The above description of the present invention is provided for the purpose of illustration, and it would be understood by those skilled in the art that various changes and modifications may be made without changing the technical conception and essential features of the present invention. Thus, it is clear that the above-described embodiments are illustrative in all aspects and do not limit the present invention. The various embodiments disclosed herein are not intended to be limiting, with the true scope and spirit being indicated by the following claims. The present invention is to be limited only by the terms of the appended claims, along with the full scope of equivalents to which such claims are entitled.

The invention claimed is:

1. A compound represented by Formula 1 below or a pharmaceutically acceptable salt thereof:

[Formula 1]

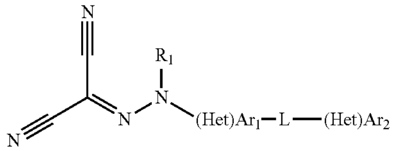

wherein, in Formula 1 above,

L is —NHCO—, —CONH—, —$NHSO_2$—, —$SO_2NH$—, or -(straight-chain or branched $C_{0-3}$ alkylene)'-O-(straight-chain or branched $C_{0-3}$ alkylene)"-;

$R_1$ is hydrogen, $C_{1-6}$ alkyl, or $C_{1-6}$ alkylcarbonyl;

(Het)$Ar_1$ is $C_{6-10}$ arylene or 5- to 10-membered heteroarylene; and (Het)$Ar_2$ is $C_{6-10}$ aryl or 5- to 10-membered heteroaryl;

wherein the $C_{6-10}$ aryl(ene) and 5- to 10-membered heteroaryl(ene) are each independently unsubstituted or substituted with at least one selected from the group consisting of $C_{1-6}$ alkyl, $C_{1-6}$ alkoxy, halogen, cyano, $C_{1-6}$ haloalkyl, and $C_{1-6}$ haloalkoxy, wherein the compound is 1. (6-(5-methylpyrazine-2-carboxamido)pyridin-3-yl)carbonohydrazonoyl dicyanide,
2. (4-(5-methylpyrazine-2-carboxamido)phenyl)carbonohydrazonoyl dicyanide,
3. (2-fluoro-4-(5-methylpyrazine-2-carboxamido)phenyl) carbonohydrazonoyl dicyanide,
4. (2-methoxy-4-(5-methylpyrazine-2-carboxamido)phenyl) carbonohydrazonoyl dicyanide,
5. (2-chloro-4-(5-methylpyrazine-2-carboxamido)phenyl) carbonohydrazonoyl dicyanide,
6. (2-methyl-4-(5-methylpyrazine-2-carboxamido)phenyl)carbonohydrazonoyl dicyanide,
7. (3-fluoro-4-(5-methylpyrazine-2-carboxamido)phenyl) carbonohydrazonoyl dicyanide,
8. (3-methyl-4-(5-methylpyrazine-2-carboxamido)phenyl)carbonohydrazonoyl dicyanide,
9. methyl(3-methyl-4-(5-methylpyrazine-2-carboxamido) phenyl) carbonohydrazonoyl dicyanide,
10. (3-methoxy-4-(5-methylpyrazine-2-carboxamido) phenyl) carbonohydrazonoyl dicyanide,
11. (3-chloro-4-(5-methylpyrazine-2-carboxamido)phenyl)carbonohydrazonoyl dicyanide,
12. (5-methyl-6-(5-methylpyrazine-2-carboxamido)pyridin-3-yl) carbonohydrazonoyl dicyanide,
13. (4-methyl-6-(5-methylpyrazine-2-carboxamido)pyridin-3-yl) carbonohydrazonoyl dicyanide,
14. (5-(5-methylpyrazine-2-carboxamido)pyridin-2-yl) carbonohydrazonoyl dicyanide,
15. (6-benzamidopyridin-3-yl)carbonohydrazonoyl dicyanide,
16. (6-(4-fluorobenzamido)pyridin-3-yl)carbonohydrazonoyl dicyanide,
17. (6-(2-fluorobenzamido)pyridin-3-yl)carbonohydrazonoyl dicyanide,
18. (6-(3-fluorobenzamido)pyridin-3-yl)carbonohydrazonoyl dicyanide,
19. (6-(3-fluoro-5-methylbenzamido)pyridin-3-yl)carbonohydrazonoyl dicyanide,
20. (6-(2-fluoro-3-methylbenzamido)pyridin-3-yl)carbonohydrazonoyl dicyanide,
21. (6-(4-fluoro-3-methylbenzamido)pyridin-3-yl)carbonohydrazonoyl dicyanide,
22. (6-(3-fluoro-4-methylbenzamido)pyridin-3-yl)carbonohydrazonoyl dicyanide,
23. (6-(4-methylbenzamido)pyridin-3-yl)carbonohydrazonoyl dicyanide,
24. (6-(3-methylbenzamido)pyridin-3-yl)carbonohydrazonoyl dicyanide,
25. (6-(2-methylbenzamido)pyridin-3-yl)carbonohydrazonoyl dicyanide,
26. (6-(3-(trifluoromethyl)benzamido)pyridin-3-yl)carbonohydrazonoyl dicyanide,
27. (6-(4-(trifluoromethyl)benzamido)pyridin-3-yl)carbonohydrazonoyl dicyanide,
28. (6-(2-(trifluoromethyl)benzamido)pyridin-3-yl)carbonohydrazonoyl dicyanide,
29. (6-(pyrimidine-2-carboxamido)pyridin-3-yl)carbonohydrazonoyl dicyanide,
30. (6-(thiophene-2-carboxamido)pyridin-3-yl)carbonohydrazonoyl dicyanide,
31. (6-(benzo[d]thiazole-2-carboxamido)pyridin-3-yl) carbonohydrazonoyl dicyanide,
32. (6-(quinoxaline-2-carboxamido)pyridin-3-yl)carbonohydrazonoyl dicyanide,
33. (2-(5-methylpyrazine-2-carboxamido)thiazolo[4,5-b] pyridin-6-yl) carbonohydrazonoyl dicyanide,
34. (6-(p-tolylcarbamoyl)pyridin-3-yl)carbonohydrazonoyl dicyanide,
35. (6-(4-methoxyphenylcarbamoyl)pyridin-3-yl)carbonohydrazonoyl dicyanide,
36. (6-(5-methylpyrazin-2-ylcarbamoyl)pyridin-3-yl)carbonohydrazonoyl dicyanide,
37. (6-(4-chlorophenylcarbamoyl)pyridin-3-yl)carbonohydrazonoyl dicyanide,
38. (6-(6-methylpyridin-3-ylcarbamoyl)pyridin-3-yl)carbonohydrazonoyl dicyanide,
39. (6-(5-methylpyridin-3-ylcarbamoyl)pyridin-3-yl)carbonohydrazonoyl dicyanide,
40. (6-(pyridin-3-ylcarbamoyl)pyridin-3-yl)carbonohydrazonoyl dicyanide,
41. (6-(6-methylpyrazin-2-ylcarbamoyl)pyridin-3-yl)carbonohydrazonoyl dicyanide,
42. (6-(pyrimidin-5-ylcarbamoyl)pyridin-3-yl)carbonohydrazonoyl dicyanide,
43. (6-(pyrimidin-2-ylcarbamoyl)pyridin-3-yl)carbonohydrazonoyl dicyanide,
44. (4-(4-methoxyphenylcarbamoyl)phenyl)carbonohydrazonoyl dicyanide,
45. (4-(5-methylpyrazin-2-ylcarbamoyl)phenyl)carbonohydrazonoyl dicyanide,
46. (4-(6-methylpyrazin-2-ylcarbamoyl)phenyl)carbonohydrazonoyl dicyanide,
47. (4-(6-methylpyridin-3-ylcarbamoyl)phenyl)carbonohydrazonoyl dicyanide,
48. (4-(5-methylpyridin-3-ylcarbamoyl)phenyl)carbonohydrazonoyl dicyanide,
49. (4-(pyridin-3-ylcarbamoyl)phenyl)carbonohydrazonoyl dicyanide,
50. (4-(pyrimidin-5-ylcarbamoyl)phenyl)carbonohydrazonoyl dicyanide,
51. (2-methoxy-4-(5-methylpyrazin-2-ylcarbamoyl)phenyl)carbonohydrazonoyl dicyanide,
52. (3-methyl-4-(5-methylpyrazin-2-ylcarbamoyl)phenyl)carbonohydrazonoyl dicyanide,
53. (3-methyl-4-(6-methylpyridin-3-ylcarbamoyl)phenyl) carbonohydrazonoyl dicyanide,
54. (3-methyl-4-(6-methylpyrazin-2-ylcarbamoyl)phenyl)carbonohydrazonoyl dicyanide,
55. (2-methyl-4-(6-methylpyridin-3-ylcarbamoyl)phenyl) carbonohydrazonoyl dicyanide,
56. (2-fluoro-4-(5-methylpyrazin-2-ylcarbamoyl)phenyl) carbonohydrazonoyl dicyanide,
57. (2-methoxy-4-(6-methylpyridin-3-ylcarbamoyl)phenyl)carbonohydrazonoyl dicyanide,
58. (6-(phenylsulfonamido)pyridin-3-yl)carbonohydrazonoyl dicyanide,
59. (6-(4-methoxyphenylsulfonamido)pyridin-3-yl)carbonohydrazonoyl dicyanide,
60. (6-(pyridine-3-sulfonamido)pyridin-3-yl)carbonohydrazonoyl dicyanide,
61. (6-(1-methyl-1H-pyrazole-4-sulfonamido)pyridin-3-yl)carbonohydrazonoyl dicyanide,
62. (6-(thiophene-2-sulfonamido)pyridin-3-yl)carbonohydrazonoyl dicyanide,
63. (6-(4-methylphenylsulfonamido)pyridin-3-yl)carbonohydrazonoyl dicyanide,
64. (6-(4-fluorophenylsulfonamido)pyridin-3-yl)carbonohydrazonoyl dicyanide,
65. (4-(N-(6-methylpyridin-3-yl)sulfamoyl)phenyl)carbonohydrazonoyl dicyanide,
66. (4-(N-(4-methoxyphenyl)sulfamoyl)phenyl)carbonohydrazonoyl dicyanide, 67. (4-(N-(5-methylpyrazin-2-yl)sulfamoyl)phenyl)carbonohydrazonoyl dicyanide,
68. (6-phenoxypyridin-3-yl)carbonohydrazonoyl dicyanide,
69. (6-(3-fluorophenoxy)pyridin-3-yl)carbonohydrazonoyl dicyanide,
70. (5-phenoxypyridin-2-yl)carbonohydrazonoyl dicyanide,
71. (3-fluoro-4-phenoxyphenyl)carbonohydrazonoyl dicyanide,
72. (3-fluoro-4-(pyridin-3-yloxy)phenyl)carbonohydrazonoyl dicyanide,
73. (4-phenoxy-3-(trifluoromethyl)phenyl)carbonohydrazonoyl dicyanide,
74. (3-methyl-4-(pyridin-3-yloxy)phenyl)carbonohydrazonoyl dicyanide,
75. methyl(5-phenoxypyridin-2-yl)carbonohydrazonoyl dicyanide,
76. (6-(3-fluorophenoxy)pyridin-3-yl)(methyl)carbonohydrazonoyl dicyanide,
77. (3-fluoro-4-phenoxyphenyl)(methyl)carbonohydrazonoyl dicyanide,
78. methyl(4-phenoxy-3-(trifluoromethyl)phenyl)carbonohydrazonoyl dicyanide,
79. (3-methyl-4-(pyridin-4-yloxy)phenyl)carbonohydrazonoyl dicyanide,
80. (3-fluoro-4-(pyridin-4-yloxy)phenyl)carbonohydrazonoyl dicyanide,
81. (3-methyl-4-(pyrimidin-5-yloxy)phenyl)carbonohydrazonoyl dicyanide,
82. (3-fluoro-4-(pyrimidin-5-yloxy)phenyl)carbonohydrazonoyl dicyanide,
83. (4-(pyridin-2-yloxy)phenyl)carbonohydrazonoyl dicyanide,
84. (4-(pyrazin-2-yloxy)phenyl)carbonohydrazonoyl dicyanide,
85. (4-(pyridin-3-yloxy)phenyl)carbonohydrazonoyl dicyanide,
86. (4-(2-cyanophenoxy)phenyl)carbonohydrazonoyl dicyanide,
87. (4-(4-cyanophenoxy)phenyl)carbonohydrazonoyl dicyanide,
88. (4-(3-cyanophenoxy)phenyl)carbonohydrazonoyl dicyanide,
89. (4-(6-(trifluoromethyl)pyridin-3-yloxy)phenyl)carbonohydrazonoyl dicyanide,
90. (4-(5-(trifluoromethyl)pyridin-2-yloxy)phenyl)carbonohydrazonoyl dicyanide,
91. (4-(pyrimidin-2-yloxy)phenyl)carbonohydrazonoyl dicyanide,
92. (4-(pyridazin-3-yloxy)phenyl)carbonohydrazonoyl dicyanide,
93. (4-(2-fluorophenoxy)phenyl)carbonohydrazonoyl dicyanide,
94. (4-(3-fluorophenoxy)phenyl)carbonohydrazonoyl dicyanide,
95. (6-(benzyloxy)pyridin-3-yl)carbonohydrazonoyl dicyanide,
96. (6-(4-(trifluoromethyl)benzyloxy)pyridin-3-yl)carbonohydrazonoyl dicyanide,
97. (4-(benzyloxy)-3-(trifluoromethyl)phenyl)carbonohydrazonoyl dicyanide,
98. (3-(trifluoromethyl)-4-(4-(trifluoromethyl)benzyloxy) Phenyl) carbonohydrazonoyl dicyanide,
99. (6-(4-methylbenzyloxy)pyridin-3-yl)carbonohydrazonoyl dicyanide,
100. (6-phenethoxypyridin-3-yl)carbonohydrazonoyl dicyanide,
101. (4-phenethoxy-3-(trifluoromethyl)phenyl)carbonohydrazonoyl dicyanide,
102. (6-(4-methoxyphenethoxy)pyridin-3-yl)carbonohydrazonoyl dicyanide,
103. (6-(4-(trifluoromethyl)phenethoxy)pyridin-3-yl)carbonohydrazonoyl dicyanide,
104. (3-methoxy-4-(5-methylpyrazin-2-ylcarbamoyl)phenyl) carbonohydrazonoyl dicyanide,
105. (3-methoxy-4-(6-methylpyrazin-2-ylcarbamoyl)phenyl) carbonohydrazonoyl dicyanide,
106. (3-chloro-4-(5-methylpyrazin-2-ylcarbamoyl)phenyl) carbonohydrazonoyl dicyanide,
107. (3-methoxy-4-(5-methylpyridin-3-ylcarbamoyl)phenyl) carbonohydrazonoyl dicyanide,
108. (3-methoxy-4-(p-tolylcarbamoyl)phenyl)carbonohydrazonoyl dicyanide,
109. (3-methoxy-4-(4-methoxyphenylcarbamoyl)phenyl) carbonohydrazonoyl dicyanide,
110. (6-(furan-3-carboxamido)pyridin-3-yl)carbonohydrazonoyl dicyanide,
111. (3-methyl-4-(thiazole-4-carboxamido)phenyl)carbonohydrazonoyl dicyanide,
112. (6-(thiazole-4-carboxamido)pyridin-3-yl)carbonohydrazonoyl dicyanide,
113. (6-(oxazole-4-carboxamido)pyridin-3-yl)carbonohydrazonoyl dicyanide,
114. (6-(oxazole-5-carboxamido)pyridin-3-yl)carbonohydrazonoyl dicyanide,
115. (6-(isoxazole-3-carboxamido)pyridin-3-yl)carbonohydrazonoyl dicyanide,
116. (4-(thiazol-2-yloxy)phenyl)carbonohydrazonoyl dicyanide,
118. (4-(4-(trifluoromethyl)benzyloxy)phenyl)carbonohydrazonoyl dicyanide,
119. (4-(4-methylbenzyloxy)phenyl)carbonohydrazonoyl dicyanide,
120. (4-(4-methoxyphenethoxy)phenyl)carbonohydrazonoyl dicyanide,
121. (4-(4-(trifluoromethyl)phenethoxy)phenyl)carbonohydrazonoyl dicyanide,
122. (4-phenethoxyphenyl)carbonohydrazonoyl dicyanide,
123. (4-(4-chlorophenethoxy)phenyl)carbonohydrazonoyl dicyanide,
124. (4-(pyridin-3-ylmethoxy)phenyl)carbonohydrazonoyl dicyanide,
125. (4-(pyrazin-2-ylmethoxy)phenyl)carbonohydrazonoyl dicyanide,
126. (4-((1H-benzo[d]imidazol-2-yl)methoxy)phenyl) carbonohydrazonoyl dicyanide,
127. (4-(pyridazin-3-ylmethoxy)phenyl)carbonohydrazonoyl dicyanide,
128. (4-(benzo[d]oxazol-2-ylmethoxy)phenyl)carbonohydrazonoyl dicyanide,
129. (4-(benzo[d]thiazol-2-ylmethoxy)phenyl)carbonohydrazonoyl dicyanide,
130. (4-(benzo[b]thiophen-2-ylmethoxy)phenyl)carbonohydrazonoyl dicyanide,
131. (6-(4-chlorophenethoxy)pyridin-3-yl)carbonohydrazonoyl dicyanide,
132. (4-(4-methylbenzyloxy)-3-(trifluoromethyl)phenyl) carbonohydrazonoyl dicyanide,
133. (4-(4-chlorophenethoxy)-3-(trifluoromethyl)phenyl) carbonohydrazonoyl dicyanide, 134. (4-(4-methoxyphenethoxy)-3-(trifluoromethyl)phenyl) carbonohydrazonoyl dicyanide,
135. (3-(trifluoromethyl)-4-(4-(trifluoromethyl) phenethoxy)phenyl) carbonohydrazonoyl dicyanide,
136. (4-(pyrimidin-2-ylmethoxy)phenyl)carbonohydrazonoyl dicyanide,
137. (4-((1H-pyrazol-4-yl)methoxy)phenyl)carbonohydrazonoyl dicyanide,
138. (4-((5-methylpyrazin-2-yl)methoxy)phenyl)carbonohydrazonoyl dicyanide,
139. (4-(1-(4-(trifluoromethyl)phenyl)ethoxy)phenyl)carbonohydrazonoyl dicyanide,
140. (4-(1-(pyridin-3-yl)ethoxy)phenyl)carbonohydrazonoyl dicyanide,
141. (4-(benzyloxy)-3-methylphenyl)carbonohydrazonoyl dicyanide,
142. (3-methyl-4-(4-methylbenzyloxy)phenyl)carbonohydrazonoyl dicyanide,
143. 3-methyl-4-(pyrimidin-2-ylmethoxy)phenyl)carbonohydrazonoyl dicyanide,
144. (3-methyl-4-(pyrazin-2-ylmethoxy)phenyl)carbonohydrazonoyl dicyanide,
145. (3-methyl-4-(pyridin-3-ylmethoxy)phenyl)carbonohydrazonoyl dicyanide,
146. (4-((1H-benzo[d]imidazol-2-yl)methoxy)-3-methylphenyl) carbonohydrazonoyl dicyanide,
147. (3-methyl-4-((5-methylpyrazin-2-yl)methoxy)phenyl)carbonohydrazonoyl dicyanide,
148. (3-methyl-4-(4-(trifluoromethyl)benzyloxy)phenyl) carbonohydrazonoyl dicyanide,
149. (3-methyl-4-(pyridazin-3-ylmethoxy)phenyl)carbonohydrazonoyl dicyanide,
150. (4-(benzo[b]thiophen-2-ylmethoxy)-3-methylphenyl)carbonohydrazonoyl dicyanide,
151. (4-((1H-pyrazol-3-yl)methoxy)-3-methylphenyl)carbonohydrazonoyl dicyanide,
152. (3-methyl-4-(thiazol-4-ylmethoxy)phenyl)carbonohydrazonoyl dicyanide,
153. (4-(benzyloxy)-3-methoxyphenyl)carbonohydrazonoyl dicyanide,
154. (3-methoxy-4-(4-methylbenzyloxy)phenyl)carbonohydrazonoyl dicyanide,
155. (3-methoxy-4-(4-(trifluoromethyl)benzyloxy)phenyl)carbonohydrazonoyl dicyanide,
156. (4-(benzo[d]oxazol-2-ylmethoxy)-3-methylphenyl) carbonohydrazonoyl dicyanide,
157. (4-(benzo[d]thiazol-2-ylmethoxy)-3-methylphenyl) carbonohydrazonoyl dicyanide,
158. (4-(benzo[b]thiophen-2-ylmethoxy)-3-methoxyphenyl) carbonohydrazonoyl dicyanide,
159. (3-methoxy-4-(pyrazin-2-ylmethoxy)phenyl)carbonohydrazonoyl dicyanide,
160. (3-methoxy-4-(pyridin-3-ylmethoxy)phenyl)carbonohydrazonoyl dicyanide,
161. (3-methoxy-4-(pyrimidin-2-ylmethoxy)phenyl)carbonohydrazonoyl dicyanide,
162. (3-methoxy-4-((5-methylpyrazin-2-yl)methoxy)phenyl) carbonohydrazonoyl dicyanide,
163. (4-((1H-benzo[d]imidazol-2-yl)methoxy)-3-methoxyphenyl) carbonohydrazonoyl dicyanide,
164. (3-methoxy-4-(pyridazin-3-ylmethoxy)phenyl)carbonohydrazonoyl dicyanide,
165. (4-(benzo[d]thiazol-2-ylmethoxy)-3-methoxyphenyl)carbonohydrazonoyl dicyanide,
166. (4-(benzo[d]oxazol-2-ylmethoxy)-3-methoxyphenyl)carbonohydrazonoyl dicyanide,
167. (3-methoxy-4-(thiazol-4-ylmethoxy)phenyl)carbonohydrazonoyl dicyanide,
168. (4-((1H-pyrazol-3-yl)methoxy)-3-methoxyphenyl) carbonohydrazonoyl dicyanide,
169. (3-methoxy-4-(pyridin-2-ylmethoxy)phenyl)carbonohydrazonoyl dicyanide,
170. (3-methoxy-4-((6-methylpyridin-3-yl)methoxy)phenyl) carbonohydrazonoyl dicyanide,
171. (3-methoxy-4-((2-methylthiazol-4-yl)methoxy)phenyl) carbonohydrazonoyl dicyanide,
172. (3-methoxy-4-(thiophen-2-ylmethoxy)phenyl)carbonohydrazonoyl dicyanide,
173. (3-methoxy-4-(thiophen-3-ylmethoxy)phenyl)carbonohydrazonoyl dicyanide,
174. (3-methoxy-4-((1-methyl-1H-pyrazol-4-yl) methoxy)phenyl) carbonohydrazonoyl dicyanide, or
175. acetyl(3-methyl-4-(4-methylbenzyloxy)phenyl)carbonohydrazonoyl dicyanide.

2. A method of preparing the compound according to claim 1, the method comprising:

a first step of reacting a compound represented by Formula 2 below including a reactive amine group at one end with sodium nitrite and malononitrile in the presence of an acid to form an imine bond; and optionally, a second step of introducing an $R_1$ substituent into a product obtained in the previous step when $R_1$ is a substituent other than hydrogen:

$H_2N$—(Het)$Ar_1$-L-(Het)$Ar_2$ [Formula 2]

wherein, in Formula 2, L, (Het)$Ar_1$, (Het)$Ar_2$, and $R_1$ are as defined in claim 1.

3. The method of claim 2, wherein the first step is performed by a series of processes comprising the steps of:

1-1) dissolving the compound of Formula 2 and sodium nitrite in a $C_{1-4}$ lower alcohol solvent and adding an aqueous acid solution thereto at a temperature of −5° C. to 5° C. to form a diazonium salt;

1-2) adding malononitrile to a reaction solution including the diazonium salt obtained in step 1-1), and performing a reaction at a temperature of 15° C. to 40° C.; and 1-3) neutralizing the reaction solution of step 1-2) by adding an aqueous base solution thereto.

4. The method of claim 2, wherein the compound represented by Formula 2 including a reactive amine group at one end is prepared from a compound represented by Formula 3 below including a nitro group by way of a reduction reaction:

$O_2N$—(Het)$Ar_1$-L-(Het)$Ar_2$ [Formula 3]

5. The method of claim 4, wherein when L is —NHCO— or —CONH—, the compound of Formula 3 is prepared by way of:

i) a reaction between a (Het)$Ar_1$ derivative including carboxyl groups at sites linked to the nitro group and L and a (Het)$Ar_2$ derivative including an amine group at a site linked to L; or ii) a reaction between a (Het)$Ar_1$ derivative including amine groups at sites linked to the nitro group and L and a (Het)$Ar_2$ derivative including a carboxyl group at a site linked to L.

6. The method of claim 4, wherein when L is —$NHSO_2$— or —$SO_2NH$—, the compound of Formula 3 is prepared by way of:

i) a reaction between a (Het)$Ar_1$ derivative including amine groups at sites linked to the nitro group and L and a (Het)$Ar_2$ derivative including a chlorosulfonyl group at a site linked to L; or ii) a reaction between a (Het)$Ar_1$ derivative including halosulfonyl groups at sites linked to the nitro group and L and a (Het)$Ar_2$ derivative including an amine group at a site linked to L.

7. The method of claim 4, wherein when L is -(straight-chain or branched $C_{0-3}$ alkylene)'-O-(straight-chain or branched $C_{0-3}$ alkylene)"-, the compound of Formula 3 is prepared by way of:

i) a reaction between a (Het)$Ar_1$ derivative including -(straight-chain or branched $C_{0-3}$ alkylene)'-OH at sites linked to the nitro group and L and a (Het)$Ar_2$ derivative including -(straight-chain or branched $C_{0-3}$ alkylene)"-X (where X is halogen) at a site linked to L; or ii) a reaction between a (Het)$Ar_1$ derivative including -(straight-chain or branched $C_{0-3}$ alkylene)'-X at sites linked to the nitro group and L and a (Het)$Ar_2$ derivative including -(straight-chain or branched $C_{0-3}$ alkylene)"-OH at a site linked to L.

8. A composition for inhibiting aggregation of tau protein comprising the compound according to claim 1 as an active ingredient.

9. A composition for inhibiting hyperphosphorylation of tau protein comprising the compound according to claim 1 as an active ingredient.

* * * * *